United States Patent [19]

Lo et al.

[11] Patent Number: 5,001,649
[45] Date of Patent: Mar. 19, 1991

[54] LINEAR POWER CONTROL FOR ULTRASONIC PROBE WITH TUNED REACTANCE

[75] Inventors: Ying-Ching Lo, Fremont; Samuel Zambre, Palo Alto; Tolentino Escorcio, San Leandro, all of Calif.

[73] Assignee: Alcon Laboratories, Inc., Fort Worth, Tex.

[21] Appl. No.: 245,837

[22] Filed: Sep. 16, 1988

Related U.S. Application Data

[63] Continuation-in-part of Ser. No. 35,128, Apr. 6, 1987, which is a continuation-in-part of Ser. No. 928,235, Nov. 7, 1986.

[51] Int. Cl.$^5$ .......................................... G01H 11/08
[52] U.S. Cl. .............................. 364/484; 364/481; 331/1 R; 331/181; 331/36 R; 324/727; 323/205; 323/206; 310/316
[58] Field of Search ............... 364/481, 484; 331/1 R, 331/181, 4, 36 R, 177 R, 179; 310/317, 318, 311; 323/205, 206, 208, 209, 211, 212, 218; 324/107, 56, 59, 60 R; 318/116, 118; 73/612, 602, 651

[56] References Cited

U.S. PATENT DOCUMENTS

| | | | |
|---|---|---|---|
| 2,752,512 | 6/1956 | Sarratt | 310/8.1 |
| 2,799,787 | 7/1957 | Guttner | 310/8.1 |
| 2,872,578 | 2/1959 | Kaplan et al. | 250/36 |

(List continued on next page.)

FOREIGN PATENT DOCUMENTS

| | | |
|---|---|---|
| 0128635 | 12/1984 | European Pat. Off. |
| 0135907 | 4/1985 | European Pat. Off. |
| 0151003 | 7/1985 | European Pat. Off. |

(List continued on next page.)

OTHER PUBLICATIONS

Chinese J. Ophthalmol., (1979), 15(3):135-137.
Chinese J. Ophthalmol., (1981), 17(1):29-31.

(List continued on next page.)

Primary Examiner—Parshotam S. Lall
Assistant Examiner—V. N. Trans
Attorney, Agent, or Firm—Ronald C. Fish

[57] ABSTRACT

There is disclosed herein a driver system for an ultrasonic probe for allowing a user to have proportional control of the power dissipated in the probe in accordance with the position of power dissipation controls operable by the user and for automatically tuning upon user request such that the driving frequency is equal to the mechanical resonant frequency of said probe and such that the reactive component of the load impedance represented by said probe is tuned out. The system uses a tunable inductor in series with the piezoelectric crystal excitation transducer in the probe which has a flux modulation coil. The bias current through this flux modulation coil is controlled by the system. It is controlled such that the inductance of the tunable inductor cancels out the capacitive reactance of the load impedance presented by the probe when the probe is being driven by a driving signal which matches the mechanical resonance frequency of the probe. The resulting overall load impedance is substantially purely resistive. The system measures the phase angle and monitors the load current. This information is used to determine the mechanical resonance frequency by sweeping through a band of driving frequencies and finding the peak load current where the slope of the load current versus frequency function is greater than a predetermined constant. After the automatic tuning to the resonant frequency, the system automatically adjusts the bias current flowing through the flux modulation coil to maintain the substantially purely resistive load impedance for changing power levels. There is also disclosed herein an analog circuit to measure the Phase angle for the load driving signal and to adjust the frequency of the driving signal for best performance. This system includes an integrator to eliminate the effect of offset errors caused by operational amplifiers.

17 Claims, 34 Drawing Sheets

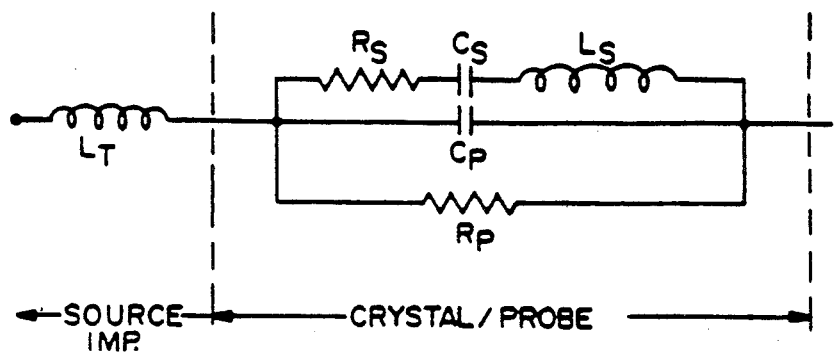
FIG. 2
FIG. 3
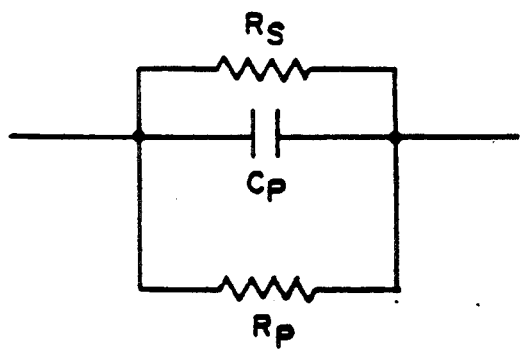
FIG. 4

FIXED FREQUENCY
PROPORTIONAL POWER
WITH TUNING INDUCTOR

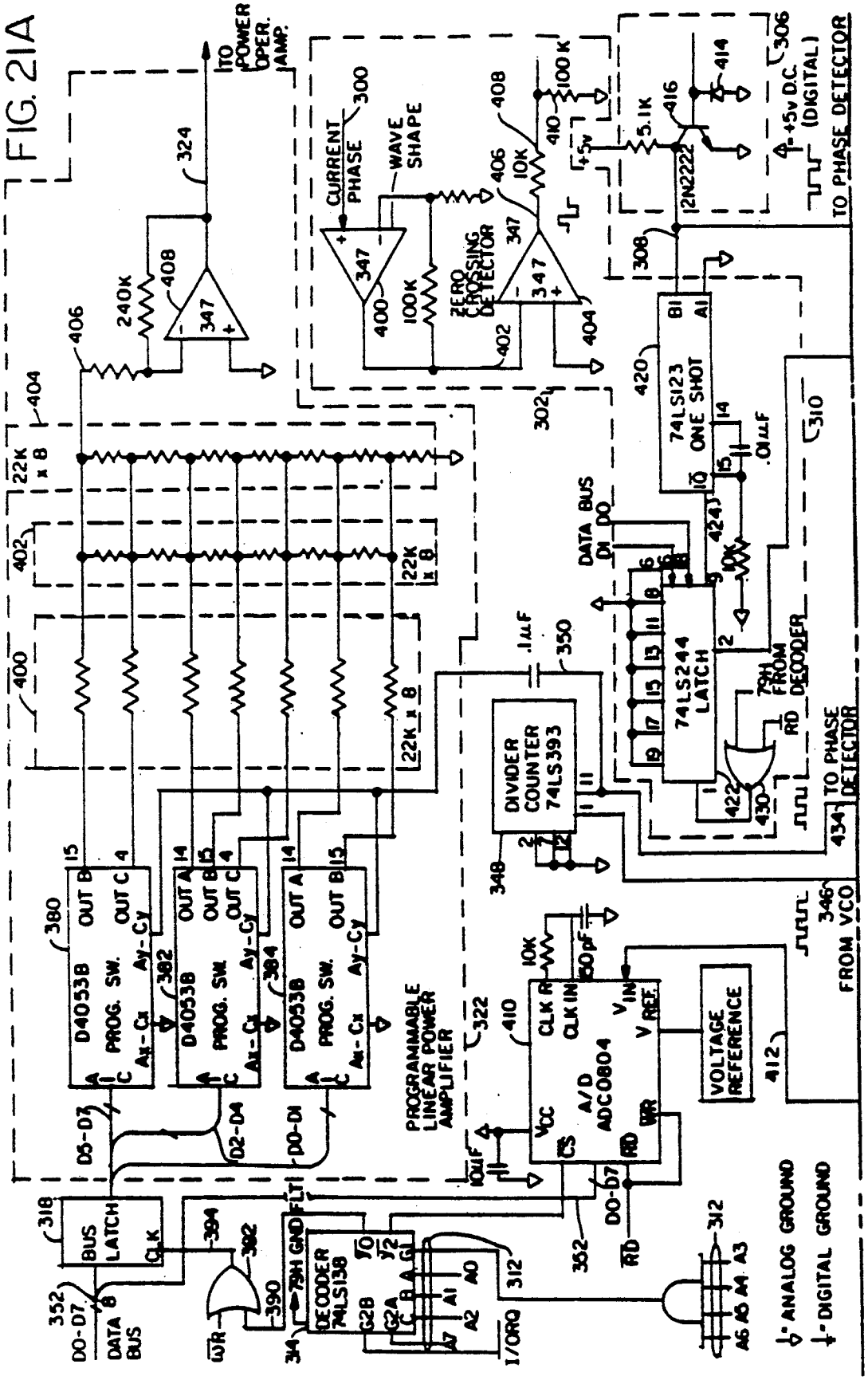

SWEEPER ROUTINE
(FREQUENCY)

LINEAR POWER CONTROL FOR ULTRASONIC PROBE WITH TUNED REACTANCE

BACKGROUND OF THE INVENTION

This is a continuation-in-part application of a U.S. Pat. application Ser. No. 035,128, by Lo et al. entitled "Linear Power Control for Ultrasonic Probe With Tuned Reactance", filed Apr. 6, 1987, which is currently co-pending, which was a continuation-in-part of a U.S. Pat. application Ser. No. 928,235, of the same title, filed Nov. 7, 1986, which also is co-pending.

The invention relates to the field of phacoemulsification probe driving apparatus, and, more particularly, to the field of tuned reactance process for phacoemulsification.

It has long been known that, in delivery of electric power to inductive loads or capacitive loads, maximum efficiency and maximum delivery of said power occurs when the phase angle between the voltage across the load and the current through the load is substantially zero. The phase angle of a system is related to the power factor. Those skilled in the art appreciate that the impedance of any network which includes inductive or capacitive elements in addition to resistive elements is the vector sum of the real component, i.e., the resistive elements, and the imaginary component caused by the presence of the inductive and capacitive elements. If the reactive component is zero, then the impedance of a system is purely resistive, and the resultant vector is coincident with the real axis. In such a circumstance, the phase angle is zero. Power factor is a measure of the relative magnitudes of the reactive and real components in a load impedance. It is related to the relative magnitude of these two vector components.

Power factor is also a measure of the efficiency of a system in delivering power to a load. Since only resistive components can actually dissipate power, the presence of an inductive or capacitive reactance component in a load impedance will decrease the efficiency of power delivery of the system, since it causes increased power dissipation in the source resistance of the power supply. The reason for this is well understood by those skilled in the art and will not be detailed here. As a consequence of the foregoing reality, it has long been known by utility companies and other practitioners of the power delivery art that to maximize the efficiency of power delivery to a load, it is useful to tune out the reactive component of the load impedance by placing it in series or parallel with an equal and opposite sign reactive component in a tuning circuit so that the resultant load impedance is purely resistive. In such a circumstance the source impedance is said to be the matched conjugate of the load impedance, and the power delivered to the load is maximized.

Power delivered to a load is given by the following expression:

$$\text{Power} = VI \cosine \theta \tag{1}$$

where V is the voltage drop across the load impedance, and I is the series current flowing through the load impedance, and coine theta is the power factor of the circuit. The power factor is said to be "leading" if the current leads the voltage, and "lagging" if the current lags the voltage.

Ultrasonic probes have traditionally been used for phacoemulsification for rupturing of cataracts in the eye coupled with aspiration of the pieces of tissue disrupted by the probe. There have been developed two classes of probes, one of which is excited by piezoelectric crystals. Such piezoelectric probes traditionally have been rods of metal, such as titanium, having piezoelectric crystals affixed therein to act as excitation sources to cause the rods to vibrate. The piezoelectric crystals are driven with electrical alternating current driving signals having high frequencies, such as 40,000 Hz. The length of the probe is such that it is a multiple of one-half the wavelength of the driving signal. Vibration of the piezoelectric crystal under the influence of the driving signal causes the rod to vibrate at its mechanical resonant frequency.

The piezoelectric crystals which are used as excitation sources in such probes, when coupled with the mass of the probe rod, can be modeled as an equivalent electrical circuit having inductive, capacitive, and resistive components. There is a capacitive component representing the elasticity of the metal of the rod and inductive component representing the mass of the probe. There is also a resistive component representing resistance to motion of the tip of the rod as it hits loads such as tissue or fluids in the eye which tend to dampen the vibration of the tip of the probe. The piezoelectric crystal itself contributes a resistive component which is related to the amount of leakage of current between the terminals of the crystal. The crystal also has a capacitive component which represents the intrinsic electrical characteristics of piezoelectric crystals, i.e., the thickness and the dielectric constant and the area.

As the temperature changes, and as load on the probe changes, the various resistive and reactive components in the equivalent circuit of the probe change values. These changes in the component values change the mechanical resonant frequency of the probe. Unless the driving frequency is changed to correspond with the changed resonant frequencies, maximum power-transfer efficiency will not be achieved.

Further, those skilled in the art understand that maximum power transfer between a source and a load occurs when the impedances of the source and the load are matched so that the load appears to be purely resistive. Therefore, in the case of an ultrasonic probe if the probe load impedance at the resonance frequency has a capacitive reactive component, the source impedance should have an inductive reactive component of equal magnitude to maximize power transfer between the source and the load. Because of the changing magnitudes of the resistive and reactive components of the combined mechanical and electrical system of a phacoemulsification probe, as the power level changes and as the temperature and load conditions of the probe change, it is difficult, if not impossible with a fixed inductor, to match the source impedance to the load impedance to cancel out the probe's reactive component over a broad range of power levels and frequency variations. An advantage of such a matched, tuned system is that low voltage components may be used since the impedance seen by the source voltage generator is minimized (looking into a two-port network including the tuning inductor).

Accordingly, there has arisen a need for a phacoemulsification probe driver which can be tuned such that the reactive component of the load is canceled as conditions such as power level, temperature, and loading change. Further, there has arisen a need for a probe driver circuit which can alter the driving frequency to match the changed mechanical resonant frequency as power level, temperature, and loading conditions change or as new probes are attached to the system. Further, a need has arisen for a phacoemulsification probe driver with proportional power control such that the user may set a desired power level and that level of power will be transmitted to the probe.

SUMMARY OF THE INVENTION

According to the teachings of the invention, there is disclosed herein a method and apparatus for providing substantially proportional power control for a phacoemulsification probe with automatic tuning to the mechanical resonance frequency of the probe and automatic tuning out of the reactive component of the load impedance. The constant tuning to cancel the load impedance reactive component allows the system to maximize the efficiency of power transfer from the driver to the probe. The apparatus and method for tuning the phacoemulsification probe driver frequency to substantially match the changing mechanical resonant frequency of the probe upon request from the user or as power level, temperature, and loading conditions change in some embodiment finds the resonant frequency by sweeping the drive frequency and finding the peak load current where the slope of the load current versus driving frequency function is greater than a predetermined constant. This constant eliminates spurious peaks from being falsely assumed to be resonant peaks.

In the preferred embodiment, the linear power control apparatus includes a microprocessor which is coupled through a serial interface to a foot pedal control manipulated by the user to set the desired level of power. The microprocessor is also coupled to a maximum power level control on the front panel, which is also manipulated by the user to establish the 100% power level. The microprocessor reads the foot pedal position and the position of the maximum power level control on the front panel and scales the signal from the foot pedal to determine the desired power level as a percentage of the maximum level set by the user at the front panel. The microprocessor then generates a digital gain number and sends it to a programmable gain linear power amplifier inside a voltage controlled oscillator. The programmable linear power amplifier amplifies the driving signal by the gain level established by the digital input from the microprocessor. The output of the linear programmable amplifier is then amplified by another power amplifier operating in class AB. The output of this amplifier is applied to a voltage step-up transformer which has its secondary coupled through a tuning inductor to the piezoelectric crystal or crystals which excite the phacoemulsification probe. The microprocessor also controls the frequency of the voltage controlled oscillator in a manner to be described below.

The tuning inductor is the means by which the source impedance of the probe driver circuitry may be adjusted so that the driver circuitry source impedance is maintained so as to cancel the reactive component of the load impedance presented by the crystal and the mechanical system of the probe. The tuning inductor, in the preferred embodiment, is comprised of a ferromagnetic core with three arms extending therefrom. Two of these arms have the DC bias coils wrapped around them. The AC driving signal is driven through a tuning inductor coil wrapped around the third leg and sets up a magnetic flux through the core, part of which passes through the arms around which the bias coils are wrapped. The magnetic flux modulating coil has a DC current flowing therein at an amplitude controlled by the microprocessor. The purpose of the tuning inductor is to allow the microprocessor to control the amount of inductance which is in series with the load impedance such that the source impedance may be tuned to cancel the reactive component of the load impedance for all load, temperature, and power level conditions. Any tunable inductor which can be used to cancel the capacitive reactance of the load will suffice for purposes of practicing the invention.

In order to control the reactive component of the source impedance, the microprocessor needs to sense the power factor or phase angle between the phasor representing the current waveform for current flowing through the piezoelectric crystal load and the waveform representing the driving voltage across the piezoelectric crystal load. A phase detector is used for this purpose. It has one input which samples the voltage waveform for the driving voltage across the crystal and it has another input which samples the current waveform for the driving current through the crystal. This current waveform sampling is taken from a current sensor in series with the primary side of the voltage step-up transformer. The feedback voltage from this current sensor is proportional to and in phase with current flowing through the primary of the step up transformer. It is the phase angle between the current flowing in the primary and the voltage across the primary as indicated by a SYNC signal from the voltage-controlled oscillator which is in phase with the driving voltage which is tuned by the system to be zero or some other user defined acceptable phase angle so as to cancel the reactive component of the load. Any other means of sensing the phase of the load current will also suffice for purposes of practicing the invention.

The phase detector generates two pulse-width modulated digital signals which represent the magnitude of the phase and its sign. These pulse-width modulated signals are summed and integrated to generate an analog signal representing the magnitude of the phase angle error. This analog signal is converted by an A/D converter to a digital number representing the phase angle error. Any phase angle other than zero represents an out-of-tune condition where the reactance of the probe impedance is not canceled. When the phase angle is nonzero (or whatever acceptable phase angle the user sets in some embodiments), the microprocessor senses this fact and alters the DC current flowing through the magnetic flux modulating coil in the tuning inductor. This alters the amount of magnetic flux in the core passing through the AC driving coils of the tuning inductor, thereby altering the inductance thereof. This process is continued with small changes to the drive current of the D.C. coil until the reactive component of the probe impedance is canceled and the source drive impedance is a matched conjugate of the probe impedance.

In the preferred embodiment, a sweeper software routine sweeps the driving frequency through a range of frequencies known to include all possible mechanical resonant frequencies of commercially useable phacoemulsification probes. During this sweep, the probe drive current is monitored and compared to the highest probe driver current to that point in time. If the current frequency of the driving signal results in a probe drive current which is greater than the current highest probe driver current, the current probe driver current is replaced with the new highest probe driver current value. Slope calculations to determine the slope of the function of load current versus driving frequency are continuously performed. This process is continued until the entire range of frequencies has been surveyed. The frequency corresponding to the highest probe driver current having a slope which is greater than a predetermined constant is then set into the VCO by sending a signal to the frequency modulation input of the VCO causing it to generate a probe driving signal having the corresponding frequency. After the proper driving frequency is determined, a software routine to tune away the phase angle as much as possible is performed. This routine determines the phase angle difference between a constant reference phase angle representing the desired or unavoidable phase angle difference and the actual phase angle. The difference is then used to adjust the D.C. coil bias drive. This process of successive approximation is then continued until the phase angle difference falls within an acceptable range.

The methods of linear power control, impedance matching over wide ranges of conditions, and source frequency tuning to match the resonant frequency according to the teachings of the invention may be understood from the above description of the functions of the apparatus that implements these processes.

The teachings of the invention can be better understood by reference to the following drawings.

BRIEF DESCRIPTION OF THE DRAWINGS

FIG. 2 is the simplified equivalent circuit model used to explain the operation of the probe and tuning inductor system.

FIGS. 3A and 3B are two expressions of the mathematical relationships needed to explain the functioning of the system.

FIG. 4 is the simplified equivalent circuit of the probe at the mechanical resonant frequency.

FIGS. 21A and 21B together comprise a more detailed schematic diagram of the analog embodiment of FIG. 20.

DETAILED DESCRIPTION OF THE PREFERRED EMBODIMENT

Figure 1:
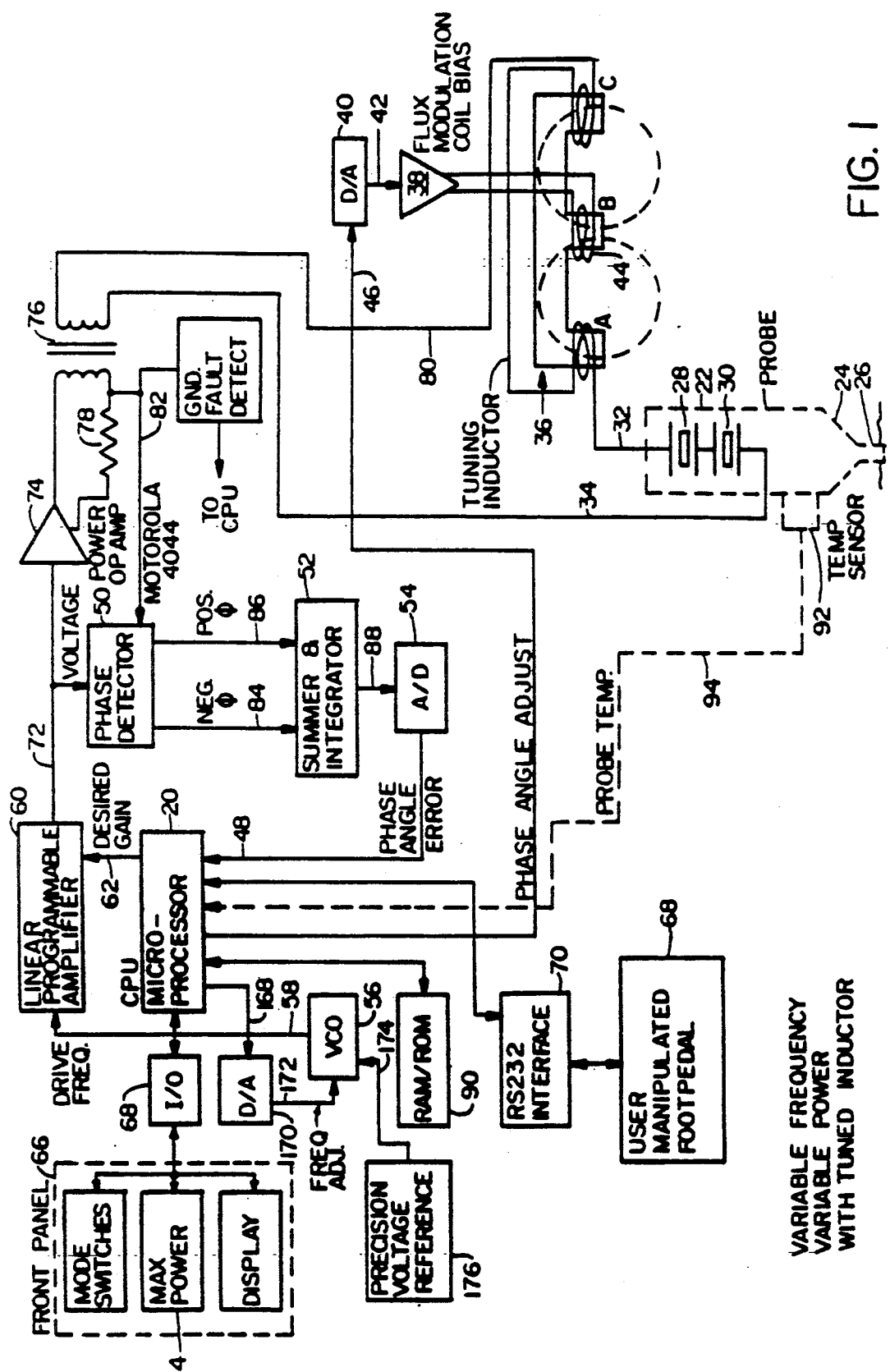
FIG. 1 is a block diagram of one embodiment of the invention which implements all teachings of the invention.

Referring to FIG. 1, there is shown a block diagram of one embodiment of the invention which implements all three aspects of the teachings of the invention. A microprocessor 20 is at the heart of the system. In one embodiment, the microprocessor 20 is part of an off-the-shelf Micro/Sys B8010 CPU card. The microprocessor 20 controls all the functions which the system performs. According to the teachings of the invention, three separate and independent function are performed, all of which can be used independently of the other functions and all of which have utility in phacoemulsification probe driver systems. The best performance, however, results from use of all three aspects of the invention in combination. The purpose and function of the various components of the system will be explained in the course of explaining each function that the system performs so that the cooperation of each individual element with the other elements in order to accomplish the function will be clear.

It is useful in phacoemulsification probe driver systems to have a substantially linear control over the amount of power dissipated in the probe. In FIG. 1, the probe 22 is a metal rod having a conical mechanical amplifier section 24 and a projecting nosepiece 26 in the form of a small diameter tube on the mechanical amplifier 24. Embedded in or otherwise mechanically attached to the metal of the probe 22 are a pair of piezoelectric crystals, 28 and 30. The purpose of the crystals 28 and 30 is to excite the metal of the probe 22 to vibrate at its mechanical resonance frequency as the crystals vibrate in response to electrical driving signals on the lines 32 and 34. Together the piezoelectric crystals 28 and 30 and the mechanical system of the probe 22 can be modeled by the equivalent circuit shown in FIG. 2. These two resistive components $R_p$ and $R_s$ represent, respectively, the leakage between lines 32 and 34 of the crystals 28 and 30 and the resistance of the mechanical load, e.g., cataract or water or other tissue, touching the tip of the projecting nosepiece 26 to movement of the projecting nosepiece 26. The value of $R_s$ changes drastically when the nosepiece 26 comes into contact with liquid such as water or other fluids in the eye versus free vibration in air. Computer simulations of the crystal/mechanical system show that $R_s$ can increase drastically with changing conditions.

As power is dissipated in the crystals, the temperature of the probe 22 can increase if sufficient amounts of power are dissipated over time. Normally the probe 22 has a fluid passageway through the nosepiece 26 to which a vacuum is applied such that tissue and eye fluids which the nosepiece comes into contact with may be aspirated through the nosepiece and into a collection cassette. This causes some cooling of the probe, so the temperature rise of the probe depends upon the thermal equilibrium between heat flowing into the probe by virtue of power dissipation in the crystal versus heat being taken out of the probe by virtue of cooler fluids being aspirated through the fluid channel (not shown) in the nosepiece 26.

As can be seen from the equivalent circuit for the crystal/mechanical probe system, the series network of capacitance and inductance representing the mechanical aspects of the probe will have a mechanical resonant frequency. Generally speaking, when the crystals 28 and 30 are driven with a frequency so as to vibrate at the mechanical resonant frequency, the series capacitance and inductance representing the mechanical aspects of the system will cancel each other out and disappear from the equivalent circuit representing the overall probe load impedance. This leaves an equivalent circuit which is dominated by the capacitance of the piezoelectric crystals as shown by FIG. 4. Thus, the load impedance has a capacitive reactance component. In order to get maximum efficiency of power transfer, this capacitive component of the load impedance must be canceled out by an equal and opposite inductive impedance in series with it. This is accomplished by use of a tuning inductor 36 having an inductance $L_T$. The tuning inductance consists of a ferromagnetic core having three legs labeled A, B, and C. Legs A and C have wound thereabout A.C. driving signal coils which are connected in series. The purpose of these coils is to provide an inductance in series with the load impedance of the probe to help cancel the capacitive reactance of the load impedance at the mechanical resonant frequency. To that end, the A.C. driving signal coils, which will hereafter be referred to as coils A and C, establish paths of magnetic flux which pass through the ferromagnetic material of legs A and C, out into the air and then back into the core through the leg B.

The leg B has wound thereabout a D.C. flux modulation coil. When D.C. is passed through this coil, the amount of magnetic flux in the ferromagnetic coil is altered. When the amount of flux in the core is altered, the inductance of the inductor changes. Thus, by controlling the magnitude of current flowing through the coil 44 wrapped around leg B (hereafter referred to as the flux modulation coil) the inductance of the tuning inductor may be changed.

The flux modulation coil 44 is coupled to the output of a voltage-to-current amplifier 38. This amplifier receives a voltage input signal from a D/A converter 40. The purpose of the voltage-to-current amplifier 38 is to convert the voltage on the line 42 from the D/A converter to a corresponding magnitude of D.C. bias current flowing through the flux modulation coil 44.

The D/A converter 40 receives as its input a phase angle adjust digital word on the bus 46 from the microprocessor. This phase angle adjust word is generated by the microprocessor 20 in response to several input data items. One of these data items is the phase angle error word on the bus 48. This phase angle error data represents the phase angle between the phasor representing the driving voltage waveform applied across the crystal load and the phasor representing the current waveform for load current flowing through the crystal. This phase angle error information is developed in part by a phase detector 50. The output of the phase detector is coupled to a summer and integrator 52, which has its output in turn coupled to an A/D converter 54.

Figure 18:
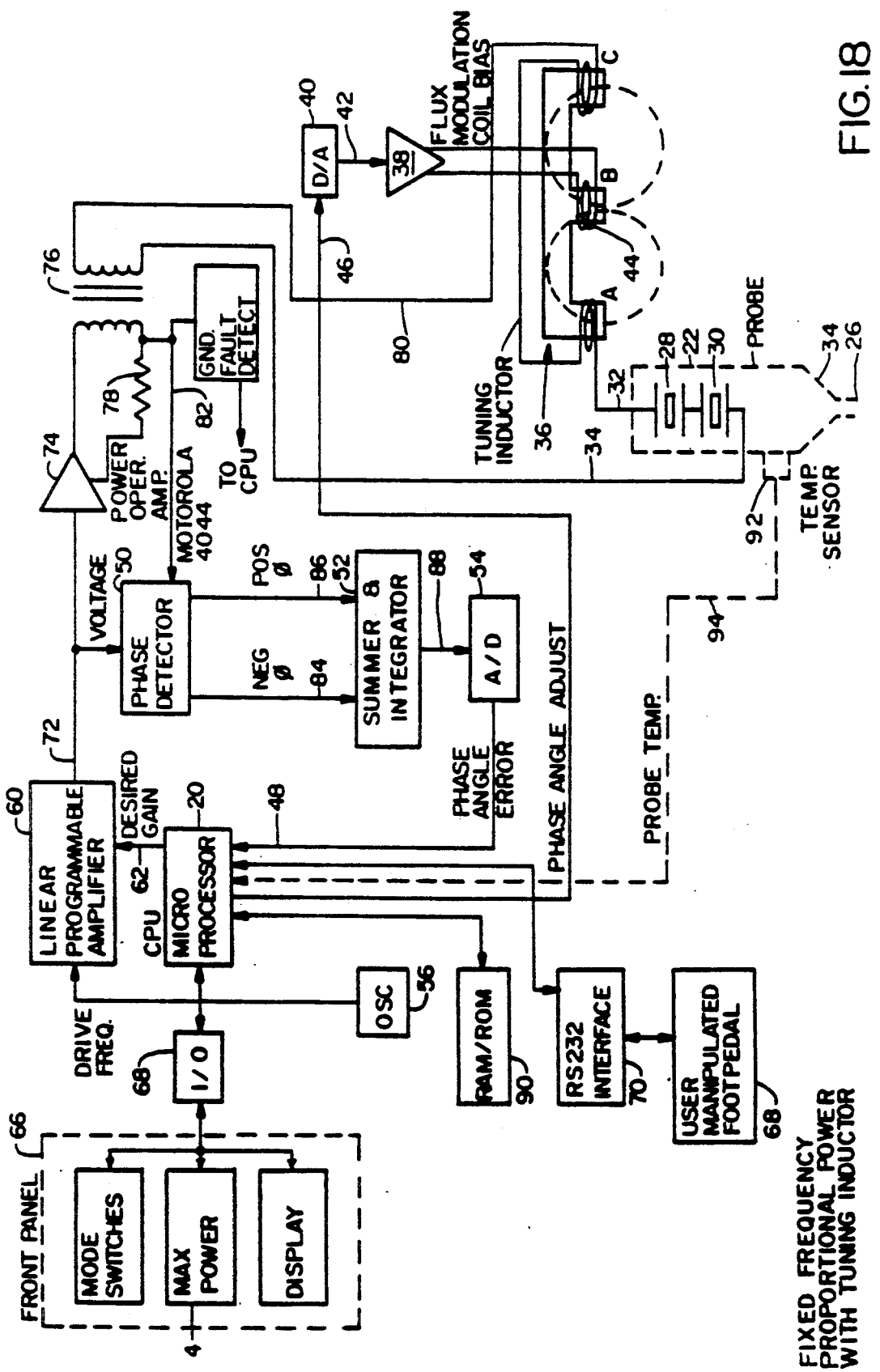
FIG. 18 is representative of a class of fixed frequency, proportional power embodiments with a tuned driving inductance to minimize the phase angle.
Figure 19:
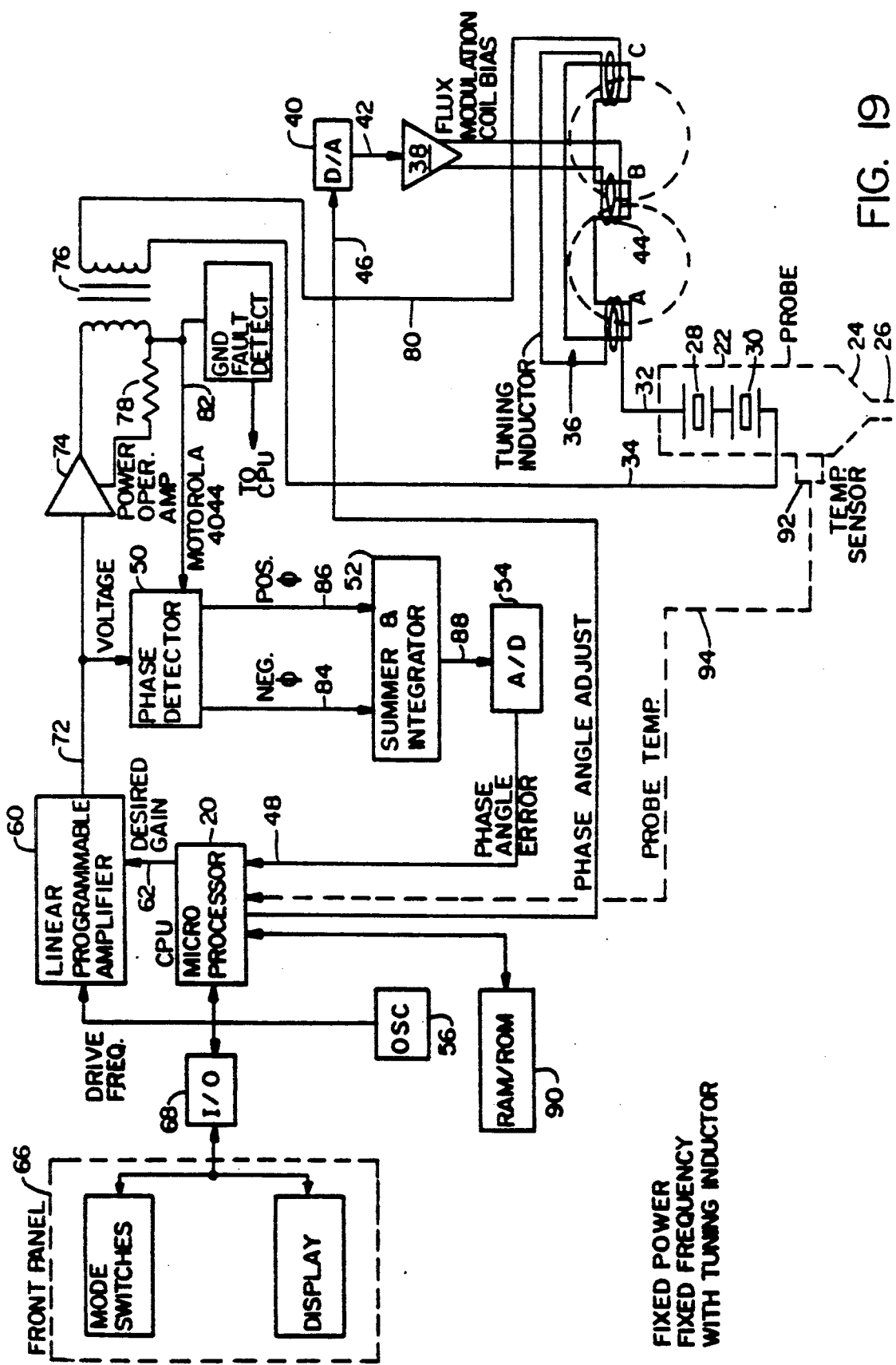
FIG. 19 is representative of a class of fixed power, fixed frequency tuned inductance embodiments.

To understand how the phase angle error adjust signal is generated on bus 48, the rest of the driving circuitry will be explained as a preliminary matter. The function of the driving circuitry is to drive the crystals 28 and 30 with an A.C. driving waveform which causes the crystals to vibrate at the mechanical resonance frequency of the probe 22. Obviously, the first step in this process is to generate a driving signal having a frequency which is equal to the mechanical resonance frequency of the probe 22. This is done, in one embodiment, by a voltage control oscillator 56. However, in some embodiments, the voltage control oscillator 56 could be a fixed frequency oscillator set at the mechanical resonant frequency for the probe for a temperature at which the probe operates most of the time. Such an embodiment is illustrated in FIGS. 18 and 19, where the FIG. 18 embodiment has proportional power control and the FIG. 19 embodiment has a fixed power level. As will be seen from discussions below, this is not an optimum situation but is acceptable under some circumstances.

The output of the oscillator on line 58 in FIG. 1 is applied to the input of a linear programmable amplifier 60. The purpose of this amplifier is to amplify the signal on the bus 58 by a gain value established by a signal on a bus 62. In one embodiment utilizing proportional power control, the data bits on the bus 62 represent the desired gain as set by the user.

In one embodiment, the user establishes the desired gain level by manipulation of two controls. The first control is the maximum power control 64 on the front panel 66. With the control 64, the user establishes the maximum power level desired. The microprocessor 20 reads this maximum power level through an I/O circuit 68 of conventional design. In one embodiment, the I/O circuit 68 is an SB8466 board manufactured by Micro/Sys of Glendale, Calif. Any conventional method and apparatus for performing the I/O transactions between the microprocessor and the front panel 66 will suffice for purposes of the invention.

The other user-operable control with which the desired power level is set is a foot pedal 68. This control allows the user to establish the desired power level as a percentage of the maximum power set by the control 64 by depressing a pedal with his foot. The depression of the foot pedal operates a transducer which may be read by the microprocessor 20 through an RS232 interface circuit 70 of conventional design. In one embodiment, the foot pedal is actually attached to a surgical instrument called the MVS-XIV or MVS-XX manufactured by Alcon Surgical, MID Labs, San Leandro, Calif. The MVS-XIV reads the foot pedal position and sends that information to the microprocessor 20 via the RS232 interface connecting the driver system of FIG. 1 to the MVS-XIV. However, this "middleman" architecture is not critical to the invention, and a direct connection between the microprocessor 20 and a foot pedal 68 with conventional interface circuitry may also be used. With the MVS-XIV present, however, the aspiration vacuum is generated to support the operation being performed with the probe. This vacuum is coupled by a vacuum line (not shown) to the probe 22.

The microprocessor 20 performs a scaling operation in the main software loop to be described below using data from the foot pedal 68 and from the maximum power control 64. The data from the foot pedal 68 is a number representing the percentage of full-scale deflection of the foot pedal. The data from the maximum power control 64 indicates the desired full power level set by the user for 100% deflection of the foot pedal. The microprocessor 20 simply combines these two numbers to determine the percentage of full-scale power currently desired by the user. This number is then output on the bus 62 to the linear programmable amplifier 60. This amplifier amplifies the driving signal on the line 58 and outputs it at the desired amplitude level on a line 72. In the fixed power embodiments such as is shown in FIG. 19, the digital word on bus 62 will be fixed, or, in some embodiments, will be one of a selected number of possible gain level steps available to the user.

The driving signal on line 72 is generally a sinusoid having an RMS voltage level related to the desired power dissipation. This signal is applied to the input of a power operational amplifier 74 for amplification in a class AB mode.

The output of the amplifier 74 is applied to the primary of a voltage step-up transformer 76. A current-sensing resistor 78 is in series with the return line from the primary of the transformer to the operational amplifier 74. The secondary of the transformer 76 is coupled to the line 34 and a line 80. The line 80 is coupled to one end of the coil C on the tuning inductor. The other terminal of coil C is coupled to one terminal of coil A. The other terminal of coil A is coupled via a line 32 to one terminal of the crystals 28 and 30 (which are coupled in series). The line 34 is coupled to the return side of the piezoelectric crystal 30. Thus the current flowing in the secondary of the step-up transformer 76 is the series current flowing through the crystals 28 and 30 of the probe 22. Note that this current also flows through the tuning inductor coils A and C.

Since the voltage waveform on line 72 is in phase with the voltage waveform across the primary of the step up transformer, the phase detector 50 can sample the voltage on the line 72 with the assurance that the waveform on the line 72 is in phase with the voltage across the step up transformer. To determine the relative efficiency of power transfer from the driver to the probe, the phase angle between the voltage across the step up transformer primary and the current through the primary must be determined. The phase detector does this by comparing the phase of the voltage waveform on the line 72 to the phase of the current flowing in the primary of the step-up transformer 76, as determined by the voltage drop across the current-sensing resistor 78. The phase detector 50 is a conventional Motorola integrated circuit or any equivalent which is commercially available.

The magnitude of the phase angle error is indicated by the width of the pulses on lines 84 and 86. The purpose of the integrator 52 is to average out the pulses over time so that the system has a smooth D.C. response to changes in the phase angle. The A/D converter 54 converts the analog phase angle error signal to a digital phase angle error word on bus 48.

The microprocessor 20 perform the linear power control, impedance-matching, and frequency-tuning functions of the invention by running a program stored in local RAM 90. This memory also includes ROM for storage of look-up tables and other information which does not change over the life of the system.

Referring to FIG. 3, equation (A), there is shown the expression which defines the relationships which exist when the piezoelectric crystals are being driven at the resonant frequency of the mechanical system (equation A). Equation B in FIG. 3 defines the value of the tuning inductance when it is in the tuned condition when the crystals are being driven at the resonant frequency of the mechanical system. Equation A represents the expression for the resonant frequency of the mechanical probe system for any particular temperature.

In FIG. 2, the mechanical system is represented by the components in the equivalent circuit, labeled $R_S$, $C_S$, and $L_S$. The value of the component $R_S$ represents the mechanical load engaged by the tip of the probe. The component $C_S$ represents the elasticity of the metal in the probe. The component $L_S$ represents the mass of the probe. The value of the components $C_S$ change with changing temperature. The temperature may change either because the ambient temperature changes or because of power dissipated in the probe through excitation of the crystals. The value of the component $R_S$ changes greatly with the loading of the probe.

The other components of the crystal/probe system equivalent circuit are $C_P$ and $R_P$. The component $C_P$ represents the parallel electrical capacitance of the crystals 28 and 30 in FIG. 1. The component $R_P$ represents the leakage of electrical current between the terminals of the crystals, i.e., the current leakage from line 32 to line 34.

At the mechanical resonance frequency, the reactive component represented by $C_S$ (jw $C_S$) is exactly equal to and opposite in sign to the reactive components $L_S$. (1/jw $L_S$). Since these two reactive components cancel each other out, the equivalent circuit for the crystal/probe system is as shown in FIG. 4. As can be seen from FIG. 4, the equivalent circuit has a substantial capacitive reactance of the crystals 28 and 30. Thus the load impedance has a real component represented by the value of the resistors $R_S$ and $R_P$ in parallel, and a reactive component of a capacitive nature represented by the capacitance $C_P$. According to the teachings of the invention, maximum power efficiency will be achieved by tuning the tuning inductor $L_T$ so as to cancel out the reactive component and the load impedance represented by $C_P$. When the crystals 28 and 30 are driven at the resonant frequency of the mechanical system for any particular temperature, the necessary value for the tuning inductance is given by equation B in FIG. 3.

As can be seen from equation B, the value for the tuning inductance is highly dependent on the value for the resistive components $R_S$ and $R_P$ and upon the value of the parallel electrical capacitance of the crystals 28 and 30. This means that the necessary value for the tuning inductance to keep the probe system in proper tune will change with changing temperature, changing loading conditions, and changes in the level of power dissipated in the probe by the driving system. The reason for this is that either changes in ambient temperature or power dissipation in the probe raises the temperature of the probe and therefore affects the elasticity of the material. This changes the value of the component $C_S$ in the equivalent circuit of FIG. 2 and therefore changes the mechanical resonant frequency as defined by equation A of FIG. 3. Changing loading conditions also change the mechanical resonant frequency because, in addition to changing the value of $R_S$ in FIG. 2, changing load also affects the value of $L_S$ because the load becomes an effective part of the mass of the system. This also changes the value of the mechanical resonant frequency defined by equation A by FIG. 3.

The teachings of the invention regarding tuning out the capacitive reactance of the crystal/probe system, when operating at its resonance frequency, may be implemented in at least two ways. One way is a coarse-tuning-only process, and the other way is a coarse-tuning process followed by a fine-tuning process. In one embodiment, the value of $L_T$ is adjusted to the level defined by equation B in FIG. 3 using a two-step process. The first step in this process is a coarse-tuning process where the phase angle error word on line 48 is used to generate an address into a look-up table. This look-up table will have stored therein experimentally determined values for the phase angle which result from various power levels. The overall effect of changes in the equivalent circuit component values with changing power levels is to alter the magnitude of the overall load impedance and its phase angle relative to its real component. The reactive component of the load impedance also changes, thereby destroying the reactive component canceling match with the source impedance. This alteration in the match of the two impedances changes the phase angle. Unless $L_T$ is changed in response to these changes, the probe will be out of tune and maximum power transfer efficiency will not be maintained.

The system of the invention uses the phase angle change resulting from the above-noted changes as an index into a look-up table from which data is obtained which defines the necessary magnitude of the tuning inductor for that phase angle condition to keep the system tuned for maximum performance. The look-up table contains experimentally determined data which defines the optimal magnitude for the inductance of the tuning inductor for a given phase angle, or power level, or temperature, or some combination of the three. Although in some embodiments the look-up table adjustment alone may be sufficient, in one embodiment, a further adjustment is made to fine tune the inductance of the tuning inductor to bring the phase angle to zero or some other predetermined acceptable level of phase angle error. The second stage in this process of tuning the tuning inductor involves incrementing the D.C. bias level of the flux modulating coil and testing the phase angle. This process is continued until the phase angle reaches the predetermined acceptable angle. The user can set any acceptable level for the phase angle including zero.

Figure 5:
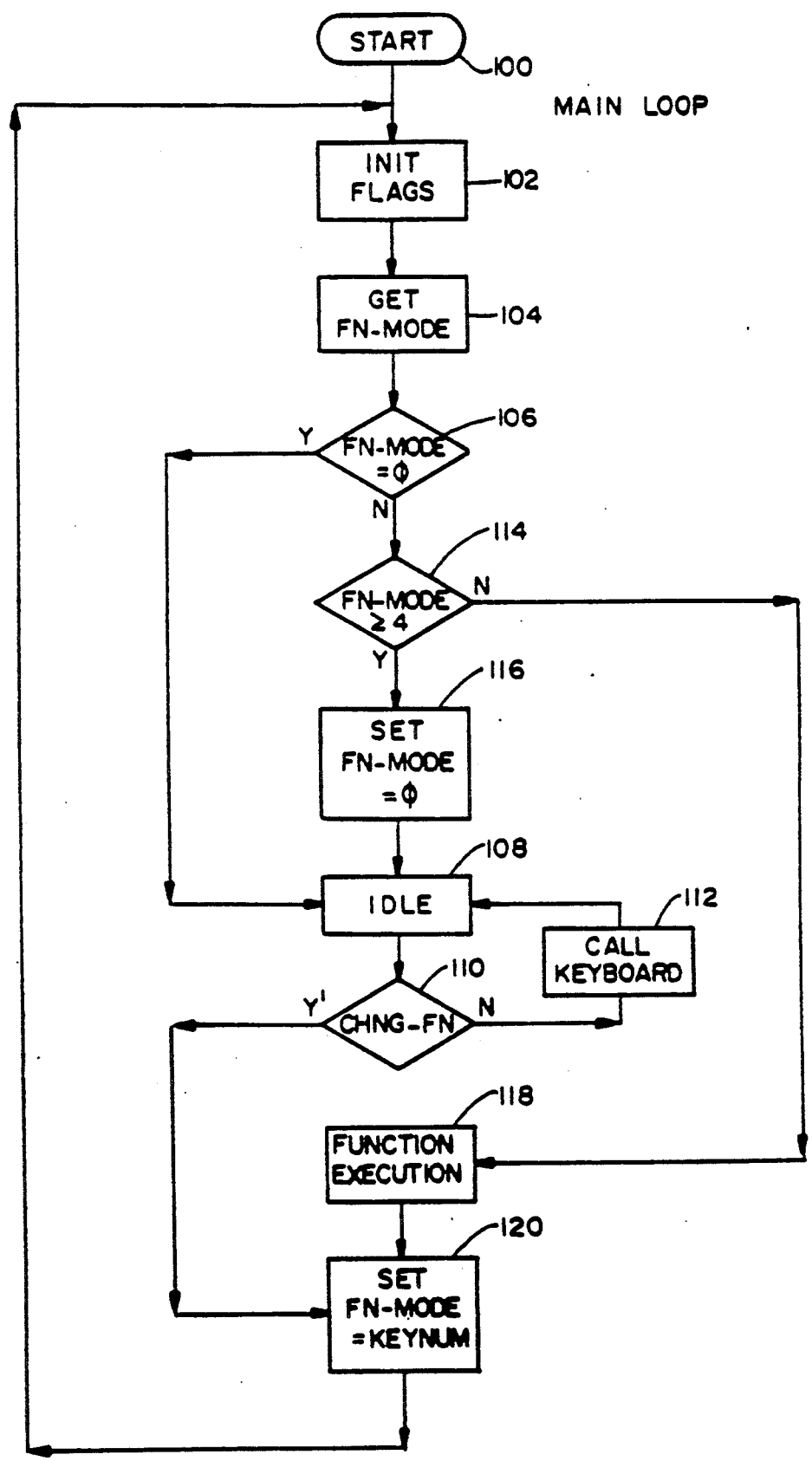
FIG. 5 is a flow diagram of the main loop of the control program that controls operations of one embodiment of the invention.

Referring to FIG. 5, there is shown a flow chart for the main loop of the software run by microprocessor 20. The purpose of the main loop of the program is: to establish the mode in which the system is to operate; to monitor the functions of the system; to provide audio responses to the user's manipulation of various controls; to handle display data on the front panel; to communicate with any system coupled to the serial part; and to perform any necessary mathematical computations such as foot pedal position scaling.

Main loop processing begins at power-up time in block 100. From there processing proceeds to block 102, where various system flags are initialized. These flags indicate the status of various conditions in the system, such as error conditions and so on, for the various functions of the system.

Processing then proceeds to block 104. In this block, the microprocessor reads the data from a buffer which contains I/O data from the function switches on the front panel. When the function switches are manipulated by the user, interrupts are generated which cause the function switches to be read by the microprocessor. Data obtained in this I/O operation is then stored in a buffer in the RAM 90 in FIG. 1. Block 104 reads this portion of memory to obtain the data and determine which function the user desires. The user can select a fixed power mode where the maximum power setting on the front panel is sent to the probe 22 or a linear power control where the desired percentage of the maximum power is sent to the probe 22.

Processing then flows to block 106. This block represents a test of the data obtained regarding the desired function. If the function data is zero, processing goes to block 108, where the machine idles waiting for something to happen. This idling occurs by continuous looping to a test block 110, where the microprocessor reads the contents of the function mode buffer and determines if there has been a change in the desired function. If there has not been a change, processing flows to block 112, which is a call to the keyboard reading subroutine. This subroutine addresses the function or mode keys on the front panel and reads the data describing their current status. This data is then written into the function mode buffer. Processing then returns to block 108.

Returning to block 106, if the test of the data in the function mode buffer indicates that the desired mode is not equal to zero, processing proceeds to the test of block 114. The purpose of block 114 is to determine whether the function mode data is equal to 4 or greater. Such function modes would be illegal and are filtered out. This filtering is done by block 116 when the answer to the test of block 114 is yes. In block 116, the data in the function mode buffer is cleared to zero, and processing proceeds to the idle block 108.

If the test of block 114 indicates that the function mode is not equal to 4 or a larger number, processing flows to block 118, where the function is executed. Function execution is simply a series of calls to subroutines which will be described when the interrupt service routines are described. Function execution also includes performing the scaling function on the foot pedal data.

After said execution, processing flows to block 120. Processing can also flow into block 120 from block 110 if the answer to the test of block 110 as to whether the function data has changed is yes. The purpose of block 120 is to write the new function mode data with the key number that was obtained by the keyboard routine when the front panel switches were read. Processing then proceeds from block 120 back to block 102 where the loop is begun again. The microprocessor will continue to loop through the processing of FIG. 5 until an interrupt occurs.

Figure 6A:
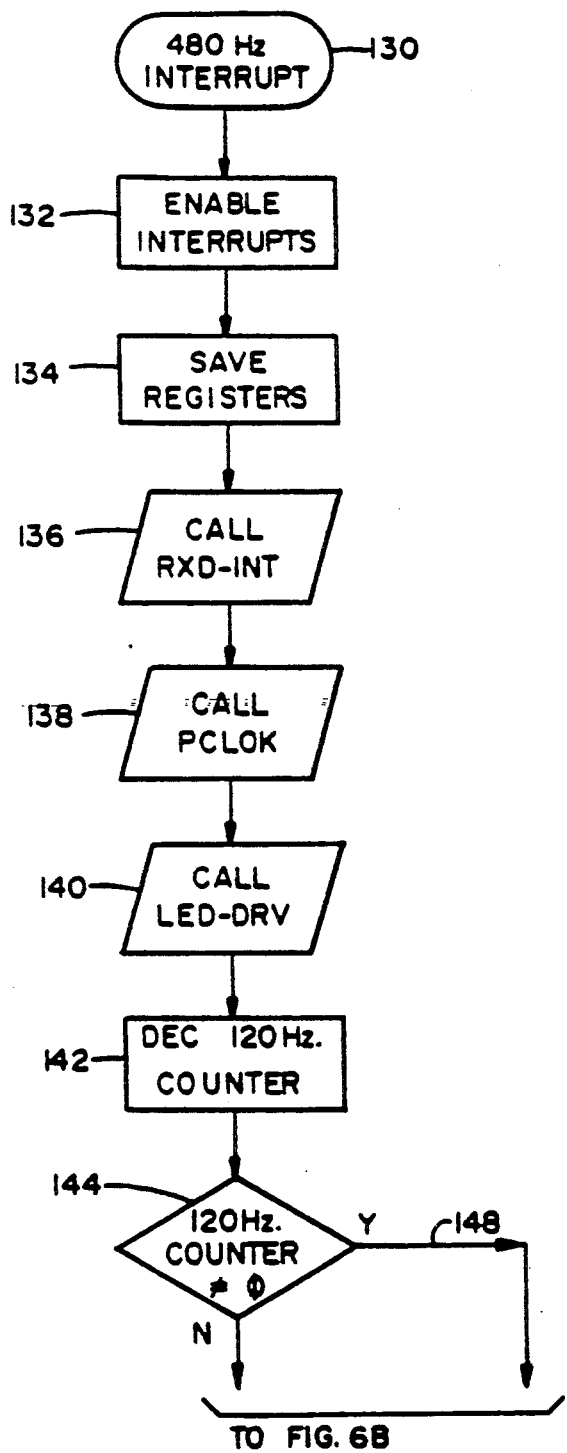
FIGS. 6A-6C are a flow diagram of the interrupt service routines of the control program of one embodiment of the invention.
Figure 6B:
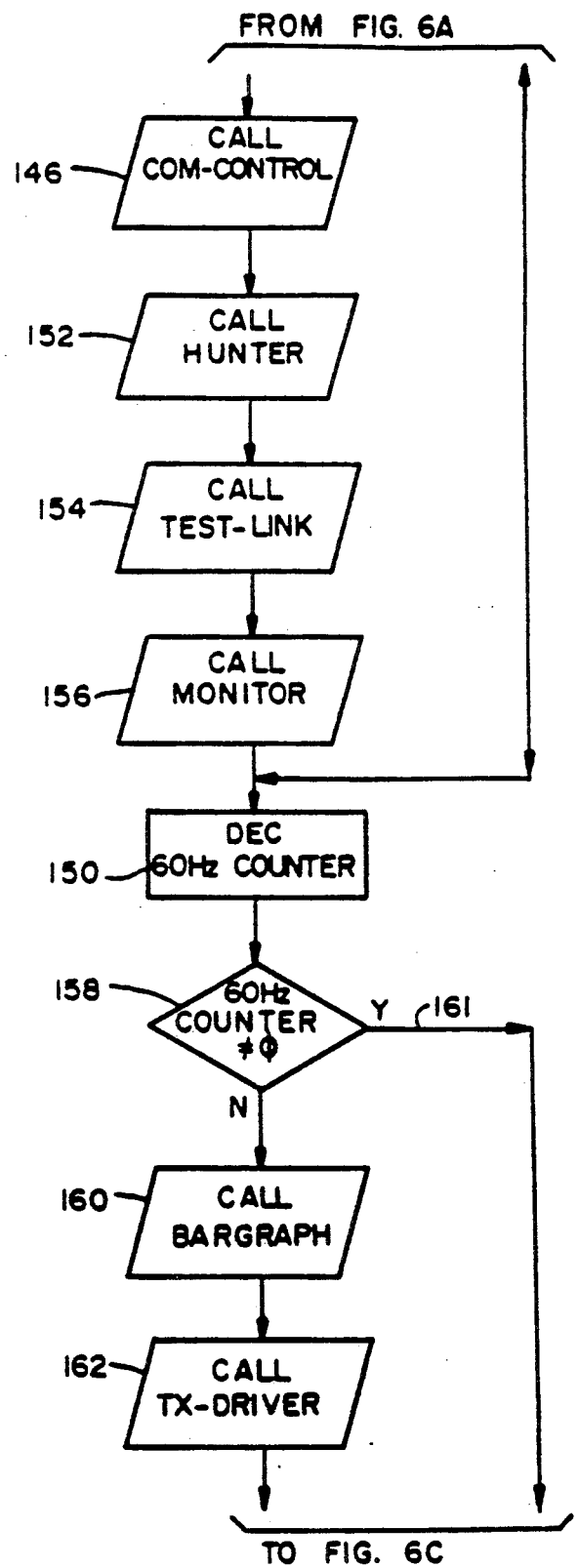
Figure 6C:
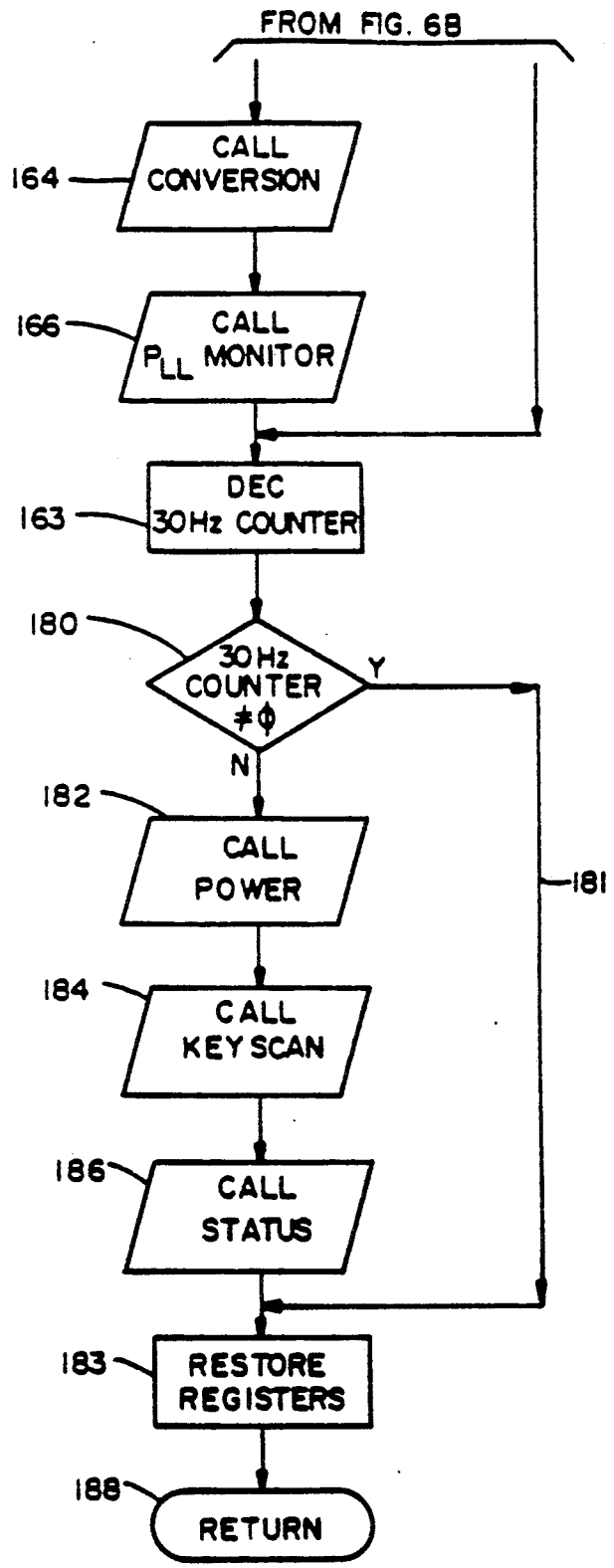
Figure 7:
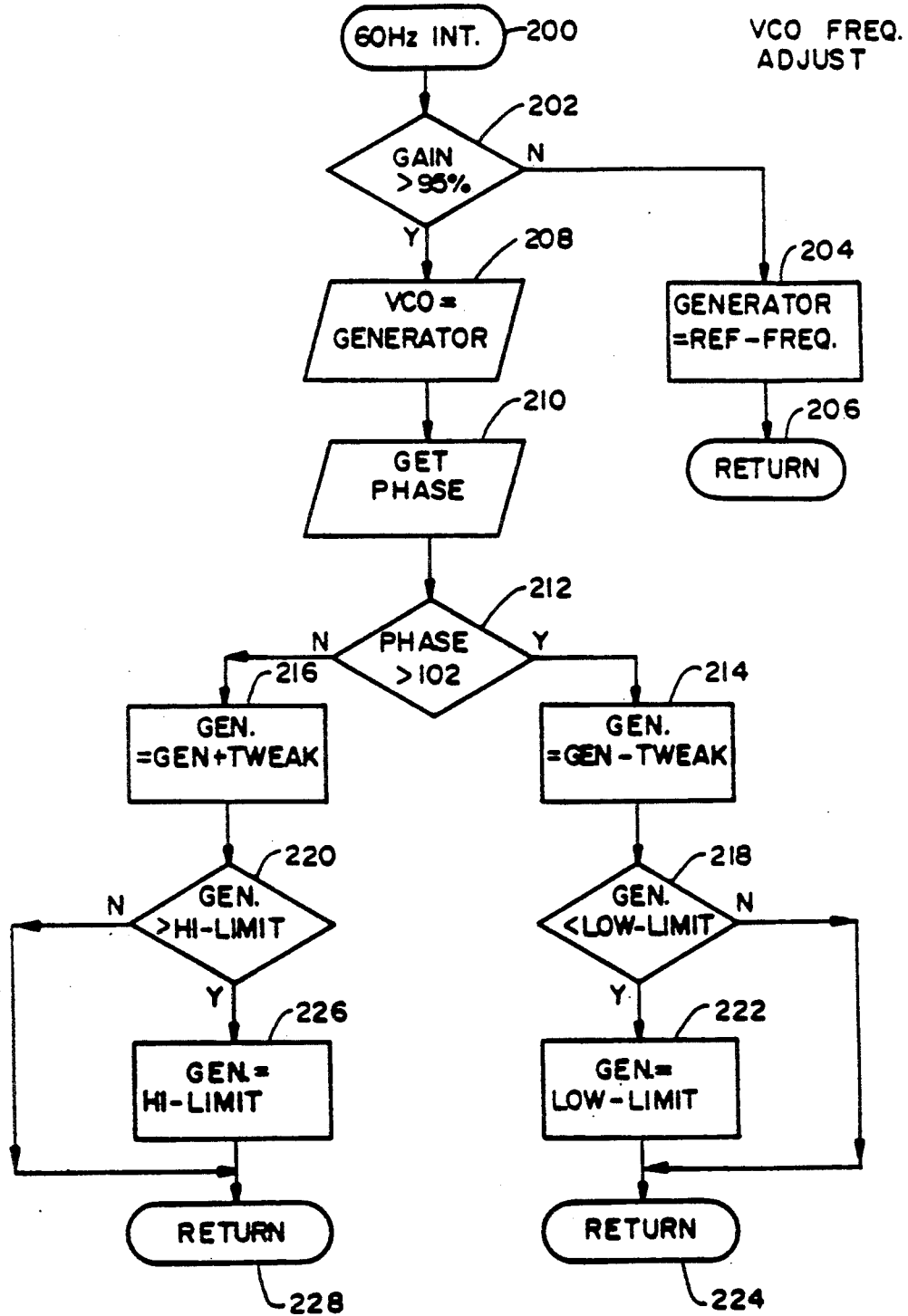
FIG. 7 is a flow chart representing further detail on the portion of the interrupt service routine that alters the VCO frequency to track changes in the mechanical resonant frequency of the probe in one embodiment of the invention.

Processing during interrupts is detailed in the flow chart of FIGS. 6A-6C and the flow chart of FIG. 7. The interrupts are generated by a multi-channel programmable counter This counter is programmed to generate the interrupt represented by block 130, 480 times per second, i.e., 480 Hz. When this interrupt occurs, processing proceeds to block 132 where further interrupts are enabled. A prioritized interrupt scheme is used. Each time the 480 Hz interrupt occurs, each of the three other channels of the counter are incremented. These channels are programmed to generate interrupt requests at different counts. Each of these interrupts has its own service routine. Processing then flows to block 134 where the microprocessor registers defining its current status are saved in RAM for later recall after the interrupt service routine is processed. Processing then proceeds to block 136, where a subroutine is called to read the buffer storing any serial data which has arrived via the RS232 interface 70 in FIG. 1. The foot pedal position data comes in through this RS232 interface and will be accessed by the microprocessor 20 and the subroutine represented by block 136.

Processing proceeds from block 136 to block 138, which increments the system clock. From there processing proceeds to block 140, which represents a subroutine to call the light-emitting diode driver hardware and cause the proper light-emitting diode for the current mode to be lit.

Processing then proceeds to block 142, where the 120 Hz interrupt counter channel is decremented. There are three additional interrupt service routines which are performed less frequently than the interrupt service routine started at block 130. One interrupt service routine is performed 120 times per second. The remaining two service routines are performed 60 times per second and 30 times per second, respectively. They start at blocks 160 and 182, respectively. After decrementing the counter in block 142, the 120 Hz counter channel value is tested in block 144. The 120 Hz counter channel is a circular counter which will count down from a value of 120 by 1 every time block 142 is executed Basically this occurs every fourth time the interrupt generated by block 130 occurs. When step 144 finds the count has reached zero, processing proceeds to block 146. Otherwise processing proceeds to block 150.

The block 146 represents the call to a communications control subroutine. This subroutine serves the same function as a telephone operator does in operating a switchboard to coordinate communications over the serial communications port of the microprocessor 20.

After block 146 is performed, processing flows to block 152 to call the hunter subroutine. The hunter subroutine tests a flag which give the status as to whether the probe is connected to the system. If the probe is not connected to the system, the hunter subroutine performs a sequence to attempt to reestablish the link.

Processing then proceeds to block 154, where a routine to test the link to the phacoemulsification probe is performed. Processing then proceeds to block 156, which calls a subroutine call monitor. The routine monitors error conditions and is not critical to the invention.

After the subroutine represented by block 156 is performed, a 60 Hz counter is decremented by block 150. The purpose of this step is to count the number of times the 480 Hz interrupt service routine has been performed, and on every eighth repetition, to perform the interrupt service routine starting at block 160. After block 150 is performed, block 158 is performed to test the value of the 60 Hz counter. If this counter value is zero, processing proceeds to block 160, which is a call to the bar graph subroutine. This subroutine addresses the bar graph display on the front panel and updates its status. This display is used to indicate the current power level If the 60 Hz counter test of block 158 indicates the 60 Hz counter value is zero, processing will proceed along path 161 to a block 163. Block 163 decrements a 30 Hz counter and marks a test for the beginning of the interrupt service routine which is performed 30 times per second.

After block 160 is performed, the subroutine represented by block 162 is called. This subroutine calls the transmitter driver which sends data out the RS232 port to any systems which are connected thereto. Design of the system is modular, such that the system may be used alone or in combination with an MVS-XIV system and other systems in a family of products related to ocular surgery. The transmit driver also determines the rate at which information is sent to any other systems coupled to the RS232 port.

Next, the subroutine represented by block 164 is called. This is a subroutine which handles the A/D and D/A conversion processes needed to change the frequency, read the phase angle error, or tune the tuning inductor. In one function of the subroutine represented by block 164, the phase angle error word on bus 48 is read by the routine of block 164. This data is needed to do the modulating of the magnetic flux in the tuning inductor to keep the phase angle error at a predetermined value.

After the phase angle error word on bus 48 has been read, the system is ready to make any necessary adjustments in the D.C. bias current flowing in the flux modulation coil. This process is performed in a subroutine represented by block 166. The subroutine represented by block 166 actually performs two separate and independent functions in one embodiment. First, it tunes the frequency generated by the voltage-controlled oscillator 56 in FIG. 1 to change the frequency to correspond with the new resonant frequency for the probe, based on the then existing power levels, phase angle, temperature, or other such criteria. The details of how the frequency is adjusted are given in FIG. 7. As will be seen from FIG. 7, this is an iterative process.

To change the frequency of the VCO 56, the microprocessor 20 generates a digital word on bus 168 representing the desired amount of change. This word is then converted to an analog signal by D/A converter 170. This analog signal is output on line 172 to the VCO, where it causes the VCO frequency to be changed slightly from the frequency established by the voltage reference signal on line 174. A precision voltage reference source 176 generates the frequency controlling signal on line 174. The combination of the analog signals on line 172 and line 174 establish the new operating frequency for the VCO 56.

Figure 8:
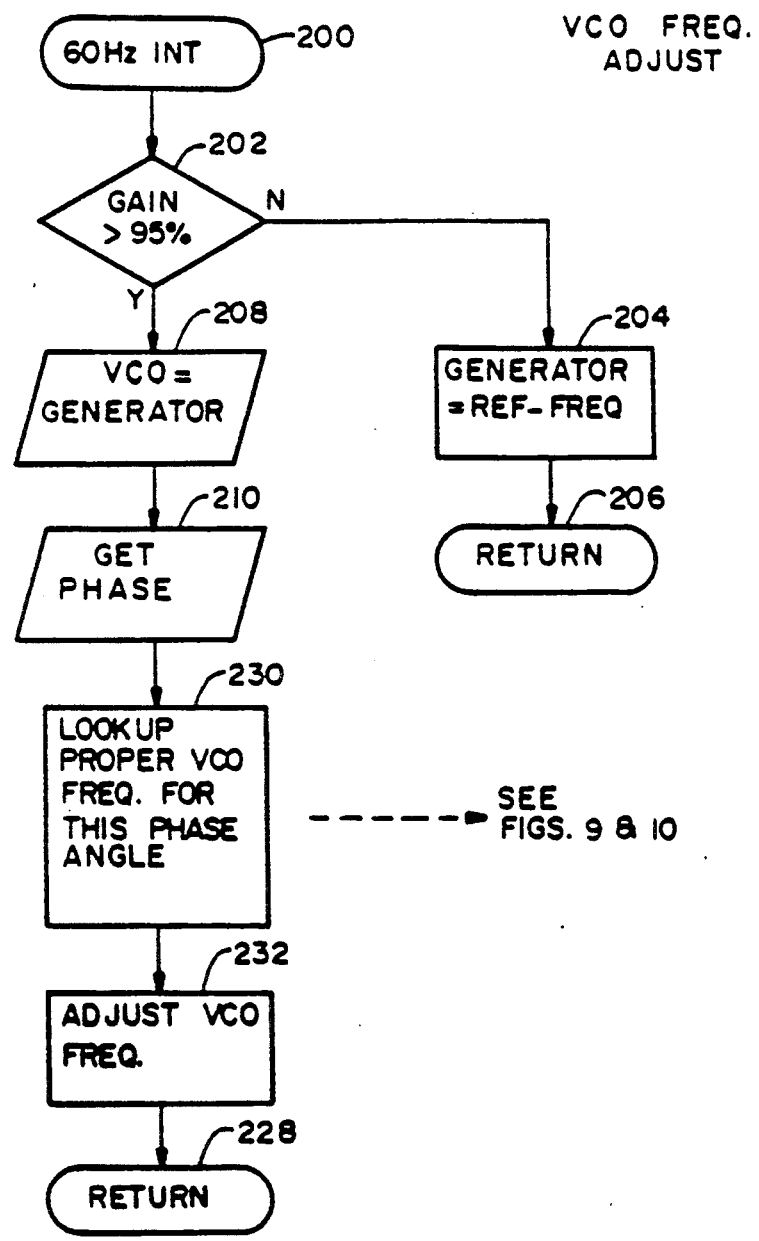
FIG. 8 is another embodiment of the VCO frequency tuning process according to an alternative embodiment of the invention.

The second thing that the subroutine of block 166 performs is the function of tuning the inductance of the tuning inductor to cancel the capacitive reactance of the probe. The flow chart defining the process by which this is done is shown in FIG. 8 and will be explained in more detail below.

In other embodiments such as those with fixed frequency and/or fixed power such as the embodiments shown in FIGS. 18 and 19, the subroutine of block 166 may only tune the tuning inductor.

After the subroutine of block 166 is performed, the 30 Hz counter channel is decremented by a count in block 163. In block 180 a test is performed to determine if the 30 Hz counter is or is not equal to zero. If the counter output is not equal to zero, a path 181 is transitioned to block 183. The process represented by block 183 is that of restoring to the microprocessor registers the values that they had when the 480 Hz interrupt occurred and the register contents were saved in the process of block 134. Processing may then resume from where it left off on the main loop.

If the test of block 180 indicates that the 30 Hz counter has reached zero, then block 182 is performed. This block represents the first step in the interrupt service routine which is performed 30 times per second. Block 182 is a call to the power control subroutine. This subroutine reads from memory or a buffer the power data which has been prepared for it by the function execution block 118 in FIG. 5 in the main loop. Part of the function of the execution block is to scale the data from the foot pedal to the maximum power level established at the front panel by the user. Therefore, if the maximum power dissipation level at the 100% foot pedal displacement position is to be 25 watts, and the foot pedal displacement is 10%, then the function execution block takes the 25 watt maximum power and multiplies it by 10% to derive a desired power level of 2.5 watts. The power routine represented by block 182 then determines whether or not the power level has to be changed from the current power level at which the probe is operating. In one embodiment there are four safety conditions which are checked before a power control word is output on the bus 62. If a change is necessary and the safety conditions are met, then the new power level desired by the user is transmitted as a digital number on the bus 62 as a desired gain for the linear programmable amplifier 60 in FIG. 1.

Next, the subroutine for scanning the keyboard is called, as symbolized by block 184. This routine performs I/O read operations and reads data from the keyboard and writes it into the mode buffer in RAM for use by the main loop. Note that this keyboard scan subroutine is shared by the interrupt service vector and by the main loop. Note that this keyboard scan subroutine is shared by the interrupt service vector and by the main loop. Next, the status subroutine is called, as symbolized by block 186. This subroutine checks various system status flags for conditions then existing in the system such as power, link present, error conditions, etc.

After block 186 is performed, the restore registers process is performed as symbolized by block 183, and the interrupts service routine terminates in block 188. This returns program control status to the main loop until the next interrupt occurs.

It will be apparent to those skilled in the art that not all the subroutines in the interrupt service routine shown in FIGS. 6A-6C are necessary for implementing the teaching's of the invention. Specifically, only those subroutines necessary for linear power control, tuning of the tuning inductor, and changing the driving frequency for the probe to match the resonant frequency of the probe for various conditions are necessary and critical to the teachings of the invention. Further, each of these critical functions may be performed independently of the others in accordance with the teachings of the invention, albeit with lower power transfer efficiency and nonproportional power control in some cases. Specifically, the tuning of the tuning inductor to maximize power transfer efficiency may be performed independently of whether or not the power dissipated in the probe is controlled proportionately. Thus, the tuning inductor may be tuned for changing temperature conditions even at a fixed power level. Likewise, the frequency of the driving signal may be adjusted for changing mechanical resonance frequency regardless of whether or not the tuning inductor is tuned to maximize the efficiency of power transfer and regardless of whether or not the power levels of power dissipated in the probe are changed. Further, the power levels for power dissipated in the probe may be changed in proportional fashion regardless of whether or not the driving frequency is altered to compensate for changes in the mechanical resonance frequency. In some embodiments, the power levels may be changed linearly in response to user input regardless of whether or not the tuning inductor is tuned to maintain maximum power transfer efficiency throughout the power range. However, if the tuning inductor is not tuned, the transfer efficiency will change over the power range, and substantial linearity of power control may not be achievable over the full range of desired power dissipation levels.

Referring to FIG. 7, there is shown a flow chart for the frequency adjustment aspect of the teachings of the invention. As noted earlier, this particular subroutine is performed 60 times per second, as symbolized by block 200 and as implemented by one channel of the multichannel counter (this counter may be in hardware or software). The first step is a test represented by block 202, which tests whether the current user-desired gain level is greater than 95%. This test is used in one embodiment such that frequency is adjusted only when gain levels are at levels greater than 95%. In other embodiments, this test may be omitted, and the frequency may be adjusted for all gain levels or may be adjusted for changing ambient conditions for a fixed gain level. In one embodiment, if the gain is less than 95%, processing flows to block 204. In block 204, the microprocessor 20 generates a frequency control word on the bus 168 which is converted to an analog signal voltage on line 172 by the D/A converter 170 to set the frequency of the VCO 56 at a known reference frequency. This reference frequency is the experimentally determined average mechanical resonance frequency of the probe at gain levels less than 95%. Processing then proceeds to block 206, where control is returned from the 60 Hz interrupt service routine to whatever processing sequence was interrupted.

If the answer to the test performed in block 202 indicates the gain is greater than 95%, processing proceeds to block 208. There the microprocessor reads the current contents of a variable called GENERATOR stored in the RAM 90. During the initialization process, the value stored in GENERATOR is the same reference frequency value used in block 204. However, during succeeding iterations through the 60 Hz interrupt service routine, the value of GENERATOR is altered in order to change the VCO frequency.

The purpose of this particular service routine for the 60 Hz interrupt is to alter the VCO driving frequency to track changes in the mechanical resonance frequency of the probe, which occur with changing gain levels and changing temperatures. The value stored in GENERATOR will determine the particular driving frequency generated by the VCO 56 in FIG. 1.

After the VCO frequency is set to the frequency dictated by the value of GENERATOR by block 208, processing proceeds to block 210, where the current phase angle error word on bus 48 is read. Next, in block 212, a test is performed on the phase angle error word read in block 210. In block 212, the phase angle error word is compared to a constant phase angle error, which is established by the user as the desired phase angle error when the system is in tune. This acceptable phase angle error will often be zero, but it need not always be so. In systems like that shown in FIG. 1, the phase angle error words on the bus 48 change around the number 102 as a center point representing zero phase angle because of use of a unipolar A/D converter 54. However, the system may be reprogrammed so that the number 102 is some other number representing the different phase angle about which the tuning of the VCO frequency is to be centered. In other embodiments, where a different type of A/D converter is used, the value used in testing the phase angle error word in block 212 may be different.

With the system of FIG. 1, if the phase angle error word on bus 48 is greater than 102, the value of GENERATOR will be decreased to change the phase angle toward zero. This process is done in block 214. Block 214 represents the process of accessing GENERATOR from RAM and subtracting from it a constant value called TWEAK, which is stored in a constants table in the RAM. The magnitude of TWEAK can be altered by the user by reprogramming the system. The value of TWEAK will set the step size by which the frequency changes are made, and therefore will control the response time and resolution of the system in adjusting VCO frequency for changed mechanical resonance frequency.

If the test of block 212 indicates that the phase angle error word is less than 102, then the value of GENERATOR must be increased by the value of TWEAK to increase the phase angle toward the test constant used in block 212. This process if performed in block 216 in the same manner as described for block 214. After the value of GENERATOR has been altered, the new value of GENERATOR must be tested against high and low limits to determine if it has been changed to an illegal, out-of-bounds value. The low limit test is symbolized by block 218, and the high limit test is symbolized by the block 220. If the answer to the test of block 218 is yes, indicating that GENERATOR has been changed to a lower value than the constant low limit, then block 222 is performed. In block 222, GENERATOR is set to the value of the low limit constant. If the answer to the test of block 218 is no, processing skips block 222 to block 224, where return from the 60 Hz interrupt service routine occurs.

A similar process is performed by block 226. Block 226 is performed if the answer to the test performed in block 220 is yes, indicating that GENERATOR as been increased beyond the value of the constant high limit. In block 226, the value of GENERATOR is set to the value of the high limit constant. Then processing proceeds to block 228, where a return from the 60 Hz interrupt service routine is performed. If the answer to the test of block 220 is no, then block 226 is skipped and block 228 is performed.

In alternative embodiments, a look-up table may be used for the frequency adjustment instead of the iterative approach shown in FIG. 7. In such an embodiment, the steps following step 210 in FIG. 7 would be replaced by a single step of using the phase as an index into the look-up table stored in ROM to derive a value to send out on bus 168 in FIG. 1. This value would be experimentally determined for that particular phase angle and would establish the driving frequency at the mechanical resonance frequency that experiments showed resulted in that phase angle. The flow chart for such an embodiment is illustrated in FIG. 8. The step 230 represents the process of looking up the proper VCO frequency for the phase angle read in step 210. This process involves generating an address using the phase angle error word on bus 48 as an index and then accessing the frequency correction data in the look-up table and storing it in a buffer. Step 232 represents the use of the frequency correction data from the look-up table to generate the proper word on the bus 168 in FIG. 1 to cause the voltage-controlled oscillator 156 to assume the frequency of the new probe mechanical resonance frequency. Step 228 represents the return from the interrupt service routine.

In yet another alternative embodiment, the step 230 in FIG. 8 can represent the look-up of the proper VCO frequency from one of several look-up tables. These look-up tables could be differentiated based upon the amount of time for which power has been applied to the probe. That is, each look-up table could contain the experimentally determined values for the probe resonant frequencies after the probe has been operated for a specific time and, possibly, at specific power levels. These different tables would contain the different experimentally determined mechanical resonant frequency values for the probe operating at different temperatures resulting from the measured time at certain power dissipation levels. In yet another alternative embodiment, an actual temperature sensor on the probe could be used. The microprocessor 20 could measure the probe temperature periodically when tuning of the driving frequency was necessary. This temperature could be used as an index to determine which look-up table to use. Once the proper look-up table is determined, either from the time for which the probe has been operating or the temperature of the probe, the phase angle or the temperature or some other variable indicative of the shift in mechanical resonance frequency may be used as an index to access the proper value in the look-up table. These alternative embodiments are illustrated in FIGS. 9 and 10, which represent breakdowns of the steps performed in block 230 for the different embodiments.

Figures 9, 10:
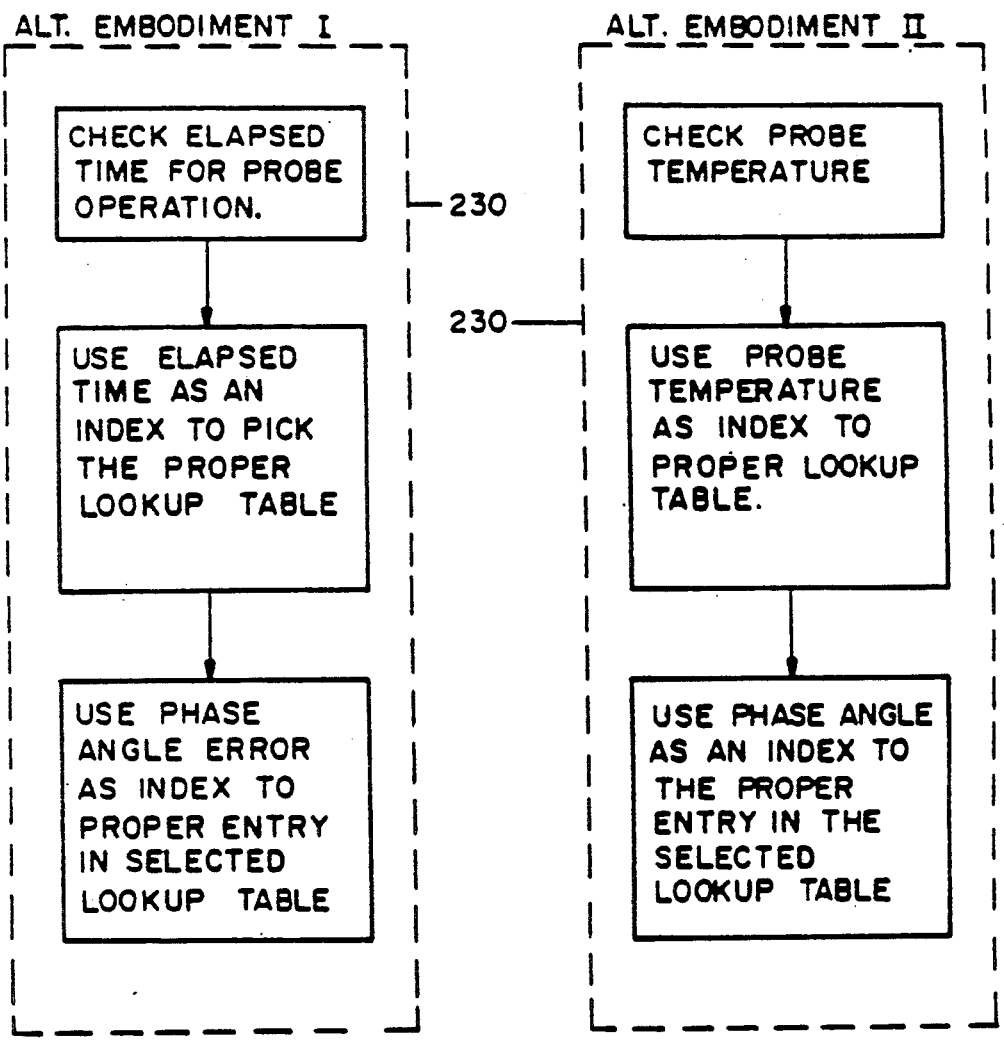
FIGS. 9 and 10 are alternative ways of performing step 230 in FIG. 8.

With respect to the embodiments shown in FIGS. 8–10 for adjustment of the VCO frequency, it should be noted that this process may occur independently of the process of tuning the tuning inductor 36 in FIG. 1. That is, the processes of FIGS. 8–10 may be performed for a fixed tuning inductor which is adjusted to cancel the reactive component of the load impedance at a specific operating temperature or gain level. At different operating temperatures and/or gain levels, the probe may be slightly out of tune by virtue of the inability to change the value of the tuning inductance, but the VCO frequency may be altered to match the changed mechanical resonance frequency for the new conditions, even through a zero phase angle cannot be achieved. That is, according to the teachings of the invention, VCO frequency alteration to track the mechanical resonance frequency drift works whether or not the tuning inductor value is changed. However, it works best when the value of the tuning inductor is changed to tune out the reactive component of the load impedance. The combination of these two adjustments by the system of FIG. 1 will insure that maximum possible power transfer efficiency is maintained over the entire power operating range of the system.

Likewise, the tuning inductor impedance may be altered to maintain proper cancellation of the reactive component of the load impedance independently of whether or not the VCO frequency is changed to track the drifting mechanical resonance frequency. The manner in which this may be done is illustrated in FIG. 11 in one embodiment.

Figure 11:
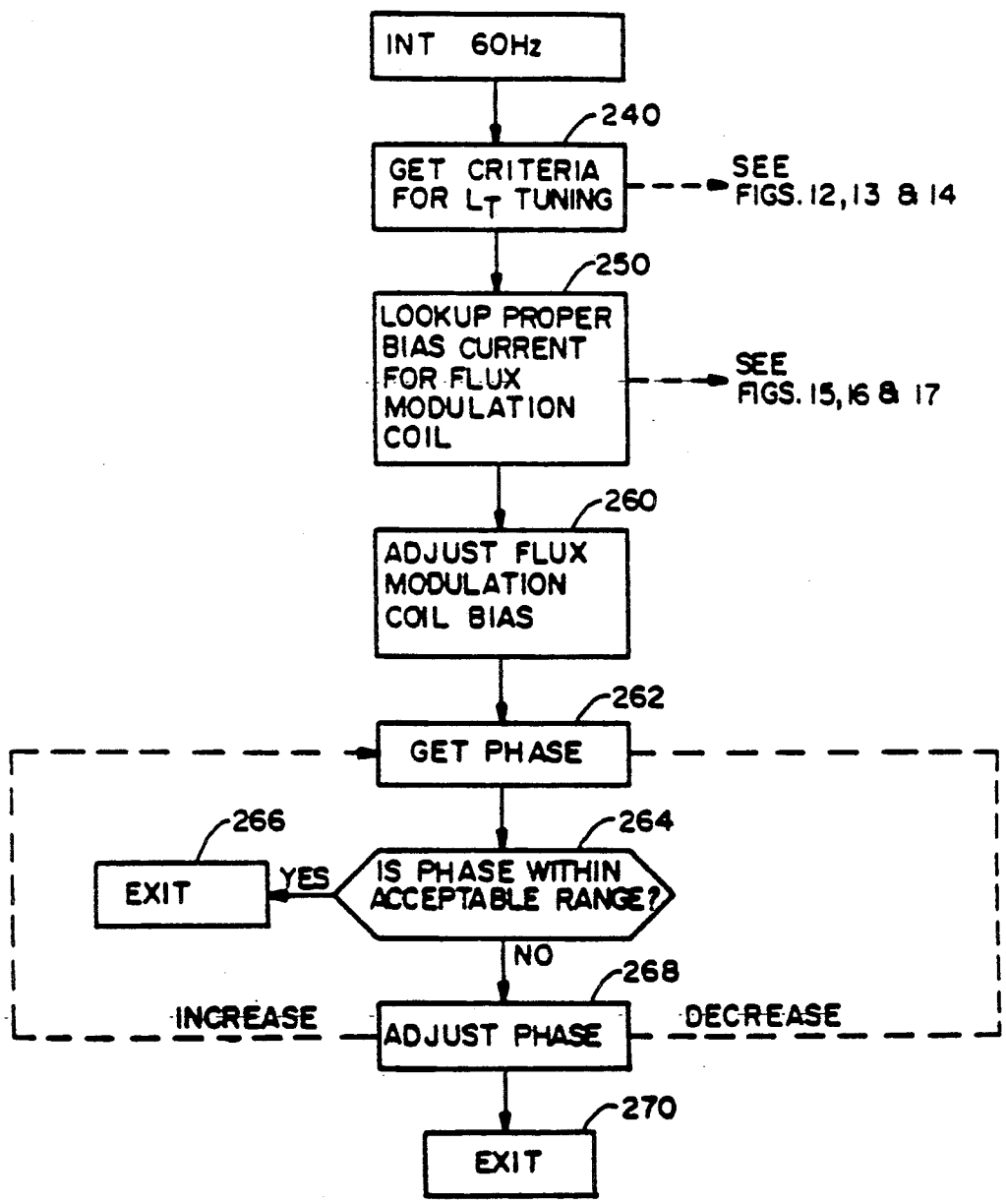
FIG. 11 is a flow chart for a process for tuning the inductance of the tuning inductor $L_T$ to cancel the reactance component of the load in one embodiment of the invention.
Figure 12:
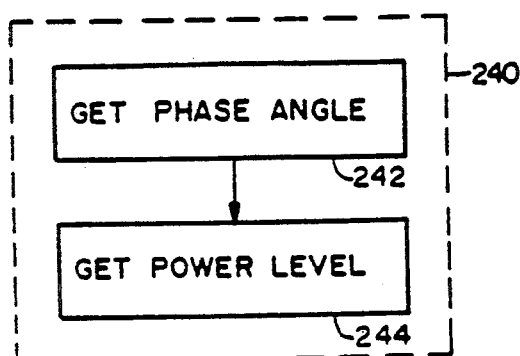
FIGS. 12, 13, and 14 are alternative ways of performing step 240 in FIG. 11.
Figure 13:
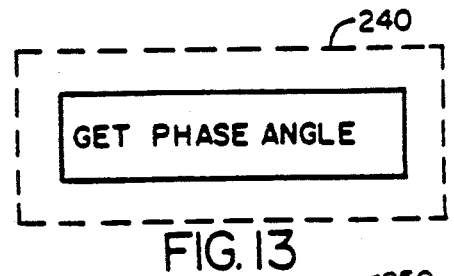

Referring to FIG. 11, there is shown the interrupt service routine for a 60 times per second interrupt to tune the value of the tuning inductor $L_T$. The function of the interrupt service routine of FIG. 11 is to tune out the reactive component of the load impedance represented by the probe. The first step in this service routine is represented by block 240. The process represented by this block is that of reading the proper criteria upon which the tuning of the tuning inductor will be based. In some embodiments, the criteria will be both the phase angle error and the power level. In such embodiments, block 240 represents the steps shown in FIG. 12. Step 242 in FIG. 12 represents the process of reading the phase angle error on the bus 48 and storing it in a memory location, and step 244 represents the process of reading the memory location which contains the current scaled power level obtained by scaling the deflection of the foot pedal 68 relative to the relative maximum power control setting 64 in FIG. 1. In other embodiments where only phase angle is used as the index, step 240 may represent only the process of getting the phase angle as shown in FIG. 13. In still other embodiments, step 240 may represent the step of obtaining the current power level, as shown in FIG. 14.

Figure 14:
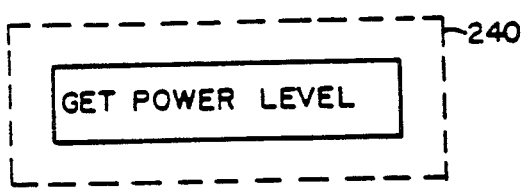

In both FIGS. 12 and 14, the step of getting the current power level may be omitted, and a step may be substituted of obtaining the current probe temperature via temperature sensor 92 and signal line 94 in FIG. 1.

Referring again to FIG. 11, after the criteria for tuning of the inductor $L_T$ has been obtained in step 240, a step 250 is performed. This step represents the process of using the criteria obtained in step 240 to look up the proper D.C. bias level for the flux modulation coil 44 in FIG. 1 to cause the tuning inductor to assume the proper inductance to cancel out the reactive component of the load impedance presented by the probe. Step 250 may represent the process of accessing a single look-up table wherein are stored experimentally determined D.C. bias current levels indexed by the criteria determined in step 240. In one embodiment, however, multiple look-up tables are used wherein the experimentally determined values in each look-up table are determined for a particular set of conditions. Typically, there will be one look-up table for a certain range of elapsed times during which the probe has been operated and another look-up table for another range of elapsed times during which the probe has been operated. In some embodiments, the look-up tables may be further divided in terms of the amount of time the probe has been operated at specific power levels, i.e., the total wattage which has been dissipated in the probe may be determined, and that wattage may be used as an index to the proper table based on the assumption that, after a given number of watts has been dissipated in the probe, the probe will have achieved a predetermined temperature. In such embodiments, the look-up tables may be indexed by the range of watts dissipated in the probe for which the entries in the table are valid. Such an embodiment is illustrated in FIG. 15.

Figure 15:
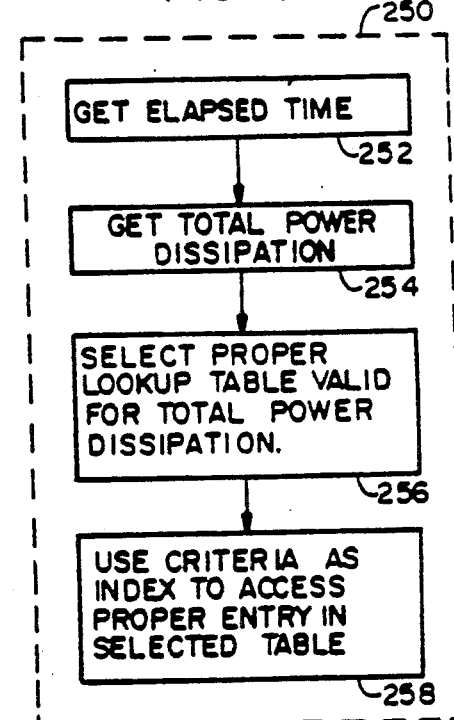

In FIG. 15, the first step is symbolized by block 252, where the elapsed time during which power has been dissipated in the probe is obtained. A step 242 represents the step of calculating the total power dissipation in the probe since its use began. This process may be an integration using the summation of the instantaneous average power level during each of a plurality of time slots multiplied by the increment of time for each time slot. This gives the total power dissipation as of the time step 250 is performed. Once the total power dissipation is determined, it is used in step 256 to point to the proper look-up table having bias current levels which are valid for that total amount of power dissipation.

Once the proper look-up table is selected in step 256, the criteria read in step 240 in FIG. 11 is used as an index to access the proper entry in the selected table. This entry will be the correct bias current for the flux modulation coil 44 to cause the tuning inductor to have the proper value to cancel out the reactive component of the probe load impedance for the particular total power dissipation up to that point.

Figure 16:
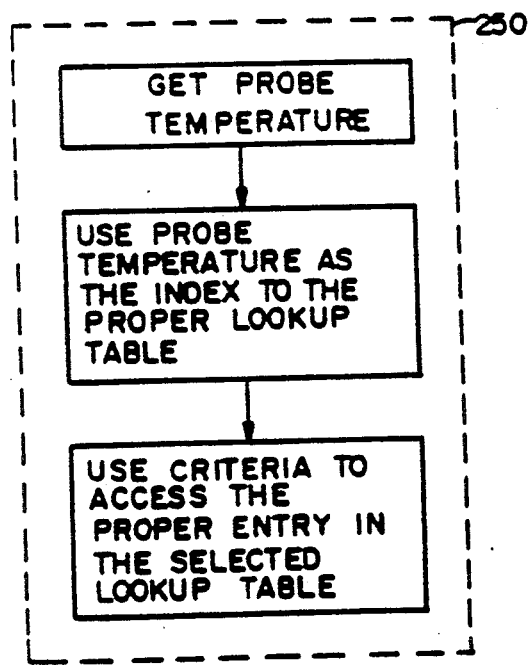
FIGS. 15, 16, and 17 are alternative ways of performing step 250 in FIG. 11.

An alternative and simpler embodiment is shown in FIG. 16. In this simple embodiment, the probe temperature is measured using the temperature sensor 92 shown in FIG. 1, and that temperature is used to select the proper look-up table. Each look-up table will cover a different range of temperatures for which its bias current entries are valid. Once the proper look-up table is selected, the criteria determined in step 240 is used to access the proper entry in that look-up table.

Figure 17:
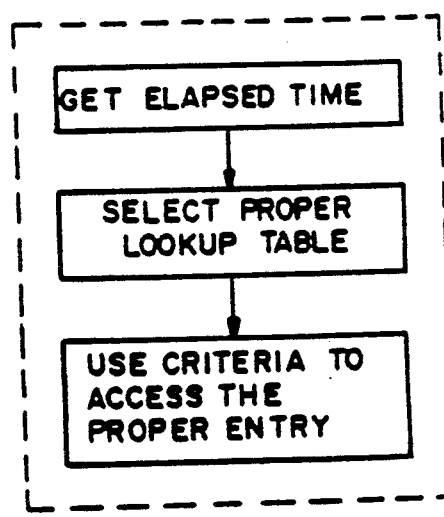

A still simpler embodiment uses only the elapsed time to select the proper look-up table. After the proper look-up table is selected, the criteria determined in step 240 is used to access the proper entry therein. This embodiment is illustrated in FIG. 17.

Returning again to FIG. 11, once the proper bias current entry has been selected from the proper look-up table, the flux modulation coil bias current is adjusted in step 260. This step represents the process of generating the proper digital word for transmission on bus 46 to D/A converter 40. The D/A converter 40 converts this number to an analog signal on line 42 which controls the amount of bias current flowing through the flux modulation coil 44.

Next a step 262 reads the phase angle error on the bus 48. This phase angle is then tested in a process symbolized by the block 264 to determined whether it is within an acceptable range defined by the user at the time of programming the system. In some embodiments, the acceptable range for phase angle error may be defined in real time by the user through the front panel.

If the phase angle is within the acceptable range, the service routine is exited in step 266, and processing resumes where it left off at the time the interrupt of FIG. 11 occurred. If the phase is not within the acceptable range, a step 268 is performed to adjust the phase in the proper direction by an incremental amount in similar fashion as shown in FIG. 7 for altering the GENERATOR constant by the constant TWEAK. That is, the phase angle error will be compared to the acceptable range and the direction of correction will be determined. The current word on the phase angle adjust signal bus 46 would then be added to a phase angle adjust constant, or the phase angle constant will be subtracted from the word on the phase angle adjust bus 46 depending on the desired direction of correction of the phase angle error. Thereafter, the interrupt service routine of FIG. 11 will be exited in step 270. In some embodiments, the adjust phase block 268 may cause looping back to step 262 to continue to loop through steps 262, 264, and 268 until exit step 266 is reached. These embodiments are symbolized by the dotted lines 272 and 274 in FIG. 11.

In other embodiments, the fine tuning of the phase angle represented by steps 262, 264, 268, and 266/270 may be omitted. In these embodiments, the phase angle adjust interrupt service routine is comprised solely of steps 240, 250, and 260, plus an exit step to return control to the point in processing where the interrupt occurred.

Finally, it should be noted that the proportional power control aspects of the teachings of the invention may be performed without either adjusting the phase angle through changing the inductance of the tuning inductor 36 and without changing the driving frequency generated by VCO 56. However, changing the power level to the probe without using at least the tuning inductor 36 to cancel out the changing reactance component of the load will not work very well, since at higher power levels, the probe temperature will begin to rise, and the system will become so far out of tune that it will be impossible to transfer enough power into the probe to maintain a linear or proportional relationship to the displacement of the foot pedal 68. However, over small ranges of power dissipation levels, the system will work adequately with proportional power control without either tuning the tuning inductor or changing the VCO frequency.

That concludes the description of the digital embodiment of the teachings of the invention. There follows a description of an analog version of the teachings of the invention.

Figure 20:
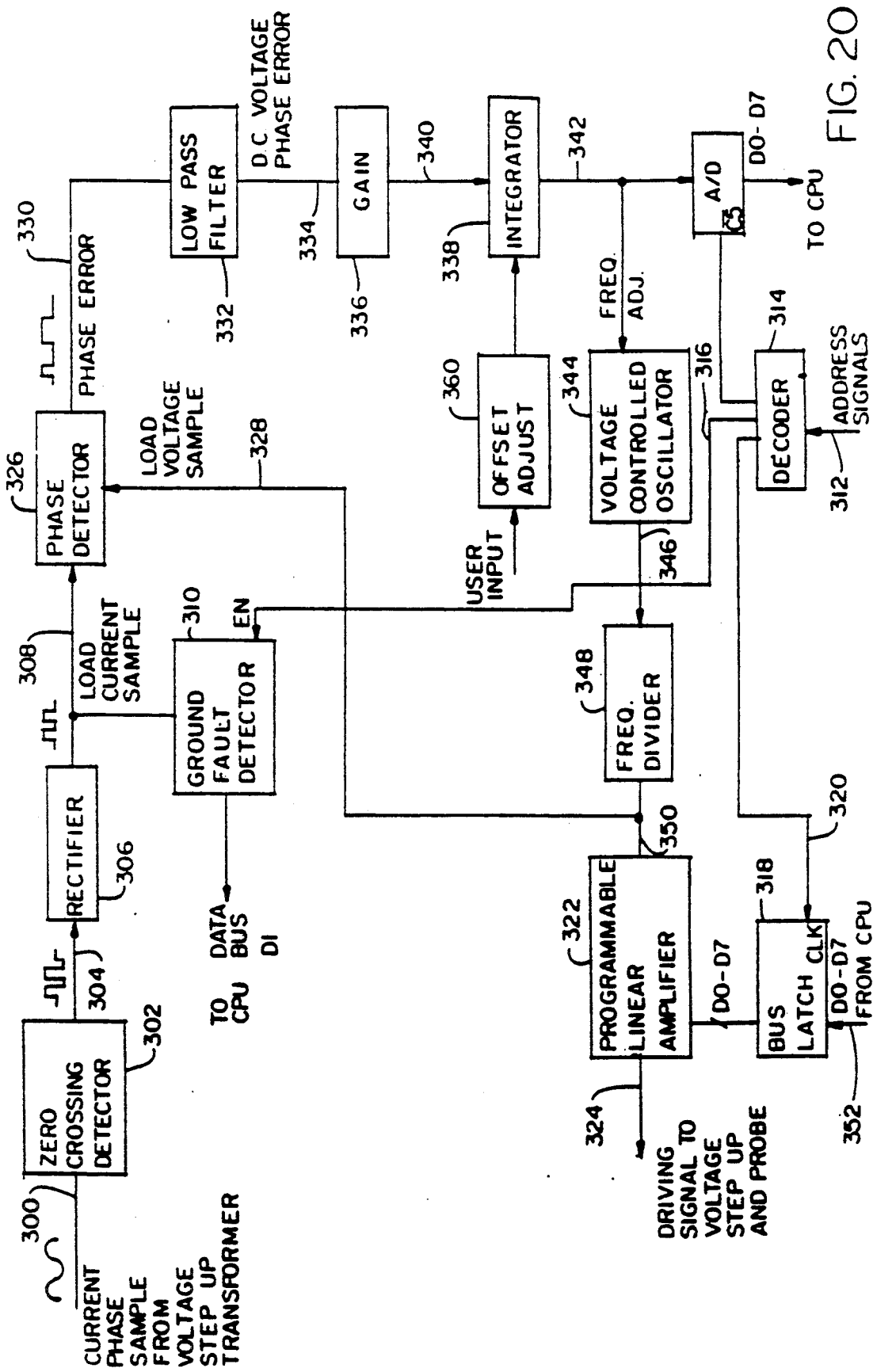
FIG. 20 is a block diagram of an analog embodiment of a subsystem to tune the VCO frequency to the mechanical resonance frequency using the phase angle as a criteria.

Referring to FIG. 20 there is shown a block diagram of an analog system for tuning the frequency of the driving signal for the probe. A sample of the current waveform through the probe enters the system on a line 300 where it is processed by a zero crossing detector 302. The zero crossing detector converts the current waveform to a square wave, alternating current waveform on a line 304. A rectifier 306 chops off one half of the square wave to convert the signal on line 304 to a pulse train of all positive or all negative pulses on line 308. A ground fault detector 310 monitors the signal on the line 308, and when no pulses occur on the line 308, a data bit D1 is latched to flag the failure of feedback from the probe. The computer (not shown) periodically addresses the ground fault detector via address signals on bus 312, decoder 314 and enable line 316 and reads the ground fault flag bit (D1). If it is set, the computer cuts off power to the probe by addressing a bus latch 318 via enable line 320 and address signals on bus 314 and by sending the proper data word to cause a programmable linear power amplifier 322 to cut off all driving signal power to the probe on line 324.

The signal on the line 308 comprises the load current sample needed by a phase detector 326 to determine the phase angle error or power factor caused by the current probe load impedance for existing conditions. The other signal needed for this determination is a sample of the phase of the voltage waveform for the voltage waveform used to drive the probe. This signal arrives on a line 328 which is coupled to the input of the programmable linear amplifier 322. The phase detector 326 compares the phase of the current waveform on line 308 to the phase of the voltage waveform on line 328 and generates a phase angle error signal on line 330. This phase angle error signal is in the form of a pulse width modulated pulse train where the pulse width is indicative of the phase angle error.

The phase angle error signal is passed through a low pass filter 332 to convert it to a direct current signal having a voltage which is indicative of the phase angle error on a line 334. This signal is applied through a gain stage 336 to an integrator 338. The purpose of the integrator 338 is to make the operation of the circuit not subject to offset errors intrinsic to operations with the operational amplifiers used to implement many of the stages shown in FIG. 20. Even the best operational amplifiers have some offset output voltage for a zero volt differential input. This offset error would exist on the line 340, and if it were not eliminated, would be applied to the voltage adjust input of the voltage controlled oscillator used to generate the driving signal.

This offset error would cause the driving frequency to always be slightly off from the desired driving frequency to match the mechanical resonance frequency. The integrator 338 acts as an infinite gain operational amplifier. When there is any voltage other than 0 volts on the line 340, the integrator 338 continually integrates (sums) it. This causes the output voltage of the integrator on the line 342 to continue to rise until the output voltage reaches the maximum voltage of one of the supply voltages to the integrator. This output voltage on line 342 is applied to the frequency control input of the voltage controlled oscillator 344 and causes the frequency generated by the voltage controlled oscillator to shift to the frequency corresponding the voltage on the line 342. This driving signal is output on the line 346 to a frequency divider 348. There it is divided down in frequency to the proper driving frequency for the probe. The linear power amplifier 322 then amplifies the signal on line 350 by the gain set by the computer via the data bus 352 and bus latch 318, and the amplified driving signal is output to the voltage step up transformer (not shown) via line 324.

Because the feedback is negative, the shift in frequency caused by the signal on the line 342 is such as to reduce the phase angle error signal on line 334. Thus if any offset error signal exists on line 340, the integration of the error and the negative feedback of the system will force the error signal on the line 340 to zero. Whenever the mechanical resonance frequency shifts because of changing conditions, the phase error signal which results therefrom will cause the integrator to force the VCO frequency to shift until the voltage on the line 340 is once again zero.

The phase angle error around which the system operates need not be zero. The user may adjust it to be some other value by use of the offset adjust circuit 360. This circuit forces the integrator 338 to tolerate a certain phase error.

Figure 21B:
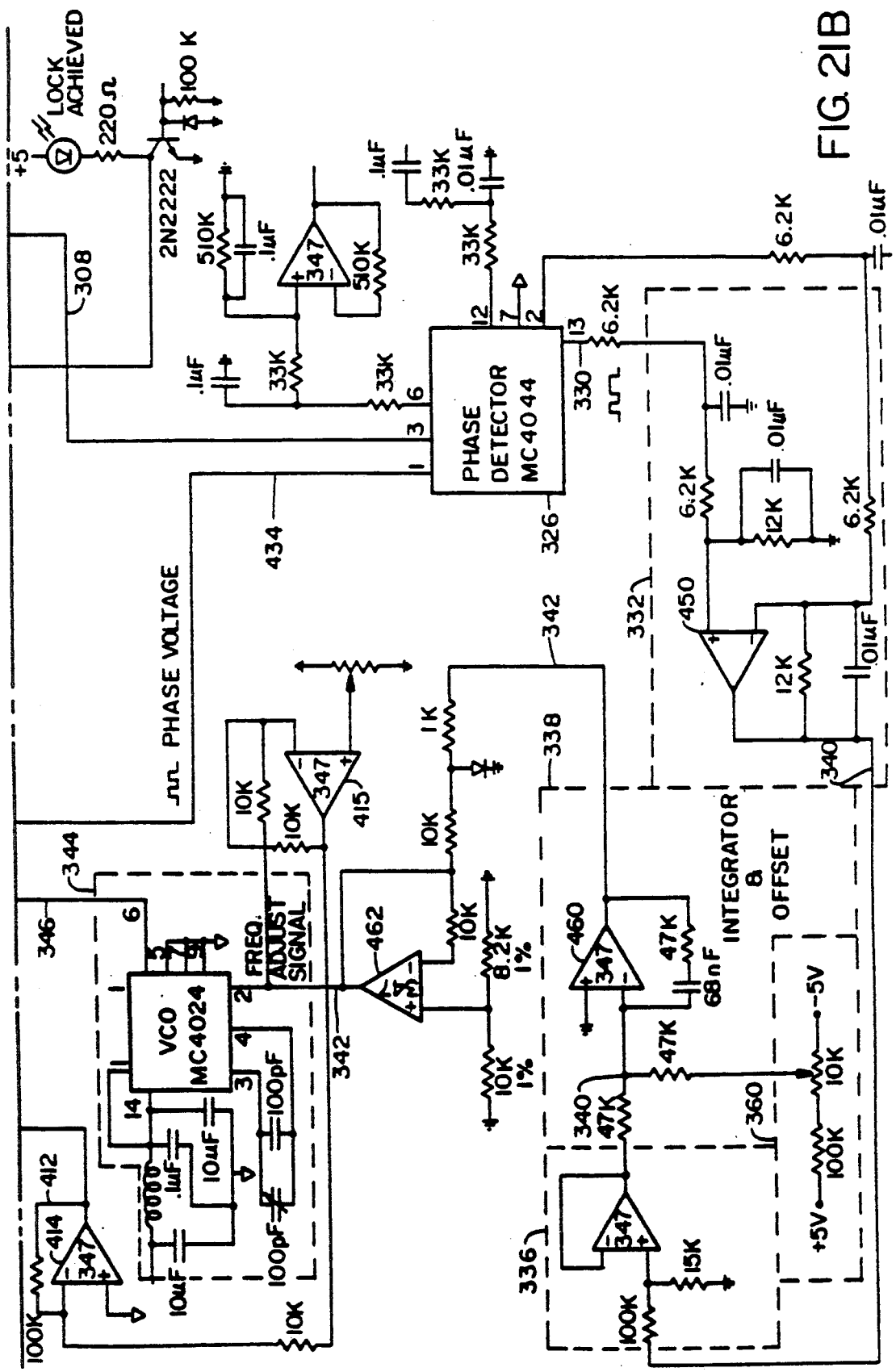

Referring now to FIGS. 21A and 21B there is shown a more detailed schematic diagram for the analog embodiment of the teachings of the invention with respect to changing the VCO frequency in response to phase angle changes. The load current phase sample enters on line 300 on the upper right corner of FIG. 21A as the CURRENT PHASE signal. This signal is processed by a waveshaper in the form of operational amplifier 400. The output of the waveshaper 400 on line 402 is an alternating current signal having the frequency and phase of the current waveform through the load.

To get this signal in a condition to be read by a phase detector, the signal must be converted to a square wave, direct current signal, i.e., it must be rectified and further waveshaped. To this end, the alternating current signal on line 402 is coupled to the negative input of an operational amplifier 404 which has its positive input coupled to analog ground and which acts as a zero crossing detector. The output on line 406 is a square wave, alternating current signal. A voltage divider comprised of resistors 408 and 410 change the maximum amplitude of the signal on line 406 to a level suitable for base drive of a transistor/diode rectifier circuit 306.

The rectifier circuit 306 converts the alternating current square wave on line 406 to a train of positive going pulses on the output line 308. This is done through use of the shunt diode 414 having its cathode coupled to the base of a transistor 416. The diode shunts all negative going pulses to analog ground, so that only the positive going pulses turn on the transistor 416 and drive line 308 to logic zero.

The computer (not shown) must know that the probe is present and is receiving the drive current to keep the driving signal power on. If the probe is not present, or the link to same is broken, the computer must shut off power to the probe as a safety feature since the voltage step up transformer steps up the driving voltage across the crystal to approximately 1000 volts. The computer must constantly monitor line 308 to determine if current phase samples are arriving. If they are, then the computer assumes that the probe is present and that the link to the probe is working. A retriggerable one shot 420 and a latch 422 are used for this purpose as the ground fault detector 310. The signal on line 308 constantly retriggers the retriggerable one shot 420 to keep its output on line 424 in a predetermined logic state constantly. When the pulses on line 308 stop, the retriggerable one shot emits a pulse on line 424 which is latched into the latch 422. This latch is periodically addressed by the computer by activating the read signal and writing the proper address to a decoder 314 to activate the 79H signal to the NOR gate 430. The computer then reads the contents of the latch 422, and, if the bit pattern is in a predetermined state, the computer knows that there has been a ground fault, and cuts off power to the probe.

To determine the correct frequency to use to drive the probe, the phase angle between the current waveform for current flowing through the crystals in the probe and the voltage waveform of the driving signal across the crystal and tuning inductor is used. This phase angle is circumstantial evidence that the impedance of the crystal/probe equivalent circuit has shifted away from the tuned condition where the combined tuning inductance and crystal/probe impedance appears to be purely resistive. When this happens, the mechanical resonance changes because the temperature changes have affected the elasticity of the probe metal thereby changing the equivalent circuit capacitance representing elasticity and changing load conditions have changed the effective mass of the probe. This alters the inductance in the equivalent circuit representing the mass of the system. The result is that the mechanical resonance frequency changes, so the driving frequency must be changed to keep the probe in tune. Further, the value of the tuning inductance should also be altered to keep the overall load impedance substantially purely resistive. The analog circuitry to alter the tunable inductance works the same as the circuit of FIG. 20, and will not be further detailed here.

To determine the phase angle, the signals on the line 308 are coupled to one sample input of a phase detector 326. This signal must be compared in phase to a sample of the voltage waveform across the tuning inductor and the crystal transducer of the probe. The voltage sample comes in on line 434 from the output of a counter/frequency divider 436 coupled so as to divide the output of the voltage controlled oscillator 344 down to the proper driving frequency for the probe (approximately 40 kilohertz).

The phase detector 326 generates a pulse width modulated phase angle error signal and outputs it on line 330. The pulse widths of the pulses in the signal on line 330 are proportional to the phase angle error. This signal is passed through a low pass filter 332 consisting of a passive network of resistors which shunt capacitors to ground and then through a gain stage consisting an operational amplifier 450 coupled as a low pass filter/integrator. The purpose of this low pass filter and integrator combination is to filter out high frequency noise components, and to convert the pulse width modulated phase error signal to a direct current voltage phase angle error signal on line 340.

After conversion of the phase angle error signal to a D.C. phase angle error voltage, the signal on line 340 is amplified in a gain stage 336. Thereafter, the D.C. phase angle error signal is applied to the input of the integrator 338. The purpose of the integrator is to eliminate the errors introduced by offset errors in the operational amplifiers preceding the integrator stage. As noted earlier, because of the high gain of the integrator and the negative nature of the feedback, the integrator will force the frequency of the driving signal to change until the D.C. phase angle error signal on line 340 is zero volts.

The integrator 338 is comprised of an operational amplifier 460 coupled with capacitive feedback so as to act as an integrator. An offset adjust circuit 360 comprised of a voltage divider with a potentiometer as the second resistor is used to adjust the voltage on the line 340 so that any phase angle desired by the user may be used as the home point around which the integrator 338 forces servo action. That is, the offset adjust circuit 360 may be used to set some phase angle such as 5 degrees as the center point. Then when a phase angle of 8 degrees is found, the integrator forces a frequency change until the phase angle moves back toward 5 degrees. Likewise, if a phase angle of 2 degrees is found, the integrator forces the frequency to change until the phase angle once again is 5 degrees. However, the voltage on the line 340 will always be maintained at a virtual ground level by virtue of the negative feedback whereby positive changes in the D.C. level of the phase error signal are applied to the negative input of the operational amplifier 460 which causes a change in the VCO frequency to reverse the direction of the change in the D.C. phase angle error signal. Any offset voltage on the line 340 will be continually integrator until the integrator output on line 342 reaches the power supply or "rail" voltage at which the integrator operates unless the phase angle change resulting from the changing voltage on the line 342 acts to remove the voltage on line 340. The voltage on the line 342 then stabilizes at that voltage necessary to cause the phase angle error signal on line 340 to be zero.

The output of the integrator on line 342 is coupled through a level shifting stage comprising operational amplifier 462 which changes the level of the signal voltage to a level suitable for application to the voltage control input of the voltage controlled oscillator 344. The oscillator generates a driving signal having a frequency which is a function of the FREQUENCY ADJUST signal on line 342. The voltage controlled oscillator 344 has a characteristic curve of frequency versus voltage which has a less sensitive portion and a more sensitive portion. In the less sensitive portion, it takes more change of voltage on the line 342 to cause a one hertz change of the output driving signal frequency than in the more sensitive portion. The level of the signal on the line 342 is set to be in the low sensitivity portion of the characteristic curve of the VCO.

The output signal from the VCO is coupled via line 346 to the divider/counter 348. This counter divides the frequency on line 346 by a factor of 32, and outputs the lower frequency driving signal on line 350. This line is coupled to the input of the programmable linear amplifier 322.

The purpose of the programmable linear amplifier is to amplify the driving signal on the line 350 by a gain factor set by the computer (not shown) via the data bus 352. The programmable amplifier is comprised of several programmable switches 380, 382 and 384 which are coupled to the data bus via a bus latch 318. When the computer wishes to control the gain level, it activates the write signal WR and writes the address of the programmable amplifier on the address bus 312 and writes the desired gain control number on the data bus 352. This causes the decoder 314 to activate the enable signal on the line 390 thereby clocking in the gain control data on the data bus 352 via the NOR gate 392 and line 394 coupling the NOR gate output to the clock input of the bus latch 318.

The gain control number causes the programmable switches to control the resistor ladder networks 400, 402 and 404 in such a way as to set the desired gain level on line 406 at the input to the final gain stage 408. The final gain stage amplifies the signal by a fixed gain and buffers it from the output line 324 so that the resistor ladder network cannot be loaded down by external impedances coupled to the line 324.

For purposes of debugging, an analog to digital converter 410 is coupled by a line 412 to the output of the VCO through a pair of isolation and level shifting stages to sample the output amplitude level of the VCO. The A/D converter can be addressed by the computer to read the digital equivalent of the VCO output signal amplitude via the data bus 352 whenever the computer needs to know this value. This aspect of the circuit is not critical to the invention.

The analog method of tuning the VCO frequency may be used independently of proportional power control or of tuning of the tuning inductor impedance. Likewise it may be used with the digital methods of performing the latter two functions as disclosed above. In yet another embodiment, the tuning of the tunable inductor may be done in analog fashion using a circuit using the same teachings of the circuit of FIG. 20.

For all embodiments where the frequency of the driving signal is to be tuned to the mechanical resonance frequency of the probe, there is an alternative way to determine the mechanical resonance frequency. In the embodiments discussed so far, the mechanical resonance frequency is inferred from the phase angle. That is, when conditions such as power level change resulting in temperature change or the load condition changes, the mechanical resonance frequency shifts and the phase angle is altered. Instead of measuring the mechanical resonance frequency itself, the resonance frequency is inferred from the resulting phase angle. This was done with either a lookup table as described with reference to FIG. 8 or by trial and error method as shown in FIG. 7.

Figure 22:
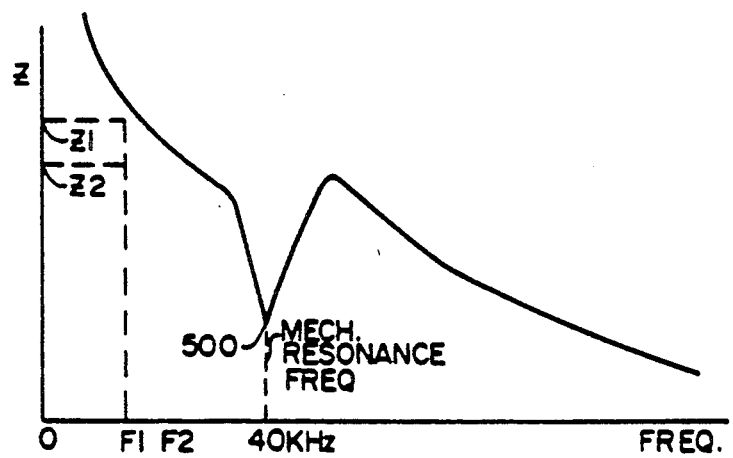
FIG. 22 is a curve showing the shape of the characteristic curve for the impedance of the probe at different frequencies surrounding the mechanical resonance frequency.
Figure 23:
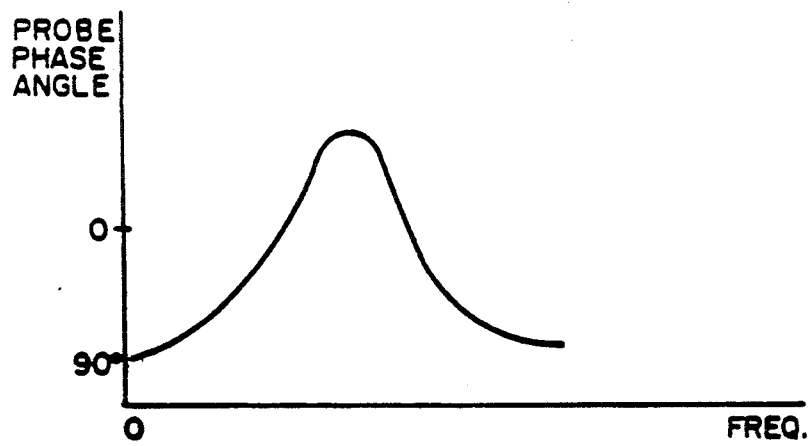
FIG. 23 is a curve showing the relationship of the phase angle to frequency for the phase between the voltage across the probe crystals and the current through the probe crystals for a given set of conditions.

Another way to determine the mechanical resonance frequency is to measure it directly using Ohm's law and the shape of the curve defining the load impedance represented by the probe. FIG. 22 shows the characteristic impedance of the probe without the tuning inductor over a range of frequencies surrounding the mechanical resonant frequency. The mechanical resonance frequency is always the frequency where the minimum impedance point 500 occurs from the equivalent circuit for the probe shown in FIG. 2. Since the impedance is higher at frequencies on either side of the mechanical resonance frequency, this fact can be used to determine the value of the mechanical resonance frequency under a given set of conditions. This can be done by measuring the current flowing through the probe at a number of different frequencies and finding the frequency where the current flow is a maximum. Once the mechanical resonance frequency is determined, the tuning inductor is tuned to reduce the phase angle to zero. FIG. 23 shows the relationship of phase angle to frequency for the phase between the voltage across the crystals and the current flowing through them under a given set of conditions.

Figure 24:
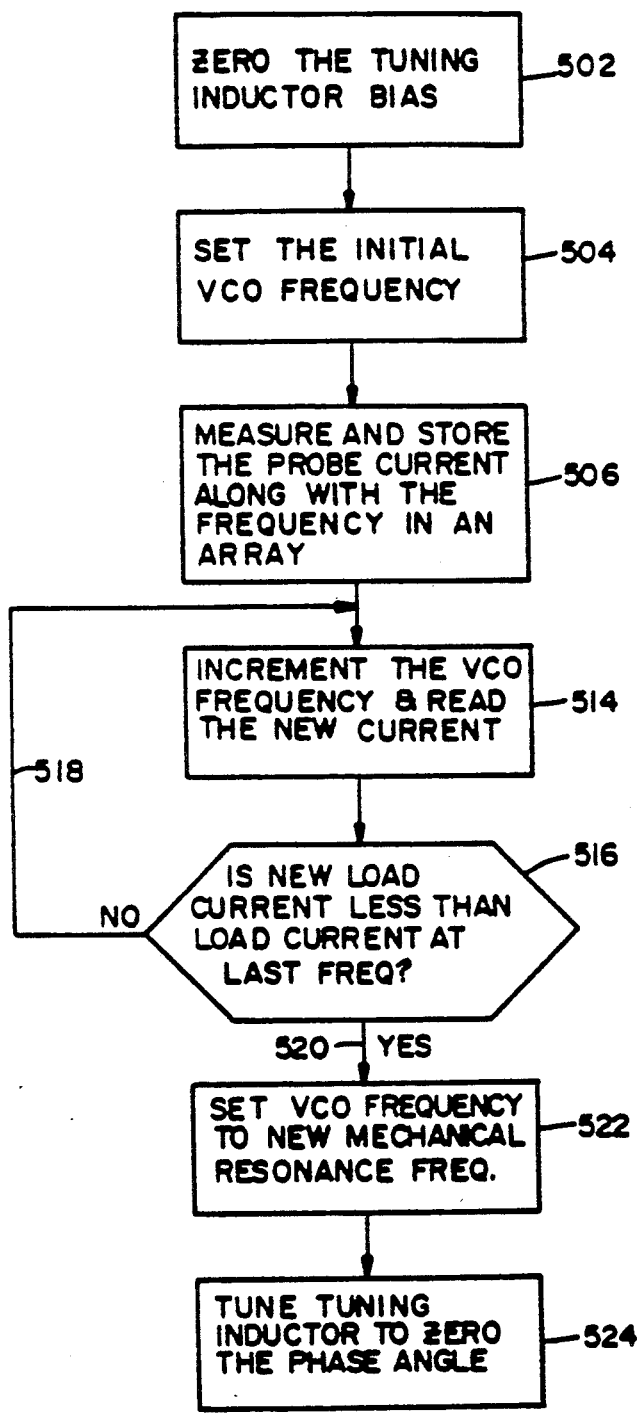
FIG. 24 is a flow chart for a method of using the shape of the characteristic curve for probe impedance to find the mechanical resonance frequency and to tune the tuning inductor for zero phase angle.

A method for tuning the probe for maximum efficiency of power transfer using the shape of the characteristic impedance of the probe as a pointer to the correct mechanical resonance frequency is shown in the flow chart of FIG. 24. The general idea is to sweep the VCO frequency through a number of frequencies on either side of the expected mechanical resonance frequency and read the current flowing through the probe at each frequency. The frequency at which the maximum amount of current flows is the mechanical resonance frequency. Once this frequency is determined, the VCO is set to this frequency, and the tuning inductor is biased to tune the phase angle to zero.

The first step in this process is to zero the bias of the tuning inductor 36 in FIG. 1 as symbolized by block 502. This entails having the microprocessor (or other analog circuitry controlling the bias of the tuning inductor) send a bias word on bus 46 to D/A converter 40 to reduce the bias current through the flux modulation coil 44 to zero. Next, an initial VCO frequency is set at some frequency less than the frequency of the impedance minimum 500 in FIG. 22. For the sake of example, assume this initial frequency is F1 in FIG. 22 which corresponds to a probe impedance of Z1. This step is symbolized by block 504 in FIG. 24, and is done by sending the proper frequency control word corresponding to frequency F1 on bus 168 in FIG. 1 to the D/A converter 170.

Block 506 represents the steps of measuring the load current drawn by the probe at frequency F1 and storing the value of the load current along with its frequency F1 in RAM 90 in FIG. 1. This done using the operational amplifier 508 in FIG. 1 along with rectifier 508 and A/D converter 510. The operational amplifier has one input coupled to line 82 which carries a signal voltage proportional to the magnitude of load current flowing through the crystals 28 and 30. The amplifier amplifies this A.C. signal and outputs it on line 509. The rectifier 508 converts the amplified load current signal on line 509 to a D.C. voltage level proportional to the load current on line 511. This signal is converted to a digital word by the A/D converter 510, and makes the digital word representing the magnitude of the load current available on bus 512 for the microprocessor to read. The microprocessor 20 then reads the word on the bus 512 and stores it in RAM 90 along with the frequency which corresponds to this particular load current in memory.

The next step, as symbolized by step 514, is to increment the VCO frequency to a slightly higher frequency F2 corresponding to a load impedance Z2 and to read the resulting load current. The system then compares the load current read in step 514 to the load current stored in step 506 to determine if the new load current is less than the previous load current. This is done in step 516. Because it is known that as soon as the frequency is incremented to a frequency above the mechanical resonance frequency, the load impedance will begin to rise having reached its minimum at the mechanical resonance frequency, it follows that as soon as the load current begins to fall, the mechanical resonance will have been passed. The system then knows that the mechanical resonance frequency for existing conditions lies between the current frequency and the last used frequency. If the new load current is not less than the previous load current, processing returns to step 514 to increment the frequency and to take another reading of the load current as symbolized by path 518. Then the test of step 516 is performed again.

If the new load current is less than the old load current, then the mechanical resonance frequency has been determined, and path 520 is taken to step 522. The next step is to set the VCO frequency at the frequency determined in step 516 to be the mechanical resonance frequency. This may be done by using the most current frequency or by interpolating between the current frequency and the last frequency used. If the step size is small, the current frequency may be used without appreciable error.

The final step is symbolized by step 524. In this step, the tuning inductor 36 is tuned in the manner described herein to zero the phase angle and make the load of the probe appear to be purely resistance. This can be done by a trial and error method by looking at the output of the phase detector, altering the tuning inductor bias and looking again at the output of the phase detector. Alternatively, the proper bias level to zero the phase angle for the current conditions of frequency, probe temperature, etc. can be looked up in a look up table. The value which emerges from the look up table can then be used to set the bias level for the current through the flux modulation coil of the tuning inductor.

Figure 25:
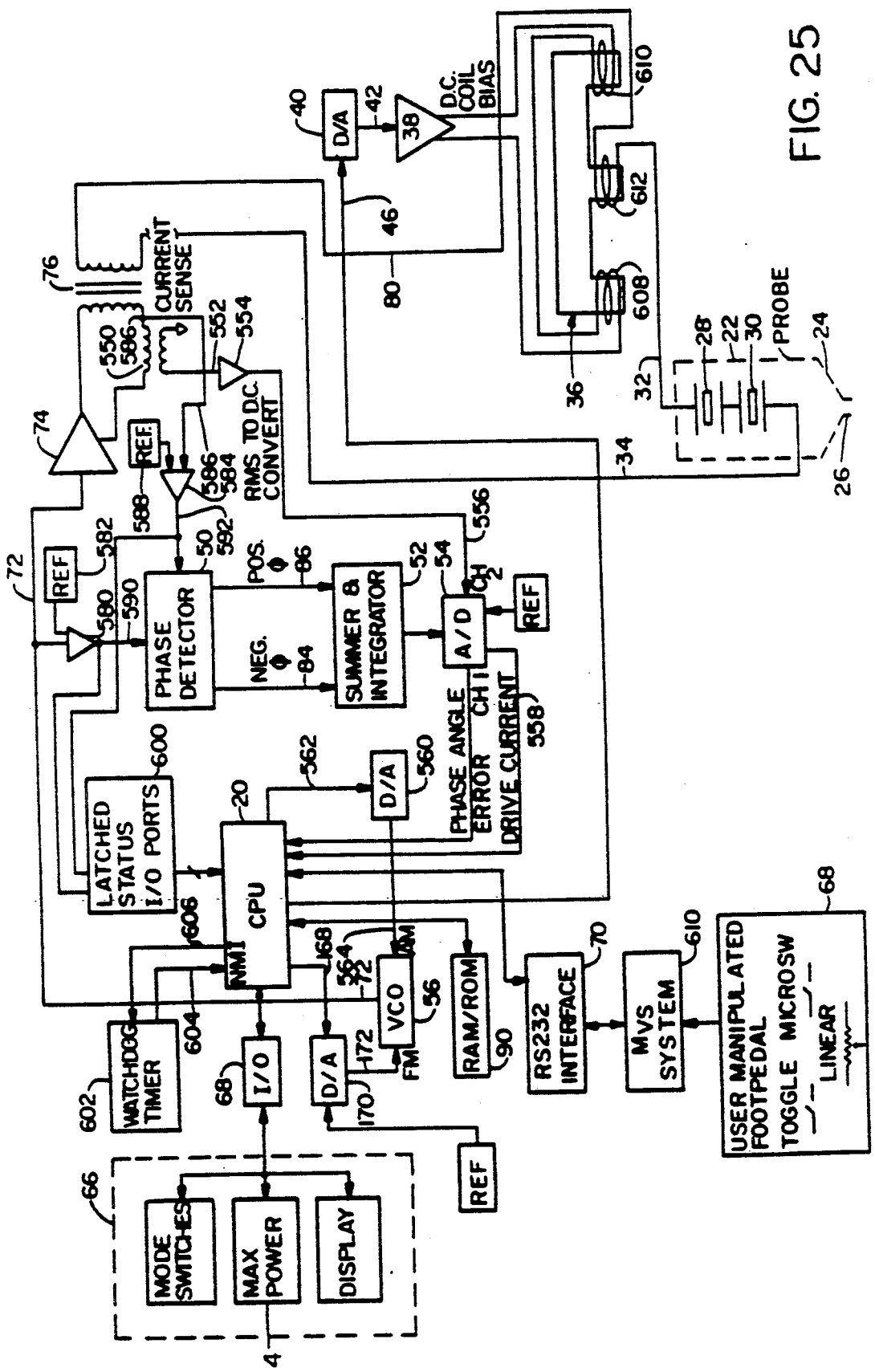
FIG. 25 is a block diagram of the hardware of an alternative embodiment of the invention.

Referring to FIG. 25, there is shown an alternative embodiment of the circuitry of the invention. The embodiment shown in FIG. 25 is substantially similar to the embodiment shown in FIG. 1 except that certain changes have been made. These changes will be described in detail. Portions of the circuitry that are identical between the embodiment of FIGS. 1 and 25 and which serve the same function in both embodiments are identified with like reference numerals in both figures. The discussion of the common elements of the circuitry given above is equally applicable to the embodiment of FIG. 25 and will not be repeated here.

The first change of significance is the substitution of a current sense transformer 550 for the current sense resistor 78. This current sense transformer has its primary in series with the primary winding of the voltage step up transformer 76. The current sense transformer 550 is, itself, a voltage step up transformer such that the voltage generated across the primary winding by the current flowing through the primary of the voltage step up transformer 76 generates a voltage in the secondary of the current sense transformer 550 which is a multiple of the voltage across the primary. The multiple depends upon the turns ratio as between the primary and the second windings of the transformer 550. The current sense transformer 550 has less parasitic inductance and parasitic capacitance than the current sense resistor 78 which eliminates one possible source of error in determining when the frequency of the driving signal is most closely matched to the mechanical resonant frequency of the probe. Since the software uses the voltage swings on the secondary of the current sense transformer 550 as part of the information needed to determine the phase angle, it is important to derive clear signals with a high signal to noise ratio. The current sense transformer 550 improves the signal to noise ratio by stepping up the voltage across the primary winding of the transformer 550 to a level well above any noise.

The R.M.S. value of the A.C. signal on the line 552 is converted to a D.C. signal value by an operational amplifier 554. The magnitude of this signal indicates the amplitude of the current flowing in the primary of the step up transformer 76 and therefore is indicative of the level of drive current in the probe 22. This D.C. signal on line 556 is coupled to one input of a two channel analog-to-digital converter 54. The analog-to-digital converter 54 converts the D.C. level on line 556 to a digital signal on the bus 558 which indicates the level of the drive current flowing in the primary winding of the step up transformer 76. This information is used by the sweeper software routine to be described below in determining the frequency of drive signal on line 72 which matches the mechanical resonance frequency of the probe 22.

When the CPU 20 determines the proper driving frequency, a digital frequency control word is written via bus 168 to a D/A converter 170. This word is converted to an analog signal level on the line 172 which is coupled to the frequency modulation control input of the voltage controlled oscillator 56. The voltage on the signal line 172 controls the frequency of the driving signal generated by the VCO 56 on the line 72.

The amplitude of the driving signal on line 72 is controlled by the CPU 20 via a digital-to-analog converter 560. The CPU 20 receives signals from the user manipulated footpedal 68 via the RS232 interface 70 regarding the level of power the user desires to be sent to the probe. The CPU 20 converts these signals to a digital word which corresponds to the desired level of power and sends this word out to a digital-to-analog converter 560 via a bus 562. This unit converts this desired power level word to an analog signal having an amplitude which corresponds to the desired level of power. This analog signal is coupled on line 564 to the amplitude modulation input of the VCO 56. The analog signal causes the VCO 56 to generate a drive signal having an amplitude on the line 72 which corresponds to the desired level of power requested by the user.

The phase angle between the voltage waveform on the line 72 and the current waveform in the primary of the transformer 76 is indicative of the degree of cancelling of the reactive component of the probe impedance by tuning of the tuning inductor 36. A small or zero phase angle indicates substantially complete cancelling of the reactive component. The phase detector 50 is used to determine this phase angle by comparing the outputs of two comparators. Comparator 580 has one input coupled to line 72 and the other input coupled to a reference voltage source 582 which generally is ground. Thus each time the signal on the line 72 makes a zero crossing, the comparator 580 changes states. Another comparator 584 has one input coupled to the line 586 in the primary circuit of the step up transformer 76 and a second input coupled to a voltage reference circuit 588 which also is a ground reference voltage in an alternative embodiment. Thus each time the signal on line 586 crosses zero, the comparator 584 changes states. These changes of states on lines 590 and 592 are coupled to the phase detector 50 and carry information regarding the then existing phase angle. Since the signal on line 72 is the driving voltage and the signal on line 586 is proportional to the current passing through the probe 22 in response to the signal on the line 72, the difference in times of occurrence of the changes of states on the lines 590 and 592 can be decoded into the corresponding phase angle.

There are also provided latched status ports 600 for allowing the CPU 20 to do ground fault detection. Two of the status ports are coupled to receive the output bits from the comparators 580 and 584. Since these bits are constantly changing, the CPU 20 can tell if the probe circuit is functioning properly by reading the status ports frequently to determine if the data indicates the zero crossings are still occurring on lines 72 and 586.

There is also provided a watchdog timer circuit 602 which serves as a safeguard. The watchdog timer is constantly counting up toward a timeout number and will be continually reset by the CPU 20 by a signal on the line 606 before the timeout number is reached as long as the CPU 20 is functioning properly. If the CPU gets trapped in an endless loop or somehow fails to reset the watchdog timer 602, the timer will time out and assert a nonmaskable interrupt on line 604. The CPU 20 is slaved to the nonmaskable interrupt and will always be vectored to the service routine which serves the nonmaskable interrupt regardless of whether the CPU is in an endless loop or not. This service routine shuts down the system as a safety precaution.

Another difference between the embodiments shown in FIG. 25 and that shown in FIG. 1 is that in the embodiment of FIG. 25, the D.C. coil or flux modulating coil of the tuning inductor 36 is comprised of the two windings on either side of the center winding which is the A.C. drive winding. That is, the D.C. winding is comprised of windings 608 and 610 while the A.C. winding is the coil 612. The A.C. winding provides an inductive reactance which cancels the capacitive reactance of the probe 22 when the tuning inductor 36 is properly tuned. The D.C. windings must be such as to be able to alter the apparent inductance of the A.C. coil 612 between 0 and 30 millihenries.

In an alternative embodiment shown in FIG. 25, the user manipulated footpedal 68 is coupled to the CPU 20 through a commercially available surgical instrument called the MVS (Trademark) system 610. This unit is available from Alcon Surgical Instrumentation Division in San Leandro, Calif., and is described in detail in a co-pending U.S. Pat. application Ser. No. 780,689, entitled "Handpiece Drive Apparatus for Powered Surgical Scissors", filed Sept. 26, 1985 which is hereby incorporated by reference. The MVS system 610 has several modes, and enables the CPU 20 when the MVS system is in the phacoemulsification mode by sending a code via the RS232 interface 70. In the phacoemulsification mode, there are two power modes available: fixed power and linear power. Which mode is entered is determined by user manipulation of the controls of the MVS system. The MVS system then sends data to the CPU 20 which controls which power mode the embodiment of the invention shown in FIG. 25 is to use. The user manipulated footpedal 68 is comprised of two switches and a potentiometer. A toggle switch is actuated between its two states when the user kicks the footpedal to the right indicating that power is to be sent to the probe. A microswitch is actuated between its two states when the user presses down on the footpedal. A linear potentiometer is also included which has its wiper mechanically coupled to the footpedal so that when the footpedal is pressed down, the wiper is moved. The MVS system 610 has an analog-to-digital converter which is coupled to the potentiometer which converts the setting of the potentiometer to a digital value indicative of the desired level of power requested by the user. The MVS system is also coupled to the toggle switch and to the microswitch through I/0 ports (not shown) so that the MVS system can read the states of these two switches. The MVS system converts the states of the two switches and the setting of the potentiometer to digital data or code words which are sent to the CPU 20 via the RS232 interface. In an alternative embodiment, the MVS system after enabling the CPU 20 in the phacoemulsification mode, generates an interrupt to the CPU 20 when the toggle switch indicates the footpedal is kicked right and when the microswitch indicates the footpedal has been pushed down. The CPU 20 is then vectored to a power control service routine which reads the data as to the toggle switch position, the microswitch position and the potentiometer setting. This service routine is described next.

Figures 29A, 29B:
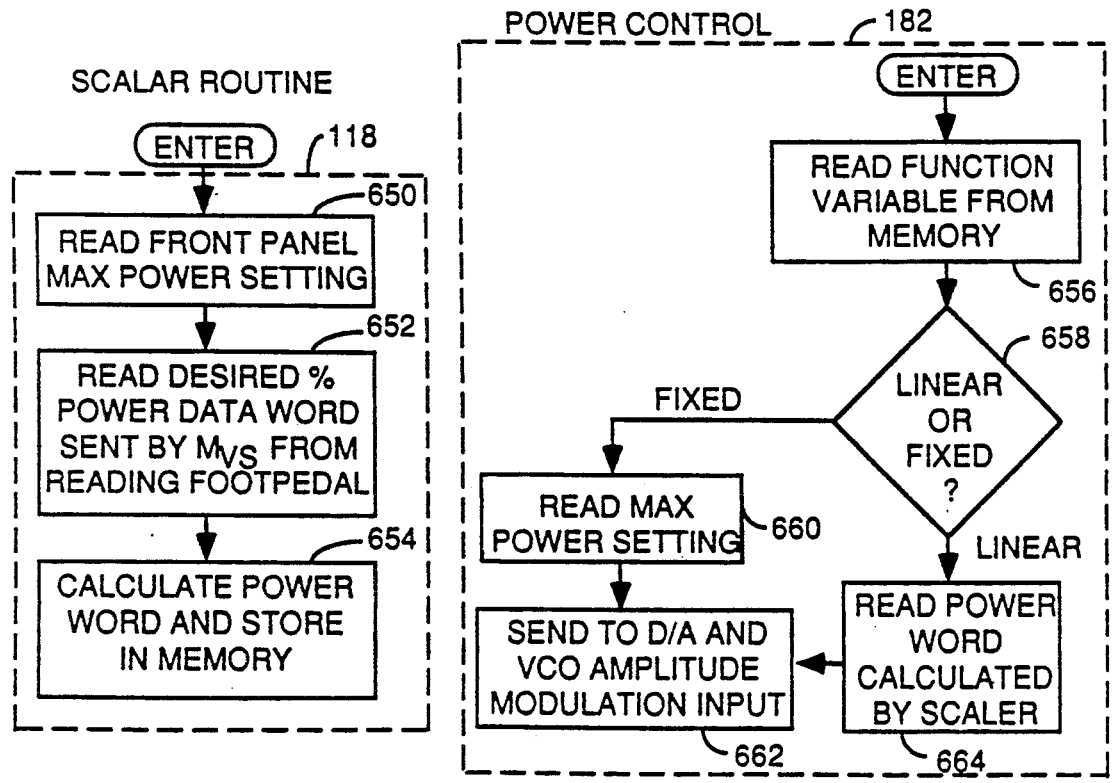
FIG. 29 is a flow chart of the power control and scaling software routines.

Referring to FIG. 29A, there is shown the details of the power control steps to control the power sent to the probe 22 during phacoemulsification operations. The embodiment of the invention shown in FIG. 25 can operate in a fixed power mode or a linear power mode. In the fixed power mode, the maximum power set by the user in the front panel switch 64 is sent to the probe 22 when the user depresses the footpedal any amount in the phacoemulsification mode of the MVS system. Of course in alternative embodiments, the MVS System 610 may be eliminated as the footpedal interface, and the footpedal 68 may be directly coupled to the CPU through appropriate, conventional interface circuitry. In the linear power control mode, a percentage of the maximum power set in the maximum power switch 64 is sent to the probe 22 where the percentage depends upon the position of the footpedal. The power control is linear such that a 10% increase in the displacement of the footpedal results in a 10% increase in power dissipation in the probe.

There is a scaler routine which is performed as part of step 118 shown in FIG. 5 which constantly performs the scaling calculation for the linear mode each time step 118 is performed. The steps of this calculation are shown in FIG. 29A. The first step is symbolized by block 650 which reads the front panel maximum power setting set by the user on switch 64. Next, step 652 reads the desired percentage of power data which is derived by the MVS system from reading the position of the potentiometer in the footpedal. The MVS system writes this data to the CPU 20 via the RS232 communications interface 70. The desired percentage of power is then multiplied by the maximum power setting to derive a power word which is stored in memory as symbolized by step 654. Processing then continues with the other operations of step 118 and from there to step 120 in FIG. 5.

The steps in FIG. 29B are the details of the power control step 182 in FIG. 6C. The flow charts of FIGS. 5 and 6A through 6C are used in the embodiment of FIG. 25, but the flow charts of FIGS. 7 through 17 are replaced by the frequency tuning and phase angle adjusting routines of FIGS. 27 and 28 respectively. The first substep in the power control step 118 is symbolized by block 656 which reads the function variable from memory. This function variable is stored in memory by the keyboard scan routine which reads the switches on the front panel to determine whether the user wishes to operate in the linear or the fixed power modes. Substep 658 determines what the function variable states regarding the mode, and vectors processing to substep 660 if the mode is fixed. Substep 660 reads the maximum power setting either from the front panel switches or from the memory location in which this data is stored by the keyboard scan routine. Next, this maximum power setting is sent as a digital word to the D/A converter 560 by the CPU 20 for conversion to an analog signal which controls the amplitude of the signal put out by the VCO 56 as symbolized by substep 662.

If substep 658 determines that the linear power control mode is selected, a step 664 is performed which reads the power word calculated by the scaler routine in step 118 and sends this power control data word to the D/A converter 560 and the VCO amplitude modulation control input to set the desired amplitude of the driving signal.

Figure 26:
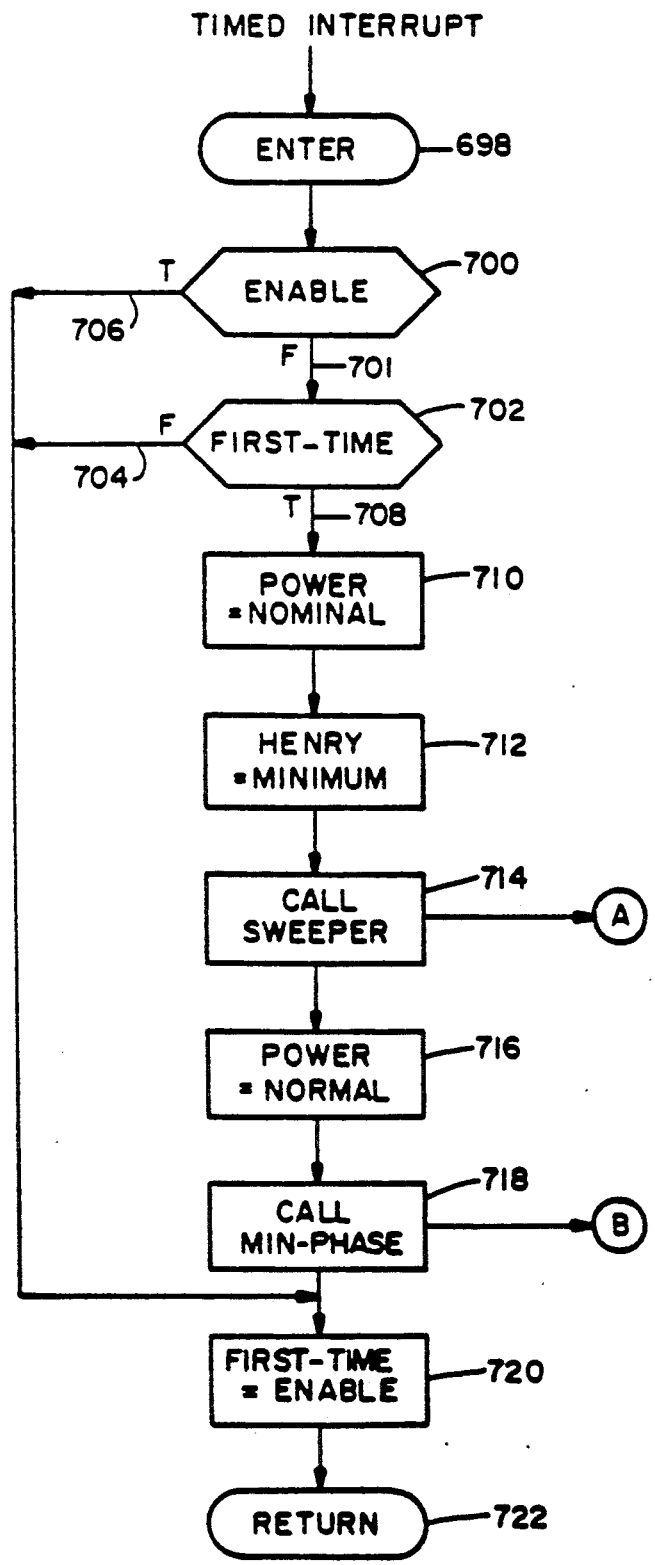
FIG. 26 is a flow chart of the software of the main loop of the control program of the invention.

Referring to FIG. 26 there is shown a flow diagram of the calibration cycle of the control program of an alternative embodiment of the invention. The calibration cycle of the program is periodically run, but the core steps that tune the frequency and minimize the phase angle are run only one time each time the user lets up on the footpedal thereby indicating that the user does not want power dissipated in the probe. Basically, the control software that controls the operation of the system of FIG. 25 is set up as a series of interrupt service routines that occur periodically. The calibration cycle routine of FIG. 26 can be one of these timed routines that performs the frequency sweep and phase angle minimization only once each time the user lets up the footpedal and bypasses these steps when the user is applying power to the probe. In alternative embodiments, other software architectures may be used. It is important however in obtaining maximum performance that whatever software architecture is chosen there be routines to find the probe resonant frequency and match the VCO driver frequency to the resonant frequency of the probe and it is important that once this is done, that the tuning inductor be tuned to minimize the phase angle as much as possible. Whatever software architecture that performs these functions and provides linear power control will suffice for purposes of practicing the invention, and the particular software architecture that is described here is not critical to the invention.

The calibration cycle essentially determines whether or not it is time to do a frequency sweep and phase angle minimization. To that end, the calibration cycle of FIG. 26 starts out with an enter step 698. This step symbolizes the timed interrupt that periodically occurs and is self generated by a timer in the CPU 20. Each time this interrupt occurs, processing jumps to step 698, and the calibration cycle is performed. The first step in the calibration cycle is the enable step 700 which checks an enable flag in RAM which indicates whether the user has taken his or her foot off the footpedal indicating the user does not wish to send power to the probe. Step 700 represents the step of checking the status flag in RAM that indicates this status and branching to the appropriate next step depending upon the condition of the status flag. A status routine (not shown) periodically reads the control codes arriving from the MVS system 610 regarding the positions of the switches in the footpedal and updates the status flags. The control codes regarding the toggle switch and the microswitch status in the footpedal are used to set the power status flag read by step 700.

Assuming that the flag status checked in step 700 indicates that the user has lifted his foot from the footpedal, processing proceeds to a step 702 to determine if this is the first time since entering at step 698 that the enable step 700 has vectored processing along the path 701. The reason for this is to prevent the calibration routine of the steps following step 702 from being performed more than once each time the user takes his foot off the footpedal. If the steps following step 702 have already been performed once since the routine of FIG. 26 was entered, then processing is vectored along path 704. Likewise, if the routine of FIG. 26 is entered at a time when the user is applying power to the probe, then the test of step 700 vectors processing along the path 706. Paths 704 and 706 bypass the calibration step following step 702.

Assuming that path 708 is followed out of step 702, a step 710 is performed. This step sets the power level to the probe to a nominal level by writing an appropriate digital word to the D/A converter 560 in FIG. 25. Next a step 712 is performed to set the inductance of the tuning inductor 36 to a minimum value. This is done by writing a digital word to the D/A converter 40 which sets the current flow through the D.C. bias coils 610 and 608 to a maximum level.

Next, a step 714 is performed to call the sweeper routine to be described below. The purpose of this routine is to sweep the frequency of the VCO 56 through an entire range of driving frequencies which will include the resonant frequency of any probe 22 attached to the system which is intended for phacoemulsification operations. At each frequency, the driving current is read and compared to the highest driving current previously recorded to determine if a new highest driving current has been found. The frequency at which the highest driving current flow is found is the resonant frequency of the probe.

After the sweeper routine finds the resonant frequency of the probe, the frequency of the VCO is set at this frequency via a write operation to the D/A converter 170, and processing proceeds to step 716.

Step 716 sets the power level to the probe back to the normal level which existed before the routine of FIG. 26 was entered.

Following step 716, a step 718 is performed which serves to minimize the phase angle at the new driving frequency. This routine will be described more below.

Finally, a step 720 is performed which sets the FIRST_TIME flag checked in step 702 to indicate that the calibration routine has been performed once since the user first removed power to the probe. Finally, processing returns from the interrupt service routine of FIG. 26 to the point in the program where processing halted when the interrupt that vectored processing to step 698 occurred. This is symbolized by step 722. Processing then proceeds from that point.

Figure 27:
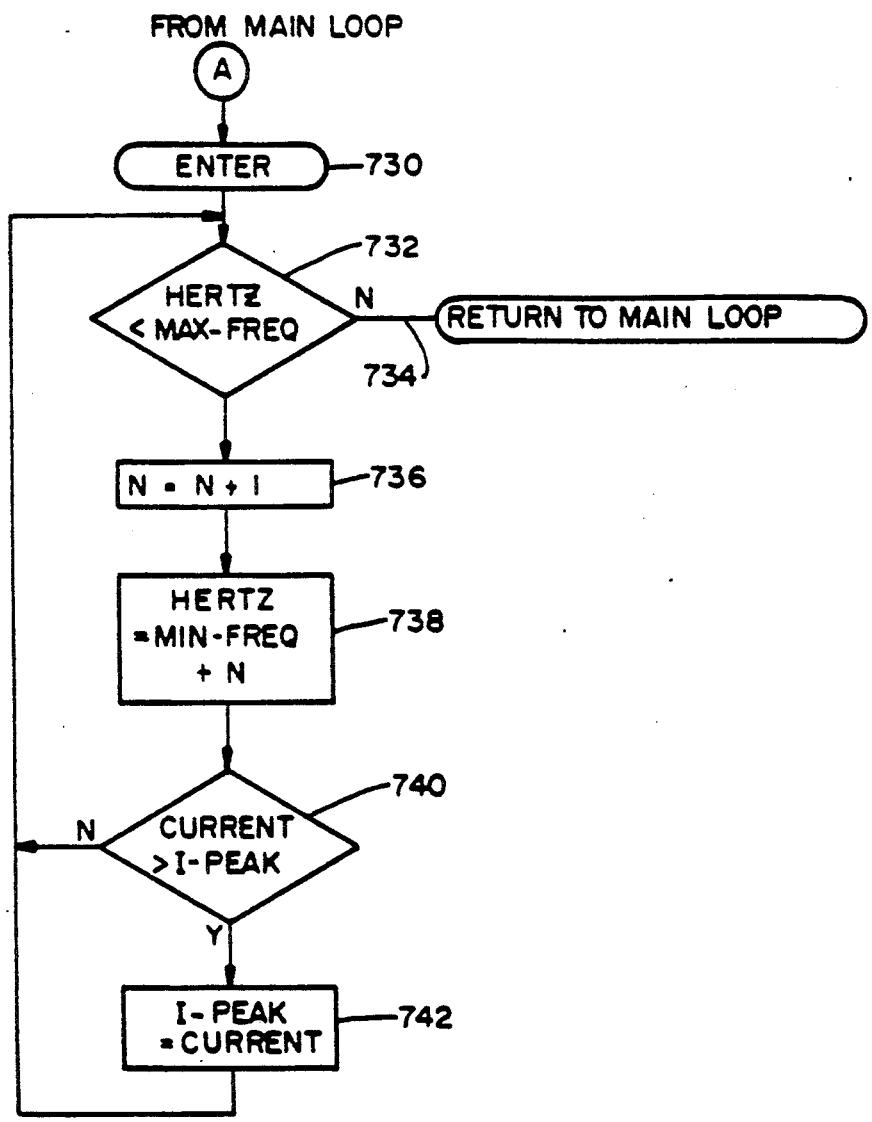
FIG. 27 is a flow chart of the frequency sweeper subroutine called upon by the main loop to determine the drive frequency which maximizes the drive current for the probe 22.

Referring to FIG. 27, the details of the sweeper routine are given. Step 730 symbolizes the call of this subroutine from step 714 in FIG. 26. Next, a test symbolized by step 732 is performed. The purpose of this test is to determine if the current operating frequency of the VCO is at or above the fixed, high frequency end of the band of frequencies through which the VCO frequency is swept to find the resonant frequency of the probe. If the frequency has been increased to the high frequency boundary or above, processing is vectored along path 734 which symbolizes the return to the routine of FIG. 26, step 716. If the frequency has not yet reached the high end of the frequency band, processing proceeds to step 736 which increments the incrementation variable N by 1 step. When the routine of FIG. 27 was entered, step, 730 initialized N to zero.

Next, a step 736 is performed. This step symbolizes the step of incrementing the VCO frequency to the next higher frequency step. The first time the loop of FIG. 27 is performed, N is zero and step 738 sets the VCO frequency to the MIN_FREQ value which is the frequency boundary at the low end of the range of frequencies through which the VCO frequency is swept. Each time the loop is performed, N is incremented by one, and the frequency of the VCO is set one step higher until the test of step 732 returns processing to the routine of FIG. 26. Step 738 also symbolizes the process of writing the digital word representing the new frequency out to the D/A converter 170 in FIG. 25 to set the VCO frequency to the new frequency.

Next, a step 740 is performed to read the new resulting drive current through the probe and compare it to the current value of the variable I_PEAK in which the maximum drive current so far recorded is stored. The first substep in this process is the addressing and reading of the digital word at the channel 2 output of the A/D converter 54 in FIG. 25. This digital word represents the magnitude of the primary current in the transformer 76 as sensed by the current sensor 550 and is proportional to the actual drive current flowing through the probe 22. Then, the value stored in the I_PEAK variable is compared against the current data just obtained to see is the drive current is now greater than the previous peak drive current. If it is, the I_PEAK variable contents are updated with the value of the drive current at the then existing drive frequency and the value of this drive frequency is recorded as associated with the drive current just written to I_PEAK. This process is symbolized by step 742. Processing is then vectored to step 732 to start the loop again.

Figure 28:
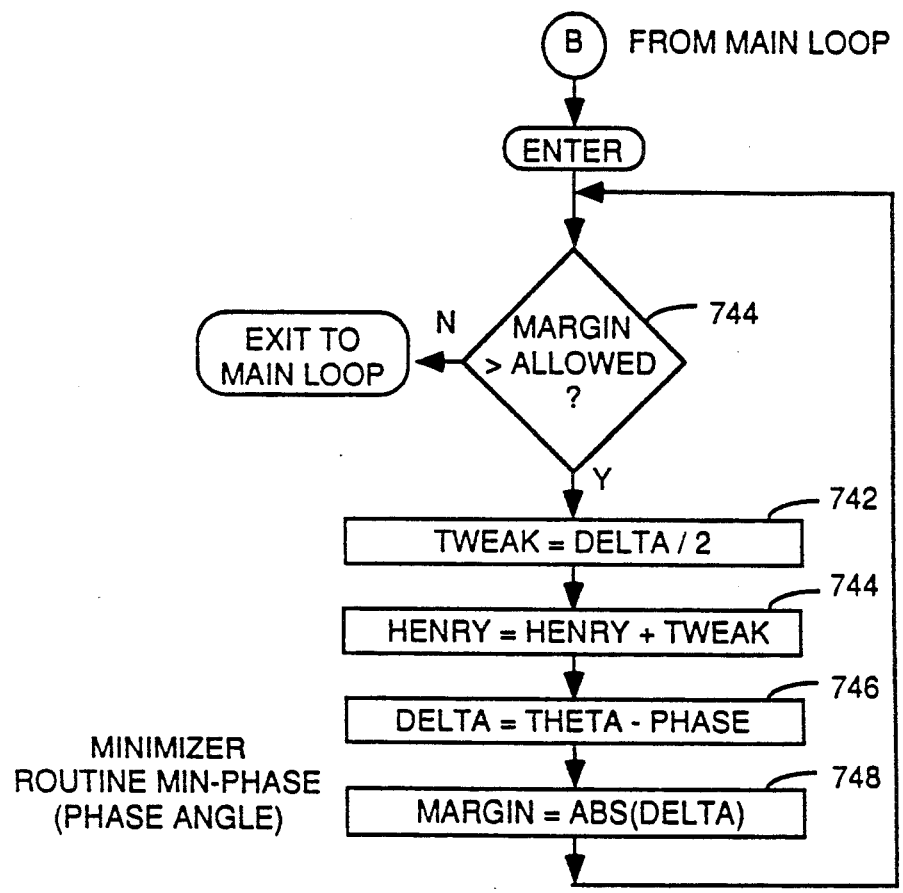
FIG. 28 is a flow chart of the phase angle minimization subroutine called upon by the main loop to tune the tuning inductor to change the inductive reactance of the source impedance to match the capacitive reactance of the probe as close as possible.

Referring to FIG. 28, the details of the phase angle minimizer routine are given. The first step in this routine when it is called from step 718 in FIG. 26 is to determine if the current phase angle is within a band of allowed phase angles centered around the desired phase angle. This test is symbolized by step 744. The reason this step is performed is to prevent the loop of FIG. 28 from being performed an infinite number of times since a successive approximation technique is used where adjustment of only half the error margin are made. The step 744 compares the contents of variable MARGIN to a constant called ALLOWED which is the maximum error margin which is allowed. If MARGIN is greater than ALLOWED, step 742 is performed which adjusts the contents of a variable TWEAK which is the amount by which the current in the D.C. bias coils 608 and 610 is to be changed to start the process of tuning away the phase angle to the minimum possible angle. TWEAK is adjusted by step 742 by an amount equal to DELTA/2 where DELTA is the signed difference between the desired phase angle (expressed in terms of the current though the D.C. bias coils) and the actual phase angle. The actual phase angle is determined by the CPU 20 by reading the channel 1 output of the A/D converter 54 in FIG. 25 to obtain the results calculated by the phase detector 50 and the summer and integrator 52. The desired phase angle can be any constant, but is usually zero.

Next, a step 744 is performed which adjusts the current level in the D.C. bias coils 608 and 610 in FIG. 25 to a new level of current in an attempt to minimize the phase angle. In step 744, a variable HENRY, which represents the current value of current flowing in the D.C. bias coils 608 and 610 expressed in terms of the digital value currently written to the D/A converter 40, is changed by the value of TWEAK.

Next, a step 746 is performed to test the new phase angle which results from the change in HENRY and the resultant change in the current level flowing in the D.C. bias coils. Step 746 computes the value of the variable DELTA by subtracting from the desired phase angle, THETA, the value of the current phase as determined by reading the channel 1 output from the A/D converter 54 as represented by the variable PHASE. Next, a step 748 is performed which computes the value of the variable MARGIN by taking the absolute value of the variable DELTA.

Finally, processing is returned to the test of 744. When the test of step 744 indicates that MARGIN is less than the value of ALLOWED, processing returns to the routine of FIG. 26, step 720.

SLOPE TEST EMBODIMENT

Figure 30:
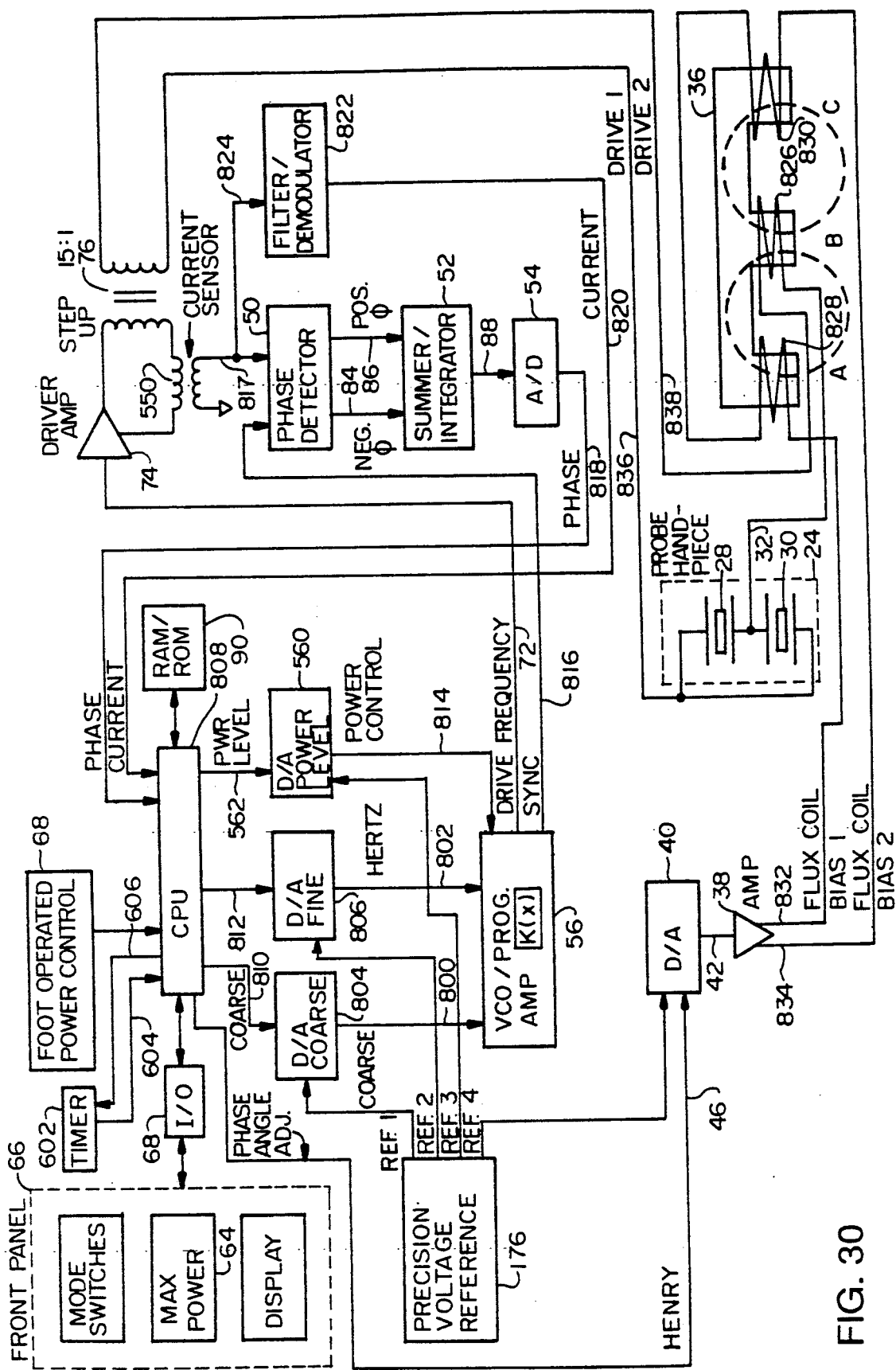
FIG. 30 is a block diagram of the preferred embodiment of an apparatus according to the teachings of the invention.

Referring to FIG. 30, there is shown a block diagram of the preferred embodiment of the circuitry of the invention. Circuit elements in FIG. 30 having the same reference numbers as blocks in the embodiment shown in FIG. 25 perform the same functions in the same way as described with reference to FIG. 25, and will not be described again here. Only the changes over the embodiment shown in FIG. 25 will be described with reference to FIG. 30.

The voltage-controlled oscillator/programmable gain amplifier 56 has two frequency control inputs: a coarse input 800 and a fine input 802. These two inputs receive the signals COARSE and HERTZ, respectively, from digital-to-analog converters 804 and 806, respectively. These digital-to-analog converters receive digital signals from the CPU 808 on lines 810 and 812, respectively. These digital signals define the analog levels for the signals on lines 800 and 802 and thereby control the frequency of the output drive signal DRIVE FREQUENCY from the voltage-controlled oscillator on line 72.

Each of the digital-to-analog converters 804 and 806 receives a reference voltage from a precision voltage reference source 176 in the form of the signals REF 1 and REF 2, which are used as reference voltages for purposes of scaling the analog voltages on lines 800 and 802.

To generate the signals on lines 810 and 812 and do the many other functions described here, the CPU 808 runs the software given in Appendix A attached hereto. The software of Appendix A is the preferred embodiment and the best mode of practicing the teachings of the invention. The CPU 808 is a Z-80 card which is commonly available. The voltage-controlled oscillator/programmable amplifier 56 is manufacture by Exar Corporation, Model XR2206.

Figure 31:
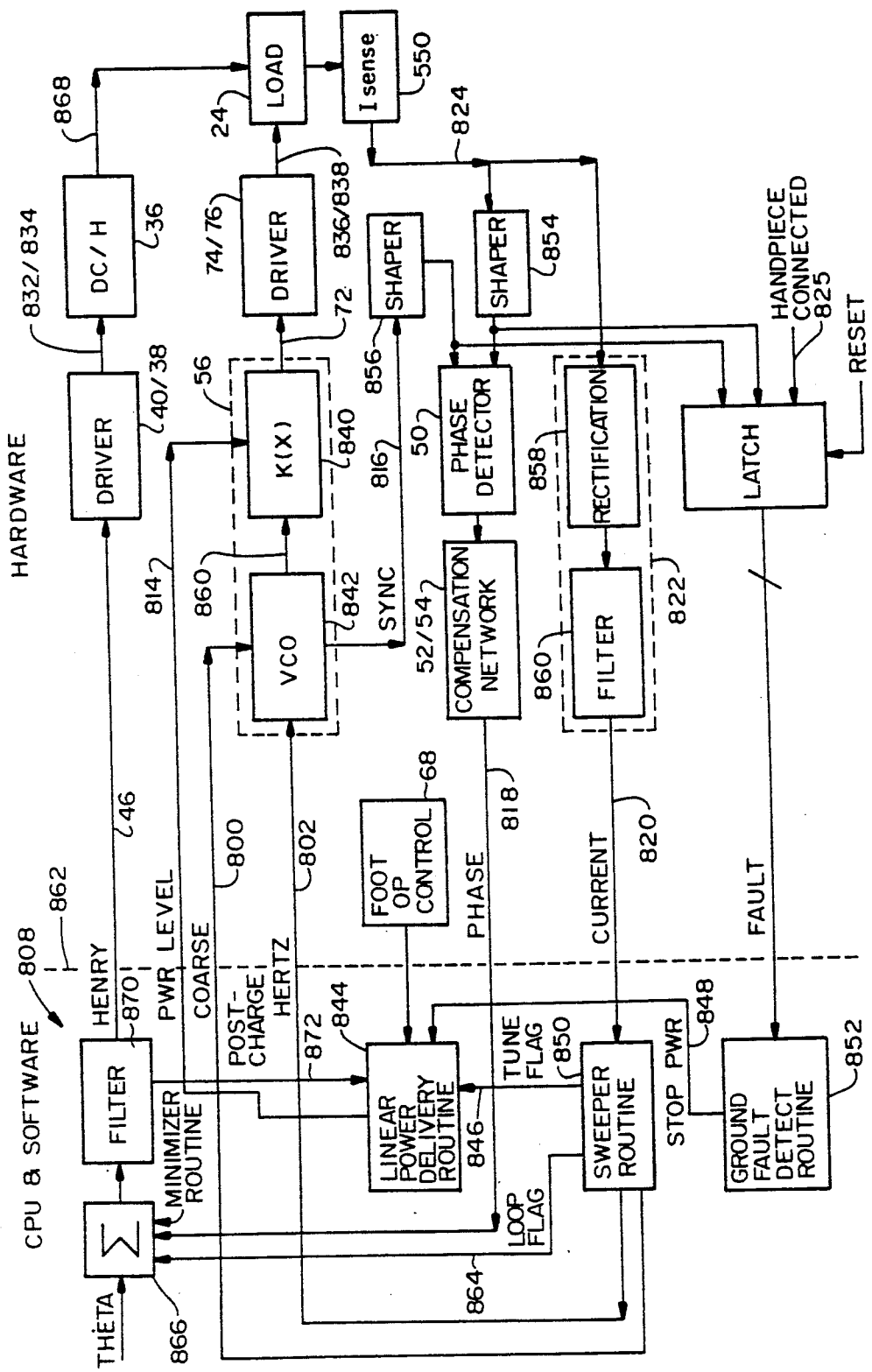
FIG. 31 is a symbolic diagram illustrating the interplay between the hardware and software elements of the system.

The power level for the DRIVE FREQUENCY signal on line 72 is controlled by the foot-operated control 68 and the CPU 808 in combination with linear power control software 844 in FIG. 31. This software has been previously herein and is included within Appendix A. The CPU 808 outputs a power control signal PWR LEVEL on line 562 to a digital-to-analog converter 560. This digital-to-analog converter also received a reference voltage input signal REF 3 from voltage reference source 176. The digital-to-analog converter 560 generates an analog control signal called POWER CONTROL on line 814 which is coupled to a gain control input for the programmable gain amplifier portion of the voltage-controlled oscillator. The signal POWER CONTROL on line 814 controls the amplitude of the output signal DRIVE FREQUENCY on line 72, thereby controlling the power delivered to the handpiece 24.

The CPU 808 needs feedback signals regarding two things to do its tuning functions. First, the CPU 808 must know the phase angle difference between the driving signal voltage and the resulting load current. Also, the CPU must know the amplitude of the current flowing in the load. To determine the phase angle difference, the phase detector 50 and a current sensor transformer 550 are used. The phase detector has one phase input coupled to the secondary winding of the current sensor 550 and has another phase input coupled to a signal SYNC on line 816 from the voltage control oscillator. As in the other embodiments described herein, when there is no phase difference, no pulses appear on either of the output lines 84 or 86. However, when positive phase difference exists, a train of pulse width modulated pulses appear on line 86 with the width of the pulses indicative of the amount of the phase angle difference. Likewise, when a negative phase angle difference exists, a train of pulse width modulated pulses appears on line 84 with the width of the pulses indicative of the magnitude of the phase angle difference. The summer/integrator 52 and analog-to-digital converter 54 operate as previously described to generate the digital signal PHASE on line 818, which is indicative of the magnitude of the phase angle error. The signal is coupled to the CPU 808. The phase detector 50 uses the SYNC signal output on line 816 from the voltage-controlled oscillator because this signal is cleaner and leads to better phase detection than where the phase detector 50 has its other input coupled to the DRIVE FREQUENCY signal on line 72.

The load current feedback signal CURRENT on line 820 is generated by a filter/demodulator circuit 822 coupled to the current sensor 550 coupled in series with the primary winding of the output transformer 76. The input signal on line 824 to this filter/demodulator is essentially a sine wave having the frequency of the driving signal on line 72 and having an amplitude which is related to the amplitude of the drive signal on line 72. The CPU 808, however, is only interested in the level of the envelope of the "peak"s of the alternating current signal on line 824. Therefore, the filter/demodulator circuitry 822 can be any conventional demodulation circuitry for AM demodulation. Specifically, it comprises a rectifier to convert the A.C. signal to a train of D.C. pulses and a filter to smooth these D.C. pulses out so as to create a D.C. signal having an amplitude which is related to the amplitude of the envelope of the signal CURRENT on line 820. This signal tells the CPU 88 how much load current the probe, i.e., handpiece, 24 is drawing through the output transformer 76. Since at resonance, the load current will be a maximum, the CURRENT signal is used to detect when then resonance occurs by detecting the "peak" load current and examining the slope of the load current versus frequency function. When the actual resonance frequency is found, the frequency of the drive signal on 72 at which this resonance occurred is noted by the CPU 808 and, thereafter, the CPU controls the voltage-controlled oscillator 56 so as to deliver this frequency at all power levels commanded by the foot-operated power control 68 until such time as retuning is performed automatically or is requested by the user. Both of these options are contemplated as within the teachings of the invention.

The process of tuning the voltage-controlled oscillator to find the resonance frequency is an ongoing foreground process which occurs whenever a routine called "sweeper" is performed. In some embodiments, the "sweeper" routine is performed periodically and in some embodiments, the "sweeper" routine is performed only when called by the main loop under conditions such as power being first applied to the handpiece, a new handpiece is attached etc. Thus, as conditions such as probe temperature and load change so as to alter the resonance frequency of the probe, the new resonance frequency is found in some embodiments, and the voltage-controlled oscillator is commanded through the digital signals on line 810 and 812 to deliver the drive signal on line 72 at the new resonance frequency.

The CPU 808 is also continually checking the phase angle difference between the drive signal voltage and the load current through monitoring of the signal PHASE on line 818. In the preferred embodiment, this process is stopped and the tuning inductor is tuned to minimum inductance during a resonance tuning interval when the "sweeper" routine is active in tuning the voltage-controlled-oscillator. A "minimizer" software routine performs the phase angle tuning. When the "minimizer" routine is actice, and the phase angle difference becomes larger than a desired value, the CPU 808 acts through a digital-to-analog converter 40 and an amplifier 38 to alter the inductance of a tunable inductor 826 so as to cancel the capacitive reactance of the load. This minimizes the phase angle difference between the driving signal voltage and the load current. The inductance of the tuning inductor 826 is altered by changing the flux in the tuning inductor core 36 through use of D.C. bias coils 828 and 830. These bias coils are connected in series and are driven by the signals FLUX COIL BIAS 1 and FLUX COIL BIAS 2 on the lines 832 and 834. The D.C. bias existing between the lines 832 and 834 is controlled by a digital signal HENRY on line 46 from the CPU 808. This digital signal is input through the digital-to-analog converter 40, which also receives a D.C. voltage reference level signal REF 4. The digital-to-analog converter converts the digital level represented by the signal HENRY to an analog signal on line 42 which controls the output of an amplifier 38 so as to drive the signal lines 832 and 834 with the appropriate D.C. bias level.

Finally, note that the drive signal to the probe handpiece on lines 836 and 838, i.e., the signals DRIVE 1 and DRIVE 2, respectively, are coupled through the tunable inductor 824 such that the DRIVE 2 signal is coupled to the common node between the crystals 28 and 30 while the DRIVE 1 signal is coupled collectively to the outer nodes of the crystals 28 and 30. In other words, center drive between the two crystals 28 and 30 is used.

Referring to FIG. 31, there is shown another representation of the combination of hardware and software which cooperates to implement the teachings of the invention. Again, like numbers between FIGS. 31 and 30 indicate that the circuitry is similar and performs a similar function. The handpiece is represented by the load 24. The variable frequency variable amplitude driving signal for the load appears on the line 836/838 and is generated by the driver 74/76. The circuitry inside the dashed line 56 represents the voltage-controlled oscillator 842 and the linear programmable amplifier 840. The gain control signal to the linear programmable amplifier 840 is the PWR LEVEL signal on line 814. The voltage-controlled oscillator 842 has a fine frequency control signal HERTZ on line 802 and a coarse frequency control signal COARSE on line 800. Power dissipation is controlled by a linear power delivery software routine 844 combined with the CPU 808 an a foot-operated control 68. This power delivery routine 844 generates the signal PWR LEVEL on line 814. The power delivery routine 844 has two interlocks represented by the TUNE flag represented by line 846 and the STOP POWER flag represented by the line 848. The TUNE flag will be set when a tuning routine called "sweeper", represented by box 850, indicates that the load 24 has not been properly tuned and that power should not be applied. The STOP POWER flag represented by line 848 will be set when a ground fault detect routine represented by box 852 indicates that a ground fault has been detected. A ground fault occurs any time certain conditions of three bits stored in a latch 823 occur. These three bits are set, respectively, by the presence of the SYNC output signal on line 816, presence of an output on line 824 from the current sensor and the presence of a connected handpiece as indicated by a signal HANDPIECE CONNECTED on line 825. A typical ground fault condition would be that no handpiece is connected. Another would be that there is a SYNC output signal but there is no output signal on line 824 indicating that no load current is flowing.

The current through the load 24 is sensed by the current sensor 550. The current sensor is coupled to a shaper circuit 854 to condition the signal on line 824 for use by the phase detector 50. The phase detector also receives the SYNC signal on line 816 through a shaper 856 which serves to condition the SYNC signal for use by the phase detector 50. The phase detector is a Motorola MC4044 integrated circuit in the preferred embodiment.

The phase detector output is coupled by a compensation network 52/54 to the CPU (not separately shown). The output of the compensation network is the signal PHASE on line 818.

The output of the current sensor 550 on line 824 is also coupled to a rectifier 858 and a filter 860 which combine to amplitude demodulate the signal on line 824 and generate a D.C. varying signal called CURRENT on line 820 which is proportional to the magnitude of the envelope of the signal on line 824. The signal CURRENT on line 820 is read by the CPU 808 and used in the "sweeper" software routine to tune the voltage-controlled oscillator 852 to output a drive signal on line 860 which has a frequency which matches the mechanical resonant frequency of the load 24. The details of the "sweeper" routine best mode are in Appendix A. The code of Appendix A will be explained functionally in terms of flow charts for a similar embodiment to be described in more detail below. The "sweeper" routine causes two main output signals to be generated by the CPU 808 to control the frequency of the voltage-controlled oscillator 842. These two digital output signals are the signals COARSE and HERTZ on lines 800 and 802, respectively.

The "sweeper" routine also sets a LOOP flag, represented by line 864, to disable the operation of a "minimizer" routine to tune away any PHASE angle error and represented by box 866. The "minimizer" routine serves to determine the current PHASE angle error between the driving signal voltage and the load current and to alter the inductance of a tuning inductor, represented by box 36, so as to minimize or eliminate this PHASE angle error. It is undesirable to perform this process while the voltage-controlled oscillator is being tuned to the resonant frequency because any inductance by the tuning inductor might lead to finding a false resonant frequency. Thus, the loop flag 864 is used to disable this process during activity by the "sweeper" routine.

The "minimizer" routine 866, when activated, causes the CPU 808 to read the signal PHASE on line 818 and to generate an output signal HENRY on line 46 to the driver 40. The output of the driver 40 is an analog D.C. bias signal on line 832/834. This signal is transformed by a D.C.-to-HENRY transformation circuit implemented by the tuning inductor 36 and represented by the box 36. Line 868 represents the effect of the changing magnetic flux in the tunable inductor 36 thereby altering the inductance of the tuning inductor in series with the load and causing the load impedance to look as close to a pure resistance as possible.

A filter 870, implemented in software as a delay function, is used to control the loop frequency response. This delay is necessary to stabilize the operation of the servo loop used to minimize or eliminate the PHASE angle error. Because this servo loop includes a tunable inductor which cannot change states as rapidly as the computer can compute correction factors, each correction is delayed until the servo loop has had a sufficient opportunity to implement the previous correction. Implementation of each correction is by alteration of the inductance of the tunable inductor. The filter 870 also represents a software routine which sets the level of the output signal HENRY on line 46 at a predetermined statistically determined nominal operating point for most handpieces prior to release of control of the power control function to the surgeon manipulating the foot-operated control 68. This operating point is empirically determined as the nominal operating point for most handpieces which can be connected to the system. The software filter routine 870 sets HENRY at this nominal operating point during a postcharge routine which is part of this filter function and sends a signal to the power delivery routine 844 to cause it to apply full power to the load for three seconds prior to release of control to the surgeon. The interaction between the software filter routine 870 and the power delivery routine 844 is represented by the line labeled postcharge 872 although the postcharge routine is software and not a signal, signal line or a flag. This postcharge routine enables smoother operation of the system since the operating point of the load has already been set at a point which is very close to the correct operating point prior to allowing the surgeon to change the system's operating conditions. As the surgeon changes the system operating conditions such as the level of power applied to the handpiece, the mechanical loading on the handpiece, the probe temperature and so on, the system automatically compensates for changes in phase angle and mechanical resonance frequency in some embodiments, thereby constantly keeping the load 24 tuned to optimum operating conditions.

Figure 32:
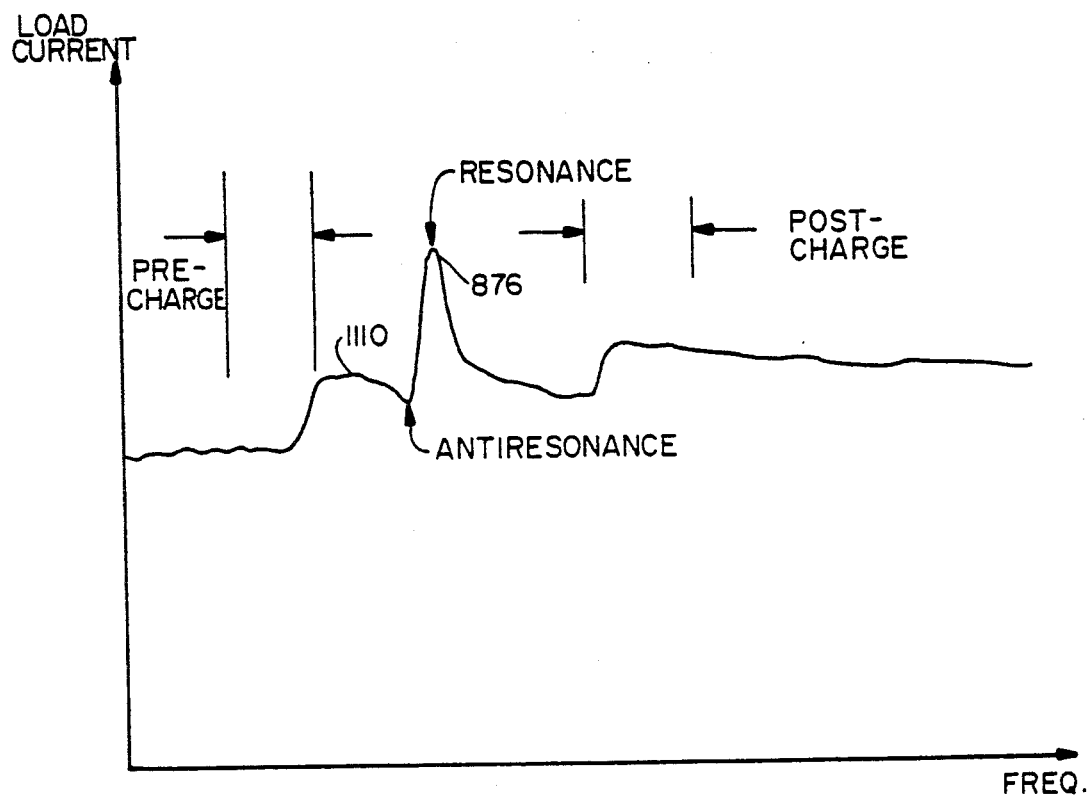
FIG. 32 is a plot of a typical load current versus frequency function illustrating the precharge and postcharge regions symbolically.

Referring to FIG. 32, there is shown a typical plot of load current versus frequency for a typical "sweeper" tuning cycle. The resonant frequency of the probe is found where the load current is at a "peak", as shown at 876, and where the slope of the load current change versus frequency change is below a specified level. The software of the "sweeper" routine finds the resonant "peak" by finding the "peak" load current and examining the slope of the function of load current versus frequency at least at this "peak". In some embodiments, continuous slope calculations are performed but this is not critical. The slope calculation can be made only at what appears to be each new "peak". If this slope at the "peak" is within predetermined limits in some embodiments or less than a predetermined slope in the preferred embodiment, then the "peak" is accepted as a legitimate resonance "peak". If not, the "peak" is rejected a spurious "peak" not at the mechanical resonance frequency. The software of the "sweeper" routine also performs specific operations during a "precharge" interval to improve performance of the servo loop for tuning the tunable inductor. During the "precharge" interval, the software of the "sweeper" routine causes the CPU to output a predetermined value for the control signal HENRY. After this predetermined level is established, a delay is imposed to allow the inductance of the tuning inductor to change to the new value established by the value of the control signal HENRY. No changes in the drive frequency to the probe are allowed during this delay of the "precharge" interval. During the "precharge" interval, the value of the control signal HENRY is changed to a very large voltage so as to cause the D.C. bias coils 828 and 830 in FIG. 30 to saturate the core of the transformer 36 with magnetic flux. This minimizes or eliminates any inductive characteristic of the tuning coil 826. This is desirable so that the inductance of the tuning inductor does not play a role in establishing the resonant frequency found by the "sweeper" routine. Since the reactance of an inductor changes with changing frequency, having the tuning inductor in the circuit during a sweep could lead to a false resonance. The "precharge" routine eliminates the possibility.

Figure 33:
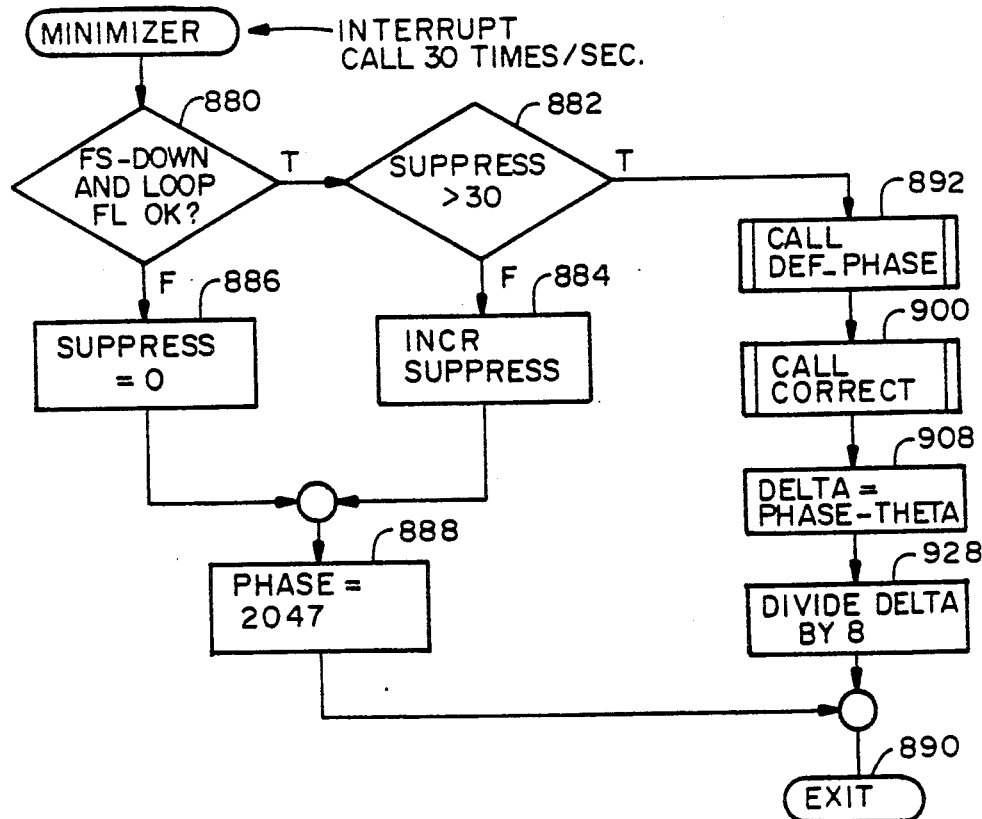
FIG. 33 is a flow chart of the "minimizer" routine to tune out the reactance component of the load impedance.

Referring to FIG. 33, there is shown a flow chart for the "minimizer" routine 866 in FIG. 31. This routine starts at step 880 with a test to determine whether the foot switch is down, indicating that the surgeon desires to apply power to the probe and that the LOOP flag is in a state indicating that the "sweeper" routine has tuned the system such that the voltage-controlled oscillator is now operating at the resonance frequency of the probe. The purpose for step 880 is to not allow the "minimizer" routine to minimize the phase angle error unless power is being applied to the probe and the system has been tuned to the mechanical resonance frequency of the probe. The "minimizer" routine is called 30 times per second by a timed interrupt. Thus the PHASE minimization function of the "minimizer" routine is performed in background to the operations in the main loop.

If both the foot switch is down and the LOOP flag indicates that tuning of the tuning conductor is permissible, processing advances to step 882. In this step, a variable SUPPRESS is tested to determine if its value is greater than 30. The SUPPRESS variable is a variable which is used to cause a delay of one second from foot pedal depression before any further corrections of the control signal HENRY are allowed. Since the "minimizer" routine is called 30 times per second, and the SUPPRESS variable is incremented by 1 by step 884 upon each call until the SUPPRESS variable has a value greater than 30, a one second delay is thereby implemented. The purpose for this delay is to improve the response of the system when the foot switch is first pressed by the surgeon. Because of the characteristics of the servo loop, when a servo correction is made, power dies momentarily while the servo loop stabilizes at its new operating point. This is because of the characteristics of the tuning inductor and the inability to change current flowing through an inductor instantaneously. Since the surgeon expects immediate response when the foot switch is pressed, the delay is used to not allow any corrections within the first second after depression of the foot switch so that power response appears to instantaneous.

Returning to step 880, if the result of this test is false, meaning either that the foot switch is not depressed or that the LOOP flag indicates that the "sweeper" routine is still tuning, processing branches to step 886, where the SUPPRESS variable is set to zero. Thereafter, processing flows to step 888, where the value of the PHASE variable is arbitrarily set to the constant 2047. Normally the PHASE variable is set by the value of the PHASE control signal on line 818 received from the compensation network 52/54 in FIG. 31. However, the PHASE variable can be set at a constant, if desired. The value of the PHASE variable can vary from zero to 4095. The midpoint of this range is 2047 and corresponds to a zero-degree phase angle error. The phase angle range of 2047±2047 corresponds to a phase angle error of plus or minus 180 degrees. Thus, step 888 is equivalent to arbitrarily setting the phase angle error at zero. Thereafter, processing flows to step 890 to exit the "minimizer" routine and return to the calling process.

Returning to step 882, if the value of the SUPPRESS variable is less than 30, the step 884 increments the variable by 1, and processing flows to steps 888 and 890. If however the value of the SUPPRESS variable is found to be greater than 30, the one-second delay implemented thereby has elapsed, and a correction of the phase angle error can begin. The first step in this process is symbolized by block 892 which calls the "default phase" subroutine.

Figure 34:
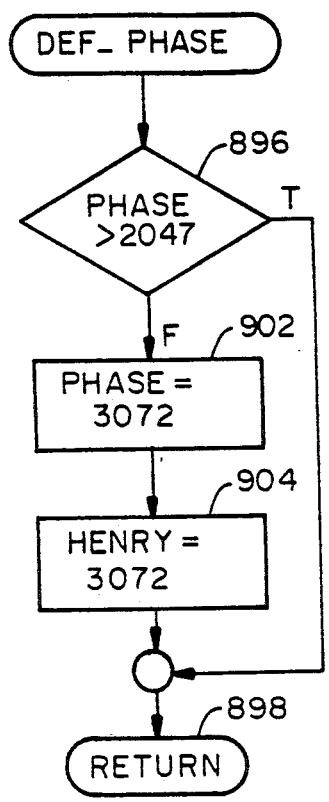
FIG. 34 is a flow chart of the "def-phase" routine to set a default value for HENRY.

Referring to FIG. 34, there is shown a flow chart of the "default phase" subroutine called by the "minimizer" routine of FIG. 33. The first step in the default phase routine is step 896, where the value of the PHASE variable is tested to determine if it is greater than the constant 2047. The PHASE variable will have been set by the value of the input signal PHASE on line 818 in FIG. 31. Since the value 2047 for the PHASE variable indicates a zero degree phase angle, step 896 is a test for the existence of a positive phase angle. If the phase angle is positive, that phase angle is used for the default phase, and processing flows to step 898 to return to the "minimizer" routine at step 900. If the phase angle error is negative, or less than 2047, processing flows to step 902 where the value of the PHASE variable is arbitrarily set to a default constant of 3072. Thereafter, processing flows to step 904, where the software causes the microprocessor to output a value for the control signal HENRY equal to 3072. Thereafter, processing returns to the "minimizer" routine of FIG. 33 at step 900.

Figure 35:
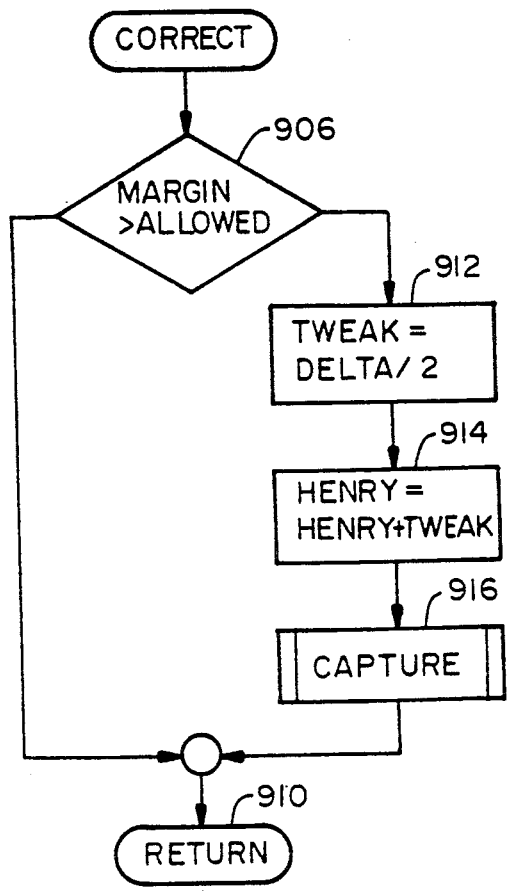
FIG. 35 is a flow chart of the "correct" routine to alter the value of HENRY.

Step 900 of the "minimizer" routine is a call to a subroutine called correct. Referring to FIG. 35, there is shown a flow chart of the subroutine "correct". The first step in the subroutine "correct" is a test of the MARGIN variable to see if it is greater than a variable ALLOWED. The variable MARGIN is equal to the absolute value of another variable called DELTA. DELTA is a variable calculated by a step 908 in FIG. 33 and is indicative of the size of the phase angle error. Specifically, step 908 in FIG. 33 calculates DELTA by subtracting a constant phase angle error THETA from the value of the PHASE variable set by the actual phase angle error. THETA is a constant phase angle error introduced by the circuitry of the servomechanism which cannot be eliminated. The ALLOWED variable sets a minimum phase angle error which is acceptable. If the MARGIN variable is greater than the ALLOWED variable, then adjustment to the tuning inductor must be made. If the MARGIN variable is less than the ALLOWED variable, then the phase angle error is within acceptable limits and no correction need be made. In this event, processing flows to step 910, which returns processing to the calling process, i.e., processing flows to step 908 in FIG. 33.

Returning to step 906, if the phase angle is greater than the allowed minimum phase angle, processing flows to step 912, where the value of a variable called TWEAK is set at the value of DELTA divided by 2. Input/output step 914 is then performed where the software causes the microprocessor to set the value of the control signal HENRY equal to the old value for HENRY plus the value of the variable TWEAK calculated in step 912. Next, a step 916 is performed wherein a subroutine called "capture" is called.

Figure 36:
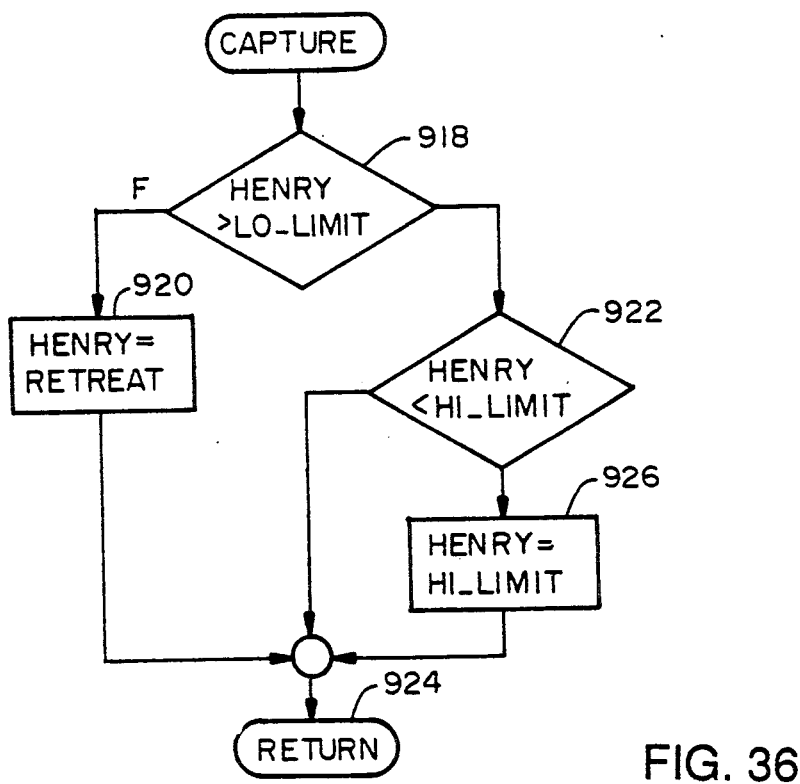
FIG. 36 is a flow chart of the "capture" subroutine to set HENRY at certain capture limits.

Referring to FIG. 36, there is shown a flow chart of the "capture" subroutine. The first step in the subroutine is the test represented by block 918. This test determines whether the value of the control signal HENRY is greater than the value of a variable called LOW-LIMIT. If the value of the control signal HENRY is less than the value of the constant LOW-LIMIT, then step 920 is performed wherein the value for the variable HENRY is set equal to a constant called RETREAT which is basically a constant at or near the opposite rail or limit. This value for HENRY is then output by the microprocessor on line 46 to the driver 40/38 in FIG. 31. If the value of the variable HENRY is greater than the constant LOW-LIMIT, then step 922 is performed, where the value of the HENRY variable is tested against a high limit symbolized by the constant HI-LIMIT. If the value of HENRY is less than HI-LIMIT, then step 924 is performed to return processing to the calling process, i.e., step 910 in the subroutine "correct", illustrated in FIG. 35. If the value of the variable HENRY is greater than the constant HI-LIMIT, then a step 926 is performed wherein the value of HENRY is set equal to the value of the constant HI-LIMIT.

The purpose of the "capture" routine is to capture the value of the variable HENRY within a range defined by the constants RETREAT and HI-LIMIT. This prevents the control signal HENRY from making excursions outside the desired range and causing the servo loop controlling the tuning inductor to have to make large corrections to minimize the phase angle. Making large corrections slows the response time of the servo loop down because each large correction requires changing the value of the tuning inductor inductance by large amounts. Since this inductor cannot change its inductance rapidly because the level of current flow in the D.C. bias coils instantly, such large changes take long intervals.

The return from the "capture" routine is to the "correct" routine at step 910. The return from step 910 of the "correct" routine is to step 908 of the "minimizer" routine shown in FIG. 33. Step 908 calculates the value of the variable DELTA by reading the current value of the PHASE variable as set by the PHASE control signal received from the compensation network 52–54 in FIG. 31. The value of PHASE has subtracted from it the value of the constant THETA.

Next, a step 928 is performed in the "minimizer" routine to divide the value of DELTA by a factor of 8. This prevents corrections of the value of the control signal HENRY which are large. Thereafter, step 890 is performed to exit the "minimizer" routine and return processing to the calling point of the main loop of the software. The above-described processing of the "minimizer" routine is performed 30 times per second.

Figure 37:
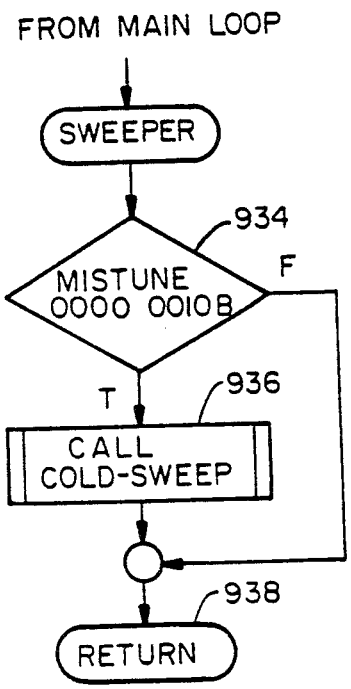
FIG. 37 is a flow chart of the "sweeper" subroutine to tune the VCO to the mechanical resonance frequency of the probe.

Referring to FIG. 37, there is shown a flow chart of the "sweeper" routine, which tunes the frequency of the voltage-controlled oscillator to match the mechanical resonance frequency of the handpiece. The first step in the "sweeper" process is symbolized by block 934, which tests a MISTUNE variable to determine if the second least significant bit is a logic one. This bit is used by other routines (not shown) in the software to manage an "analysis" subroutine to be described further below. If for any reason the handpiece must be retuned, the second least significant bit of the MISTUNE variable will be set to a logic 1. This can occur when a new handpiece has been connected, or for other reasons such as a user request in some embodiments. For present purposes, the "analysis" subroutine should be understood as the software which causes the microprocessor to alter the frequency of the voltage-controlled oscillator until the mechanical resonance frequency of the handpiece is found or, for some reason, the resonance is not found and a FAILURE flag is set.

If the second least significant bit of the MISTUNE variable is found to be a logic 1, processing flows to step 936, which represents a call to the "cold-sweep" subroutine. The "cold-sweep" subroutine calls the "analysis" subroutine after setting up appropriate input conditions so as to tune the voltage-controlled oscillator. Upon return from the "cold-sweep" subroutine, the return step 938 in the "sweeper" routine is performed to return control to the calling process in the main loop (not shown).

If the second least significant bit of the MISTUNE variable is a logic 0, then processing flows to step 938, which represents a return to the calling process in the main loop. The details of the main loop of the program, including the calling process, are not critical to understanding the invention, and are not described further herein.

Figure 38A:
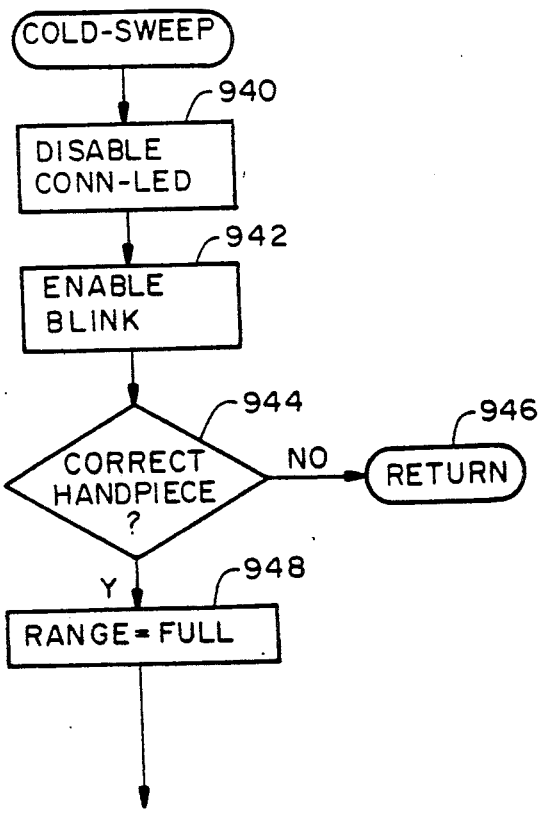
FIGS. 38A and 38B are a flow chart of the "coldsweep" routine which calls the "analysis" routine to do the VCO tuning and manages user interface functions.

Referring to FIG. 38A, there is shown a flow chart of the "cold-sweep" subroutine. The purpose of the "cold-sweep" subroutine is to tune the handpiece by invoking the "analysis" subroutine and to handle user interface functions in the form of audible feedback and a light-emitting diode on the front console to give the status of the tuning process. The "cold-sweep" subroutine also invokes the "postcharge" subroutine previously described. As earlier noted, the "sweeper" routine disables the PHASE "minimizer" routine 866 in FIG. 31 through use of the LOOP flag 864 in FIG. 31 during the tuning process.

To implement the function of visual feedback to the user, step 940 disables a light-emitting diode on the front panel near the connector where the handpiece is attached to the system. The next step, symbolized by block 942, is to cause this light emitting diode to blink. Thus, the user knows that a tuning process is underway when the light emitting diode is blinking.

It is important that only compatible phacoemulsification handpieces be connected to the system. To this end, a step 944 is performed to test the connected handpiece to determine if it is compatible. Any sensing scheme to determine the compatibility of the handpiece will suffice for purposes of practicing the invention, and the details of this sensing are not critical to understanding of the invention. If the test of block 944 determines that an incompatible handpiece has been connected to the system, then step 946 is performed to return processing to the calling routine, i.e., "sweeper", at step 938. Return step 938 then returns processing to the calling process in the main loop. Thus, when an incompatible handpiece is connected to the system, "cold-sweep" does not invoke the "analysis" subroutine, and no tuning can occur.

If test 944 determines that a compatible handpiece is connected, a step 948 is performed wherein a RANGE variable is set to a constant FULL. The RANGE variable is a control variable used to enable or disable performance of the "analysis" subroutine. If RANGE is set to full, the "analysis" subroutine will perform its tuning function. If, on the other hand, the RANGE variable is set to the value of a variable called MINIMUM, then the "analysis" routine will simply return immediately upon being called without having performed any tuning activity.

Figure 38B:
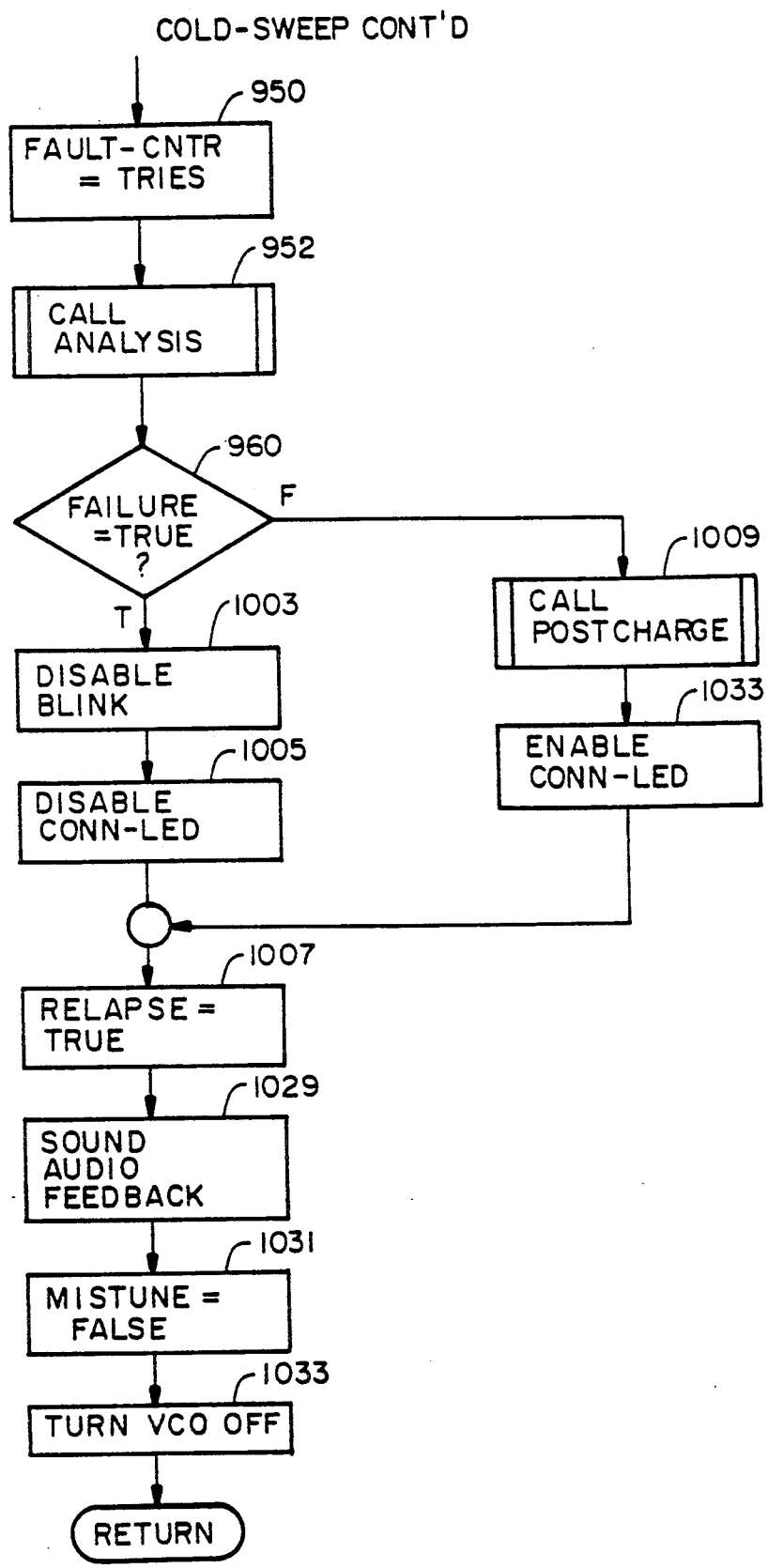

The next step in the "cold-sweep" routine is symbolized by block 950 on FIG. 38B. This step sets the value of a variable called FAULT-CNTR equal to a constant called TRIES. This establishes the number of tuning attempts which will be made before a FAILURE flag is set indicating no successful tuning of the handpiece has been accomplished.

Next, the "cold-sweep" routine calls the "analysis" subroutine, as symbolized by block 952. The details of the "analysis" subroutine will now be described.

Figure 39:
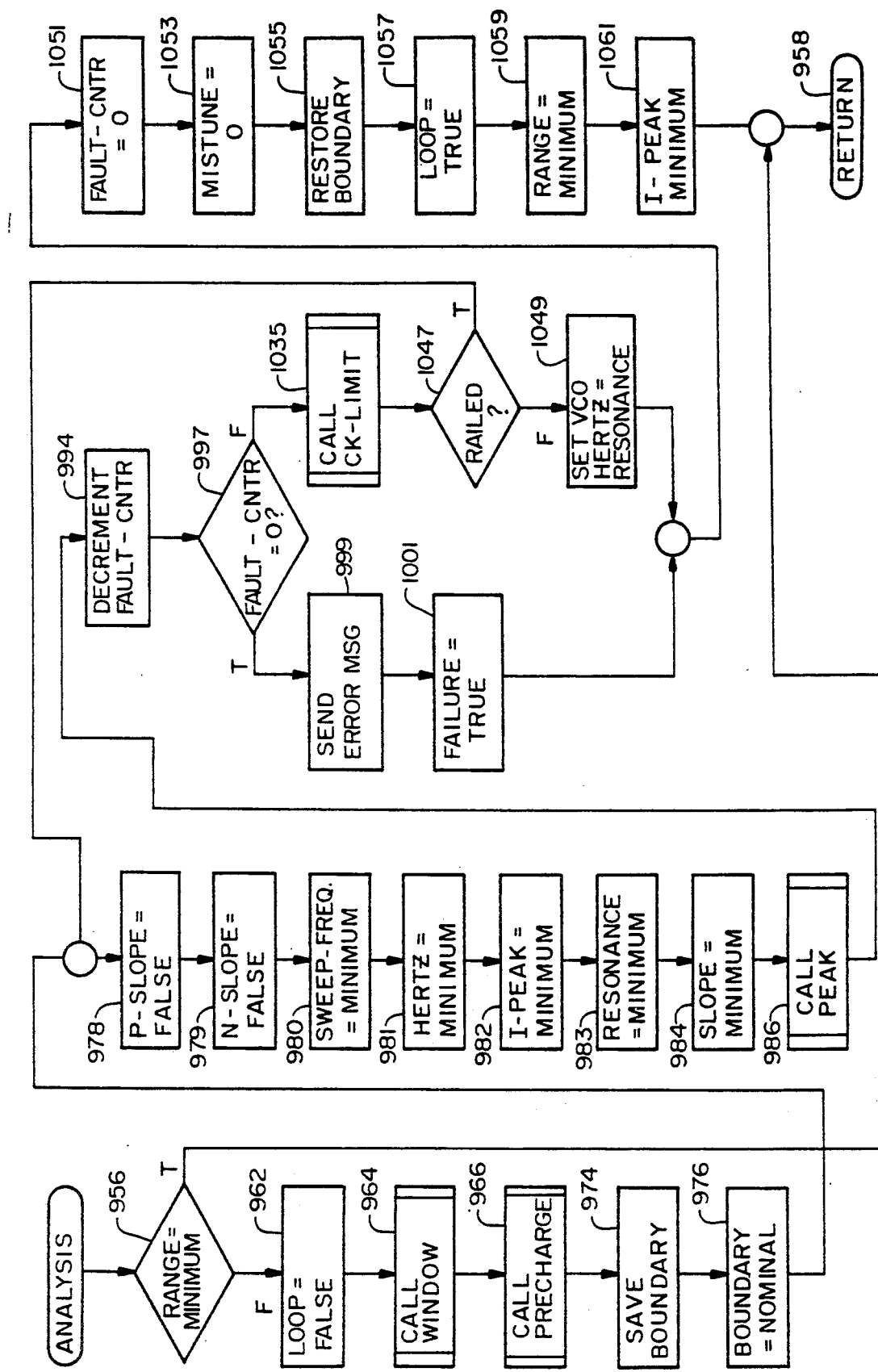

Referring to FIG. 39, there is shown a flow chart of the "analysis" subroutine. The first step in the "analysis" subroutine is a test to determine the value of the RANGE variable as symbolized by block 956. If the RANGE variable is equal to a constant called MINIMUM, then processing flows immediately to step 958, which returns processing to step 960 in the "cold-sweep" routine shown in FIG. 38B. Processing by steps 960 and following of the "cold-sweep" routine will be described in more detail below. If the value of the RANGE variable is found to be not equal to the constant MINIMUM, then a step 962 is performed wherein the LOOP flag is set to a false condition. This disables the operation of the phase "minimizer" routine previously described.

Next, a step 964 is performed to call a WINDOW subroutine. This routine calculates the minimum frequency and maximum frequency between which the voltage-controlled oscillator will be tuned during the tuning process. Basically the window subroutine calculates a variable called MINIMUM which sets the lower boundary of the tuning window. In the preferred embodiment, the variable MINIMUM is set at zero. The "window subroutine" also sets a variable called MAX-FREQ to a value of 4096. These two numbers establish a window for tuning of the voltage-controlled oscillator by variation of the fine tuning control signal HERTZ. The coarse tuning is controlled by the value of a variable COARSE which is set by a "chk-limit" subroutine to be described below to move the center frequency of the fine tuning window throughout the tuning band. Basically, the process is to set COARSE, sweep HERTZ and look for a resonance peak within the inner 50% of frequencies swept by HERTZ. If no resonance peak is found within this inner 50% of frequencies, hereafter called the ACCEPTABLE band, then COARSE is incremented to move the center frequency of the fine tuning window up 800 Hertz and the process is started again. The details of why only the inner 50% of frequencies of the fine tuning window are used will be given below.

The control signal HERTZ can vary between analog voltages which are proportional to digital values for the variable HERTZ. These values range between zero and 4096. When the value of the HERTZ variable is 2047, the voltage-controlled oscillator will operate at the center frequency established by the control signal COARSE. For each count of the variable HERTZ below the value 2047, the voltage-controlled oscillator will operate at a frequency of 1.6 hertz below the frequency established by the control signal COARSE. For every count of the variable HERTZ above a value of 2047, the frequency of the voltage-controlled oscillator will be 1.6 HERTZ above the frequency established by the control signal COARSE standing alone. The variable SWEEP-FREQ set by the subroutine "window" represented by block 964 in FIG. 39 represents a pointer for the current operating frequency, i.e., the position within the fine-tuning window at which the voltage-controlled oscillator is currently operating. The variable MAX-FREQ establishes the upper limit for the window and an upper limit for the pointer variable SWEEP-FREQ.

It is now time to tune out the effect of the tuning inductor prior to a resonance tuning phase. To this end, the "analysis" subroutine calls the "precharge" subroutine, as symbolized by block 966 in FIG. 39. The details of this subroutine are shown in the flow chart of FIG. 40.

Figure 40:
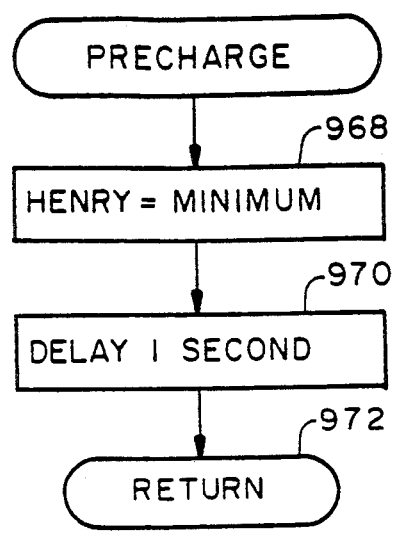
FIG. 40 is a flow chart of the "precharge" routine.

Referring to FIG. 40, the first step in the "precharge" subroutine is to set the value of the variable HENRY to a constant to reduce the inductance of the tuning inductor to a minimum. This causes the microprocessor to set the value of the control signal HENRY to the driving circuitry for the tuning inductor such that the D.C. bias is increased to the point where flux saturation occurs and the inductance of the tuning inductor is thereby minimized. This process is symbolized by block 968.

Next, a delay of one second is implemented to allow the inductance of the tuning inductor to catch up with the changes in the value of the control signal HENRY. This step is symbolized by block 970. Thereafter, step 972 is performed wherein return to the next step in the "analysis" subroutine is performed.

Returning to consideration of the "analysis" subroutine, it is now necessary to set an appropriate power level to the probe. This process starts with the step symbolized by block 974 wherein the value of a variable BOUNDARY is saved. The BOUNDARY variable is an offset value controlling the power applied to the handpiece. Power applied to the handpiece is set at a level which is equal to the value of the variable BOUNDARY plus the value of a relative offset from the BOUNDARY value established by the position of the foot operated power control. The power control software, some embodiments, has numerous safety interlocks which will not allow power to be applied to the handpiece through use of the foot operated control unless certain conditions are satisfied. However, the value of the BOUNDARY variable is not protected and can be altered by the CPU without first satisfying the various conditions. Therefore, power can be applied by the software and the CPU to the handpiece simply by varying the value of the BOUNDARY variable. The step 974 saves the current BOUNDARY value for later restoration after the tuning process, since a nominal power level will be established by the software for the tuning process per se. This nominal power level is established in step 976 by setting the value of the BOUNDARY variable to the value of a constant called NOMINAL.

Steps 978 through 984 are preparation steps for setting the values of various variables prior to calling the subroutine "peak". This subroutine determines when a peak of load current has occurred and calculates the slope of the change in load current versus the change in operating frequency of the voltage-controlled oscillator. Steps 978 and 979 are optional and set flags labelled P-SLOPE and N-SLOPE. Step 980 sets the sweep frequency pointer variable SWEEP-FREQ to the value of the variable MINIMUM calculated by the window subroutine 964 to set the frequency pointer at the lower boundary of the tuning window. Step 981 sets the value of the HERTZ variable equal to the value of the variable MINIMUM to set the frequency of the voltage-controlled oscillator at the lowest frequency in the tuning window.

Step 982 sets the value of a variable I-PEAK equal to the value of the variable MINIMUM. The variable I-PEAK is used as a register to store the highest recorded value for the load current recorded to date.

Step 983 sets the value of a variable RESONANCE equal to the value of the variable MINIMUM. The RESONANCE variable is used to record the value of the variable SWEEP-FREQ at the point where the mechanical resonance frequency of the handpiece has been found.

The step 984 sets the value of a variable SLOPE equal to the value of the variable MINIMUM. The SLOPE variable is used to record the result of the slope calculation performed in the "peak" subroutine. Thus, steps 978 through 984 simply initialize the value of the various variables such that they are in a known state prior to calling the subroutine "peak".

Step 986 represents the call to the subroutine "peak". The details of the "peak" subroutine and the subroutines called by this subroutine will be discussed below. Upon return from the "peak" subroutine, the step 994 is performed. This step decrements a variable FAULT-CNTR and is performed upon each return from the "peak" subroutine indicating that a another try to find the resonance frequency has been performed. Once the "peak" subroutine is called, the variable SWEEP-FREQ is continuously incremented and load current tests and slope calculations are performed at the various operating frequencies until the upper frequency in the tuning window has been reached. At that time, peak returns to step 994 of the "analysis" subroutine indicating that a complete sweep through the current tuning window has been performed.

Next, a step 997 is performed wherein the value of the variable FAULT-CNTR is compared to zero to determine is the alloted number of tries or sweeps has been performed. If the alloted number of tries has been performed and no resonance frequency has been found, step 997 will find FAULT-CNTR equal to zero, and will branch to step 999 where an error message will be sent to the console. Thereafter, in step 1001, a FAILURE flag will be set indicating that no resonance frequency has been found in the alloted number of tries. Then, return step 958 is performed to return to step 960 of the "cold-sweep" subroutine.

Returning to consideration of the "cold-sweep" subroutine, step 960 tests the condition of the FAILURE flag. If it is set, step 1003 is performed to disable a blink routine to stop blinking of the light-emitting diode (LED) on the front panel of the system. Next, a step 1005 is performed to disable to LED thereby keeping the LED dark and indicating to the user that the tuning has not been successful for some reason. The user can then investigate the problem.

If the test of step 960 determined that the FAILURE flag is not set, then a successful tuning phase has been performed and the VCO is now tuned to operate at the mechanical resonance frequency of the probe. In this event, a call to the "postcharge" subroutine is performed as symbolized by step 1009. The flow chart for this subroutine is given in FIG. 41.

Figure 41:
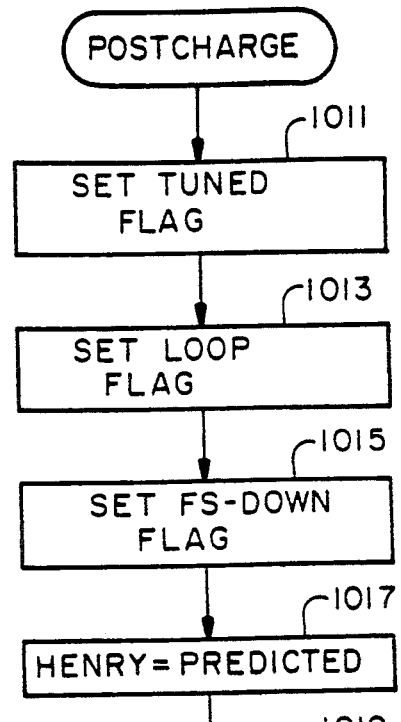
FIG. 41 is a flow chart of the "postcharge" routine.

Referring to FIG. 41, the first step in the "postcharge" subroutine is to set the TUNED flag to enable the power delivery routine in the main loop to deliver power on demand to the handpiece. Next, a step 1013 is performed to set a LOOP flag to enable operation by the "minimizer" routine to tune away any phase angle.

A step 1015 sets a flag FS-DOWN to artificially simulate a request for power. This is done because part of the function of the "postcharge" routine is to apply power for 3 seconds to allow the handpiece and tuning inductor to settle at an operating point which will be somewhat close to the actual operating point which be set following the "postcharge" routine. To apply power, the flag FS-DOWN must be set.

Next, a step 1017 is performed to set the variable HENRY and control signal HENRY to the value of a variable PREDICTED. This variable is a statistically empiracally determined value which approximates the normal operating point for the tuning inductor when coupled to most probes.

Step 1019 raises the BOUNDARY variable to send full power to the handpiece. This is followed by a three second delay/settling time symbolized by step 1021.

Finally, in steps 1023 and 1025, respectively, the old boundary value is set to restore power to its original level and the old FS-DOWN flag status is restored. Processing then flows via step 1027 to step 1033 in the "cold-sweep" routine to enable the LED thereby indicating to the user that a successfull tuning phase has been completed. Next, a step 1007 is performed to set a RELAPSE flag. This causes an elapsed timer to be reset to zero time. The elapsed timer is used to control a display on the front panel used by the user to keep track of how much energy has been dissipated inside the eye.

Returning to consideration of "cold-sweep", an optional step 1029 is performed to sound a tone or play a tune to indicate that the machine is done with the tuning phase and reminding the user to check the LED for status.

Step 1031 resets the bit of the MISTUNE variable that controls access to the ANALYSIS routine thereby disabling the analysis routine until the next call thereto.

Finally, a step 1033 is performed to turn off the VCO thereby preventing amplification of noise, and processing returns to step 938 of "sweeper" and thence to the calling process in the main loop.

Returning to the consideration of the "analysis" subroutine, if test 997 determines that the maximum number of tries to find the resonance frequency have not been expended, then a step 1035 to call the subroutine "ck-limit" is performed. This routine is detailed in FIG. 42.

Figure 42:
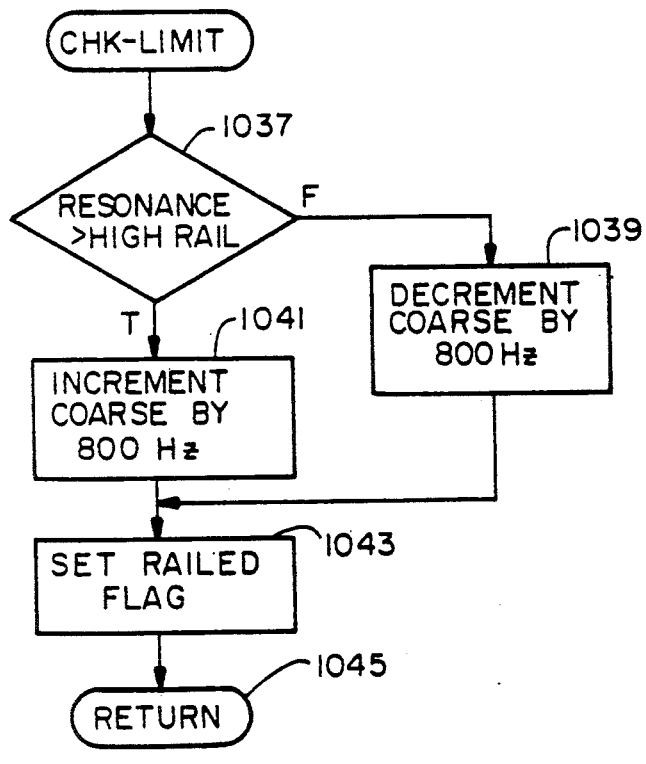
FIG. 42 is a flow chart of the "chk-limit" routine to move the tuning window.

Referring to FIG. 42, a flow chart of the "ck-limit" subroutine is shown. The purpose of this routine is to adjust the value of the variable COARSE to change the center frequency of the fine tuning window in an attempt to locate the window such that the resonance peak load current can be found within the center 50% of frequencies of the window. The first step in the "ck-limit" subroutine is to test the frequency represented by the variable RESONANCE against a variable HIGH RAIL. The variable RESONANCE has its value set by the "peak" routine to be described below at a peak load current frequency where the slope of the function of load current versus frequency is less than a predetermined amount. This test is symbolized by block 1037. The variable HIGH RAIL is set such that if the resonance frequency is found too far away from the center frequency of the tuning window, the variable COARSE will be adjusted to move the window to place the resonance frequency closer thereto. The variable HIGH RAIL is set at a frequency which is 75% up from the bottom of the tuning window. The value of this variable is calculated in the "window" subroutine of the "analysis" subroutine. The reason for the "ck-limit" subroutine is to alter the COARSE variable until the resonance peak occurs somewhere in the middle 50% of frequencies of the tuning window. This is desirable because certain voltage transients and other non-repeatable behaviors occur when operating in frequencies in the lower 25% and the upper 25% of the tuning window. Moving the tuning window in the aforedescribed manner tends to lead to finding the real resonance peak as opposed to a false peak caused by some non-repeatable phenomenon.

If the value of RESONANCE is found to be less than HIGH RAIL, step 1039 is performed to decrement the value of COARSE by the equivalent of 800 Hertz. If the value of RESONANCE is found to be greater than HIGH RAIL, step 1041 is performed to decrement the value of COARSE by the equivalent of 800 Hertz. Finally, in step 1043, the RAILED flag is set-to indicate that the resonance peak was not found within the acceptable range of frequencies. Setting the RAILED flag vectors processing back to the "peak" routine to sweep the operating frequency through a new window. This is done via the return step 1045 which returns processing to step 1047 of the "analysis" routine.

Step 1047 on FIG. 39 tests the RAILED flag and vectors processing back to step 978 if the flag is true.

If the RAILED flag is not set, step 1049 is performed to set the VCO at the resonance frequency. This is done by setting the value of the variable HERTZ equal to the value of the variable RESONANCE.

Next, conditions are set back to the way they were when "analysis" was called. First, FAULT-CNTR is set to zero in step 1051 and the second least significant bit of MISTUNE is set to 0 in step 1053. In step 1055 BOUNDARY is set back to its original value, and the LOOP flag is set to enable operations by the "minimizer" routine in step 1057. Finally, in steps 1059 and 1061, respectively, RANGE is set to MINIMUM and I-PEAK is set to MINIMUM. Thereafter, return to the calling process "cold-sweep" at step 960 is performed by step 958.

Figure 43A:
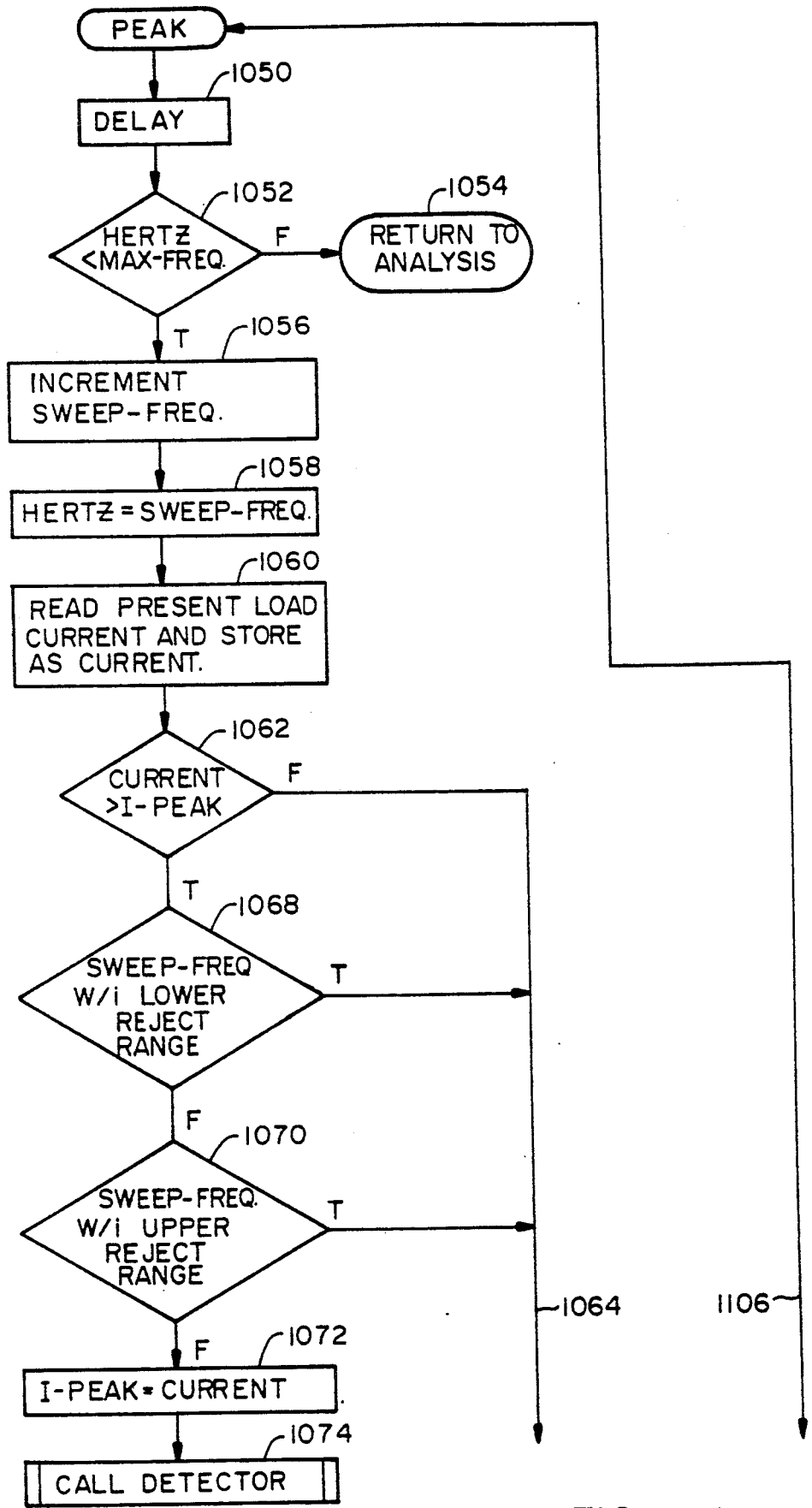
FIGS. 43A and 43B are a flow chart of the "peak" routine that finds the resonance peak by monitoring load current.
Figure 43B:
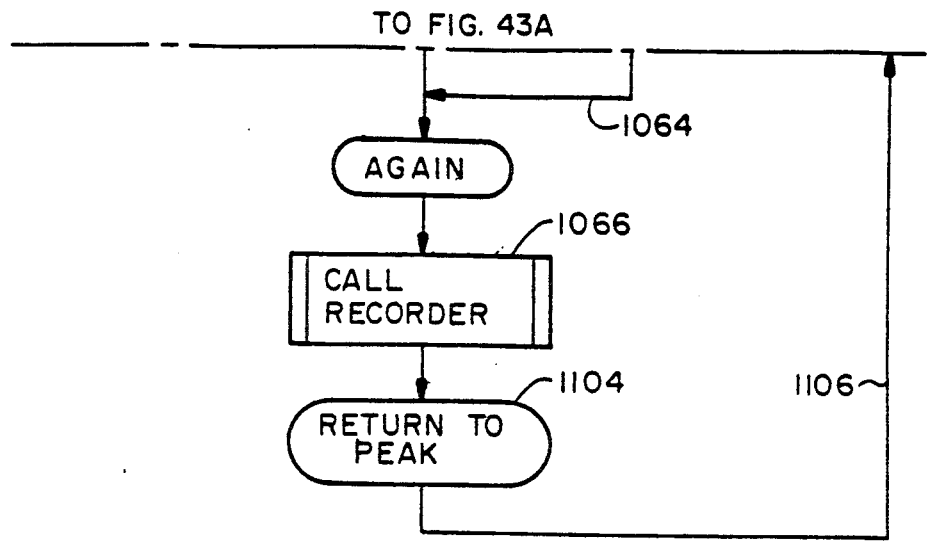

Referring to FIG. 43 comprised of FIGS. 43A and 43B, the details of the "peak" subroutine are given in flow chart form. Block 1050 is the first step in the "peak" subroutine and implements a delay to allow the value of the tuning inductor to stabilized at the inductance established by the level of the control signal HERTZ set by step 981 in FIG. 39.

Step 1052 is a test to determine whether the value of the variable HERTZ is less than the value of the variable MAX-FREQ calculated buy the subroutine "window" in FIG. 39 and establishing the upper frequency for the current tuning window. If the value of HERTZ is greater than the value of the maximum frequency, step 1054 is performed to return processing to step 994 of the "analysis" subroutine.

If HERTZ is less than the maximum frequency, step 1056 is performed to increment the value of the variable SWEEP-FREQ. Next, step 1058 is performed to set the value of the HERTZ variable equal to the value of the SWEEP-FREQ variable.

After the HERTZ variable has been established at its new level, the voltage-controlled oscillator changes frequency, and the amount of load current drawn at the new frequency will generally change from the amount of load current which was drawn at the previous operating frequency. It is necessary to know this new value for the load current. To that end, step 1060 is performed wherein the value of the present load current at the current operating frequency is read and stored as the variable CURRENT. This is accomplished by an input/output operation by the CPU 808 in FIG. 30 reading the value of the signal CURRENT on line 820.

Step 1062 represents a test to compare the value of the CURRENT variable to the value of the previously highest recorded load current as represented by the variable I-PEAK. If CURRENT is less than I-PEAK, a jump symbolized by line 1064 to an again address is performed and a step 1066 is performed to call the "recorder" subroutine. No new I-PEAK is recorded. If CURRENT is greater than I-PEAK, then a test 1068 is performed to determine if SWEEP-FREQ is within the lower reject range which is defined as the lower 25% of frequencies in the current tuning window. If this condition is true, a jump to again along line 1064 occurs and "recorder" is called and no new I-PEAK is recorded. If SWEEP-FREQ is not within the lower reject range, the test of step 1070 is performed to determine if SWEEP-FREQ is within an upper reject range. This range is defined as the upper 25% of frequencies in the current tuning window. If this condition is false, step 1072 is performed to record CURRENT as the new I-PEAK. If SWEEP-FREQ is within the upper reject range, a jump to again along line 1064 is performed.

After step 1072 is performed, a call to the "detector" subroutine is performed where the slope of the load current versus frequency function is compared to a constant. The slope is calculated by the "recorder" subroutine, so examination of that routine is now in order.

Figure 44A:
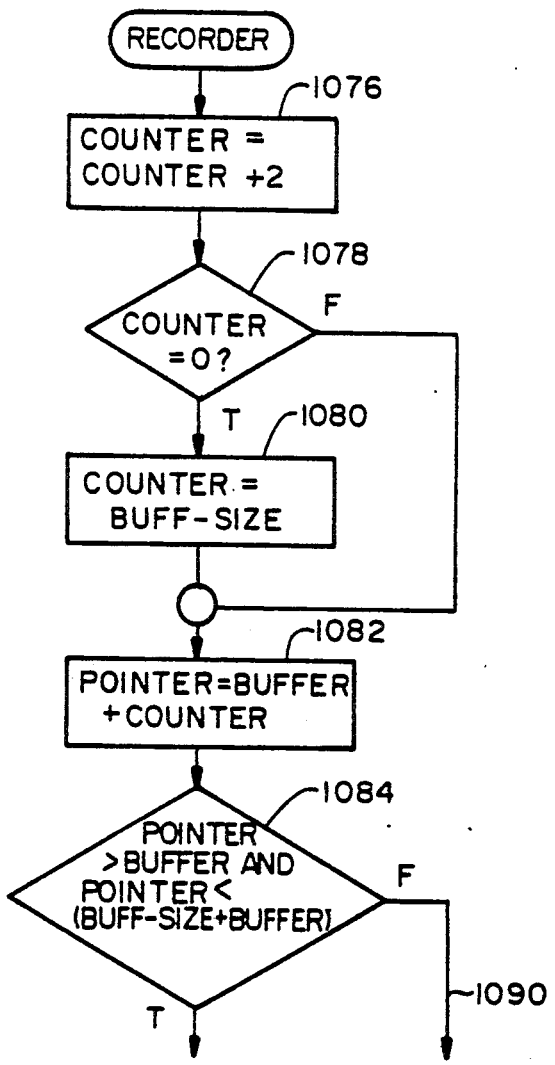
FIGS. 44A and 44B are a flow chart of the "recorder" routine which records load current data and calculates slope.
Figure 44B:
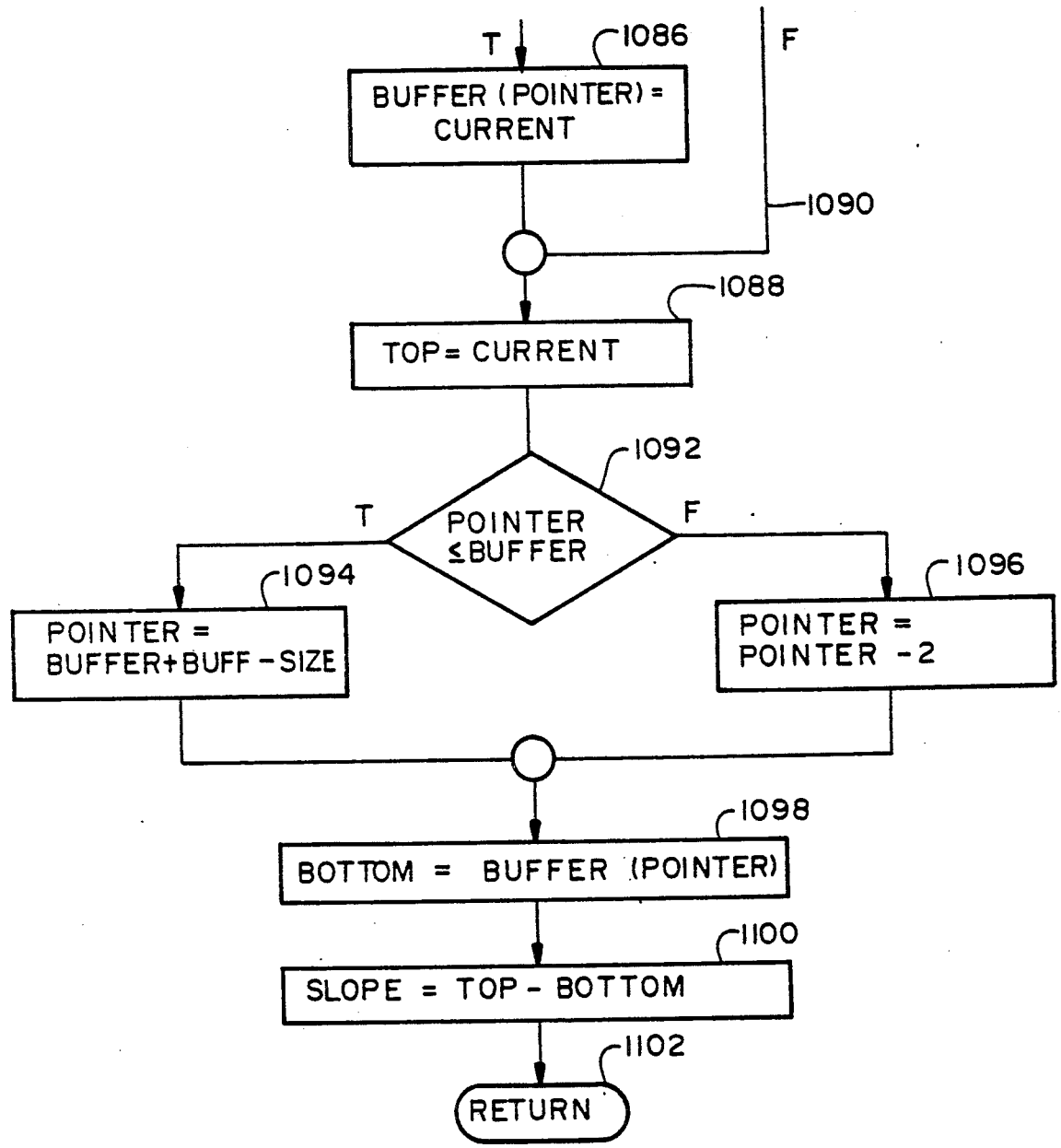

Referring to FIGS. 44A and 44B there is shown a flow chart of the "recorder" routine. The first step is to set a variable COUNTER to COUNTER+2 as symbolized by step 1076. COUNTER is a pointer in a circular buffer used to store load current samples or points on the load current versus frequency curve. Each load current sample is two bytes in length, so incrementing the COUNTER is done by adding 2 to point to the next pair of addresses. This incrementation is symbolized by step 1076. Next, COUNTER is tested against zero in step 1078. If COUNTER has reached zero, the buffer has been filled (it is filled from the highest pair of addresses to the lowest pair of addresses), and COUNTER is reset to the top of the buffer by setting it equal to a constant BUFF-SIZE in step 1080. BUFF-SIZE is equal to the size of the buffer. If test 1078 determines that COUNTER is not zero, a step 1082 is performed to set an address pointer POINTER equal to BUFFER+COUNTER. BUFFER is the lowest address in the circular buffer, so step 1082 sets POINTER at an appropriate address in said buffer.

Next, a test 1084 is performed wherein POINTER is tested to see if it is still within the bounds of the buffer. Specifically, POINTER is compared to BUFFER and to BUFF-SIZE+BUFFER which mark the two ends of the buffer. If POINTER is within the buffer, the address pointed to by POINTER is loaded with the latest value of CURRENT in step 1086. If POINTER points to either end address of the buffer, a step 1088 is performed to set a variable TOP equal to the latest value of CURRENT as symbolized by line 1090.

Next, a step 1092 is performed to determine if POINTER is less than or equal to BUFFER, the lowest address in the buffer. If it is, POINTER is set equal to BUFFER+BUFF-SIZE in step 1094. This resets POINTER to the highest address in the buffer. If POINTER is greater than BUFFER, step 1096 is performed to set POINTER to POINTER−2. Then a step 1098 is performed to set a variable BOTTOM equal to the contents of the buffer at the address pointed to by POINTER. Finally, in step 1100, a variable SLOPE is calculated as TOP−BOTTOM. SLOPE is thus equal to the latest value of CURRENT minus the value of CURRENT stored either at the highest pair of addresses in the buffer or the previous pair of addresses. SLOPE is proportional to the slope of the load current versus drive frequency function at the current drive frequency and load current coordinates. Then processing flows via step 1102 back to step 1104 of the "peak" subroutine which vectors processing back to step 1050 of "peak" along path 1106 to increment the drive frequency again.

Figure 45:
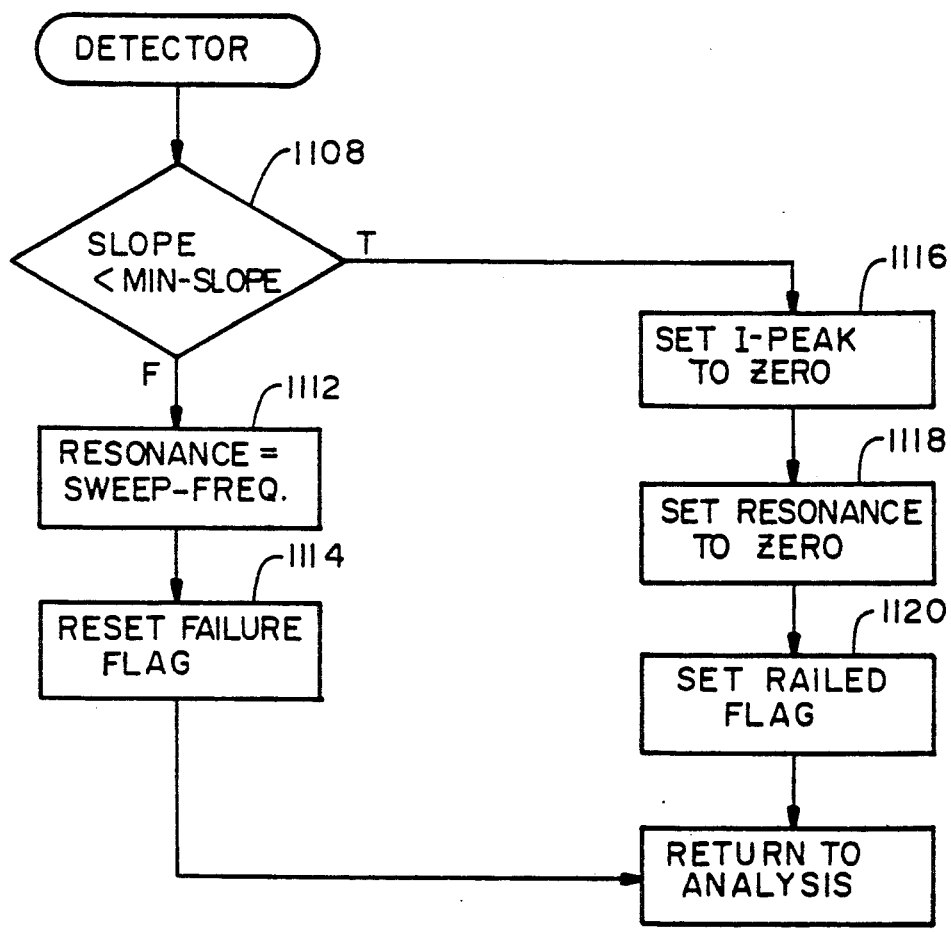
FIG. 45 is a flow chart of the "detector" routine which checks the slope of the load current function against a minimum slope.

Returning to step 1074 of "peak", the "detector" routine is called to evaluate SLOPE at the latest I-PEAK against a constant which will separate false peaks from the real resonant peak. FIG. 45 is flow chart of the "detector" routine. The first step is a test to determine if SLOPE is less than a constant MIN-SLOPE. MIN-SLOPE is picked to separate the peak at 1110 in FIG. 32 from the actual resonance peak at 876. The value of MIN-SLOPE is positive and greater than the slope of any spurious antiresonance peaks or other transients. Thus, unless SLOPE is greater than MIN-SLOPE, step 1112 is never reached. Step 1112 is the step where RESONANCE is set equal to SWEEP-FREQ thereby acknowledging that the frequency at which the latest value of I-PEAK was found is probably the actual mechanical resonance frequency of the probe under the current loading condition. Note that in the preferred embodiment, this tuning process is performed upon request by the user after the user attaches the probe, places it in water and presses a button (now shown) on the front panel requesting a tuning process.

After updating RESONANCE, the flag FAILURE is reset in step 1114 to indicate that tuning was successful.

If SLOPE was less than MIN-SLOPE, step 1116 is performed to start the process of rejecting the current peak as the legitimate resonance peak by setting I-PEAK to zero. Next, step 1118 sets RESONANCE to zero, and step 1120 sets the RAILED flag to zero. Finally, step 1122 returns processing to step 994 of "analysis" where processing proceeds as previously described.

Although the invention has been described in terms of the preferred and alternative embodiments disclosed herein, those skilled in the art will appreciate many modifications which may be made without departing from the true spirit and scope of the invention. All such embodiments are intended to be included within the scope of the claims appended hereto.

```
                    PHACO SYSTEM DRIVER (Z80 STD BUS)        1

1 0000                         TITLE    'PHACO SYSTEM DRIVER (Z80 STD BUS)'
 2                              NAME     PINIT_MAIN_MODULE
 3                              STKLN    255
 4                              PAGESZ   66
 5                              CSEG
 6 0000                         ORG      00H
 7                      ;
 8                      ;xxxxxxxxxxxxxxxxxxxxxxxxxxxxxxxxxxxxxxxxxxxxxxxxxxxxxxxxxxxxxxxx;
 9                      ;                                                                ;
10                      ;                      PHACO INITIALIZATION                     ;
11                      ;                                                                ;
12                      ;================================================================;
13                      ;          xxxxxxx CHANGE HISTORY xxxxxxx                        ;
14                      ;                                                                ;
15                      ;          Author        Date         Change Purpose             ;
16                      ;          -----------------------------------------             ;
17                      ;                                                                ;
18                      ;          F.Lian        4/14/86      Creation (Code)            ;
19                      ;          F. LIAN       4/21/86      audio change               ;
20                      ;          F. LIAN       4/23/86      audio change               ;
21                      ;          T.Escorcio    7/8/86       comm. interface            ;
22                      ;          T.Escorcio    7/29/86      correction and cleanup     ;
23                      ;          T.Escorcio    11/1/86      add pseudo code documentation ;
24                      ;          T.Escorcio    10/21/87     Restructure and add restart ;
25                      ;                                       capability, WARM_START   ;
26                      ;                                                                ;
27                      ;================================================================;
28                      ;
29                      ;----------------------------------------------------------------;
30                      ;                                                                ;
31                      ;          Function: Initialize Phaco system variables.          ;
32                      ;                                                                ;
33                      ;          Register: AF, BC, DE, HL, IX, IY, SP                  ;
34                      ;          Accepts:  None                                        ;
35                      ;          Returns:  TM120HZ, TM60HZ, TM30HZ, LASTPC, BEEP, SENTINEL ;
36                      ;                    SEC03, DURATION, TUNE, BEEP_TIME, ALERT, LINK ;
37                      ;                    SPEECH, SAY                                 ;
38                      ;          Calls:    MASTER, SET_TABLE, IO_INIT, USART_INIT, CTC_INIT ;
39                      ;                    SPEAK                                       ;
40                      ;          Flags:    LINK, SAY, ALERT                            ;
41                      ;          Variables: TM120HZ, TM60HZ, TM30HZ, BEEP, SENTINEL, SEC03, ;
42                      ;                     DURATION, TUNE, ALERT, LINK, SPEECH,       ;
43                      ;                     SAY, BEEP_TIME                             ;
44                      ;          Constants: RAM, RAM_END, ELAPS1, ELAPS2, ELAPS3, INT_TABLE ;
```

```
45  ;
46  ;               Pseudo Code:
47  ;               START
48  ;                       (Disable Interrupts)
49  ;                       STACK = 0FFFFh
50  ;                       IX = 0
51  ;                       IY = 0
52  ;                       do while ((RAM_END - RAM) <> 0)
53  ;                               (RAM) = 0       (null contents)
54  ;                               RAM = RAM + 1
55  ;                       enddo
56  ;                       TM120HZ = 0
57  ;                       TM60HZ = 0
58  ;                       TM30HZ = 0
```

PHACO  SYSTEM DRIVER (Z80 STD BUS)         2

```
59  ;                       LASTFC = 1
60  ;                       BEEP = 00001110b
61  ;                       SENTINEL = ELAPS1
62  ;                       SEC03 = ELAPS3
63  ;                       goto REV_UP
64  ;               NMI_HANDLR
65  ;                       call MASTER
66  ;               REV_UP
67  ;                       call SET_TABLE
68  ;                       call IO_INIT
69  ;                       call USART_INIT
70  ;                       call CTC_INIT
71  ;                       I (interrupt register) = INT_TABLE
72  ;                       (enable interrupts)
73  ;                       TUNE = 10
74  ;                       BEEP_TIME = 10h
75  ;                       ALERT = 1
76  ;                       LINK = 0
77  ;                       goto MAIN_LOOP
78  ;
79  ;-----------------------------------------------------------------;
80  ;-----------------------------------------------------------------;
81  ;
82  ;       NOTE
83  ;           - The CTC decodes the RETI instruction to clear any pending
84  ;             interrupts. To perform a COLD_START (or restart), it is
85  ;             absolutely imperative that an RETI be issued before
86  ;             attempting to re-initialize the CTC.
                                        ;
87  ;
88  ;-----------------------------------------------------------------;
89  ;
90  ;
91 0000 31 00 00     S  START   LD      SP,STACK        ;SET STACK POINTER
```

```
 92 0003 C3 6B 00    C            JP      COLD_START   ;
 93 0006                          DS      2            ;
 94 0008 C3 97 00    C   RSTRT1   JP      WARM_START   ;
 95 000B                          DS      5            ;
 96 0010 C3 97 00    C   RSTRT2   JP      WARM_START   ;
 97 0013                          DS      5            ;
 98 0018 C3 97 00    C   RSTRT3   JP      WARM_START   ;
 99 001B                          DS      5            ;
100 0020 C3 97 00    C   RSTRT4   JP      WARM_START   ;
101 0023                          DS      5            ;
102 0028 C3 97 00    C   RSTRT5   JP      WARM_START   ;
103 002B                          DS      5            ;
104 0030 C3 97 00    C   RSTRT6   JP      WARM_START   ;
105 0033                          DS      5            ;
106 0038 C3 97 00    C   RSTRT7   JP      WARM_START   ;
107                                                    ;
108 0205                 REV      EQU     205H         ;Num to be written to the display
109 003B 56 32 2E 30     VERSION  DEFM    'V2.05'              ;Record in ROM
    003F 35
110 0040 43 4F 50 59              DEFM    'COPYRIGHT 1988 '   ;
    0044 52 49 47 48
    0048 54 20 31 39
    004C 38 38 20 20
111 0050 41 4C 43 4F              DEFM    'ALCON LABS PHACO'  ;
    0054 4E 20 4C 41
    0058 42 53 20 50
    005C 48 41 43 4F
112                                                    ;
113                                                    ;37 bytes allowed for message
114                      ;
115                      ;------ NMI HANDLER
116                      ;
117 0066                          ORG     66H          ;LOCATE THE HANDLER
118                                                    ;
119                      NMI_HANDLR                    ;
120 0066 CD 00 00    E            CALL    MASTER       ;
121 0069 ED 45                    RETN                 ;
122                                                    ;
123                      ;
124                      ;------ BEGIN FORMAL INITIALIZATION
125                      ;
126                      COLD_START                    ;
127 006B AF                       XOR     A            ;CLEAR THE INTERRUPT REGISTER FIRST
128 006C ED 47                    LD      I,A          ;
129 006E F3                       DI                   ;DISABLE INTERRUPTS FOR NOW
130 006F ED 46                    IM      0            ;CONTROL DEFAULT INTERRUPT MODE
131                                                    ;
132 0071 DD 21 00 00              LD      IX,0H        ;SET INDEX POINTER
```

```
133 0075 FD 21 00 00              LD    IY,0H         ;
134 0079 3E 00                    LD    A,0           ;PRELOAD REGISTERS
135 007B 06 00                    LD    B,0           ;    .       .
136 007D 0E 00                    LD    C,0           ;    .       .
137 007F 16 00                    LD    D,0           ;    .       .
138 0081 1E 00                    LD    E,0           ;    .       .
139 0083 26 00                    LD    H,0           ;    .       .
140 0085 2E 00                    LD    L,0           ;    .       .
141                         ;
142                         ;----- CLEAR RAM SPACE
143                         ;
144 0087 CD FF 00   C             CALL  CLEAN         ;BUMP WATCHDOG SUPERVISOR TO BUY SOME TIME
145                                                   ; SINCE NEXT PROCESS TAKES TIME
146 008A AF                       XOR   A             ;USE BLOCK TRANSFER METHOD
147 008B 21 00 00   D             LD    HL,RAM        ; TO CLEAR 8K RAM
148 008E 11 01 00   D             LD    DE,RAM+1      ;
149 0091 77                       LD    (HL),A        ;
150 0092 01 00 80                 LD    BC,RAM_END    ;
151 0095 ED B0                    LDIR                ;
152                                                   ;
153                         WARM_START                ;
154                                                   ;
155 0097 CD D9 00   C             CALL  INT_COUNTR    ;Load the interrupt counters
156                                                   ;
157                         ;
158                         ;----- SETUP INTERRUPT TABLE INDEX POINTER AND ENABLE
159                         ;
160 009A 21 00 00   D             LD    HL,INT_TABLE  ;POINT TO INTERRUPT TABLE BASE ADDR.
161 009D 7C                       LD    A,H           ;KEEP UPPER BYTE FOR REFERENCE
162 009E ED 47                    LD    I,A           ;PLACE UPPER BYTE IN THE INDEX REG.
163 00A0 ED 5E                    IM    2             ;>>>>>> MODE 2 INTERRUPT <<<<<<
164                                                   ;
165 00A2 CD 00 00   E             CALL  SET_TABLE     ;SETUP INTERRUPT TABLE IN RAM
166                                                   ;

167                         ;
168                         ;----- Special initialization of CTC (see note)
169 00A5
170 00A5 CD FB 00   C             CALL  BREAK         ;
171                                                   ;
172 00A8 CD 00 00   E             CALL  CTC_INIT      ;CTC (MK3882)
173 00AB FB                       EI                  ;ENABLE INTERRUPTS NOW
174                                                   ;
175                         ;
176                         ;----- Initialize the other I/O chips
177                         ;
178 00AC CD 00 00   E             CALL  IO_INIT       ;TWO 8255 CHIPS
179 00AF CD 00 00   E             CALL  USART_INIT    ;8251A
180                                                   ;
```

```
181 00B2 CD 04 01    C           CALL    SET_COUNTRS     ;Load default vals into system counters
182 00B5 CD 00 00    E           CALL    VCO_OFF         ;Deactivate the VCO
183                                                      ;
184                      ;
185                      ;------ Interrogate the keyboard and service switch for diagnostic mode
186                      ;
187                      DIAGS?                          ;Check for a diagnostic mode request
188 00B8 DB 71                   IN      A,(IO_P1)       ;Poll the keyboard once
189 00BA E6 3F                   AND     00111111B       ;Mask off handpiece select bits
190 00BC FE 00                   CP      0               ;Any keys pressed ?
191 00BE CA C4 00    C           JP      Z,DIAG1         ;If not, continue
192                                                      ;
193 00C1 C3 00 00    E           JP      DIAGNOSTIC      ; otherwise enter the diagnostic mode
194                                                      ;
195                      DIAG1                           ;Check for a service mode request
196 00C4 DB 7E                   IN      A,(SERVICE)     ;Poll the service switch once
197 00C6 E6 FC                   AND     11111100B       ;Mask off Power Detection bits
198 00C8 FE 00                   CP      0               ;Any keys pressed ?
199 00CA CA D0 00    C           JP      Z,NORM_MODE     ;If not, continue
200                                                      ;
201 00CD C3 00 00    E           JP      SRVC_LOOP       ; otherwise enter the service loop mode
202                                                      ;
203                      NORM_MODE                       ;
204 00D0 CD 39 01    C           CALL    ANNUNCIATOR     ;Indicate normal init to user
205                                                      ;
206 00D3 CD 4A 01    C           CALL    DECLARE         ;
207                                                      ;
208 00D6 C3 00 00    E           JP      MAIN_LOOP       ;Enter main program loop
209                                                      ;
210                                                                                              ;
211                      ;----------------------------------------------------------------------;
212                      ;       SUBROUTINES                                                    ;
213                      ;----------------------------------------------------------------------;
214                      ;
215                      ;
216                      ;------ SYSTEM INTERRUPT TIMING VARIABLE INIT
217                      ;
218                      INT_COUNTR                      ;
219 00D9 3E 02                   LD      A,DIV480HZ+0    ;
220 00DB 32 00 00    E           LD      (TM480HZ),A     ;480 Hz INTERRUPT COUNTER (2.4KHz/5)
221 00DE 3E 05                   LD      A,DIV240HZ+1    ;
222 00E0 32 00 00    E           LD      (TM240HZ),A     ;240 Hz INTERRUPT COUNTER
223 00E3 3E 0A                   LD      A,DIV120HZ+2    ;
224 00E5 32 00 00    E           LD      (TM120HZ),A     ;120 Hz INTERRUPT COUNTER
225 00E8 3E 13                   LD      A,DIV60HZ+3     ;
226 00EA 32 00 00    E           LD      (TM60HZ),A      ; 60 HZ INTERRUPT COUNTER
227 00ED 3E 24                   LD      A,DIV30HZ+4     ;
228 00EF 32 00 00    E           LD      (TM30HZ),A      ; 30 HZ INTERRUPT COUNTER
229 00F2 3E 65                   LD      A,DIV10HZ+5     ;
230 00F4 32 00 00    E           LD      (TM10HZ),A      ; 10 HZ INTERRUPT COUNTER
231                                                      ;
232 00F7 C9                      RET                     ;
233                                                      ;
234                      ;
235                      ;------ Clear the CTC from any pending interrupts
236                      ;
```

```
237 00FB                    BREAK
238 00FB 21 FE 00    C              LD    HL,RECOVER         ;LOCATE THE NEXT INSTRUCTION
239 00FB E5                         PUSH  HL                 ;SAVE IT AS THE "RETURN" ADDRESS
240 00FC ED 4D                      RETI                     ;RETURN THERE, (REQUIRED CTC OVERHEAD)
241                         RECOVER                          ;CONTINUE
242 00FE C9                         RET                      ;
243                                                          ;
244                         ;
245                         ;----- Set the CTC system interrupt channel to the reset condition
246                         ;
247                         CLEAN                            ;
248 00FF 3E 33                      LD    A,00110011B        ;CHANNEL 1 CONTROL WORD
249 0101 D3 F1                      OUT   (CTC_C1),A         ;NO INTERRUPT AND TIMER MODE (MODIFIABLE)
250                                                          ;
251 0103 C9                         RET                      ;
252                                                          ;
253                         ;
254                         ;----- LOAD COUNTERS
255                         ;
256                         SET_COUNTRS                      ;
257 0104 01 F4 01                   LD    BC,BUFF_SIZE       ;Fetch buffer size
258 0107 ED 43 00 00  E              LD    (COUNTR),BC        ;
259                                                          ;
260 010B 01 69 01                   LD    BC,ELAPS1          ;LOAD SENTINEL COUNTER WITH 3 SECOND
261 010E ED 43 00 00  E              LD    (SENTINEL),BC      ; COUNT VALUE
262                                                          ;
263 0112 01 A0 05                   LD    BC,ELAPS2          ;START REPLY COUNTER
264 0115 ED 43 00 00  E              LD    (SEC03),BC         ;
265                                                          ;
266 0119 01 78 00                   LD    BC,ELAPS5          ;LOAD SCANNER INTERVAL
267 011C ED 43 00 00  E              LD    (LATENCY),BC       ;
268                                                          ;
269 0120 21 00 08                   LD    HL,FULL            ;DEFAULT RESONANCE AT CENTER FREQUENCY
270 0123 22 00 00    E              LD    (RESONANCE),HL     ; UNTIL FULL SWEEP CAN BE PERFORMED
271                                                          ;
272 0126 AF                         XOR   A                  ;
273 0127 32 00 00    E              LD    (LINK),A           ;HUNTER WILL SENSE AND ATTEMPT
274                                                          ; LINK UNTIL POS. REPLY REC'D
275 012A 3E 01                      LD    A,1                ;
276 012C 32 00 00    E              LD    (LASTPC),A         ;INVOKE HANDPIECE CHECK AT INIT.
277                                                          ;
278                                                          ;
279 012F 21 40 06                   LD    HL,BEGINNING       ;Set course freq. adjust to default
280 0132 22 00 00    E              LD    (OLD_COURSE),HL    ;
281 0135 22 00 00    E              LD    (COURSE),HL        ;
282                                                          ;
284                                                          ;
285                         ;
286                         ;----- SOUND A QUICK ALARM BURST TO SIGNAL SUCCESSFUL INITIALIZATION
287                         ;
288                         ANNUNCIATOR                      ;
289 0139 3E 01                      LD    A,1                ;Set the RYTHM for audio feedback
290 013B 32 00 00    E              LD    (RYTHM),A          ;
291 013E 21 00 00    E              LD    HL,SONG0           ;Point to the SONG
292 0141 22 00 00    E              LD    (MELODY),HL        ;
293 0144 21 00 00    E              LD    HL,CONDUCTOR       ;Set the CONDUCTOR's queue
```

```
294 0147 CB C6              SET     0,(HL)          ;
295                                                 ;
296 0149 C9                  RET                    ;
297                                                 ;
298                      ;
299                      ;------
300                      ;
301                      DECLARE                    ;
302                                                 ;
303                      STALL                      ;
304 014A 01 FF FF            LD      BC,0FFFFH ;2 SECS    ;Load delay counter (29cnts/SEC)
305                      STLL1                      ;
306 014D 21 05 02            LD      HL,REV          ;
307 0150 22 00 00   E        LD      (DISPLAY),HL    ;
308                                                  ;
309 0153 0B                  DEC     BC              ;Subtract 1
310 0154 79                  LD      A,C             ;Sum upper with lower
311 0155 B0                  OR      B               ;
312 0156 C2 4D 01   C        JP      NZ,STLL1        ;Continue until it is zero
313                                                  ;
314 0159 21 00 00   E        LD      HL,RELAPSE      ;
315 015C CB C6               SET     0,(HL)          ;
316                                                  ;
317 015E C9                  RET                     ;
318                                                  ;
319                                                  ;
320                                                                                          ;
321                      ;==============================================================;
322                      ;     DATA SEGMENT                                              ;
323                      ;==============================================================;
324                      ;
= 325 015F                   INCLUD  EQU.INC         ;
= 326                    ;==============================================================;
= 327                    ;                                                              ;
= 328                    ;     EQU.INC       PHACO SYSTEM GLOBAL EQUATES                ;
= 329                    ;                                                              ;
= 330                    ;==============================================================;
= 331                    ;
= 332                    ;         ######### CHANGE HISTORY #########                   ;
= 333                    ;                                                              ;
= 334                    ;         AUTHOR       DATE         CHANGE PURPOSE             ;
= 335                    ;         --------------------------------------------         ;
= 336                    ;         T. LO        3 FEB 86     CREATION                   ;
= 337                    ;         F. Lian      10 Feb. 86   Update                     ;
= 338                    ;         F. Lian      10 April 86  Update                     ;
= 339                    ;         T. Escorcio  24 June 86   Update                     ;
= 340                    ;         T. Escorcio  7 July 86    Update                     ;
```

```
= 341               ;       T. Escorcio      4/1/87      add adaptive tuning constants   ;
= 342               ;                                                                    ;
= 343               ;--------------------------------------------------------------------;
= 344               ;
= 345               ;------ TOP OF RAM MARKER
= 346               ;
= 347 8000          RAM_END         EQU     8000H           ;32K CONFIGURATION
= 348               ;
= 349               ;------ INTERRUPT LOOP TIMING CONSTANTS
= 350               ;
= 351 01EB          SAMPFRQ         EQU     489+2           ;INTERRUPT SAMPLING FREQUENCY
= 352 0002          DIV480HZ        EQU     2               ;480 HZ DIVIDER
= 353 0004          DIV240HZ        EQU     4               ;240 HZ DIVIDER
= 354 0008          DIV120HZ        EQU     8               ;120 HZ DIVIDER
= 355 0010          DIV60HZ         EQU     16              ; 60 HZ DIVIDER
= 356 0020          DIV30HZ         EQU     32              ; 30 HZ DIVIDER
= 357 0060          DIV10HZ         EQU     96              ; 10 HZ DIVIDER
= 358                                                       ;
= 359               ;
= 360               ;------ System counter parameters
= 361               ;
= 362 0168          ELAPS1          EQU     168H            ;3 SECOND TIMER VALUE (HUNTER)
= 363 05A0          ELAPS2          EQU     5A0H            ;3 SECOND TIMER VALUE (COM. REPLY)
= 364 0020          ELAPS3          EQU     020H            ;BEEPER DURATION
= 365 0300          ELAPS4    -     EQU     0300H           ;BEEPER COUNTER SAMPLING RATE
= 366 0078          ELAPS5          EQU     120             ;SCANNER INTERVAL
= 367                                                       ;
= 368               ;
= 369               ;------ PROGRAM THRESHOLD LEVELS
= 370               ;
= 371 0000          MIN             EQU     00H             ;
= 372 00FF          MAX             EQU     0FFH            ;
= 373 0001          TRUE            EQU     00000001B       ;
= 374 0000          FALSE           EQU     00000000B       ;
= 375 01F4          BUFF_SIZE       EQU     500             ;
= 376 000A          KEY_RYTHM       EQU     10              ;Key music duration time       ;
= 377 0004          KEY_TIME        EQU     4               ;
= 378 000F          BEEP_TIME       EQU     15              ;
= 379 0640          BEGINNING       EQU     1600            ;
= 380 0800          FULL            EQU     2048            ;
= 381                                                       ;
= 382               ;====================================================================;
= 383 015F
= 384 015F
= 385 015F                          INCLUD  ADDRESS.INC   ;
= 386               ;====================================================================;
= 387               ;                                                                    ;
= 388               ;       ADDRESS.INC     PHACO SYSTEM GLOBAL EQUATES                  ;
= 389               ;                                                                    ;
= 390               ;====================================================================;
= 391               ;                                                                    ;
= 392               ;             !!!!!!!!! CHANGE HISTORY !!!!!!!!!                     ;
= 393               ;                                                                    ;
= 394               ;       AUTHOR          DATE            CHANGE PURPOSE               ;
= 395               ;       ---------------------------------------------------          ;
= 396               ;       T. LO           3 FEB 86        CREATION                     ;
= 397               ;       F. Lian         10 Feb. 86      Update                       ;
= 398               ;       F. Lian         10 April 86     Update                       ;
```

```
= 399                    ;       T. Escorcio     24 June 86      Update                          ;
= 400                    ;       T. Escorcio     7 July 86       Update                          ;
= 401                    ;       T. Escorcio     4/1/87          add adaptive tuning constants   ;
= 402                    ;                                                                       ;
= 403                    ;-----------------------------------------------------------------------;
= 404                    ;
= 405                    ;------ DIGITAL I/O BOARD ADDRESSES
= 406                    ;
= 407 0070               DIO_BASE        EQU     70H             ;BASE ADDRESS OF SB8466 CARD
= 408 0070               BITIOAD         EQU     DIO_BASE+0      ;
= 409 0070               IO_P0           EQU     DIO_BASE+0      ; PORT A OF 8255 #1
= 410 0071               IO_P1           EQU     DIO_BASE+1      ; PORT B OF 8255 #1
= 411 0072               IO_P2           EQU     DIO_BASE+2      ; PORT C OF 8255 #1
= 412 0073               IO_C1           EQU     DIO_BASE+3      ; CONTROL WORD ADDR. OF 8255 #1
= 413 0074               IO_P3           EQU     DIO_BASE+4      ; PORT A OF 8255 #2
= 414 0075               IO_P4           EQU     DIO_BASE+5      ; PORT B OF 8255 #2
= 415 0076               IO_P5           EQU     DIO_BASE+6      ; PORT C OF 8255 #2
= 416 0077               IO_C2           EQU     DIO_BASE+7      ; CONTROL WORD ADDR. OF 8255 #2
= 417                                                            ;
= 418                    ;
= 419                    ;------ COUNTER TIMER CHIP ADDRESSES
= 420                    ;
= 421 00F0               CTC_BASE        EQU     0F0H            ;BASE ADDRESS OF CTC
= 422 00F0               CTCADR          EQU     CTC_BASE+0      ;
= 423 00F0               CTC_C0          EQU     CTC_BASE+0      ; CHANNEL 0
= 424 00F1               CTC_C1          EQU     CTC_BASE+1      ; CHANNEL 1
= 425 00F2               CTC_C2          EQU     CTC_BASE+2      ; CHANNEL 2
= 426 00F3               CTC_C3          EQU     CTC_BASE+3      ; CHANNEL 3
= 427                    ;
= 428                    ;------ SERIAL PORT ADDRESSES
= 429                    ;
= 430 00F4               SIO_BASE        EQU     0F4H            ;BASE ADDRESS OF 8251A (USART)
= 431 00F4               SERADR          EQU     SIO_BASE+0      ;
= 432 00F4               SER_PORT        EQU     SIO_BASE+0      ; SERIAL PORT ADDR.
= 433 00F5               SER_CONTROL     EQU     SIO_BASE+1      ; 8251A CONTROL PORT ADDR.
= 434                                                            ;
= 435 007C               PWR_PORT        EQU     7CH             ;
= 436                                                            ;
= 437 007E               SERVICE         EQU     7EH             ;SERVICE SWITCH ADDRESS
= 438                                                            ;
= 439                                                            ;
= 440                    ;=======================================================================;
  441                                                    ;
  442                    ;
  443                    ;------ GLOBAL VARIABLES
  444                    ;
  445                            DSEG                            ;
  446                    RAM                                     ;***** RAM STARTS HERE *****
  447 0000               INT_TABLE       DS      16              ;LOCATE AND RESERVE 16 BYTES FOR THE
  448                                                            ; INTERRUPT VECTOR TABLE
  449                                                            ;
  450 0010 00            FN_MODE         DB      0               ;FUNCTION MODE NO.
  451 0011 00            CHNG_FN         DB      0               ;REQUEST TO CHANGE FUNCTION MODE IF > 0
  452 0012 00            SECURITY        DB      0               ;KEYBOARD LOCKOUT
  453 0013 00            INITIAL         DB      0               ;INITIAL PHASE ACQUIRED DURING BOOTUP
  454 0014 00            SWITCH          DB      0               ;TUNING ACTIVATION FLAG
  455                                                            ;
  456                                                            ;
```

```
457                                                                                 ;
458             ;----------------------------------------------------------------;
459             ;                                                                ;
460             ;           EXTERNAL VARIABLE DECLARATION                        ;
461             ;                                                                ;
462             ;----------------------------------------------------------------;
463             ;
464                     EXTRN   RYTHM, MELODY, CONDUCTOR, MASTER, RESONANCE, SET_TABLE
465                     EXTRN   IO_INIT, USART_INIT, CTC_INIT; MAIN_LOOP, SENTINEL
466                     EXTRN   LATENCY, LINK, COURSE, TM480HZ, TM120HZ, TM60HZ, TM30HZ
467                     EXTRN   COUNTR, SEC03, LASTPC, REPEAT, ALARM, SONG0, VCO_OFF
468                     EXTRN   DIAGNOSTIC, SRVC_LOOP, TM240HZ, TM10HZ, OLD_COURSE
469                     EXTRN   DISPLAY, RELAPSE
470                                                                                 ;
471             ;----------------------------------------------------------------;
472             ;                                                                ;
473             ;           PUBLIC VARIABLE DECLARATION                          ;
474             ;                                                                ;
475             ;----------------------------------------------------------------;
476             ;
477                     PUBLIC  RSTRT1, RSTRT2, RSTRT3, RSTRT4, RSTRT5, RSTRT6, RSTRT7
478                     PUBLIC  RAM, INT_TABLE, FN_MODE, CHNG_FN, SECURITY, INITIAL
479                     PUBLIC  START, SWITCH
480                                                                                 ;
481             ;================================================================;
482             ;
483             ;IIIIIIIIIIIIIIIIIIIIIIIIIIIIIIIIIIIIIIIIIIIIIIIIIIIIIIIIIIIIIIII;
484             ;
485 0015                END
```

ERRORS = 0000

```
ALARM  E 0015   ANNUNC C 0139   BEEP_T   000F   BEGINN   0640
BITIDA   0070   BREAK  C 00F8   BUFF_S   01F4   CHNG_F D 0011
CLEAN  C 00FF   COLD_S C 006B   CONDUC E 0002   COUNTR E 0012
COURSE E 000C   CTCADR   00F0   CTC_BA   00F0   CTC_CO   00F0
CTC_C1   00F1   CTC_C2   00F2   CTC_C3   00F3   CTC_IN E 0008
DECLAR C 0144   DIAG1  C 00C4   DIAGNO E 0019   DIAG5? C 00B9
DIO_BA   0072   DISPLA E 001E   DIV10H   0060   DIV120   0008
DIV240   0004   DIV30H   0020   DIV480   0002   DIV60H   0010
ELAPS1   0168   ELAPS2   05A0   ELAPS3   0020   ELAPS4   0300
ELAPS5   0078   FALSE    0000   FN_MOD D 0010   FULL     0800
INITIA D 0012   INT_CO C 00D9   INT_TA D 0000   IO_C1    0073
IO_C2    0077   IO_INI E 0006   IO_PO    0070   IO_P1    0071
IO_P2    0072   IO_P3    0074   IO_P4    0075   IO_P5    0076
KEY_RY   0002   KEY_TI   0004   LASTPC E 0014   LATENC E 000B
LINK   E 000C   MAIN_L E 0009   MASTER E 0003   MAX      00FF
MELODY E 0001   MEMORY M 0000   MIN      0000   NMI_HA C 0068
NORM_M C 0022   OLD_CO E 001D   PWR_PD   007C   RAM    D 0000
RAM_EN   8000   RECOVE C 00FE   RELAPS E 001F   REPEAT E 0015
RESONA E 0004   REV      0205   RSTRT1 C 0008   RSTRT2 C 0010
RSTRT3 C 0018   RSTRT4 C 0020   RSTRT5 C 0028   RSTRT6 C 0030
RSTRT7 C 0038   RYTHM  E 0000   SAMPFR   01EB   SEC03  E 0013
SECURI D 0012   SENTIN E 000A   SERADR   00F4   SERVIC   007E
SER_CO   00F5   SER_PO   00F4   SET_CO C 0104   SET_TA E 0005
SIO_BA   00F4   SONG0  E 0017   SRVC_L E 001A   STACK  S 0000
```

```
STALL  C 014A   START  C 0000   STLL1  C 014D   SWITCH D 0014
TM10HZ E 001C   TM120H E 000F   TM240H E 001B   TM30HZ E 0011
TM480H E 00CE   TM60HZ E 0010   TRUE     0001   USART_ E 0007
VCO_OF E 0012   VERSIO C 003B   WARM_S C 0097
```

```
                PHACO  SYSTEM DRIVER (Z80 STD BUS)          1

1 0000                           TITLE  'PHACO  SYSTEM DRIVER (Z80 STD BUS)'
 2                                NAME   PMAIN_MAIN_MODULE
 3                                CSEG
 4                                PAGESZ 66
 5                        ;
 6                        ;;;;;;;;;;;;;;;;;;;;;;;;;;;;;;;;;;;;;;;;;;;;;;;;;;;;;;;;;;;;;;;;;;;;;;;;
 7                        ;                                                                      ;
 8                        ;                       PHACO MAIN PROGRAM                             ;
 9                        ;                                                                      ;
10                        ;======================================================================;
11                        ;          ;;;;;;;; CHANGE HISTORY ;;;;;;;;                            ;
12                        ;                                                                      ;
13                        ;          Author       Date         Change Purpose                    ;
14                        ;          ----------------------------------------------              ;
15                        ;                                                                      ;
16                        ;          F.Lian       4/14/86      Creation (Code)                   ;
17                        ;          F. LIAN      4/21/86      audio change                      ;
18                        ;          F. LIAN      4/23/86      audio change                      ;
19                        ;          T.Escorcio   7/8/86       comm. interface                   ;
20                        ;          T.Escorcio   7/29/86      correction and cleanup            ;
21                        ;          T.Escorcio   10/5/87      Re-structure and documentation    ;
22                        ;                                    edit.                             ;
23                        ;                                                                      ;
24                        ;======================================================================;
25                        ;
26                        ;----------------------------------------------------------------------;
27                        ;                       MAIN PROGRAM LOOP                              ;
28                        ;----------------------------------------------------------------------;
29                        ;
30                        MAIN_LOOP                         ;
31 0000 21 00 00    E              LD     HL,CHNG_FN       ;Use flag to determine conditions
32 0003 CB 46                      BIT    0,(HL)           ;
33 0005 CA 0B 00    C              JP     Z,PROCESS        ;If true, invoke new mode
34                                                         ; otherwise, re-execute
35                        CHANGE                           ;
36 0008 CD 00 00    E              CALL   NEW_MODE         ;Request new mode
37                        PROCESS                          ;
38 000B CD 14 00    C              CALL   INITIAL          ;Request INITIAL EXECUTION conditions
39 000E CD 00 00    E              CALL   EXECUTION        ;Execute function
40                                                         ;
41 0011 C3 00 00    C              JP     MAIN_LOOP        ;
42                                                         ;
43                        ;
44                        ;------ Establish INITIAL EXECUTION conditions of main program loop
45                        ;
```

```
46 0014                 INITIAL
47 0014 21 00 00    E           LD      HL,CHNG_FN      ;Reset the change flag
48 0017 CB 86                   RES     0,(HL)          ;
49                                                      ;
50                      EXIT                            ;
51 0019 C9                      RET                     ;
52                                                      ;
53                                                      ;
54                      ;=================================================================;
55                      ;       DATA SEGMENT                                              ;
56                      ;=================================================================;
57                      ;
= 58 0014                       INCLUD  EQU.INC         ;INCLUDE ALL CONSTANTS IN ASSEMBLY
```

PHACO  SYSTEM DRIVER (Z80 STD BUS)          2

```
= 59            ;=================================================================;
= 60            ;                                                                 ;
= 61            ;       EQU.INC         PHACO SYSTEM GLOBAL EQUATES               ;
= 62            ;                                                                 ;
= 63            ;=================================================================;
= 64            ;                                                                 ;
= 65            ;              ttttttttt CHANGE HISTORY ttttttttt                 ;
= 66            ;                                                                 ;
= 67            ;       AUTHOR          DATE            CHANGE PURPOSE            ;
= 68            ;       ------------------------------------------------------    ;
= 69            ;       T. LO           3 FEB 86        CREATION                  ;
= 70            ;       F. Lian         10 Feb. 86      Update                    ;
= 71            ;       F. Lian         10 April 86     Update                    ;
= 72            ;       T. Escorcio     24 June 86      Update                    ;
= 73            ;       T. Escorcio     7 July 86       Update                    ;
= 74            ;       T. Escorcio     4/1/87          add adaptive tuning constants ;
= 75            ;                                                                 ;
= 76            ;-----------------------------------------------------------------;
= 77            ;
= 78            ;------ TOP OF RAM MARKER
= 79            ;
= 80 8000       RAM_END         EQU     8000H           ;32K CONFIGURATION
= 81            ;
= 82            ;------ INTERRUPT LOOP TIMING CONSTANTS
= 83            ;
= 84 01E3       SAMPFRQ         EQU     489+2           ;INTERRUPT SAMPLING FREQUENCY
= 85 0002       DIV480HZ        EQU     2               ;480 HZ DIVIDER
= 86 0004       DIV240HZ        EQU     4               ;240 HZ DIVIDER
= 87 0008       DIV120HZ        EQU     8               ;120 HZ DIVIDER
= 88 0010       DIV60HZ         EQU     16              ; 60 HZ DIVIDER
= 89 0020       DIV30HZ         EQU     32              ; 30 HZ DIVIDER
= 90 0060       DIV10HZ         EQU     96              ; 10 HZ DIVIDER
= 91                                                    ;
= 92            ;
= 93            ;------ System counter parameters
= 94            ;
= 95 0168       ELAPS1          EQU     168H            ;3 SECOND TIMER VALUE (HUNTER)
```

```
=  96 05AC              ELAPS2      EQU     5A0H            ;3 SECOND TIMER VALUE (COM. REPLY)
=  97 0020              ELAPS3      EQU     020H            ;BEEPER DURATION
=  98 0300              ELAPS4      EQU     0300H           ;BEEPER COUNTER SAMPLING RATE
=  99 0078              ELAPS5      EQU     120             ;SCANNER INTERVAL
= 100                                                       ;
= 101                   ;
= 102                   ;------ PROGRAM THRESHOLD LEVELS
= 103                   ;
= 104 0000              MIN         EQU     00H             ;
= 105 00FF              MAX         EQU     0FFH            ;
= 106 0001              TRUE        EQU     00000001B       ;
= 107 0000              FALSE       EQU     00000000B       ;
= 108 01F4              BUFF_SIZE   EQU     500             ;
= 109 000A              KEY_RYTHM   EQU     10              ;Key music duration time     ;
= 110 0004              KEY_TIME    EQU     4               ;
= 111 000F              BEEP_TIME   EQU     15              ;
= 112 0640              BEGINNING   EQU     1600            ;
= 113 0800              FULL        EQU     2048            ;
= 114                                                                                    ;
= 115                   ;=====================================================================;
= 116 001A
```

PHACO  SYSTEM DRIVER (Z80 STD BUS)        3

```
= 117 001A
  118                                       ;
  119                                                                                        ;
  120                   ;----------------------------------------------------------------;
  121                   ;                                                                ;
  122                   ;       EXTERNAL VARIABLE DECLARATION                            ;
  123                   ;                                                                ;
  124                   ;----------------------------------------------------------------;
  125                   ;
  126                           EXTRN   CHNG_FN, FN_MODE, EXECUTION, NEW_MODE
  127
  128                   ;----------------------------------------------------------------;
  129                   ;                                                                ;
  130                   ;       PUBLIC VARIABLE DECLARATION                              ;
  131                   ;                                                                ;
  132                   ;----------------------------------------------------------------;
  133                   ;
  134                           PUBLIC  MAIN_LOOP
  135
  136                   ;=================================================================;
  137                   ;
  138                   ;!!!!!!!!!!!!!!!!!!!!!!!!!!!!!!!!!!!!!!!!!!!!!!!!!!!!!!!!!!!!!!!!;
  139                   ;
  140 001A                      END
```

ERRORS = 0000

```
                    PHACO SYSTEM Z80 INTERRUPT HANDLER        1

1 0000                           TITLE   'PHACO SYSTEM Z80 INTERRUPT HANDLER'
 2                                NAME    PINTR_MODULE
 3                                CSEG
 4                                PAGESZ  66
 5                        ;
 6                        ;xxxxxxxxxxxxxxxxxxxxxxxxxxxxxxxxxxxxxxxxxxxxxxxxxxxxxxxxxxxxxxxxx;
 7                        ;                                                                 ;
 8                        ;              PHACO SYSTEM INTERRUPT HANDLER                     ;
 9                        ;                                                                 ;
10                        ;=================================================================;
11                        ;            xxxxxxx CHANGE HISTORY xxxxxxx                       ;
12                        ;                                                                 ;
13                        ;         Author         Date         Change Purpose              ;
14                        ;         ------------------------------------------------        ;
15                        ;         F.Lian         4/13/86      Creation (Code)             ;
16                        ;         F. LIAN        4/21/86      audio control change        ;
17                        ;         F. LIAN        4/23/86      audio control change        ;
18                        ;         F. Lian        5/01/86      bargraph pattern gen.       ;
19                        ;         T.Escorcio     7/8/86       comm. interrupt calls       ;
20                        ;         T.Escorcio     7/29/86      correction and cleanup      ;
21                        ;                                                                 ;
22                        ;=================================================================;
23                        ;
24                        ;-----------------------------------------------------------------;
25                        ;              CTC CHANNEL 2 INTERRUPT                            ;
26                        ;-----------------------------------------------------------------;
27                        ;
28                        CHAN3                           ;SERVICING 977HZ INTERRUPT
29 0000 FB                LEVEL1  EI                      ;ENABLE NESTED INTERRUPT
30 0001 F5                        PUSH    AF              ;
31 0002 C5                        PUSH    BC              ;
32 0003 D5                        PUSH    DE              ;
33 0004 E5                        PUSH    HL              ;
34 0005 CD 00 00    E              CALL   A_TO_D          ;SERVICE THE CONTROLLER BOARD
35 0008 CD 00 00    E              CALL   FILTER          ;
36 000B CD 00 00    E              CALL   POWER_          ;
37                                                        ;
38                        ;
39                        ;------ 480 HZ ROUTINES
40                        ;
41 000E 21 00 00    D     LEVEL2  LD      HL,TM480HZ      ;DIVIDE 977HZ BY 2
42 0011 35                        DEC     (HL)            ;DEC. THE COUNT
43 0012 C2 29 00    C             JP      NZ,LEVEL3       ;
44 0015 36 02                     LD      (HL),DIV480HZ   ;RELOAD COUNT
45                                                        ;
46 0017 CD 00 00    E             CALL    LED_DRV         ;REFRESH LEDS
47 001A CD 00 00    E             CALL    PCLOCK          ;UPDATE PHACO CLOCK
48 001D CD 00 00    E             CALL    RXD_INT         ;SERVICE INCOMING COMMUNICATION
49 0020 CD 00 00    E             CALL    COM_CONTROL     ;SERIAL COM. DRIVER
50 0023 CD 00 00    E             CALL    MONITOR         ;READ INCOMING CODES INTO FLAGS
51 0026 CD 00 00    E             CALL    WATCHDOG        ;REPORT TO THE SUPERVISOR
52                                                        ;
53                        ;
54                        ;------ 120 Hz ROUTINES
```

```
55                        ;
56 0029 21 02 00   D   LEVEL3  LD    HL,TM120HZ    ;DIVIDE 977HZ BY 8
57 002C 35                     DEC   (HL)          ;DEC. THE COUNT
58 002D C2 41 00   C           JP    NZ,LEVEL4     ;
```

PHACO SYSTEM Z80 INTERRUPT HANDLER        2

```
59 0030 36 08                  LD    (HL),DIV120HZ ;RELOAD COUNT
60                                                 ;
61 0032 CD 00 00   E           CALL  SOUND         ;Play music requests
62 0035 CD 00 00   E           CALL  HUNTER        ;VERIFY OR ESTABLISH LINK
63 0038 CD 00 00   E           CALL  TEST_LINK     ;WATCH FOR ABSENCE OF FOOTSWITCH
64 003B CD 00 00   E           CALL  D_TO_A        ;SERVICE THE D/A
65 003E CD 00 00   E           CALL  SDAC          ;
66                                                 ;
67                        ;
68                        ;------ 60 HZ ROUTINES
69                        ;
70 0041 21 03 00   D   LEVEL4  LD    HL,TM60HZ     ;DIVIDE 977HZ BY 16
71 0044 35                     DEC   (HL)          ;DEC. THE COUNT
72 0045 C2 50 00   C           JP    NZ,LEVEL5     ;
73 0048 36 10                  LD    (HL),DIV60HZ  ;RELOAD COUNT
74                                                 ;
75 004A CD 00 00   E           CALL  TXDRIVER      ;COMMUNICATIONS
76 004D CD 00 00   E           CALL  WINK          ;
77                                                 ;
78                        ;
79                        ;------ 30 HZ ROUTINES
80                        ;
81 0050 21 04 00   D   LEVEL5  LD    HL,TM30HZ     ;DIVIDE 977HZ BY 32
82 0053 35                     DEC   (HL)          ;DEC. THE COUNT
83 0054 C2 5F 00   C           JP    NZ,LEVEL6     ;RETURN IF NOT ZERO
84 0057 36 20                  LD    (HL),DIV30HZ  ;RELOAD COUNT
85                                                 ;
86 0059 CD 00 00   E           CALL  MINIMIZER     ;ITTERAVELY REDUCE PHASE MARGIN
87 005C CD 00 00   E           CALL  KEYSCAN       ;KEY SCAN AND UPDATE KEY STATE
88                                                 ;
89                        ;
90                        ;------ 10 HZ ROUTINES
91                        ;
92 005F 21 05 00   D   LEVEL6  LD    HL,TM10HZ     ;DIVIDE 977HZ BY 96
93 0062 35                     DEC   (HL)          ;DEC. THE COUNT
94 0063 C2 77 00   C           JP    NZ,LEVEL_OUT  ;RETURN IF NOT ZERO
95 0066 36 60                  LD    (HL),DIV10HZ  ;RELOAD COUNT
96                                                 ;
97 0068 CD 00 00   E           CALL  POWER         ;POWER OUTPUT CONTROL
98 006B CD 00 00   E           CALL  STATUS        ;Check the error and connector status
99 006E CD 00 00   E           CALL  FLAGS         ;
100 0071 CD 00 00  E           CALL  HSWITCH       ;
101 0074 CD 00 00  E           CALL  SERROR        ;
102                                                ;
```

```
103                     LEVEL_OUT               ;
104 0077 E1                 POP    HL           ;RESTORE REGISTERS
105 0078 D1                 POP    DE           ;
106 0079 C1                 POP    BC           ;
107 007A F1                 POP    AF           ;
108 007B ED 4D              RETI                ;RETURN FROM INTERRUPT
109                                             ;
110                     ;
111                     ;------ Reserve the addresses of future interrupt routines for CTC
112                     ;
113                     CHAN0                   ;Current assignment: Baud Rate
114 007D C9                 RET                 ;
115                                             ;
116                     CHAN1                   ;Current assignment: Watchdog
```

PHACO SYSTEM Z80 INTERRUPT HANDLER       3

```
117 007E C9                 RET                 ;
118                                             ;
119                                             ;
120                     ;=====================================================;
121                     ;   DATA SEGMENT                                      ;
122                     ;=====================================================;
123                     ;
= 124 007F                  INCLUD EQU.INC      ;INCLUDE THE CONSTANTS IN ASSEMBLY
= 125                   ;=====================================================;
= 126                   ;                                                     ;
= 127                   ;   EQU.INC     PHACO SYSTEM GLOBAL EQUATES           ;
= 128                   ;                                                     ;
= 129                   ;=====================================================;
= 130                   ;                                                     ;
= 131                   ;        !!!!!!!!! CHANGE HISTORY !!!!!!!!!           ;
= 132                   ;                                                     ;
= 133                   ;   AUTHOR         DATE         CHANGE PURPOSE        ;
= 134                   ;   ----------------------------------------------    ;
= 135                   ;   T. Lo          3 FEB 86     CREATION              ;
= 136                   ;   F. Lian        10 Feb. 86   Update                ;
= 137                   ;   F. Lian        10 April 86  Update                ;
= 138                   ;   T. Escorcio    24 June 86   Update                ;
= 139                   ;   T. Escorcio    7 July 86    Update                ;
= 140                   ;   T. Escorcio    4/1/87       add adaptive tuning constants ;
= 141                   ;                                                     ;
= 142                   ;-----------------------------------------------------;
= 143                   ;
= 144                   ;------ TOP OF RAM MARKER
= 145                   ;
= 146 8000              RAM_END        EQU   8000H      ;32K CONFIGURATION
= 147                   ;
= 148                   ;------ INTERRUPT LOOP TIMING CONSTANTS
= 149                   ;
= 150 01E3              SAMPFRQ        EQU   489+2      ;INTERRUPT SAMPLING FREQUENCY
= 151 0002              DIV480HZ       EQU   2          ;480 HZ DIVIDER
```

```
= 152 0004             DIV240HZ    EQU    4           ;240 HZ DIVIDER
= 153 0008             DIV120HZ    EQU    8           ;120 HZ DIVIDER
= 154 0010             DIV60HZ     EQU    16          ; 60 HZ DIVIDER
= 155 0020             DIV30HZ     EQU    32          ; 30 HZ DIVIDER
= 156 0060             DIV10HZ     EQU    96          ; 10 HZ DIVIDER
= 157                                                 ;
= 158                  ;
= 159                  ;------ System counter parameters
= 160                  ;
= 161 0168             ELAPS1      EQU    168H        ;3 SECOND TIMER VALUE (HUNTER)
= 162 05A0             ELAPS2      EQU    5A0H        ;3 SECOND TIMER VALUE (COM. REPLY)
= 163 0020             ELAPS3      EQU    020H        ;BEEPER DURATION
= 164 0300             ELAPS4      EQU    0300H       ;BEEPER COUNTER SAMPLING RATE
= 165 0078             ELAPS5      EQU    120         ;SCANNER INTERVAL
= 166                                                 ;
= 167                  ;
= 168                  ;------ PROGRAM THRESHOLD LEVELS
= 169                  ;
= 170 0000             MIN         EQU    00H         ;
= 171 00FF             MAX         EQU    0FFH        ;
= 172 0001             TRUE        EQU    00000001B   ;
= 173 0000             FALSE       EQU    00000000B   ;
= 174 01F4             BUFF_SIZE   EQU    500         ;

PHACO SYSTEM Z80 INTERRUPT HANDLER      4

= 175 000A             KEY_RYTHM   EQU    10          ;Key music duration time
= 176 0004             KEY_TIME    EQU    4           ;
= 177 000F             BEEP_TIME   EQU    15          ;
= 178 0640             BEGINNING   EQU    1600        ;
= 179 0800             FULL        EQU    2048        ;
= 180                                                 ;
= 181                  ;================================================================;
= 182 007F
= 183 007F
  184                                                 ;
  185                           DSEG                  ;
  186                                                 ;
  187 0000 00          TM480HZ     DB     0           ;480 HZ FREQ. DIVIDER (FROM 977HZ)
  188 0001 00          TM240HZ     DB     0           ;240 HZ FREQ. DIVIDER (FROM 977HZ)
  189 0002 00          TM120HZ     DB     0           ;120 HZ FREQ. DIVIDER (FROM 977HZ)
  190 0003 00          TM60HZ      DB     0           ;60 HZ FREQ. DIVIDER (FROM 977HZ)
  191 0004 00          TM30HZ      DB     0           ;30 HZ FREQ. DIVIDER (FROM 977HZ)
  192 0005 00          TM10HZ      DB     0           ;10 HZ FREQ. DIVIDER (FROM 977HZ)
  193                                                 ;
  194
  195                  ;----------------------------------------------------------------;
  196                  ;
  197                  ;       EXTERNAL VARIABLE DECLARATION
  198                  ;
  199                  ;----------------------------------------------------------------;
  200                  ;
```

```
201         EXTRN   RXD_INT, PCLOCK, WINK, LED_DRV, A_TO_D, D_TO_A
202         EXTRN   COM_CONTROL, HUNTER, TEST_LINK, POWER, BARGRAPH, MONITOR
203         EXTRN   TXDRIVER, KEYSCAN, STATUS, MINIMIZER, SOUND, WATCHDOG
204         EXTRN   FLAGS, HSWITCH, SDAC, FILTER, POWER_, SERROR
205                                                                              ;
206     ;----------------------------------------------------------------;
207     ;                                                                ;
208     ;           PUBLIC VARIABLE DECLARATION                          ;
209     ;                                                                ;
210     ;----------------------------------------------------------------;
211         ;
212         PUBLIC  TM480HZ, TM120HZ, TM60HZ, TM30HZ, CHAN0, CHAN1, CHAN3
213         PUBLIC  TM240HZ, TM10HZ
214                                                                              ;
215     ;================================================================;
216     ;
217     ;;;;;;;;;;;;;;;;;;;;;;;;;;;;;;;;;;;;;;;;;;;;;;;;;;;;;;;;;;;;;;;;;;
218         ;
219 0006    END
```

ERRORS = 0000

PHACO DIGITAL FILTER ALGORYTHM              1

```
            TITLE   'PHACO DIGITAL FILTER ALGORYTHM'
            NAME    PFILTER_INT_MODULE
            PAGESZ  66
            CSEG
                                                                                 ;
        ;;;;;;;;;;;;;;;;;;;;;;;;;;;;;;;;;;;;;;;;;;;;;;;;;;;;;;;;;;;;;;;;;;
        ;                                                                ;
        ;            PHACO DIGITAL FILTER ALGORYTHM                      ;
        ;                                                                ;
        ;                                                                ;
        ;================================================================;
        ;           ;;;;;;; CHANGE HISTORY ;;;;;;;                        ;
        ;                                                                ;
        ;   Author       Date         Change Purpose                     ;
        ;   ----------------------------------------------               ;
        ;                                                                ;
        ;                                                                ;
        ;================================================================;
        ;
        ;----------------------------------------------------------------
        ;
        ;    Function:
        ;
        ;    Registers:
```

```
24                      ;         Accepts:                                        ;
25                      ;         Returns:                                        ;
26                      ;           Flags:                                        ;
27                      ;       Variables:                                        ;
28                      ;       Constants:                                        ;
29                      ;                                                         ;
30                      ;     Pseudo Code:                                        ;
31                      ;                                                         ;
32                      ;---------------------------------------------------------;
33                      ;---------------------------------------------------------;
34                      ;                                                         ;
35                      ;   Notes:                                                ;
36                      ;                                                         ;
37                      ;     Transfer function of this digital filter            ;
38                      ;                                                         ;
39                      ;                     -t/RC                               ;
40                      ;       Eout = Ein[1 - e    ]                             ;
41                      ;                                                         ;
42                      ;         or,                                             ;
43                      ;                                                         ;
44                      ;         1         -t/RC                                 ;
45                      ;       d Ein[1 - e    ]                                  ;
46                      ;       t=0                                               ;
47                      ;                                                         ;
48                      ;---------------------------------------------------------;
49                      ;
50              FILTER                                                            ;
51                                                                                ;
52                                                                                ;
53 0000 DB 7E                   IN      A,(SERVICE)     ;Poll the service switch once
54 0002 E6 F4                   AND     11110100B       ;Mask off Power Detection bits
55 0004 FE 00                   CP      0               ;Any keys pressed ?
56 0006 C0                      RET     NZ              ;

57                                                                                ;
58 0007 06 04                   LD      B,TAU           ;COUNTR > TAU ?
59 0009 3A 0D 00    D           LD      A,(COUNTR)      ;
60 000C B8                      CP      B               ;
61 000D DA 1E 00    C           JP      C,FIL2          ;If false, branch
62                                                      ; otherwise, process output
63 0010 3E 00                   LD      A,NULL          ;
64 0012 32 0D 00    D           LD      (COUNTR),A      ;
65                                                      ;
66 0015 3A 00 00    E           LD      A,(AMPLITUDE)   ;
67 0018 32 02 00    D           LD      (NEW),A         ;
68                                                      ;
69 001B CD 39 00    C           CALL    OUTPUT          ;
70                                                      ;
```

```
71                      FIL2
72 001E 3E 04                   LD      A,TAU           ;TAU = 0 ?
73 0020 FE 00                   CP      0               ;
74 0022 CA 2E 00    C           JP      Z,FIL3          ;If true, branch
                                                        ; otherwise,
75
76 0025 3A 0E 00    D           LD      A,(RESULT)      ;US_PWR = RESULT
77 0028 32 00 00    E           LD      (US_PWR),A      ;
78 002B C3 34 00    C           JP      EXIT            ;
79                      FIL3                            ;
80 002E 3A 02 00    D           LD      A,(NEW)         ;US_PWR = NEW
81 0031 32 00 00    E           LD      (US_PWR),A      ;
82                                                      ;
83                      EXIT                            ;
84 0034 21 0D 00    D           LD      HL,COUNTR       ;
85 0037 34                      INC     (HL)            ;
86                                                      ;
87 0038 C9                      RET                     ;
88                                                      ;
89              ;-----------------------------------------------------------;
90              ;       SUBROUTINES                                         ;
91              ;-----------------------------------------------------------;
92              ;-----------------------------------------------------------;
93              ;                                                           ;
94              ;       Function:                                           ;
95              ;                                                           ;
96              ;       Registers:                                          ;
97              ;          Accepts:                                         ;
98              ;           Returns:                                        ;
99              ;             Flags:                                        ;
100             ;         Variables:                                        ;
101             ;         Constants:                                        ;
102             ;                                                           ;
103             ;       Pseudo Code:                                        ;
104             ;                                                           ;
105             ;-----------------------------------------------------------;
106             ;
107                     OUTPUT                          ;
108                                                     ;
109                     UP?                             ;
110 0039 3A 04 00   D           LD      A,(OLD)         ;NEW > OLD ?
111 003C 21 02 00   D           LD      HL,NEW          ;
112 003F BE                     CP      (HL)            ;
113 0040 D2 5F 00   C           JP      NC,DOWN?        ;

114                                                     ;
115 0043 21 01 00   D           LD      HL,DNWARD       ;
116 0046 CB 86                  RES     0,(HL)          ;
117                                                     ;
118 0049 21 00 00   D           LD      HL,UPWARD       ;
```

```
119 004B CB C6                       SET    0,(HL)            ;
120                                                           ;
121 004D 3E 00                       LD     A,NULL            ;
122 004F 32 07 00    D               LD     (INDEXER),A       ;
123                                                           ;
124 0052 3A 02 00    D               LD     A,(NEW)           ;
125 0055 21 04 00    D               LD     HL,OLD            ;
126 0058 96                          SUB    (HL)              ;
127 0059 32 03 00    D               LD     (DELTA),A         ;
128                                                           ;
129 005C C3 82 00    C               JP     COMPLETION        ;
130                                                           ;
131                          DOWN?                            ;
132 005F 3A 02 00    D               LD     A,(NEW)           ;NEW <OLD ?
133 0062 21 04 00    D               LD     HL,OLD            ;
134 0065 BE                          CP     (HL)              ;
135 0066 D2 82 00    C               JP     NC,COMPLETION     ;
136                                                           ;
137 0069 21 00 00    D               LD     HL,UPWARD         ;
138 006C CB 86                       RES    0,(HL)            ;
139                                                           ;
140 006E 21 01 00    D               LD     HL,DNWARD         ;
141 0071 CB C6                       SET    0,(HL)            ;
142                                                           ;
143 0073 3E 00                       LD     A,NULL            ;
144 0075 32 07 00    D               LD     (INDEXER),A       ;
145                                                           ;
146 0078 3A 02 00    D               LD     A,(NEW)           ;
147 007B 21 04 00    D               LD     HL,OLD            ;
148 007E 96                          SUB    (HL)              ;
149 007F 32 03 00    D               LD     (DELTA),A         ;
150                                                           ;
151                          COMPLETION                       ;
152                                                           ;
153 0082 CD DD 00    C               CALL   FALLING           ;Implement FALLING power curve.
154 0085 CD 8F 00    C               CALL   RISING            ;Implement RISING power curve.
155                                                           ;
156 0088 3A 02 00    D               LD     A,(NEW)           ;Keep track of amplitude to differentiate
157 008B 32 04 00    D               LD     (OLD),A           ; positive or negative slope
158                                                           ;
159 008E C9                          RET                      ;
160                                                           ;
161                  ;----------------------------------------------------------------;
162                  ;                                                                ;
163                  ;    Function:                                                   ;
164                  ;                                                                ;
165                  ;    Registers:                                                  ;
166                  ;      Accepts:                                                  ;
167                  ;      Returns:                                                  ;
168                  ;        Flags:                                                  ;
169                  ;    Variables:                                                  ;
170                  ;    Constants:                                                  ;
```

```
171                 ;
172                 ;       Pseudo Code:
173                 ;
174                 ;----------------------------------------------------------
175                 ;
176                 ;------ Condition RISING voltage swing
177                 ;
178                       RISING                              ;
179                                                           ;
180 008F 21 00 00  D       LD    HL,UPWARD                   ;
181 0092 CB 46              BIT   0,(HL)                      ;
182 0094 CA DC 00  C       JP    Z,BRANCH                    ;
183                                                           ;
184 0097 3A 07 00  D       LD    A,(INDEXER)                 ;EXP_RISE < TABL_SIZE ?
185 009A FE 80             CP    TABL_SIZE                   ;
186 009C D2 DC 00  C       JP    NC,BRANCH                   ;
187                                                           ;
188 009F 3C               INC   A                           ;
189 00A0 3C               INC   A                           ;
190 00A1 32 07 00  D       LD    (INDEXER),A                 ;
191                                                           ;
192 00A4 21 2E 01  C       LD    HL,TABLE                    ;COEFFICIENT = TABLE(INDEXER)
193 00A7 ED 5B 07 00 D     LD    DE,(INDEXER)                ;
194 00AB 19                ADD   HL,DE                       ;
195 00AC 22 09 00  D       LD    (POINTR),HL                 ;
196                                                           ;
197 00AF 01 02 00          LD    BC,2                        ;
198 00B2 2A 09 00  D       LD    HL,(POINTR)                 ;
199 00B5 11 0B 00  D       LD    DE,COEFFICIENT              ;
200 00B8 ED B0             LDIR                              ;
201                                                           ;
202 00BA 2A 0B 00  D       LD    HL,(COEFFICIENT)            ;
203 00BD ED 5B 03 00 D     LD    DE,(DELTA)                  ;CORRECTION = (DELTA x COEFFICIENT)/1024
204 00C1 16 00             LD    D,NULL                      ;
205 00C3 CD 00 00  E       CALL  MUL16                       ;
206 00C6 3E 09             LD    A,DIVISOR                   ;Will result in a truncated real number
207                                                           ; in integer form once it is REFINEd
208                      REFIN_                              ;Divide by the divisor
209 00C8 CB 3C             SRL   H                           ;
210 00CA CB 1D             RR    L                           ;
211 00CC 3D               DEC   A                           ;
212 00CD FE 00             CP    0                           ;
213 00CF C2 C8 00  C       JP    NZ,REFIN_                   ;
214                                                           ;
215 00D2 3A 02 00  D       LD    A,(NEW)                     ;RESULT = NEW - CORRECTION
216 00D5 9D               SBC   A,L                         ;
217 00D6 DA DC 00  C       JP    C,BR2                       ;
218 00D9 32 0E 00  D       LD    (RESULT),A                  ;
219                      BR2                                 ;
220                                                           ;
221                      BRANCH                              ;
222                                                           ;
223 00DC C9               RET                               ;
224                                                           ;
```

```
225          ;----------------------------------------------------------;
226          ;                                                          ;
227          ;    Function:                                             ;
228          ;                                                          ;
229          ;    Registers:                                            ;
230          ;      Accepts:                                            ;
231          ;      Returns:                                            ;
232          ;        Flags:                                            ;
233          ;    Variables:                                            ;
234          ;    Constants:                                            ;
235          ;                                                          ;
236          ;  Pseudo Code:                                            ;
237          ;                                                          ;
238          ;----------------------------------------------------------;
239          ;
240          ;------ Condition FALLING voltage swing
241          ;
242          FALLING                             ;
243                                              ;
244 00DD 21 01 00    D      LD    HL,DNWARD     ;
245 00E0 CB 46              BIT   0,(HL)        ;
246 00E2 CA 2D 01    C      JP    Z,OUTBRANCH   ;
247                                              ;
248 00E5 3A 07 00    D      LD    A,(INDEXER)   ;INDEXER < TABL_SIZE ?
249 00E8 FE 80              CP    TABL_SIZE     ;
250 00EA D2 2D 01    C      JP    NC,OUTBRANCH  ;
251                                              ;
252 00ED 3C                 INC   A             ;
253 00EE 3C                 INC   A             ;
254 00EF 32 07 00    D      LD    (INDEXER),A   ;
255                                              ;
256 00F2 21 2E 01    C      LD    HL,TABLE      ;COEFFICIENT = TABLE(INDEXER)
257 00F5 ED 5B 07 00 D      LD    DE,(INDEXER)  ;
258 00F9 19                 ADD   HL,DE         ;
259 00FA 22 09 00    D      LD    (POINTR),HL   ;
260                                              ;
261 00FD 01 02 00           LD    BC,2          ;
262 0100 2A 09 00    D      LD    HL,(POINTR)   ;
263 0103 11 0B 00    D      LD    DE,COEFFICIENT;
264 0106 ED B0              LDIR                ;
265                                              ;
266 0108 2A 0B 00    D      LD    HL,(COEFFICIENT) ;
267 010B 3A 03 00    D      LD    A,(DELTA)     ;
268 010E E6 7F              AND   01111111B     ;
269 0110 2F                 CPL                 ;
270 0111 06 80              LD    B,128         ;
271 0113 90                 SUB   B             ;
272 0114 5F                 LD    E,A           ;CORRECTION = (DELTA x COEFFICIENT)/1024
273 0115 16 00              LD    D,NULL        ;
274 0117 CD 00 00    E      CALL  MUL16         ;
275 011A 3E 09              LD    A,DIVISOR     ;Will result in a truncated real number
276                                              ;
277          REFINE                              ; in integer form once it is REFINEd
278 011C CB 3C              SRL   H             ;Divide by the divisor
279 011E CB 1D              RR    L             ;
```

```
280 0120 3D                      DEC   A               ;
281 0121 FE 00                   CP    0               ;
282 0123 C2 1C 01    C           JP    NZ,REFINE       ;
283                                                    ;
284 0126 3A 02 00    D           LD    A,(NEW)         ;RESULT = NEW + CORRECTION
285 0129 8D                      ADC   A,L             ;

286 012A 32 0E 00    D           LD    (RESULT),A      ;
287                                                    ;
288                              OUTBRANCH             ;
289                                                    ;
290 012D C9                      RET                   ;
291                                                    ;
292                                                                                ;
293                    ;================================================================;
294                    ;         DATA SEGMENT
295                    ;================================================================;
296                    ;
297                              CSEG                  ;
298                                                    ;
299                    ;   The following is a table of 64 exponential coefficients,
300                    ;   which should be scaled 1:512 to obtain the valid result.
301                    ;
302                    ;
303                                                    ;
304 012E 00 02       TABLE       DEFW  512, 459, 412, 369, 331, 297, 266, 238
    0130 CB 01
    0132 9C 01
    0134 71 01
    0136 4B 01
    0138 29 01
    013A 0A 01
    013C EE 00
305 013E D6 00                   DEFW  214, 192, 172, 154, 138, 124, 111, 100
    0140 C0 00
    0142 AC 00
    0144 9A 00
    0146 8A 00
    0148 7C 00
    014A 6F 00
    014C 64 00
306 014E 59 00                   DEFW  89, 80, 72, 64, 58, 52, 46, 42
    0150 50 00
    0152 48 00
    0154 40 00
    0156 3A 00
    0158 34 00
    015A 2E 00
    015C 2A 00
```

```
307 015E 25 00              DEFW    37, 34, 30, 27, 24, 22, 20, 18
    0160 22 00
    0162 1E 00
    0164 1B 00
    0166 18 00
    0168 16 00
    016A 14 00
    016C 12 00
308 016E 10 00              DEFW    16, 14, 13, 12, 10, 9, 8, 7
    0170 0E 00
    0172 0D 00
    0174 0C 00
    0176 0A 00
    0178 09 00
    017A 08 00

017C 07 00
309 017E 07 00              DEFW    7, 6, 5, 5, 4, 4, 4, 3
    0180 06 00
    0182 05 00
    0184 05 00
    0186 04 00
    0188 04 00
    018A 04 00
    018C 03 00
310 018E 03 00              DEFW    3, 3, 2, 2, 2, 2, 2, 1
    0190 03 00
    0192 02 00
    0194 02 00
    0196 02 00
    0198 02 00
    019A 02 00
    019C 01 00
311 019E 01 00              DEFW    1, 1, 1, 1, 1, 1, 1, 1
    01A0 01 00
    01A2 01 00
    01A4 01 00
    01A6 01 00
    01A8 01 00
    01AA 01 00
    01AC 01 00
312 01AE 00 00              DEFW    0, 0, 0, 0, 0, 0, 0, 0
    01B0 00 00
    01B2 00 00
    01B4 00 00
    01B6 00 00
    01B8 00 00
    01BA 00 00
    01BC 00 00
```

```
313                                                     ;
314                                                     ;
315 007E           SERVICE      EQU    7EH      ;SERVICE SWITCH ADDRESS
316 0080           TABL_SIZE    EQU    6412     ;
317 0000           NULL         EQU    0        ;
318 0009           DIVISOR      EQU    9        ;
319 0004           TAU          EQU    4        ;
320 000A           RATE         EQU    10       ;
321                                                     ;
322                     DSEG                            ;
323                                                     ;
324 0000 00        UPWARD       DB     0        ;
325 0001 00        DNWARD       DB     0        ;
326 0002 00        NEW          DB     0        ;
327 0003 00        DELTA        DB     0        ;
328 0004 00        OLD          DB     0        ;
329 0005 00 00     EXP_RISE     DEFW   0        ;TABLE index
330 0007 00 00     INDEXER DEFW 0              ;TABLE index
331 0009 00 00     POINTR       DEFW   0        ;
332 000B 00 00     COEFFICIENT  DEFW   0        ;
333 000D 00        COUNTR       DB     0        ;
334 000E 00        RESULT       DB     0        ;
335 000F 00        SCORE        DB     0        ;
336                                                     ;
337                                                     ;
338                                                                                                 ;
339           ;----------------------------------------------------------------;
340           ;                                                                ;
341           ;         EXTERNAL VARIABLE DECLARATION                          ;
342           ;                                                                ;
343           ;----------------------------------------------------------------;
344           ;
345                   EXTRN   MUL16, US_PWR, AMPLITUDE, POWER_
346                                                                                                 ;
347           ;----------------------------------------------------------------;
348           ;                                                    ;
349           ;       PUBLIC VARIABLE DECLARATION
350           ;                                                    ;
351           ;----------------------------------------------------------------;
352           ;
353           ;       PUBLIC   FILTER
354                                                                                                 ;
355           ;================================================================;
356           ;
357           ;;;;;;;;;;;;;;;;;;;;;;;;;;;;;;;;;;;;;;;;;;;;;;;;;;;;;;;;;;;;;;;;;
358           ;
359 0010              END

ERRORS = 0000
```

```
                    PHACO VCO AMPLITUDE CONTROL              1

1  0000                        TITLE   'PHACO VCO AMPLITUDE CONTROL'
2                              NAME    _INT_MODULE
3                              PAGESZ  66
4                              CSEG
5                                                                        ;
6                   ;%%%%%%%%%%%%%%%%%%%%%%%%%%%%%%%%%%%%%%%%%%%%%%%%%%%%%;
7                   ;                                                    ;
8                   ;              PHACO VCO AMPLITUDE CONTROL            ;
9                   ;                                                    ;
10                  ;====================================================;
11                  ;            %%%%%%% CHANGE HISTORY %%%%%%%            ;
12                  ;                                                    ;
13                  ;      Author         Date         Change Purpose     ;
14                  ;      --------------------------------------------   ;
15                  ;                                                    ;
16                  ;====================================================;
17                  ;
18                  ;----------------------------------------------------;
19                  ;
20                  ;     Function:                                      ;
21                  ;     Registers:                                     ;
22                  ;       Accepts:                                     ;
23                  ;       Returns:                                     ;
24                  ;         Flags:                                     ;
25                  ;     Variables:                                     ;
26                  ;     Constants:                                     ;
27                  ;                                                    ;
28                  ;    Pseudo Code:                                    ;
29                  ;
30                  ;----------------------------------------------------;
31                  ;----------------------------------------------------;
32                  ;                                                    ;
33                  ;    Notes:                                          ;
34                  ;     - D/A control parameters:                      ;
35                  ;           6Vda = 0% VCO ouput, 2Vda = 100 % VCO output ;
36                  ;                                                    ;
37                  ;
38                  ;----------------------------------------------------;
39                  ;
40                  ;    VCO overhead to generate 0 to 100% amplitude modulation.
41                  ;
42                  POWER_
43                                                                       ;
44 0000 DB 7E                  IN      A,(SERVICE)     ;Poll the service switch once
45 0002 E6 F4                  AND     11110100B       ;Mask off Power Detection bits
46 0004 FE 00                  CP      0               ;Any keys pressed ?
47 0006 C2 1F 00    C          JP      NZ,EXIT         ;
48                                                     ;
49 0009 3A 00 00    D          LD      A,(US_PWR)      ;
```

```
50          ;
51          ;         LD      A,(AMPLITUDE)   ;IIIIIIIIIIIIIIIIIIIIIIIIIIIIIIIIII
52          ;                                 ;THIS PATCH USEFULL FOR MONITORING
53          ;         CALL    BN2BCD          ; THE ACTUAL VALUE ON 7 SEG. DISPLAY
54          ;         LD      (DISPLAY),HL    ;DISPLAY the result
55          ;                                 ;IIIIIIIIIIIIIIIIIIIIIIIIIIIIIIIIII
56                                            ;

57 000C CD 29 00  C            CALL    FETCH         ;Get the value from the table
58                                                   ; (returned in DE)
59 000F 21 02 0C               LD      HL,VOFFSET    ;
60 0012 ED 52                  SBC     HL,DE         ;
61 0014 EA 1F 00  C            JP      PE,EXIT       ;Don't use result if overflow occurs
62                                                   ;
63                                                   ;
64                                                   ;
65               ;              LD      B,0           ;CLEAR UPPER BYTE
66               ;              LD      C,A           ; AND PASS N TO LOW BYTE
67               ;              LD      H,B           ;
68               ;              LD      L,C           ;
69               ;                                    ;
70               ;              LD      A,(US_PWR)    ;
71               ;              LD      B,0           ;CLEAR UPPER BYTE
72               ;              LD      C,A           ; AND PASS N TO LOW BYTE
73               ;              LD      H,B           ;
74               ;              LD      L,C           ;
75               ;                              ; UPSCALE, POWER = 22 X N = (N X 16) + (N X 6)
76               ;              ADD     HL,HL         ; X 2
77               ;              ADD     HL,HL         ; X 4            (N X 16)
78               ;              ADD     HL,HL         ; X 8
79               ;              ADD     HL,HL         ; X 16
80               ;                                    ;
81               ;              LD      D,H           ;PUT IT ASIDE FOR NOW
82               ;              LD      E,L           ;
83               ;              LD      H,B           ;GET N AGAIN
84               ;              LD      L,C           ;
85               ;              ADD     HL,HL         ; X 2
86               ;              ADD     HL,HL         ; X 4            (N X 6)
87               ;              ADD     HL,BC         ; + N
88               ;              ADD     HL,BC         ; + N
89               ;                                    ;
90               ;              ADD     HL,DE         ;COMBINE THE PRODUCTS
91               ;                                    ;
92               ;              LD      A,H           ;COMPLEMENT THE RESULT
93               ;              CPL                   ;
94               ;              LD      H,A           ;
95               ;              LD      A,L           ;
96               ;              CPL                   ;
97               ;              LD      L,A           ;
```

```
98                                     LD      C,PWR_PORT      ;
99  0017 0E 7C                         CALL    WRITE           ;
100 0019 CD 20 00      C                                       ;
101                                                            ;
102 001C 22 00 00      E               LD      (PWR_LEVEL),HL  ;
103                          EXIT                              ;
104 001F C9                            RET                     ;
105                                                            ;
106                          ;---------------------------------------------;
107                          ;                                             ;
108                          ;         SUBROUTINES                         ;
109                          ;                                             ;
110                          ;---------------------------------------------;
111                          ;                                             ;
112                          ;    Function:                                ;
113                          ;                                             ;
114                          ;     Accepts:                                ;
115                          ;     Returns:                                ;
116                          ;       Flags:                                ;
117                          ;   Variables:                                ;
118                          ;   Constants:                                ;
119                          ;                                             ;
120                          ;  Pseudo Code:                               ;
121                          ;                                             ;
122                          ;---------------------------------------------;
123                          ;---------------------------------------------;
124                          ;                                             ;
125                          ;  Notes:                                     ;
126                          ;                                             ;
127                          ;                                             ;
128                          ;---------------------------------------------;
129                          WRITE                              ;Write upper byte first
130                                                            ;
131 0020 7C                            LD      A,H             ;
132 0021 0C                            INC     C               ;
133 0022 ED 79                         OUT     (C),A           ;
                                                                ;Now write lower byte
134                                                            ;
135 0024 7D                            LD      A,L             ;
136 0025 0D                            DEC     C               ;
137 0026 ED 79                         OUT     (C),A           ;
138                                                            ;
139 0028 C9                            RET                     ;
140                                                            ;
141                          ;------ Get the appropriate control count from the TABLE
142                          ;
143                          ;
144                          FETCH                              ;
```

```
145
146 0029 21 37 00      C         LD      HL,TABLE        ;
147 002C E6 7F                   AND     01111111B       ;
148 002E 87                      ADD     A,A             ;index = index * 2, for word indexing
149
150 002F 16 00                   LD      D,0
151 0031 5F                      LD      E,A             ;
152                                                      ;
153 0032 19                      ADD     HL,DE           ;
154                                                      ;
155 0033 5E                      LD      E,(HL)          ;
156 0034 23                      INC     HL              ;
157 0035 56                      LD      D,(HL)          ;
158                                                      ;
159                      LEAVE                           ;
160 0036 C9                      RET                     ;
161                                                      ;
162                                                                                              ;
163                      ;===========================================================;
164                      ;       DATA SEGMENT
                                                         ;
165                      ;===========================================================;
166                      ;
= 167 0037                       INCLUD  ADDRESS.INC     ;
= 168                    ;===========================================================;
= 169                    ;
= 170                    ;       ADDRESS.INC     PHACO SYSTEM GLOBAL EQUATES          ;

= 171                                                                                            ;
= 172                    ;===========================================================;
= 173                    ;                                                            ;
= 174                    ;       !!!!!!!!! CHANGE HISTORY !!!!!!!!!                   ;
= 175                    ;                                                            ;
= 176                    ;       AUTHOR          DATE            CHANGE PURPOSE       ;
= 177                    ;       -----------------------------------------------      ;
= 178                    ;       T. LO           3 FEB 86        CREATION             ;
= 179                    ;       F. Lian         10 Feb. 86      Update               ;
= 180                    ;       F. Lian         10 April 86     Update               ;
= 181                    ;       T. Escorcio     24 June 86      Update               ;
= 182                    ;       T. Escorcio     7 July 86       Update               ;
= 183                    ;       T. Escorcio     4/1/87          add adaptive tuning constants ;
= 184                    ;                                                            ;
= 185                    ;------------------------------------------------------------;
= 186
= 187                    ;------ DIGITAL I/O BOARD ADRESSES
= 188                    ;
= 189 0070               DIO_BASE        EQU     70H             ;BASE ADDRESS OF SBB466 CARD
= 190 0070               BITIOAD         EQU     DIO_BASE+0      ;
= 191 0070               IO_P0           EQU     DIO_BASE+0      ; PORT A OF 8255 #1
```

United States Patent Office

PTO - BOYERS, PA Duty Station

BEST AVAILABLE COPY
BEST AVAILABLE C...

MISSING PAGE TEMPORARY NOTICE

PATENT # _5001649_ FOR ISSUE DATE _3-19-1991_

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # _111 - 112_

N/A at Boyers
7/30/92

Data Conversion Operation
Boyers, Pa

```
240                  ;       DEFW    691,678,666,653,640,627,614,602
241                  ;       DEFW    589,576,563,563,550,538,538,525
242                  ;       DEFW    512,499,474,461,448,435,422,410
243                  ;       DEFW    397,384,371,358,346,333,320,307
244                  ;       DEFW    294,282,269,256,243,230,218,205
245                  ;       DEFW    192,179,166,154,141,128,115,102
246                  ;       DEFW    90,77,64,51,38,26,13,0
247                  ;                                               ;
248                  ;                                               ;
249                  ;
250                  ;------ Lookup table to provide VCO AM control range of 0 to 4v
251                  ;
252  0037 00 00      TABLE   DEFW    0,13,26,38,51,64,77,90
     0039 0D 00
     003B 1A 00
     003D 26 00
     003F 33 00
     0041 40 00
     0043 4D 00
     0045 5A 00
253  0047 66 00              DEFW    102,115,128,141,154,166,179,192
     0049 73 00
     004B 80 00
     004D 8D 00
     004F 9A 00
     0051 A6 00
     0053 B3 00
     0055 C0 00
254  0057 CD 00              DEFW    205,218,230,243,256,269,282,294
     0059 DA 00
     005B E6 00
     005D F3 00
     005F 00 01
     0061 0D 01
     0063 1A 01
     0065 26 01
255  0067 33 01              DEFW    307,320,333,346,358,371,384,397
     0069 40 01
     006B 4D 01
     006D 5A 01
     006F 66 01
     0071 73 01
     0073 80 01
     0075 8D 01
256  0077 9A 01              DEFW    410,422,435,448,461,474,486,499
     0079 A6 01
     007B B3 01

007D C0 01
```

```
          007F CD 01
          0081 DA 01
          0083 E6 01
          0085 F3 01
257       0087 00 02                DEFW    512,525,538,550,563,576,589,602
          0089 0D 02
          008B 1A 02
          008D 26 02
          008F 33 02
          0091 40 02
          0093 4D 02
          0095 5A 02
258       0097 66 02                DEFW    614,627,640,653,666,679,691,704
          0099 73 02
          009B 80 02
          009D 8D 02
          009F 9A 02
          00A1 A6 02
          00A3 B3 02
          00A5 C0 02
259       00A7 CD 02                DEFW    717,730,742,755,768,781,794,806
          00A9 DA 02
          00AB E6 02
          00AD F3 02
          00AF 00 03
          00B1 0D 03
          00B3 1A 03
          00B5 26 03
260       00B7 33 03                DEFW    819,832,845,858,870,883,896,909
          00B9 40 03
          00BB 4D 03
          00BD 5A 03
          00BF 66 03
          00C1 73 03
          00C3 80 03
          00C5 8D 03
261       00C7 9A 03                DEFW    922,934,947,960,973,986,998,1011
          00C9 A6 03
          00CB B3 03
          00CD C0 03
          00CF CD 03
          00D1 DA 03
          00D3 E6 03
          00D5 F3 03
262       00D7 00 04                DEFW    1024,1037,1050,1062,1075,1088,1101,1114
          00D9 0D 04
          00DB 1A 04
          00DD 26 04
          00DF 33 04
          00E1 40 04
          00E3 4D 04
          00E5 5A 04
263       00E7 66 04                DEFW    1126,1139,1152,1164,1177,1190,1203,1216
          00E9 73 04
          00EB 80 04
          00ED 8D 04
```

```
         00EF F9 04

00F1 A6 04
         00F3 B3 04
         00F5 C0 04
264      00F7 CD 04              DEFW    1228,1241,1254,1267,1280,1292,1305,1318
         00F9 D9 04
         00FB E6 04
         00FD F3 04
         00FF 00 05
         0101 0C 05
         0103 19 05
         0105 26 05
265      0107 33 05              DEFW    1331,1343,1356,1369,1395,1407,1420,1433
         0109 3F 05
         010B 4C 05
         010D 59 05
         010F 73 05
         0111 7F 05
         0113 8C 05
         0115 99 05
266      0117 A6 05              DEFW    1446,1459,1471,1481,1497,1510,1523,1535
         0119 B3 05
         011B BF 05
         011D C9 05
         011F D9 05
         0121 E6 05
         0123 F3 05
         0125 FF 05
267      0127 0C 06              DEFW    1548,1561,1574,1587,1599,1612,1625,1638
         0129 19 06
         012B 26 06
         012D 33 06
         012F 3F 06
         0131 4C 06
         0133 59 06
         0135 66 06
268                                                              ;
269                                                              ;
270                              DSEG                            ;
271                                                              ;
272 0000 00              US_PWR  DB      0                       ;
273                                                              ;
274
275                      ;--------------------------------------------------------;
276                      ;                                                        ;
277                      ;           EXTERNAL VARIABLE DECLARATION                ;
278                      ;                                                        ;
279                      ;--------------------------------------------------------;
```

```
280                ;
281                        EXTRN   AMPLITUDE, PWR_LEVEL, BN2BCD, DISPLAY
282                                                                                    ;
283                ;------------------------------------------------------------------;
284                ;
                                                                    ;
285                ;        PUBLIC VARIABLE DECLARATION
                                        ;
286                ;
                                                            ;
287                ;------------------------------------------------------------------;

288                ;
289                        PUBLIC  POWER_, US_PWR
290                                                                                    ;
291                ;==================================================================;
292                ;
293                ;IIIIIIIIIIIIIIIIIIIIIIIIIIIIIIIIIIIIIIIIIIIIIIIIIIIIIIIIIIIIIIIIII;
294                ;
295 0001                    END
```

ERRORS = 0000

PHACO STDBUS SYSTEM COMPONENT INIT        1

```
                    TITLE  'PHACO STDBUS SYSTEM COMPONENT INIT'
                    NAME   PSYS_MODULE
                    CSEG
                    PAGESZ 66

;
;;;;;;;;;;;;;;;;;;;;;;;;;;;;;;;;;;;;;;;;;;;;;;;;;;;;;;;;;;;;;;;;;;;;;;;;;;;;;;;
;                                                                             ;
;                         I/O INITIALIZATION                                  ;
;                                                                             ;
;=============================================================================;
;                                                                             ;
;            ;;;;;;; CHANGE HISTORY ;;;;;;;                                   ;
;                                                                             ;
;          Author        Date          Change Purpose                         ;
;          --------------------------------------------                       ;
;                                                                             ;
;          Lian, F.      10 Feb. 86    Creation (Design)                      ;
;          T. Escorcio   7/30/86       Clean-up                               ;
;                                                                             ;
;=============================================================================;
;
;-----------------------------------------------------------------------------;
;                                                                             ;
;     This module contains the subroutines to initialize CTC chip and         ;
;     8251A (USART), and also the I/O chips (8255) on the I/O card.           ;
;                                                                             ;
;     I/O Map:                                                                ;
;           CTC chip (U5) - channel 0 :    F0H (CTC_C0)                       ;
;                           channel 1 :    F1H (CTC_C1)                       ;
;                           channel 2 :    F2H (CTC_C2)                       ;
;                           channel 3 :    F3H (CTC_C3)                       ;
;                                                                             ;
;           8251A (U3) -   Data port :     F4H (SER_PORT)                     ;
;                          Control port:   F5H (SER_CONTROL)                  ;
;                                                                             ;
;     The definition of these addresses is contained in the                   ;
;     include file, EQU.INC.                                                  ;
;-----------------------------------------------------------------------------;
;
;-----------------------------------------------------------------------------;
; Subroutine: CTC_INIT                                                        ;
; Accepts:    None                                                            ;
; Returns:    None                                                            ;
; Function:   This routine configures CTC's four channels; channel 0 is;
;             used for 8251A Baud Rate generation (4800) and in counter;
;             mode, channel 1 is in counter mode for receiver interrupt;
;             (RxRDY), channel 2 is in counter mode for transmitter    ;
;             interrupt (TxRDY), and channel 3 is in timer mode and    ;
;             generates a 480 Hz interrupt. The interrupt vector is set;
;             at 800H.                                                 ;
;-----------------------------------------------------------------------------;
;
CTC_INIT                                ;
```

```
52 0000 3E 57          LD     A,01010111B    ;CHANNEL 0 CONTROL WORD
53 0002 D3 F0          OUT    (CTC_C0),A     ;NO INTERRUPT AND COUNTER MODE
54 0004 3E 0D          LD     A,13           ;TIME CONSTANT
55 0006 D3 F0          OUT    (CTC_C0),A     ;4800 BAUD FOR 8251A
56 0008 3E 00          LD     A,00H          ;INTERRUPT VECTOR
57 000A D3 F0          OUT    (CTC_C0),A     ;LOWER ADDR. BYTE 800H
58                                           ;
```

PHACO STDBUS SYSTEM COMPONENT INIT     2

```
59 000C 3E 37          LD     A,00110111B    ;CHANNEL 1 CONTROL WORD
60 000E D3 F1          OUT    (CTC_C1),A     ;NO INTERRUPT AND TIMER MODE (MODIFIABLE)
61 0010 3E FF          LD     A,255          ;TIME CONSTANT
62 0012 D3 F1          OUT    (CTC_C1),A     ;POSITIVE EDGE TRIGGER
63                                           ;
64 0014 3E 33          LD     A,00110011B    ;CHANNEL 2 CONTROL WORD (JUST ITITIALIZE)
65 0016 D3 F2          OUT    (CTC_C2),A     ;NO INTERRUPT AND TIMER MODE (MODIFIABLE)
66                                           ;
67 0018 3E B7          LD     A,10110111B    ;CHANNEL 3 CONTROL WORD
68 001A D3 F3          OUT    (CTC_C3),A     ;INTERRUPT AND TIMER MODE, PRESCALE = 256
69 001C 3E 10          LD     A,16           ;TIME CONSTANT, 977Hz (4MHZ CLOCK)
70 001E D3 F3          OUT    (CTC_C3),A     ;POSITIVE EDGE TRIGGER
71                                           ;
72 0020 C9             RET                   ;END
73                                           ;
74                                                                                      ;
75                     ;----------------------------------------------------------------;
76                     ; Subroutine:   USART_INIT                                       ;
77                     ; Accepts:      None                                             ;
78                     ; Returns:      None                                             ;
79                     ; Function:     This routine initializes 8251A into an UART with 4800 ;
80                     ;               baud rate (factor = 16), one stopt bit, no parity, and ;
81                     ;               8 bit data.                                      ;
82                     ;----------------------------------------------------------------;
83                     ;
84 0021                USART_INIT:
85 0021 AF             XOR    A              ;CLEAR A
86 0022 D3 F5          OUT    (SER_CONTROL),A ;DO A SAFE RESET SEQUENCE
87 0024 D3 F5          OUT    (SER_CONTROL),A ;
88 0026 D3 F5          OUT    (SER_CONTROL),A ;
89 0028 3E 40          LD     A,40H          ;RESET COMMAND
90 002A D3 F5          OUT    (SER_CONTROL),A ;INTERNAL RESET OF USART
91 002C 3E 4E          LD     A,01001110B    ;MODE WORD
92 002E D3 F5          OUT    (SER_CONTROL),A ;SET 8251A MODE
93 0030 3E 15          LD     A,00010101B    ;COMMAND WORD: ENABLE RECEIVE AND
94 0032 D3 F5          OUT    (SER_CONTROL),A ;TRANSMIT
95 0034 C9             RET                   ;END
96                                           ;
97                     ;----------------------------------------------------------------;
98                     ;    IO_INIT                                                     ;
99                     ;    This module initializes the two 8255 chips on the SB8466 I/O ;
```

```
100             ;       card. Mode 0 control word #2 is assumed for both chips that    ;
101             ;       programs port A and C as output ports and port B as input.     ;
102             ;       The I/O addresses of the 8 ports, including the control ports, ;
103             ;       are listed below:                                               ;
104             ;                                                                       ;
105             ;       8255 #1 (U5):                                                   ;
106             ;              Port A(0):    70H (IO_P0)    output                      ;
107             ;              Port B(1):    71H (IO_P1)    input                       ;
108             ;              Port C(2):    72H (IO_P2)    output                      ;
109             ;              Control:      73H (IO_C1)    <-- 82H                     ;
110             ;       8255 #2 (U2):                                                   ;
111             ;              Port A(3):    74H (IO_P3)    output                      ;
112             ;              Port B(4):    75H (IO_P4)    input                       ;
113             ;              Port C(5):    76H (IO_P5)    output                      ;
114             ;              Control:      77H (IO_C2)    <-- 82H                     ;
115             ;       The bit definition of each port is defined in the include file, ;
116             ;       EQU.INC.                                                        ;
```

PHACO STDBUS SYSTEM COMPONENT INIT        3

```
117             ;                                                                       ;
118             ;-----------------------------------------------------------------------;
119             ;
120 0035        IO_INIT:
121             ;
122             ;       INITIALIZE THE FIRST 8255
123             ;
124 0035 3E 82          LD      A,10000010B     ;PORT A AND C OUTPUT, B INPUT
125 0037 D3 73          OUT     (IO_C1),A       ;
126             ;
127             ;       INITIALIZE THE SECOND 8255
128             ;
129 0039 D3 77          OUT     (IO_C2),A       ;
130             ;
131             ;       SET OUTPUT BITS
132             ;
133 003B AF             XOR     A               ;CLEAR A
134 003C 2F             CPL                     ;COMPLEMENT A
135 003D D3 70          OUT     (IO_P0),A       ;PORT A OF 1st 8255
136 003F D3 72          OUT     (IO_P2),A       ;PORT C OF 1st 8255
137 0041 D3 74          OUT     (IO_P3),A       ;PORT A OF 2nd 8255
138 0043 D3 76          OUT     (IO_P5),A       ;PORT C OF 2nd 8255
139 0045 C9             RET                     ;
140                                             ;
141             ;=======================================================================;
142             ;       DATA SEGMENT                                                    ;
143             ;=======================================================================;
144             ;
= 145 0046              INCLUD  ADDRESS.INC     ;
= 146           ;=======================================================================;
= 147           ;                                                                       ;
```

```
= 148        ;           ADDRESS.INC    PHACO SYSTEM GLOBAL EQUATES                    ;
= 149        ;                                                                          ;
= 150        ;==========================================================================;
= 151        ;                                                                          ;
= 152        ;              !!!!!!!!! CHANGE HISTORY !!!!!!!!!                          ;
= 153        ;                                                                          ;
= 154        ;           AUTHOR        DATE         CHANGE PURPOSE                      ;
= 155        ;           -----------------------------------------------------          ;
= 156        ;           T. LO         3 FEB 86     CREATION                            ;
= 157        ;           F. Lian       10 Feb. 86   Update                              ;
= 158        ;           F. Lian       10 April 86  Update                              ;
= 159        ;           T. Escorcio   24 June 86   Update                              ;
= 160        ;           T. Escorcio   7 July 86    Update                              ;
= 161        ;           T. Escorcio   4/1/87       add adaptive tuning constants       ;
= 162        ;                                                                          ;
= 163        ;--------------------------------------------------------------------------;
= 164        ;
= 165        ;------ DIGITAL I/O BOARD ADDRESSES
= 166        ;
= 167 0070   DIO_BASE      EQU   70H           ;BASE ADDRESS OF SB8466 CARD
= 168 0070   BITIOAD       EQU   DIO_BASE+0    ;
= 169 0070   IO_P0         EQU   DIO_BASE+0    ; PORT A OF 8255 #1
= 170 0071   IO_P1         EQU   DIO_BASE+1    ; PORT B OF 8255 #1
= 171 0072   IO_P2         EQU   DIO_BASE+2    ; PORT C OF 8255 #1
= 172 0073   IO_C1         EQU   DIO_BASE+3    ; CONTROL WORD ADDR. OF 8255 #1
= 173 0074   IO_P3         EQU   DIO_BASE+4    ; PORT A OF 8255 #2
= 174 0075   IO_P4         EQU   DIO_BASE+5    ; PORT B OF 8255 #2

PHACO STDBUS SYSTEM COMPONENT INIT      4

= 175 0076   IO_P5         EQU   DIO_BASE+6    ; PORT C OF 8255 #2
= 176 0077   IO_C2         EQU   DIO_BASE+7    ; CONTROL WORD ADDR. OF 8255 #2
= 177                                          ;
= 178        ;
= 179        ;------ COUNTER TIMER CHIP ADDRESSES
= 180        ;

PHACO COMMUNICATIONS DRIVER             1

1 0000              TITLE  'PHACO COMMUNICATIONS DRIVER'
2                   NAME   FUNCOMM_MODULE
3                   CSEG
4                   PAGESZ 66
5            ;
6            ;!!!!!!!!!!!!!!!!!!!!!!!!!!!!!!!!!!!!!!!!!!!!!!!!!!!!!!!!!!!!!!!!!!!!!!!!!;
```

PHACO COMMUNICATIONS DRIVER                1

```
1 0000              TITLE   'PHACO COMMUNICATIONS DRIVER'
2                   NAME    NETCOMM_MODULE
3                   CSEG
4                   PAGESZ  66
5           ;
6           ;;;;;;;;;;;;;;;;;;;;;;;;;;;;;;;;;;;;;;;;;;;;;;;;;;;;;;;;;;;;;;;;;;;;;;;;;
```

PHACO COMMUNICATIONS LINK MONITOR          1

```
1 0000              TITLE   'PHACO COMMUNICATIONS LINK MONITOR'
2                   NAME    PHUNT_MODULE
3                   CSEG
4                   PAGESZ  66
5           ;
6           ;;;;;;;;;;;;;;;;;;;;;;;;;;;;;;;;;;;;;;;;;;;;;;;;;;;;;;;;;;;;;;;;;;;;;;;;;
```

PHACO SYSTEM CLOCK                         1

```
1 0000              TITLE   'PHACO SYSTEM CLOCK'
2                   NAME    PCLOK_MODULE
3                   CSEG
4                   PAGESZ  66
5           ;
6           ;;;;;;;;;;;;;;;;;;;;;;;;;;;;;;;;;;;;;;;;;;;;;;;;;;;;;;;;;;;;;;;;;;;;;;;;;
```

PHACO DIAGNOSTIC ROUTINES                  1

```
1 0000              TITLE   'PHACO DIAGNOSTIC ROUTINES'
2                   NAME    DIAGNOSTIC_INT_MODULE
3                   CSEG
4
5           ;;;;;;;;;;;;;;;;;;;;;;;;;;;;;;;;;;;;;;;;;;;;;;;;;;;;;;;;;;;;;;;;;;;;;;;;;
6           ;                                                                       ;
7           ;                                                                       ;
8           ;                                                                       ;
9           ;=======================================================================;
10          ;               ;;;;;;; CHANGE HISTORY ;;;;;;;                           ;
11          ;                                                                       ;
12          ;       Author          Date           Change Purpose                   ;
13          ;       ---------------------------------------------------             ;
14          ;       T. Escorcio     11/30/87       Creation                         ;
15          ;                                                                       ;
16          ;                                                                       ;
17          ;=======================================================================;
18          ;                                                                       ;
19          ;-----------------------------------------------------------------------;
20          ;                                                                       ;
21          ;       Function:                                                       ;
                                                                    ;
22          ;       Registers:                                                      ;
23          ;       Accepts:
24          ;       Returns:
```

```
25                    ;        Flags:                                                      ;
26                    ;        Variables:                                                  ;
27                    ;        Constants:                                                  ;
28                    ;                                                                    ;
29                    ;     Pseudo Code:                                                   ;
30                    ;                                                                    ;
31                    ;--------------------------------------------------------------------;
32                    ;--------------------------------------------------------------------;
33                    ;                                                                    ;
34                    ;  Notes:                                                            ;
35                    ;                                                                    ;
36                    ;--------------------------------------------------------------------;
37                    ;
38                           DIAGNOSTIC                    ;
39                                                         ;
40 0000 DB 71                 IN      A,(IO_P1)            ;
41 0002 32 00 00   D          LD      (SNAPSHOT),A         ;
42                         DIAG1                           ;
43 0005 21 00 00   E          LD      HL,CHNG_FN           ;Use flag to determine conditions
44 0008 CB 46                 BIT     0,(HL)               ;
45 000A CA 10 00   C          JP      Z,PROCESS            ;If true, invoke new mode
46                                                         ; otherwise, re-execute
47                         ALTER                           ;
48 000D CD 75 00   C          CALL    NEW_MODE             ;Request new mode
49                         PROCESS                         ;
50 0010 21 00 00   E          LD      HL,CHNG_FN           ;Reset the change flag
51 0013 CB 86                 RES     0,(HL)               ;
52                                                         ;
53 0015 CD 1B 00   C          CALL    EXECUTION            ;Execute function
54                                                         ;
55 0018 C3 05 00   C          JP      DIAG1                ;
56                                                         ;
57

59                    ;--------------------------------------------------------------------;
59                    ;                 SUBROUTINES                                        ;
60                    ;--------------------------------------------------------------------;
61                    ;
62                         EXECUTION                       ;
63                                                         ;
64 001B CD 39 00   C          CALL    SET_LED              ;Illuminate the appropriate mode led
65 001E CD 30 00   C          CALL    WAITKEY              ;Wait here, (before executing new mode),
66                         INVOKE                          ;
67 0021 21 00 00   E          LD      HL,CHNG_FN           ;Test for a mode change condition
68 0024 CB 46                 BIT     0,(HL)               ;
69 0026 C2 2F 00   C          JP      NZ,EXIT              ;If not, continue execution
70                                                         ; otherwise, leave
71 0029 CD 65 00   C          CALL    DOLIST               ;Execute standard functions
72                                                         ;
```

```
 73 002C C3 21 00    C              JP      INVOKE          ;Continue
 74                                                         ;
 75                         EXIT                            ;
 76 002F C9                         RET                     ;Leave to process new mode
 77                                                         ;
 78                         ;
 79                         ;----- Wait here until the key is released
 80                         ;
 81                         WAITKEY                         ;
 82 0030 3A 00 00    E              LD      A,(KEYNUM)      ;Keep checking to see if key is released
 83 0033 FE 00                      CP      0               ;
 84 0035 C2 30 00    C              JP      NZ,WAITKEY      ;If not, continue waiting
 85                                                         ; otherwise, send the release code
 86                         EX_WAIT                         ;
 87 0038 C9                         RET                     ;Leave with RELEASE condition satisfied
 88                                                         ;
 89                         ;
 90                         ;----- Here is where the mode leds are updated to reflect the selection
 91                         ;
 92                         SET_LED                         ;
 93 0039 3A 02 00    D              LD      A,(FUNCTION)    ;Get current mode
 94                         ZERO?                           ;
 95 003C FE 00                      CP      0               ;Mode 0 ?
 96 003E C2 46 00    C              JP      NZ,ONE?         ;If false, continue
 97 0041 3E 00                      LD      A,00000000B     ; otherwise, assign pattern
 98 0043 C3 61 00    C              JP      SET             ;
 99                         ONE?                            ;
100 0046 FE 01                      CP      1               ;Mode 1 ?
101 0048 C2 50 00    C              JP      NZ,TWO?         ;If false, continue
102 004B 3E 30                      LD      A,00110000B     ; otherwise, assign pattern
103 004D C3 61 00    C              JP      SET             ;
104                         TWO?                            ;
105 0050 FE 02                      CP      2               ;Mode 2 ?
106 0052 C2 5A 00    C              JP      NZ,THREE?       ;If false, continue
107 0055 3E 0C                      LD      A,00001100B     ; otherwise, assign pattern
108 0057 C3 61 00    C              JP      SET             ;
109                         THREE?                          ;
110 005A FE 03                      CP      3               ;Mode 3 ?
111 005C C2 64 00    C              JP      NZ,EX_SET       ;If false, don't set anything
112 005F 3E 03                      LD      A,00000011B     ; otherwise, assign pattern
113                                                         ;
114 0061 32 00 00    E     SET      LD      (MODELED),A     ;Write result
115                                                         ;
116                         EX_SET                          ;
117 0064 C9                         RET                     ;Leave with led  properly set
118                                                         ;
119                         ;
120                         ;----- Diagnostic execution list
```

```
121                     ;
122             DOLIST
123 0065 CD 00 00   E       CALL    KEYBOARD        ;Watch the keyboard for input
124 0069 CD D9 01   C       CALL    XTREE           ;
125 006B CD 33 02   C       CALL    STAND_ALONE     ;
126 006E CD 9F 02   C       CALL    AUDIO           ;
127 0071 CD C3 02   C       CALL    SHOW_PEDAL      ;
128                                                 ;
129 0074 C9                 RET
130                                                 ;
131                     ;
132                     ;------
133                     ;
134             NEW_MODE                            ;
135                                                 ;
136 0075 21 00 00   E       LD      HL,STANDALONE   ;
137 0079 CB C6              SET     0,(HL)          ;
138                                                 ;
139 007A 3A 02 00   D       LD      A,(FUNCTION)    ;Remember last mode...
140 007D 32 01 00   D       LD      (LAST_MODE),A   ; ...should request be denied
141                                                 ;
142 0080 3A 00 00   E       LD      A,(KEYNUM)      ;Set new FUNCTION
143 0083 32 02 00   D       LD      (FUNCTION),A    ;
144             MODE_0?                             ;
145 0086 FE 00              CP      0               ;Is it mode 0 ?
146 0088 C2 8E 00   C       JP      NZ,MODE_1?      ;If not, try MODE_1

147                                                 ; otherwise, leave
148 008B C3 C4 00   C       JP      RETURN          ;
149                                                 ;
150             MODE_1?                             ;
151 008E FE 01              CP      1               ;Is it mode 1 ?
152 0090 C2 9C 00   C       JP      NZ,MODE_2?      ;If not, try MODE_2
153                                                 ; otherwise, continue
154 0093 21 00 00   E       LD      HL,SONG1        ;Point to the SONG
155 0096 22 00 00   E       LD      (MELODY),HL     ;
156                                                 ;
157 0099 C3 B5 00   C       JP      BROADCAST       ;Mode reported, so leave
158             MODE_2?                             ;
159 009C FE 02              CP      2               ;Is it mode 2 ?
160 009E C2 AA 00   C       JP      NZ,MODE_3?      ;If not, try MODE_3
161                                                 ; otherwise, continue
162 00A1 21 00 00   E       LD      HL,SONG2        ;Point to the SONG
163 00A4 22 00 00   E       LD      (MELODY),HL     ;
164                                                 ;
165 00A7 C3 B5 00   C       JP      BROADCAST       ;Mode reported, so leave
166             MODE_3?                             ;
167 00AA FE 03              CP      3               ;Is it mode 3 ?
168 00AC C2 C4 00   C       JP      NZ,RETURN       ;If not, leave
169                                                 ; otherwise, continue
170 00AF 21 00 00   E       LD      HL,SONG3        ;Point to the SONG
171 00B2 22 00 00   E       LD      (MELODY),HL     ;
172                                                 ;
173             BROADCAST                           ;
```

```
174 00B5 21 00 00    E        LD      HL,RYTHM         ;Set the RYTHM for audio feedback
175 00B8 36 0A                LD      (HL),KEY_RYTHM   ;
176                                                    ;
177 00BA 21 00 00    E        LD      HL,CONDUCTOR     ;Set the CONDUCTOR's queue
178 00BD CB C6                SET     0,(HL)           ;
179                                                    ;
180 00BF 21 00 00    E        LD      HL,NOTE          ;Force pointr to zero, this will
181 00C2 36 00                LD      (HL),0           ; override any pending music
182                                                    ;
183                  RETURN                            ;
184 00C4 C9                   RET                      ;
185                                                    ;
186
187         ;----------------------------------------------------------;
188         ;                                                          ;
189         ;    Function:                                             ;
190         ;                                                          ;
191         ;    Registers:                                            ;
192         ;      Accepts:                                            ;
193         ;      Returns:                                            ;
194         ;        Flags:                                            ;
195         ;    Variables:                                            ;
196         ;    Constants:                                            ;
197         ;                                                          ;
198         ;    Pseudo Code:                                          ;
199         ;                                                          ;
200         ;----------------------------------------------------------;
201         ;----------------------------------------------------------;
202         ;                                                          ;
203         ;    Notes:                                                ;
204         ;                                                          ;
205         ;         SYST_FLAG  ---------------------------|          ;
206         ;         FS_DOWN    --------------------------|  |        ;
207         ;         PEDAL      -------------------------| |  |       ;
208         ;         LOCKOUT    ------------------------| | |  |      ;
209         ;                                            | | | |       ;
210         ;                          D7 D6 D5 D4  D3 D2 D1 D0        ;
211         ;                          X  X  X  X   X  X  X  X         ;
212         ;                          | | | |                         ;
213         ;         LINK       -----| | | |                          ;
214         ;         CHNG_FN    -------| | |                          ;
215         ;         ASPIRATION -------- | |                          ;
216         ;         PHACO      ---------- |                          ;
217                                                                    ;
218         ;----------------------------------------------------------;
219
220                  FLAGS                              ;
221 00C5 21 00 00    E        LD      HL,SYST_FLAG     ;Get the flag
222 00C8 7E                   LD      A,(HL)           ;Place it 1st
223                                                    ;
224 00C9 21 00 00    E        LD      HL,FS_DOWN       ;Get the flag
225 00CC 46                   LD      B,(HL)           ;
226 00CD CB 10                RL      B                ;Place it 2nd
227 00CF B0                   OR      B                ;
```

```
228                                                          ;
229 00D0 21 00 00    E      LD    HL,PEDAL        ;Get the flag
230 00D3 46                 LD    B,(HL)          ;
231 00D4 CB 10              RL    B               ;Place it 3rd 232 00D6 CB 10              RL    B               ;
233 00D8 B0                 OR    B               ;
234                                                          ;
235 00D9 21 00 00    E      LD    HL,LOCKOUT      ;Get the flag
236 00DC 46                 LD    B,(HL)          ;
237 00DD CB 10              RL    B               ;Place it 4th
238 00DF CB 10              RL    B               ;
239 00E1 CB 10              RL    B               ;
240 00E3 B0                 OR    B               ;
241                                                          ;
242 00E4 21 00 00    E      LD    HL,PHACO        ;Get the flag
243 00E7 46                 LD    B,(HL)          ;
244 00E8 CB 10              RL    B               ;Place it 5th
245 00EA CB 10              RL    B               ;
246 00EC CB 10              RL    B               ;
247 00EE CB 10              RL    B               ;
248 00F0 B0                 OR    B               ;
249                                                          ;
250 00F1 21 00 00    E      LD    HL,ASPIRATION   ;Get the flag
251 00F4 46                 LD    B,(HL)          ;
252 00F5 CB 10              RL    B               ;Place it 6th
253 00F7 CB 10              RL    B               ;
254 00F9 CB 10              RL    B               ;
255 00FB CB 10              RL    B               ;
256 00FD CB 10              RL    B               ;
257 00FF B0                 OR    B               ;
258                                                          ;
259 0100 21 00 00    E      LD    HL,MOMENTARY    ;Get the flag
260 0103 46                 LD    B,(HL)          ;
261 0104 CB 10              RL    B               ;Place it 7th
262 0106 CB 10              RL    B               ;
263 0108 CB 10              RL    B               ;
264 010A CB 10              RL    B               ;
265 010C CB 10              RL    B               ;
266 010E CB 10              RL    B               ;
267 0110 B0                 OR    B               ;
268                                                          ;
269 0111 21 00 00    E      LD    HL,LINK         ;Get the flag
270 0114 46                 LD    B,(HL)          ;
271 0115 CB 10              RL    B               ;Place it 8th
272 0117 CB 10              RL    B               ;
273 0119 CB 10              RL    B               ;
274 011B CB 10              RL    B               ;
275 011D CB 10              RL    B               ;
```

```
276 011F CB 10              RL      B         ;
277 0121 CB 10              RL      B         ;
278 0123 B0                 OR      B         ;
279                                           ;
280 0124 D3 74              OUT     (IO_P3),A ;Write it to the I/O port
281                                           ;
282 0126 C9                 RET               ;
283                                           ;
284                  ;
285                  ;------ Hidden service switch
286                  ;
287                  HSWITCH                  ;
288 0127 3A 06 00  D        LD      A,(POLL)  ;
289 012A 3C                 INC     A         ;
290 012B 32 06 00  D        LD      (POLL),A  ;
291                                           ;
292 012E 06 03              LD      B,3       ;
293 0130 B8                 CP      B         ;
294 0131 DA 56 01  C        JP      C,LEAVE   ;
295                                           ;
296 0134 3E 00              LD      A,0       ;
297 0136 32 06 00  D        LD      (POLL),A  ;
298                                           ;
299 0139 DB 75              IN      A,(IO_P4) ;
300 013B 32 05 00  D        LD      (HSERVICE),A ;
301                                           ;
302 013E FE 00              CP      0         ;
303 0140 CA 56 01  C        JP      Z,LEAVE   ;
304                                           ;
305                  ;
306                  ;------ Audio feedback
307                  ;
308 0143 3E 01              LD      A,1       ;Set the RYTHM for audio feedback
309 0145 32 00 00  E        LD      (RYTHM),A ;
310 0148 21 0A 00  E        LD      HL,SCALE+10 ;Point to the SONG
311 014B 22 00 00  E        LD      (MELODY),HL ;
312 014E 21 00 00  E        LD      HL,CONDUCTOR ;Set the CONDUCTOR's queue
313 0151 CB C6              SET     0,(HL)    ;
314                                           ;
315 0153 CD 57 01  C        CALL    FIDDLER   ;
316                                           ;
317                  LEAVE                    ;
318 0156 C9                 RET               ;
319                                           ;
320                  ;
321                  ;------
322                  ;
323                  FIDDLER                  ;
```

```
324 0157 3A 05 00    D           LD      A,(HSERVICE)    ;
325 015A FE 00                   CP      0               ;
326 015C CA C2 01    C           JP      Z,OVER          ;
327                                                      ;
328 015F FE 80                   CP      10000000B       ;
329 0161 C2 75 01    C           JP      NZ,FIDD0        ;
330                                                      ;
331 0164 2A 00 00    E           LD      HL,(HERTZ)      ;
332 0167 11 01 00                LD      DE,1            ;
333 016A ED 5A                   ADC     HL,DE           ;
334 016C E2 BF 01    C           JP      PO,FIDDL        ;
335 016F 2A 00 00    E           LD      HL,(HERTZ)      ;
336                                                      ;
337 0172 C3 C2 01    C           JP      OVER            ;
338                      FIDD0                           ;
339 0175 FE 40                   CP      01000000B       ;
340 0177 C2 8B 01    C           JP      NZ,FIDD1        ;
341                                                      ;
342 017A 2A 00 00    E           LD      HL,(HERTZ)      ;
343 017D 11 01 00                LD      DE,1            ;
344 0180 ED 52                   SBC     HL,DE           ;
345 0182 E2 BF 01    C           JP      PO,FIDDL        ;
346 0185 2A 00 00    E           LD      HL,(HERTZ)      ;
347                                                      ;

348 0188 C3 C2 01    C           JP      OVER            ;
349                      FIDD1                           ;
350 018B 3A 05 00    D           LD      A,(HSERVICE)    ;
351 018E FE 00                   CP      0               ;
352 0190 CA C2 01    C           JP      Z,OVER          ;
353                                                      ;
354 0193 FE 20                   CP      00100000B       ;
355 0195 C2 A9 01    C           JP      NZ,FIDD2        ;
356                                                      ;
357 0198 2A 00 00    E           LD      HL,(HERTZ)      ;
358 019B 11 1E 00                LD      DE,30           ;
359 019E ED 5A                   ADC     HL,DE           ;
360 01A0 E2 BF 01    C           JP      PO,FIDDL        ;
361 01A3 2A 00 00    E           LD      HL,(HERTZ)      ;
362                                                      ;
363 01A6 C3 C2 01    C           JP      OVER            ;
364                      FIDD2                           ;
365 01A9 FE 10                   CP      00010000B       ;
366 01AB C2 C2 01    C           JP      NZ,OVER         ;
367                                                      ;
368 01AE 2A 00 00    E           LD      HL,(HERTZ)      ;
369 01B1 11 1E 00                LD      DE,30           ;
370 01B4 ED 52                   SBC     HL,DE           ;
371 01B6 E2 BF 01    C           JP      PO,FIDDL        ;
```

```
372 01BF 2A 00 00      E           LD    HL,(HERTZ)       ;
373                                                       ;
374 01BC C3 C2 01      C           JP    OVER             ;
375                        FIDDL                          ;
376 01BF 22 00 00      E           LD    (HERTZ),HL       ;
377                                                       ;
378                        OVER                           ;
379 01C2 2A 00 00      E           LD    HL,(PHASE)       ;
380 01C5 22 00 00      E           LD    (SDAC01),HL      ;
381 01C8 2A 00 00      E           LD    HL,(CURRENT)     ;
382 01CB 22 00 00      E           LD    (SDAC02),HL      ;
383                                                       ;
384 01CE FE 02                     CP    00000010B        ;
385 01D0 C2 D9 01      C           JP    NZ,BRANCH        ;
386                                                       ;
387 01D3 21 00 00      E           LD    HL,RELAPSE       ;
388 01D6 CB C6                     SET   0,(HL)           ;
389                                                       ;
390                        BRANCH                         ;
391 01D9 C9                        RET                    ;
392                                                       ;
393                        ;                              ;
394                        ;------                        ;
395                        ;                              ;
396                        XTREE                          ;
397 01DA 3A 02 00      D           LD    A,(FUNCTION)     :
398 01DD FE 02                     CP    2                ;
399 01DF C2 06 02      C           JP    NZ,XTREE1        ;
400                                                       ;
401 01E2 AF                        XOR   A                ;
402 01E3 2F                        CPL                    ;
403 01E4 32 00 00      E           LD    (MAX35),A        ;
404 01E7 32 00 00      E           LD    (MAX70),A        ;
405 01EA 32 00 00      E           LD    (MAX100),A       ;

406 01ED 32 00 00      E           LD    (ACT35),A        ;
407 01EF 32 00 00      E           LD    (ACT70),A        ;
408 01F2 32 00 00      E           LD    (ACT100),A       ;
409 01F5 32 00 00      E           LD    (MODELED),A      ;
410 01F8 32 00 00      E           LD    (CONN_LED),A     ;
411                                                       ;
412 01FB 21 00 00      E           LD    HL,DISPLAY       ;Write 888 to the display
413 01FE 36 88                     LD    (HL),136         ;
414 0200 23                        INC   HL               ;
415 0201 36 88                     LD    (HL),136         ;
416                                                       ;
417 0203 C3 2C 02      C           JP    GONE             ;
418                                                       ;
419                        XTREE1                         ;
```

```
420 0206 3A 02 00      D         LD      A,(FUNCTION)    ;
421 0209 21 03 00      D         LD      HL,OLDFUNC      ;
422 020C BE                      CP      (HL)            ;
423 020D CA 2C 02      C         JP      Z,GONE          ;
424                                                      ;
425 0210 AF                      XOR     A               ;
426 0211 32 00 00      E         LD      (MAX35),A       ;
427 0214 32 00 00      E         LD      (MAX70),A       ;
428 0217 32 00 00      E         LD      (MAX100),A      ;
429 021A 32 00 00      E         LD      (ACT35),A       ;
430 021D 32 00 00      E         LD      (ACT70),A       ;
431 0220 32 00 00      E         LD      (ACT100),A      ;
432                          ;   LD      (MODELED),A     ;
433 0223 32 00 00      E         LD      (CONN_LED),A    ;
434                                                      ;
435 0226 21 00 00      E         LD      HL,DISPLAY      ;
436 0229 77                      LD      (HL),A          ;
437 022A 23                      INC     HL              ;
438 022B 77                      LD      (HL),A          ;
439                                                      ;
440                       GONE
441 022C 3A 02 00      D         LD      A,(FUNCTION)    ;
442 022F 32 03 00      D         LD      (OLDFUNC),A     ;
443                                                      ;
444 0232 C9                      RET                     ;
445                                                      ;
446                          ;
447                          ;------
448                          ;
449                       STAND_ALONE                    ;
450                                                      ;
451 0233 3A 02 00      D         LD      A,(FUNCTION)    ;
452 0236 FE 01                   CP      1               ;
453 0238 C2 6D 02      C         JP      NZ,STND1        ;
454                                                      ;
455 023B CD 00 00      E         CALL    VCO_ON          ;
456                                                      ;
457 023E 21 00 00      E         LD      HL,SYST_FLAG    ;
458 0241 CB C6                   SET     0,(HL)          ;
459                                                      ;
460 0243 21 00 00      E         LD      HL,FN_MODE      ;
461 0246 36 01                   LD      (HL),1          ;
462                                                      ;
463 0248 21 00 00      E         LD      HL,PHACO        ;

464 024B CB C6                   SET     0,(HL)          ;
465                                                      ;
466 024D 21 00 00      E         LD      HL,LOCKOUT      ;
467 0250 CB C6                   SET     0,(HL)          ;
```

```
468
469  0252 21 00 00      E         LD      HL,PEDAL            ;
470  0255 CB C6                   SET     0,(HL)              ;
471                                                           ;
472  0257 21 00 00      E         LD      HL,FS_DOWN          ;
473  025A CB C6                   SET     0,(HL)              ;
474                                                           ;
475  025C 21 00 00      E         LD      HL,TUNED            ;
476  025F CB C6                   SET     0,(HL)              ;
477                                                           ;
478  0261 CD 00 00      E         CALL    BARGRAPH            ;
479  0264 CD 00 00      E         CALL    BEEPER              ;
480  0267 CD 00 00      E         CALL    SWEEPER             ;
481                                                           ;
482  026A C3 98 02      C         JP      DEPART              ;
483                                                           ;
484                             STND1                         ;
485  026D 3A 02 00      D         LD      A,(FUNCTION)        ;
486  0270 21 04 00      D         LD      HL,LASTFUNC         ;
487  0273 BE                      CP      (HL)                ;
488  0274 CA 98 02      C         JP      Z,DEPART            ;
489                                                           ;
490  0277 21 00 00      E         LD      HL,FN_MODE          ;
491  027A 36 00                   LD      (HL),0              ;
492                                                           ;
493  027C 21 00 00      E         LD      HL,PHACO            ;
494  027F CB 86                   RES     0,(HL)              ;
495                                                           ;
496  0281 21 00 00      E         LD      HL,LOCKOUT          ;
497  0284 CB 86                   RES     0,(HL)              ;
498                                                           ;
499  0286 21 00 00      E         LD      HL,PEDAL            ;
500  0289 CB 86                   RES     0,(HL)              ;
501                                                           ;
502  028B 21 00 00      E         LD      HL,FS_DOWN          ;
503  028E CB 86                   RES     0,(HL)              ;
504                                                           ;
505  0290 21 00 00      E         LD      HL,TUNED            ;
506  0293 CB 86                   RES     0,(HL)              ;
507                                                           ;
508  0295 CD 00 00      E         CALL    VCO_OFF             ;
509                                                           ;
510                             DEPART                        ;
511  0298 3A 02 00      D         LD      A,(FUNCTION)        ;
512  029B 32 04 00      D         LD      (LASTFUNC),A        ;
513                                                           ;
514  029E C9                      RET                         ;
515                                                           ;
516                         ;                                 ;
517                         ;------                           ;
518                         ;                                 ;
519                             AUDIO                         ;
520  029F 3A 02 00      D         LD      A,(FUNCTION)        ;
521  02A2 FE 03                   CP      3                   ;
```

```
522 02A4 C2 C7 02    C              JP      NZ,FINI          ;
523                                                           ;
524 02A7                     LOOP                             
525 02A7 21 00 00    E              LD      HL,CONDUCTOR     ;Set the CONDUCTOR's queue
526 02AA CB 46                      BIT     0,(HL)           ;
527 02AC C2 A7 02    C              JP      NZ,LOOP          ;
528                                                           ;
529 02AF 3E 14                      LD      A,20             ;Set the RYTHM for audio feedback
530 02B1 32 00 00    E              LD      (RYTHM),A        ;
531 02B4 21 00 00    E              LD      HL,GLISSANDO     ;Point to the SONG
532 02B7 22 00 00    E              LD      (MELODY),HL      ;
533 02BA 21 00 00    E              LD      HL,CONDUCTOR     ;Set the CONDUCTOR's queue
534 02BD CB C6                      SET     0,(HL)           ;
535 02BF 21 00 00    E              LD      HL,NOTE          ;Force pointr to zero, this will
536 02C2 36 00                      LD      (HL),0           ; override any pending music
537                                                           ;
538 02C4 C3 A7 02    C              JP      LOOP             ;
539                          FINI                             ;
540 02C7 C9                         RET                       ;
541                                                           ;
542                          ;
543                          ;
544                          ;
545                          SHOW_PEDAL                        ;
546                                                           ;
547 02C8 3A 00 00    D              LD      A,(SNAPSHOT)     ;
548 02CB E6 08                      AND     00001000B        ;
549 02CD FE 00                      CP      0                ;
550 02CF CA DE 02    C              JP      Z,BRNCH          ;
551                          SHW_PDL                           ;
552 02D2 3A 00 00    E              LD      A,(POSITION)     ;
553 02D5 CD 00 00    E              CALL    BN2BCD           ;
554 02D8 22 00 00    E              LD      (DISPLAY),HL     ;DISPLAY the result
555                                                           ;
556 02DB C3 D2 02    C              JP      SHW_PDL          ;
557                                                           ;
558                          BRNCH                             ;
559 02DE C9                         RET                       ;
560                                                           ;
561                          ;================================================================;
562                          ;     DATA SEGMENT                                                ;
563                          ;================================================================;
564                          ;
=565 02DF                           INCLUD  EQU.INC          ;INCLUDE THE CONSTANTS IN ASSEMBLY
=566                          ;================================================================;
=567                          ;                                                                ;
=568                          ;     EQU.INC        PHACO SYSTEM GLOBAL EQUATES                 ;
=569                          ;                                                                ;
=570                          ;================================================================;
=571                          ;                                                                ;
=572                          ;          IIIIIIIII CHANGE HISTORY IIIIIIIII                    ;
=573                          ;                                                                ;
=574                          ;     AUTHOR         DATE           CHANGE PURPOSE               ;
=575                          ;     ----------------------------------------------------       ;
```

```
= 576              ;       T. LO           3 FEB 86        CREATION                          ;
= 577              ;       F. Lian         10 Feb. 86      Update                            ;
= 578              ;       F. Lian         10 April 86     Update                            ;

= 579              ;       T. Escorcio     24 June 86      Update                            ;
= 580              ;       T. Escorcio     7 July 86       Update                            ;
= 581              ;       T. Escorcio     4/1/87          add adaptive tuning constants     ;
= 582              ;
= 583              ;-----------------------------------------------------------------;
= 584              ;
= 585              ;------ TOP OF RAM MARKER
= 586              ;
= 587 8000         RAM_END         EQU     8000H           ;32K CONFIGURATION
= 588              ;
= 589              ;------ INTERRUPT LOOP TIMING CONSTANTS
= 590              ;
= 591 01E9         SAMPFRQ         EQU     489+2           ;INTERRUPT SAMPLING FREQUENCY
= 592 0002         DIV480HZ        EQU     2               ;480 HZ DIVIDER
= 593 0004         DIV240HZ        EQU     4               ;240 HZ DIVIDER
= 594 0008         DIV120HZ        EQU     8               ;120 HZ DIVIDER
= 595 0010         DIV60HZ         EQU     16              ; 60 HZ DIVIDER
= 596 0020         DIV30HZ         EQU     32              ; 30 HZ DIVIDER
= 597 0060         DIV10HZ         EQU     96              ; 10 HZ DIVIDER
= 598                                                      ;
= 599              ;
= 600              ;------ System counter parameters
= 601              ;
= 602 0168         ELAPS1          EQU     168H            ;3 SECOND TIMER VALUE (HUNTER)
= 603 05A0         ELAPS2          EQU     5A0H            ;3 SECOND TIMER VALUE (COM. REPLY)
= 604 0020         ELAPS3          EQU     020H            ;BEEPER DURATION
= 605 0300         ELAPS4          EQU     0300H           ;BEEPER COUNTER SAMPLING RATE
= 606 0078         ELAPS5          EQU     120             ;SCANNER INTERVAL
= 607                                                      ;
= 608              ;
= 609              ;------ PROGRAM THRESHOLD LEVELS
= 610              ;
= 611 0000         MIN             EQU     00H             ;
= 612 00FF         MAX             EQU     0FFH            ;
= 613 0001         TRUE            EQU     00000001B       ;
= 614 0000         FALSE           EQU     00000000B       ;
= 615 01F4         BUFF_SIZE       EQU     500             ;
= 616 000A         KEY_RYTHM       EQU     10              ;Key music duration time
= 617 0004         KEY_TIME        EQU     4               ;
= 618 000F         BEEP_TIME       EQU     15              ;
= 619 0640         BEGINNING       EQU     1600            ;
= 620 0800         FULL            EQU     2048            ;
= 621
= 622              ;=================================================================;
= 623 020F
```

```
= 624 02DF
= 625 02DF                  INCLUD  ADDRESS.INC    ;
= 626                ;==========================================================;
= 627                ;                                                          ;
= 628                ;    ADDRESS.INC    PHACO SYSTEM GLOBAL EQUATES            ;
= 629                ;                                                          ;
= 630                ;==========================================================;
= 631                ;                                                          ;
= 632                ;          ********** CHANGE HISTORY **********            ;
= 633                ;                                                          ;
= 634                ;     AUTHOR          DATE         CHANGE PURPOSE          ;
= 635                ;     --------------------------------------------         ;
= 636                ;     T. LO           3 FEB 86     CREATION                ;
= 637                ;     F. Lian         10 Feb. 86   Update                  ;
= 638                ;     F. Lian         10 April 86  Update                  ;
= 639                ;     T. Escorcio     24 June 86   Update                  ;
= 640                ;     T. Escorcio     7 July 86    Update                  ;
= 641                ;     T. Escorcio     4/1/87       add adaptive tuning constants ;
= 642                ;                                                          ;
= 643                ;----------------------------------------------------------;
= 644                ;
= 645                ;------ DIGITAL I/O BOARD ADDRESSES
= 646                ;
= 647 0070           DIO_BASE        EQU     70H              ;BASE ADDRESS OF SS466 CARD
= 648 0070           BITIOAD         EQU     DIO_BASE+0       ;
= 649 0070           IO_P0           EQU     DIO_BASE+0       ; PORT A OF 8255 #1
= 650 0071           IO_P1           EQU     DIO_BASE+1       ; PORT B OF 8255 #1
= 651 0072           IO_P2           EQU     DIO_BASE+2       ; PORT C OF 8255 #1
= 652 0073           IO_C1           EQU     DIO_BASE+3       ; CONTROL WORD ADDR. OF 8255 #1
= 653 0074           IO_P3           EQU     DIO_BASE+4       ; PORT A OF 8255 #2
= 654 0075           IO_P4           EQU     DIO_BASE+5       ; PORT B OF 8255 #2
= 655 0076           IO_P5           EQU     DIO_BASE+6       ; PORT C OF 8255 #2
= 656 0077           IO_C2           EQU     DIO_BASE+7       ; CONTROL WORD ADDR. OF 8255 #2
= 657                                                         ;
= 658
= 659                ;------ COUNTER TIMER CHIP ADDRESSES
= 660                ;
= 661 00F0           CTC_BASE        EQU     0F0H             ;BASE ADDRESS OF CTC
= 662 00F0           CTCADR          EQU     CTC_BASE+0       ;
= 663 00F0           CTC_C0          EQU     CTC_BASE+0       ; CHANNEL 0
= 664 00F1           CTC_C1          EQU     CTC_BASE+1       ; CHANNEL 1
= 665 00F2           CTC_C2          EQU     CTC_BASE+2       ; CHANNEL 2
= 666 00F3           CTC_C3          EQU     CTC_BASE+3       ; CHANNEL 3
= 667                ;
= 668                ;------ SERIAL PORT ADDRESSES
= 669                ;
= 670 00F4           SIO_BASE        EQU     0F4H             ;BASE ADDRESS OF 8251A (USART)
= 671 00F4           SERADR          EQU     SIO_BASE+0       ;
= 672 00F4           SER_PORT        EQU     SIO_BASE+0       ; SERIAL PORT ADDR.
= 673 00F5           SER_CONTROL     EQU     SIO_BASE+1       ; 8251A CONTROL PORT ADDR.
= 674                                                         ;
= 675 007C           PWR_PORT        EQU     7CH              ;
= 676                                                         ;
= 677 007E           SERVICE         EQU     7EH              ;SERVICE SWITCH ADDRESS
= 678                                                         ;
= 679                                                         ;
= 680                ;==========================================================;
```

```
681
682                         DSEG                    ;
683                                                 ;
684 0000 00        SNAPSHOT     DB      0           ;Record keypad during invocation
685 0001 00        LAST_MODE    DB      0           ;Track the most current mode
686 0002 00        FUNCTION     DB      0           ;Store current mode request
687 0003 00        OLDFUNC      DB      0           ;Store last mode request
688 0004 00        LASTFUNC     DB      0           ;Store last mode request
689
690 0005 00        HSERVICE     DB      0           ;
691 0006 00        POLL         DB      0           ;
692                                                                                 ;
693                ;-------------------------------------------------------------;
694                ;                                                             ;

695                ;     EXTERNAL VARIABLE DECLARATION                           ;
696                ;                                                             ;
697                ;-------------------------------------------------------------;
698                ;
699                        EXTRN   SYST_FLAG, FS_DOWN, PEDAL, LOCKOUT, PHACO, ASPIRATION
700                        EXTRN   CHNG_FN, LINK, MOMENTARY, HERTZ, SWEEPER, FN_MODE
701                        EXTRN   RYTHM, SCALE, MELODY, CONDUCTOR, BEEPER, BARGRAPH
702                        EXTRN   CURRENT, PHASE, SDAC01, SDAC02, SDAC03, GLISSANDO
703                        EXTRN   SONG1, SONG2, SONG3, NOTE, KEYBOARD, KEYNUM, MODELED
704                        EXTRN   STANDALONE, VCO_ON, VCO_OFF, RELAPSE, TUNED
705                        EXTRN   MAX35, MAX70, MAX100, ACT35, ACT70, ACT100
706                        EXTRN   CONN_LED, DISPLAY, POSITION, BN2BCD
707                                                                              ;
708                ;-------------------------------------------------------------;
709                ;                                                             ;
710                ;     PUBLIC VARIABLE DECLARATION                             ;
711                ;                                                             ;
712                ;-------------------------------------------------------------;
713                ;
714                        PUBLIC  FLAGS, HSWITCH, HSERVICE
715                        PUBLIC  DIAGNOSTIC
716                                                                              ;
717                ;=============================================================;
718                ;
719                ;IIIIIIIIIIIIIIIIIIIIIIIIIIIIIIIIIIIIIIIIIIIIIIIIIIIIIIIIIIIII;
720                ;
721 0007                   END

ERRORS = 0000
```

PHACO FUNCTION CHANGE CONTROLLER 1

```
1 0000                          TITLE   'PHACO FUNCTION CHANGE CONTROLLER'
2                               NAME    PCHNG_MAIN_MODULE
3                               CSEG
4                               PAGESZ  66
5                         ;
6                         ;IIIIIIIIIIIIIIIIIIIIIIIIIIIIIIIIIIIIIIIIIIIIIIIIIIIIIIIIIIIIIIIIIIII;
```

PHACO SYSTEM Z80 INTERRUPT HANDLER 1

```
1 0000                          TITLE   'PHACO SYSTEM Z80 INTERRUPT HANDLER'
2                               NAME    PINTR_MODULE
3                               CSEG
4                               PAGESZ  66
5                         ;
6                         ;IIIIIIIIIIIIIIIIIIIIIIIIIIIIIIIIIIIIIIIIIIIIIIIIIIIIIIIIIIIIIIIIIIII;
7                         ;                                                                    ;
8                         ;              PHACO SYSTEM INTERRUPT HANDLER                        ;
9                         ;                                                                    ;
10                        ;====================================================================;
11                        ;            IIIIIII CHANGE HISTORY IIIIIII                          ;
12                        ;                                                                    ;
13                        ;       Author        Date         Change Purpose                    ;
14                        ;       ----------------------------------------------               ;
15                        ;       F.Lian        4/13/86      Creation (Code)                   ;
16                        ;       F. LIAN       4/21/86      audio control change              ;
17                        ;       F. LIAN       4/23/86      audio control change              ;
18                        ;       F. Lian       5/01/86      bargraph pattern gen.             ;
19                        ;       T.Escorcio    7/8/86       comm. interrupt calls             ;
20                        ;       T.Escorcio    7/29/86      correction and cleanup            ;
21                        ;                                                                    ;
22                        ;====================================================================;
23                        ;--------------------------------------------------------------------;
24                        ;          SETUP THE INTERRUPT TABLE IN RAM                          ;
25                        ;--------------------------------------------------------------------;
26                        ;
27 0000                   SET_TABLE
28                                                           ;IIIII PRIORITY 2 INTERRUPT IIIII
29 0000 11 00 00    E            LD      DE,CHAN0            ;      ( SET IN COUNTER MODE )
30 0003 ED 53 00 00 E            LD      (INT_TABLE+0),DE    ;CTC CHANNEL ASSIGNED TO BAUD RATE
31                                                           ; GENERATION
32                                                           ;IIIII PRIORITY 3 INTERRUPT IIIII
33 0007 11 00 00    E            LD      DE,CHAN1            ;
34 000A ED 53 02 00 E            LD      (INT_TABLE+2),DE    ;
35                                                           ;IIIII PRIORITY 4 INTERRUPT IIIII
36 000E 11 00 00    E            LD      DE,CHAN2            ;
37 0011 ED 53 04 00 E            LD      (INT_TABLE+4),DE    ;
38                                                           ;IIIII PRIORITY 5 INTERRUPT IIIII
39 0015 11 00 00    E            LD      DE,CHAN3            ;
40 0019 ED 53 06 00 E            LD      (INT_TABLE+6),DE    ;
41                                                           ;
42 001C C9                       RET                         ;
43                                                           ;
44                        ;====================================================================;
45                        ;       DATA SEGMENT                                                 ;
46                        ;====================================================================;
```

```
      47       ;
=  48 0010            INCLUD  EQU.INC       ;INCLUDE THE CONSTANTS IN ASSEMBLY
=  49          ;=================================================================;
=  50          ;                                                                 ;
=  51          ;      EQU.INC        PHACO SYSTEM GLOBAL EQUATES                 ;
=  52          ;                                                                 ;
=  53          ;=================================================================;
=  54          ;                                                                 ;
=  55          ;         !!!!!!!!! CHANGE HISTORY !!!!!!!!!                      ;
=  56          ;                                                                 ;
=  57          ;      AUTHOR        DATE          CHANGE PURPOSE                 ;
=  58          ;      ----------------------------------------------             ;

PHACO SYSTEM Z80 INTERRUPT HANDLER         2

=  59          ;      T. Lo         3 FEB 86      CREATION                       ;
=  60          ;      F. Lian       10 Feb. 86    Update                         ;
=  61          ;      F. Lian       10 April 86   Update                         ;
=  62          ;      T. Escorcio   24 June 86    Update                         ;
=  63          ;      T. Escorcio   7 July 86     Update                         ;
=  64          ;      T. Escorcio   4/1/87        add adaptive tuning constants  ;
=  65          ;                                                                 ;
=  66          ;-----------------------------------------------------------------;
=  67          ;
=  68          ;------ TOP OF RAM MARKER
=  69          ;
=  70 8000     RAM_END         EQU     8000H           ;32K CONFIGURATION
=  71          ;
=  72          ;------ INTERRUPT LOOP TIMING CONSTANTS
=  73          ;
=  74 01E3     SAMPFRQ         EQU     489+2           ;INTERRUPT SAMPLING FREQUENCY
=  75 0002     DIV480HZ        EQU     2               ;480 HZ DIVIDER
=  76 0004     DIV240HZ        EQU     4               ;240 HZ DIVIDER
=  77 0008     DIV120HZ        EQU     8               ;120 HZ DIVIDER
=  78 0010     DIV60HZ         EQU     16              ; 60 HZ DIVIDER
=  79 0020     DIV30HZ         EQU     32              ; 30 HZ DIVIDER
=  80 0060     DIV10HZ         EQU     96              ; 10 HZ DIVIDER
=  81                                                  ;
=  82          ;
=  83          ;------ System counter parameters
=  84          ;
=  85 0168     ELAPS1          EQU     168H            ;3 SECOND TIMER VALUE (HUNTER)
=  86 05A0     ELAPS2          EQU     5A0H            ;3 SECOND TIMER VALUE (COM. REPLY)
=  87 0020     ELAPS3          EQU     020H            ;BEEPER DURATION
=  88 0300     ELAPS4          EQU     0300H           ;BEEPER COUNTER SAMPLING RATE
=  89 0078     ELAPS5          EQU     120             ;SCANNER INTERVAL
=  90                                                  ;
=  91          ;
=  92          ;------ PROGRAM THRESHOLD LEVELS
=  93          ;
=  94 0000     MIN             EQU     00H             ;
```

```
=  95 00FF               MAX         EQU    0FFH           ;
=  96 0001               TRUE        EQU    00000001B      ;
=  97 0000               FALSE       EQU    00000000B      ;
=  98 01F4               BUFF_SIZE   EQU    500            ;
=  99 000A               KEY_RYTHM   EQU    10             ;Key music duration time
= 100 0004               KEY_TIME    EQU    4              ;
= 101 000F               BEEP_TIME   EQU    15             ;
= 102 0640               BEGINNING   EQU    1600           ;
= 103 0800               FULL        EQU    2048           ;
= 104                                                      ;
= 105                    ;==========================================================;
= 106 0010
= 107 0010
  108                                                                               ;
  109                    ;----------------------------------------------------------;
  110                    ;                                                          ;
  111                    ;       EXTERNAL VARIABLE DECLARATION                      ;
  112                    ;                                                          ;
  113                    ;----------------------------------------------------------;
  114                    ;
  115                            EXTRN   INT_TABLE, CHAN0, CHAN1, CHAN2, CHAN3
  116                                                                               ;
```

PHACO SYSTEM Z80 INTERRUPT HANDLER        3

```
  117                    ;----------------------------------------------------------;
  118                    ;                                                          ;
  119                    ;       PUBLIC VARIABLE DECLARATION                        ;
  120                    ;                                                          ;
  121                    ;----------------------------------------------------------;
  122                    ;
  123                            PUBLIC  SET_TABLE
  124                                                                               ;
  125                    ;==========================================================;
  126                    ;
  127                    ;IIIIIIIIIIIIIIIIIIIIIIIIIIIIIIIIIIIIIIIIIIIIIIIIIIIIIIIIII;
  128                    ;
  129 0010                       END
```

ERRORS = 0000

Z80 ASSEMBLER VER.  3.7PC            1

```
  1 0000
  2 0010                          TITLE   'PHACO SYSTEM Z80 KEYBOARD HANDLER'
  3                               NAME    PKEY_MODULE
  4                               CSEG
  5                               PAGESZ  66
  6                       ;
  7                       ;IIIIIIIIIIIIIIIIIIIIIIIIIIIIIIIIIIIIIIIIIIIIIIIIIIIIIIIII;
```

PHACO ERROR COMMUNICATION

```
      TITLE   'PHACO ERROR COMMUNICATION'
      NAME    PERR_MODULE
      CSEG
      PAGESZ  66
;
;IIIIIIIIIIIIIIIIIIIIIIIIIIIIIIIIIIIIIIIIIIIIIIIIIIIIIIIIIIIIIIIIIIIII;
```

PHACO CONTROLLER CARD DRIVER

```
      TITLE   'PHACO CONTROLLER CARD DRIVER'
      NAME    PAQ_MODULE
      PAGESZ  66.

;IIIIIIIIIIIIIIIIIIIIIIIIIIIIIIIIIIIIIIIIIIIIIIIIIIIIIIIIIIIIIIIIIIIII;
;                                                                     ;
;                    PHACO CONTROLLER CARD                            ;
;                                                                     ;
;=====================================================================;
;           IIIIIII    CHANGE HISTORY  IIIIIII                        ;
;                                                                     ;
;       Author       Date        Change Purpose                       ;
;       ----------------------------------------------                ;
;                                                                     ;
;       T.Escorcio   2/25/87     Creation                             ;
;       T.Escorcio   11/6/87     Add 4th D/A to control vco COURSE adj.;
;                                                                     ;
;=====================================================================;
;                                                                     ;
;---------------------------------------------------------------------;
;                                                                     ;
;      Function: Designed to service the Phaco Controller.            ;
;                                                                     ;
;      Register: AF, BC, DE, HL                                       ;
;       Accepts: None                                                 ;
;       Returns: DATA_BASE                                            ;
;         Calls: None                                                 ;
;         Flags: Z                                                    ;
;     Variables: DATA_BASE, ADIN0, ADIN1, ADIN2, ADIN3, DAOUT0        ;
;                DAOUT1, DAOUT2, DAOUT3                               ;
;     Constants: DUMMY, DA_BASE, AD_BASE, AD0, AD1, AD2, AD3, DA0LO   ;
;                DA0HI, DA1LO, DA1HI, DA2LO, DA2HI                    ;
;   Pseudo Code:                                                      ;
;                                                                     ;
;   A_TO_D                                                            ;
;       PORT_SELECT = and (PORT_SELECT, 00001111b)                    ;
;       index_y = AD_BASE + PORT_SELECT                               ;
;       index_x = DATA_BASE + PORT_SELECT                             ;
;       output (index_y, DUMMY)                                       ;
;       if (busy_flag) then                                           ;
;           input (hi_data, index_y+1)                                ;
;           input (lo_data, index_y+0)                                ;
;           hi_data = and (hi_data, 00001111b)                        ;
```

```
44   ;              output (index_x+1, hi_data)                ;
45   ;              output (index_x+0, lo_data)                ;
46   ;              increment PORT_SELECT                      ;
47   ;              increment PORT_SELECT                      ;
48   ;          endif                                          ;
49   ;       D_TO_A                                            ;
50   ;          counter = 8                                    ;
51   ;          port = DA_BASE + 5                             ;
52   ;          buffer = DATA_BASE + 15                        ;
53   ;          do while (count > 0)                           ;
54   ;              output port, buffer(contents)              ;
55   ;              decrement port                             ;
56   ;              decrement port                             ;
57   ;              decrement counter                          ;
58   ;          endo                                           ;
```

PHACO CONTROLLER CARD DRIVER                2

```
59   ;       EXIT                                              ;
60   ;          return                                         ;
61   ;                                                         ;
62   ;---------------------------------------------------------;
63   ;       NOTES                                             ;
64   ;       - This module is intended to be serviced by the 480 Hz ;
65   ;                interrupt.                               ;
66   ;       - Execution time is 148 fsec                      ;
67   ;                                                         ;
68   ;---------------------------------------------------------;

69                   CSEG                    ;
70   ;
71   ;---    PROCESS THE FOUR CHANNEL A/D CONVERTER, ONE PORT AT A TIME
72   ;
73 0000            A_TO_D
74 0000 3A 01 00  D     LD    A,(PORT_SELECT)   ;Get pointer
75 0003 E6 07           AND   00000111B         ;
76                                              ;
77 0005 6F              LD    L,A               ;Point to A/D converter address
78 0006 26 00           LD    H,0               ;
79 0008 11 F8 FF        LD    DE,AD_BASE        ;
80 000B 19              ADD   HL,DE             ;
81 000C E5              PUSH  HL                ;
82 000D FD E1           POP   IY                ;
83                                              ;
84 000F 6F              LD    L,A               ;Point to buffer
85 0010 26 00           LD    H,0               ;
86 0012 11 04 00  D     LD    DE,DATA_BASE+2    ;Place pointer at start of buffer
87 0015 19              ADD   HL,DE             ;
88 0016 E5              PUSH  HL                ;
89 0017 DD E1           POP   IX                ;
90                                              ;
```

```
91 0019 3A 00 00    D       LD      A,(WAIT)            ;Wait until auto-zero cycle done,
92 001C FE 00               CP      0                   ; before doing additional writes
93 001E C2 2F 00    C       JP      NZ,READ_CYCLE       ;If true, don't write
94                                                      ;
95 0021 01 00 00            LD      BC,DUMMY            ;Write DUMMY data
96 0024 FD 70 01            LD      (IY+1),B            ;
97 0027 FD 71 00            LD      (IY+0),C            ;
98                                                      ;
99 002A 3E 01               LD      A,1                 ;Request that subsequent writes
100 002C 32 00 00   D       LD      (WAIT),A            ; be delayed until busy is false
101                                                     ;
102                 READ_CYCLE                          ;
103 002F FD 7E 01           LD      A,(IY+1)            ;Test busy flag
104 0032 CB 7F              BIT     7,A                 ;If false, not busy, data valid
105 0034 C2 54 00   C       JP      NZ,EXIT             ; otherwise, wait until next time
106                                                     ;
107 0037 3E 00              LD      A,0                 ;Clear wait status
108 0039 32 00 00   D       LD      (WAIT),A            ;
109                                                     ;
110 003C FD 46 01           LD      B,(IY+1)            ;Get port contents
111 003F FD 4E 00           LD      C,(IY+0)            ;
112                                                     ;
113 0042 3E 0F              LD      A,00001111B         ;Mask off high nibble
114 0044 A0                 AND     B                   ;
115 0045 47                 LD      B,A                 ;

116                                                     ;
117 0046 DD 70 01           LD      (IX+1),B            ;Write result in data buffer
118 0049 DD 71 00           LD      (IX+0),C            ;
119                                                     ;
120 004C 3A 01 00   D       LD      A,(PORT_SELECT)     ;Increment pointer to next port
121 004F 3C                 INC     A                   ;
122 0050 3C                 INC     A                   ;
123 0051 32 01 00   D       LD      (PORT_SELECT),A     ;
124                                                     ;
125                 EXIT                                ;
126 0054 C9                 RET                         ;
127                                                     ;
128                 ;
129                 ;--- DISTRIBUTE CURRENT BUFFER CONTENTS TO RESPECTIVE D/A'S
130                 ;
131 0055            D_TO_A
132 0055 3E 08              LD      A,8                 ;Set counter
133 0057 0E 7F              LD      C,DA_BASE+7         ;Set pointers
134 0059 21 13 00   D       LD      HL,DATA_BASE+17     ;
135                 NEXT                                ;
136 005C 46                 LD      B,(HL)              ;
137 005D ED 41              OUT     (C),B               ;
138 005F 0D                 DEC     C                   ;
```

```
139 0060 2B                       DEC     HL              ;
140 0061 3D                       DEC     A               ;
141 0062 FE 00                    CP      0               ;
142 0064 C2 5C 00    C            JP      NZ,NEXT         ;
143                                                       ;
144                       LEAVE                           ;
145 0067 C9                       RET                     ;
146                                                       ;
147                       ;
148                       ;--- DISTRIBUTE BUFFER CONTENTS TO RESPECTIVE DIAGNOSTIC D/A'S
149                       ;
150                       SDAC                            ;!!!!!!! SERVICE DAC !!!!!!!!!!!!!
151 0068 3E 08                    LD      A,8             ;Set counter
152 006A 0E 87                    LD      C,DAC_BASE+7    ;Set pointers
153 006C 21 1B 00    D            LD      HL,DATA_BASE+17+8 ;
154                       NEXT_DAC                        ;
155 006F 46                       LD      B,(HL)          ;
156 0070 ED 41                    OUT     (C),B           ;
157 0072 0D                       DEC     C               ;
158 0073 2B                       DEC     HL              ;
159 0074 3D                       DEC     A               ;
160 0075 FE 00                    CP      0               ;
161 0077 C2 5C 00    C            JP      NZ,NEXT         ;
162                                                       ;
163                       BACK                            ;
164 007A C9                       RET                     ;
165                                                       ;
166                       ;==================================================================;
167                       ;       DATA SEGMENT                                                ;
168                       ;==================================================================;
169                       ;
170 0000                  DUMMY           EQU     0000H           ;
171                                                               ;
172 FFF8                  AD_BASE         EQU     0FFF8H          ;Address of the A/D converters
173 FFF8                  AD0             EQU     AD_BASE+0       ;

174 FFFA                  AD1             EQU     AD_BASE+2       ;
175 FFFC                  AD2             EQU     AD_BASE+4       ;
176 FFFE                  AD3             EQU     AD_BASE+6       ;
177                                                               ;
178 0078                  DA_BASE         EQU     78H             ;Address of the D/A converters
179 0078                  DA0LO           EQU     DA_BASE+0       ;
180 0079                  DA0HI           EQU     DA_BASE+1       ;
181 007A                  DA1LO           EQU     DA_BASE+2       ;
182 007B                  DA1HI           EQU     DA_BASE+3       ;
183 007C                  DA2LO           EQU     DA_BASE+4       ;
184 007D                  DA2HI           EQU     DA_BASE+5       ;
185 007E                  DA3LO           EQU     DA_BASE+6       ;
186 007F                  DA3HI           EQU     DA_BASE+7       ;
```

```
187                                                             ;
188 0080            DAC_BASE      EQU    80H            ;Address of the special DACS
189 0080            DAC0LO        EQU    DAC_BASE+0     ;
190 0081            DAC0HI        EQU    DAC_BASE+1     ;
191 0082            DAC1LO        EQU    DAC_BASE+2     ;
192 0083            DAC1HI        EQU    DAC_BASE+3     ;
193 0084            DAC2LO        EQU    DAC_BASE+4     ;
194 0085            DAC2HI        EQU    DAC_BASE+5     ;
195 0086            DAC3LO        EQU    DAC_BASE+6     ;
196 0087            DAC3HI        EQU    DAC_BASE+7     ;
197                                                     ;
198                        DSEG                         ;
199 0000 00         WAIT          DB     0H            ;
200 0001 00         PORT_SELECT   DB     0H            ;
201                                                    ;
202 0002            DATA_BASE     DS     2             ;
203 0004            PHASE         DS     2             ;
204 0006            CURRENT       DS     2             ;
205 0008            ADIN2         DS     2             ;
206 000A            ADIN3         DS     2             ;
207 000C            HERTZ         DS     2             ;
208 000E            HENRY         DS     2             ;
209 0010            PWR_LEVEL     DS     2             ;
210 0012            COURSE        DS     2             ;
211 0014            SDAC01        DS     2             ;Special diagnostic DACs
212 0016            SDAC02        DS     2             ;
213 0018            SDAC03        DS     2             ;
214 001A            SDAC04        DS     2             ;
215                                                    ;
216         ;-----------------------------------------------------------;
217         ;                                                           ;
218         ;        EXTERNAL VARIABLE DECLARATION                      ;
219         ;                                                           ;
220         ;-----------------------------------------------------------;
221         ;
222         ;-----------------------------------------------------------;
223         ;                                                           ;
224         ;        PUBLIC VARIABLE DECLARATION                        ;
225         ;                                                           ;
226         ;-----------------------------------------------------------;
227         ;
228                 PUBLIC  DATA_BASE, A_TO_D, D_TO_A, CURRENT, HERTZ, HENRY, COURSE
229                 PUBLIC  PHASE, PWR_LEVEL, SDAC01, SDAC02, SDAC03, SDAC04, SDAC
230                 PUBLIC  ADIN2, ADIN3
231                                                                      ;

232         ;===========================================================;
233         ;
234         ;!!!!!!!!!!!!!!!!!!!!!!!!!!!!!!!!!!!!!!!!!!!!!!!!!!!!!!!!!!!;
235         ;
236 001C           END

ERRORS = 0000
```

PHACO SYSTEM Z80 STATUS MONITOR          1

```
1 0000                    TITLE   'PHACO SYSTEM Z80 STATUS MONITOR'
2                   NAME  PSTAT_MODULE
3                   CSEG
4                   PAGESZ 66
5             ;
6             ;IIIIIIIIIIIIIIIIIIIIIIIIIIIIIIIIIIIIIIIIIIIIIIIIIIIIIIIIIIIIIIIIIII;
```

PHACO SYSTEM Z80 DISPLAY CONTROLLER       1

```
1 0000                    TITLE   'PHACO SYSTEM Z80 DISPLAY CONTROLLER'
2                   NAME  PSEG_INT_MODULE
3                   CSEG
4                   PAGESZ 66
5             ;
6             ;IIIIIIIIIIIIIIIIIIIIIIIIIIIIIIIIIIIIIIIIIIIIIIIIIIIIIIIIIIIIIIIIIII;
```

PHACO SYSTEM STATUS ANNUNCIATOR           1

```
1  0000                   TITLE   'PHACO SYSTEM STATUS ANNUNCIATOR'
2                   NAME  PMUSIC_MODULE
3                   PAGESZ 66
4                   CSEG
5             ;
6             ;IIIIIIIIIIIIIIIIIIIIIIIIIIIIIIIIIIIIIIIIIIIIIIIIIIIIIIIIIIIIIIIIIII;
7             ;                                                                    ;
8             ;                      PHACO MUSIC GENERATOR                         ;
9             ;                                                                    ;
10            ;====================================================================;
11            ;                     IIII CHANGE HISTORY IIIII                      ;
```

PHACO SYSTEM Z80 INTERRUPT HANDLER          1

```
1 0000                  TITLE   'PHACO SYSTEM Z80 INTERRUPT HANDLER'
2                       NAME    PINTR_MODULE
3                       CSEG
4                       PAGESZ  66
5               ;
6               ;IIIIIIIIIIIIIIIIIIIIIIIIIIIIIIIIIIIIIIIIIIIIIIIIIIIIIIIIIIIIIIIIII;
7               ;                                                                  ;
8               ;               PHACO SYSTEM INTERRUPT HANDLER                     ;
9               ;                                                                  ;
10              ;==================================================================;
11              ;           IIIIIII CHANGE HISTORY IIIIIII                         ;
12              ;                                                                  ;
13              ;       Author          Date            Change Purpose             ;
14              ;       ------------------------------------------------           ;
15              ;       F.Lian          4/13/86         Creation (Code)            ;
16              ;       F. LIAN         4/21/86         audio control change       ;
17              ;       F. LIAN         4/23/86         audio control change       ;
18              ;       F. Lian         5/01/86         bargraph pattern gen.      ;
19              ;       T.Escorcio      7/8/86          comm. interrupt calls      ;
20              ;       T.Escorcio      7/29/86         correction and cleanup     ;
21              ;                                                                  ;
22              ;==================================================================;
23              ;
24              ;------------------------------------------------------------------;
25              ;       NMI (NON MASKABLE INTERRUPT) HANDLER                       ;
26              ;       When the NMI line goes low, the Z80 jumps to 66h where     ;
27              ;       it finds an interrupt service routine that calls this sub- ;
28              ;       routine, called MASTER. MASTER handles NMI processing.     ;
29              ;                                                                  ;
30              ;       Note:                                                      ;
31              ;       - Currently, this non-maskable interrupt is not used.      ;
32              ;                                                                  ;
33              ;------------------------------------------------------------------;
34              ;
35              MASTER                                  ;
36 0000 FB              EI                              ;
37 0001 C7              RST     0H                      ;
38                                                      ;
39 0002 08              EX      AF,AF'                  ;USE ALTERNATE REGISTER BANK
40 0003 D9              EXX                             ;
41                                                      ;
42              ;       LD      HL,SWITCH               ;REQUEST SOME USER TRIGGERED EVENT
43              ;       SET     0,(HL)                  ;
44              ;                                       ;
45              ;                                       ;PLAY A GLISSANDO
46              ;       LD      HL,RYTHM                ;
47              ;       LD      (HL),3                  ;
48              ;                                       ;
49              ;       LD      HL,CONDUCTOR            ;
50              ;       SET     0,(HL)                  ;
51              ;       RES     1,(HL)                  ;
52              ;                                       ;
53              ;       LD      HL,REPEAT               ;
```

```
54            ;       LD      (HL),0          ;
55            ;                               ;
56            ;       LD      HL,SLISSANDO    ;
57            ;       LD      (MELODY),HL     ;
58                                            ;
```

PHACO SYSTEM Z80 INTERRUPT HANDLER      2

```
59                        EXIT                      ;
60 0004 D9                EXX                       ;RESTORE ORIGINAL REGISTER BANK
61 0005 08                EX      AF,AF'            ;
62 0006 C9                RET                       ;GO BACK TO NORMAL SYSTEM OPERATION
63                                                  ;
64            ;===========================================================;
65            ;       DATA SEGMENT                                         ;
66            ;===========================================================;
67            ;
= 68 0007                 INCLUD  EQU.INC           ;INCLUDE THE CONSTANTS IN ASSEMBLY
= 69          ;===========================================================;
= 70          ;
= 71          ;       EQU.INC         PHACO SYSTEM GLOBAL EQUATES          ;
= 72          ;
= 73          ;===========================================================;
= 74          ;
= 75          ;            ::::::::: CHANGE HISTORY :::::::::
= 76          ;
= 77          ;       AUTHOR          DATE            CHANGE PURPOSE
= 78          ;       ----------------------------------------------------
= 79          ;       T. LO           3 FEB 86        CREATION
= 80          ;       F. Lian         10 Feb. 86      Update
= 81          ;       F. Lian         10 April 86     Update
= 82          ;       T. Escorcio     24 June 86      Update
= 83          ;       T. Escorcio     7 July 86       Update
= 84          ;       T. Escorcio     4/1/87          add adaptive tuning constants
= 85          ;
= 86          ;----------------------------------------------------------;
= 87          ;
= 88          ;------ TOP OF RAM MARKER
= 89          ;
= 90 8000     RAM_END         EQU     8000H           ;32K CONFIGURATION
= 91          ;
= 92          ;------ INTERRUPT LOOP TIMING CONSTANTS
= 93          ;
= 94 01EE     SAMPFRQ         EQU     489+2           ;INTERRUPT SAMPLING FREQUENCY
= 95 0002     DIV480HZ        EQU     2               ;480 HZ DIVIDER
= 96 0004     DIV240HZ        EQU     4               ;240 HZ DIVIDER
= 97 0008     DIV120HZ        EQU     8               ;120 HZ DIVIDER
= 98 0010     DIV60HZ         EQU     16              ; 60 HZ DIVIDER
= 99 0020     DIV30HZ         EQU     32              ; 30 HZ DIVIDER
= 100 0060    DIV10HZ         EQU     96              ; 10 HZ DIVIDER
= 101                                                 ;
= 102         ;
= 103         ;------ System counter parameters
= 104         ;
```

```
= 105 0168          ELAPS1      EQU     168H        ;3 SECOND TIMER VALUE (HUNTER)
= 106 05A0          ELAPS2      EQU     5A0H        ;3 SECOND TIMER VALUE (COM. REPLY)
= 107 0020          ELAPS3      EQU     020H        ;BEEPER DURATION
= 108 0300          ELAPS4      EQU     0300H       ;BEEPER COUNTER SAMPLING RATE
= 109 0078          ELAPS5      EQU     120         ;SCANNER INTERVAL
= 110                                               ;
= 111                           ;
= 112                           ;------ PROGRAM THRESHOLD LEVELS
= 113                           ;
= 114 0000          MIN         EQU     00H         ;
= 115 00FF          MAX         EQU     0FFH        ;
= 116 0001          TRUE        EQU     00000001B   ;
```

PHACO SYSTEM Z80 INTERRUPT HANDLER         3

```
   17 0000          FALSE       EQU     00000000B   ;
=  18 01F4          BUFF_SIZE   EQU     500         ;
= 119 000A          KEY_RYTHM   EQU     10          ;Key music duration time
= 120 0004          KEY_TIME    EQU     4           ;
= 121 000F          BEEP_TIME   EQU     15          ;
= 122 0640          BEGINNING   EQU     1600        ;
= 123 0800          FULL        EQU     2048        ;
= 124                                                                                      ;
= 125                           ;=====================================================;
= 126 0007
= 127 0007
  128                                                                                      ;
  129                           ;-----------------------------------------------------;
  130                           ;                                                     ;
  131                           ;       EXTERNAL VARIABLE DECLARATION                 ;
  132                           ;                                                     ;
  133                           ;-----------------------------------------------------;
  134                           ;
  135                                   EXTRN   SWITCH, RYTHM, CONDUCTOR, GLISSANDO, MELODY, REPEAT
  136                                   EXTRN   SONGO, ALARM
  137                                                                                      ;
  138                           ;-----------------------------------------------------;
  139                           ;                                                     ;
  140                           ;       PUBLIC VARIABLE DECLARATION                   ;
  141                           ;                                                     ;
  142                           ;-----------------------------------------------------;
  143                           ;
  144                                   PUBLIC  MASTER
  145                                                                                      ;
  146                           ;=====================================================;
  147                           ;
  148                           ;!!!!!!!!!!!!!!!!!!!!!!!!!!!!!!!!!!!!!!!!!!!!!!!!!!!!!;
  149                           ;
  150 0017                              END
```

ERRORS = 0000

```
;================================================================;
;                                                                ;
;     EQU.INC         PHACO SYSTEM GLOBAL EQUATES                ;
;                                                                ;
;================================================================;

;                                                                ;
;            xxxxxxxxx CHANGE HISTORY xxxxxxxxx                  ;
;                                                                ;
;      AUTHOR         DATE            CHANGE PURPOSE             ;
;      ----------------------------------------------------      ;
;                                                                ;
;      T. Lo          3 FEB 86        CREATION                   ;
;      F. Lian        10 Feb. 86      Update                     ;
;      F. Lian        10 April 86     Update                     ;
;      T. Escorcio    24 June 86      Update                     ;
;      T. Escorcio    7 July 86       Update                     ;
;      T. Escorcio    4/1/87          add adaptive tuning constants ;
;                                                                ;
;----------------------------------------------------------------;

;------ TOP OF RAM MARKER
;
RAM_END         EQU     8000H           ;32K CONFIGURATION
;
;------ INTERRUPT LOOP TIMING CONSTANTS
;
SAMPFRQ         EQU     489+2           ;INTERRUPT SAMPLING FREQUENCY
DIV480HZ        EQU     2               ;480 HZ DIVIDER
DIV240HZ        EQU     4               ;240 HZ DIVIDER
DIV120HZ        EQU     8               ;120 HZ DIVIDER
DIV60HZ         EQU     16              ; 60 HZ DIVIDER
DIV30HZ         EQU     32              ; 30 HZ DIVIDER
DIV10HZ         EQU     96              ; 10 HZ DIVIDER
                                        ;
;
;------ System counter parameters
;
ELAPS1          EQU     168H            ;3 SECOND TIMER VALUE (HUNTER)
ELAPS2          EQU     5A0H            ;3 SECOND TIMER VALUE (COM. REPLY)
ELAPS3          EQU     020H            ;BEEPER DURATION
ELAPS4          EQU     0300H           ;BEEPER COUNTER SAMPLING RATE
ELAPS5          EQU     120             ;SCANNER INTERVAL
                                        ;
;
;------ PROGRAM THRESHOLD LEVELS
;
MIN             EQU     00H             ;
MAX             EQU     0FFH            ;
TRUE            EQU     00000001B       ;
FALSE           EQU     00000000B       ;
BUFF_SIZE       EQU     500             ;
KEY_RYTHM       EQU     10              ;Key music duration time
KEY_TIME        EQU     4               ;
BEEP_TIME       EQU     15              ;
BEGINNING       EQU     1600            ;
FULL            EQU     2048            ;

;================================================================;
```

PHACO HANDPIECE CHARACTERIZER                1

```
1  0010              TITLE   'PHACO HANDPIECE CHARACTERIZER'
2                    NAME    PSWEEP_MODULE
3                    PAGESZ  66
4                    CSEG
5           ;
6           ;IIIIIIIIIIIIIIIIIIIIIIIIIIIIIIIIIIIIIIIIIIIIIIIIIIIIIIIIIIIIIIIIIII ;
7           ;                                                                   ;
8           ;              PHACO HANDPIECE CHARACTERIZER                        ;
9           ;                                                                   ;
10          ;===================================================================;
11          ;            IIIIIII    CHANGE HISTORY IIIIIII                      ;
12          ;                                                                   ;
13          ;      Author        Date        Change Purpose                     ;
14          ;      ----------------------------------------------------         ;
15          ;                                                                   ;
16          ;      T.Escorcio    3/31/87     Creation                           ;
17          ;      T.Escorcio    5/3/87      Slope detection criteria  added    ;
18          ;      T.Escorcio    9/11/87     Documentation edit, comments       ;
19          ;      T.Escorcio    3/31/87     Add VCO control                    ;
20          ;      T.Escorcio    3/31/87     Modify VCO off condition           ;
21          ;                                                                   ;
22          ;===================================================================;
23          ;
24          ;------------------------------------------------------------------ ;
25          ;                                                                   ;
26          ;      Function: Do a frequency sweep of the handpiece to find      ;
27          ;                mechanical resonance.                              ;
28          ;                                                                   ;
29          ;      Register: AF, BC, DE, HL                                     ;
30          ;       Accepts: None                                               ;
31          ;       Returns: DE = SWEEP_FREQ, I_PEAK                            ;
32          ;         Calls: None                                               ;
33          ;         Flags: Carry                                              ;
34          ;     Variables: SWEEP_FREQ, HERTZ, I_PEAK, CURRENT                 ;
35          ;     Constants: TRANSIENT, MAX_FREQ, MINIMUM                       ;
36          ;                                                                   ;
37          ;    Pseudo Code:                                                   ;
38          ;      SWEEPER                                                      ;
39          ;          SWEEP_FREQ = MINIMUM                                     ;
40          ;          HERTZ = MINIMUM                                          ;
41          ;          I_PEAK = MINIMUM                                         ;
42          ;      SWPR                                                         ;
43          ;          Do while (HERTZ < MAX_FREQ)                              ;
44          ;              SWEEP_FREQ = SWEEP_FREQ + 1                          ;
45          ;              HERTZ = SWEEP_FREQ                                   ;
46          ;              countr = 5                                           ;
47          ;              Do while (countr <> 0.)                              ;
48          ;                  Dec counter                                      ;
49          ;              enddo                                                ;
50          ;              If (CURRENT > I_PEAK) then                           ;
51          ;                  I_PEAK = CURRENT                                 ;
```

```
52      ;                   endif
53      ;                 enddo
54      ;               return
55      ;
56      ;
57      ;------------------------------------------------------------
58      ;       NOTES
```

PHACO HANDPIECE CHARACTERIZER        2

```
59      ;       - To request an appropriate ANALYSIS, enter with MISTUNE
60      ;         flag set as folows:
61      ;
62      ;         MISTUNE Flag                D7 D6 D5 D4 D3 D2 D1 D0
63      ;                                     ---------|  |  |  |  |  |  |  |
64      ;                                     ------------|  |  |  |  |  |  |
65      ;                                     ---------------|  |  |  |  |  |
66      ;                                     ------------------|  |  |  |  |
67      ;                                     ---------------------|  |  |  |
68      ;         Warm Sweep Invoke           ------------------------|  |  |
69      ;         Cold Sweep Invoke           ---------------------------|  |
70      ;         Direct Invoke               ------------------------------|
71      ;
72      ;------------------------------------------------------------
73      ;
74      ;
75                      SWEEPER
76 0000 3A 00 00   E        LD    A,(HSERVICE)      ;
77 0003 FE 01               CP    1                 ;
78 0005 CA 25 03   C        JP    Z,TWEEKR          ;.
79                                                  ;
80                    ;     LD    A,(PEDAL)         ;Avoid SWEEPER when
81                    ;     BIT   0,A               ; PEDAL kicked to the left
82                    ;     JP    NZ,SWPR           ;If true, continue
83                    ;     LD    HL,MISTUNE        ; otherwise, reset MISTUNE...
84                    ;     LD    (HL),0            ;
85                    ;     JP    EXIT              ; ...and leave
86                                                  ;
87                      SWPR                        ;
88 0008 3A 00 00   E        LD    A,(CONDUCTOR)     ;Never invoke SWEEPER during
89 000B CB 47               BIT   0,A               ; annunciator modes
90 000D C2 28 00   C        JP    NZ,EXIT           ;User needs to be aware of alarms
91                                                  ;
92 0010 21 16 02   D        LD    HL,MISTUNE        ;Check MISTUNE flag
93 0013 CB 56               BIT   2,(HL)            ;If true, do a WARM_SWEEP
94 0015 C4 29 00   C        CALL  NZ,WARM_SWEEP     ; otherwise, continue
95                                                  ;
96 0018 21 16 02   D        LD    HL,MISTUNE        ;Check MISTUNE flag
97 001B CB 4E               BIT   1,(HL)            ;If true, do a COLD_SWEEP
98 001D C4 2A 00   C        CALL  NZ,COLD_SWEEP     ; otherwise, continue
```

```
 99                                                                         ;
100 0020 21 16 02    D              LD      HL,MISTUNE           ;Check MISTUNE flag
101 0023 CB 46                      BIT     0,(HL)               ;If true, invoke ANALYSIS directly
102 0025 C4 95 00    C              CALL    NZ,ANALYSIS          ; otherwise, return
103                                                                         ;
104                         EXIT                                            ;
105                                                                         ;
106 0028 C9                         RET                                     ;
107
108                         ;
109                         ;------ This function invokes ANALYSIS using arbitrary sweep ranges
110                         ;
111                         WARM_SWEEP                                      ;
112                         ;    < NO FUNCTION AT THIS TIME >               ;
113                                                                         ;
114 0029 C9                         RET                                     ;
115                                                                         ;

116                         ;
117                         ;------ This function invokes ANALYSIS using max sweep range
118                         ;
119                         COLD_SWEEP                                      ;
120 002A 21 00 00    E              LD      HL,CONN_LED          ;
121 002D CB 86                      RES     0,(HL)               ;Disable led...
122 002F CB 8E                      RES     1,(HL)               ; ...if not already off
123 0031 21 12 02    D              LD      HL,BLINK             ;
124 0034 36 02                      LD      (HL),2               ;
125                                                                         ;
126 0036 3A 00 00    E              LD      A,(HANDPC)           ;Validate handpiece...
127 0039 FE 40                      CP      PHACOPC              ; ..only phaco handpiece is ok
128 003B C2 87 00    C              JP      NZ,EX_COLD           ;If false, forget it
129 003E 21 00 08                   LD      HL,FULL              ; otherwise establish sweep RANGE
130 0041 22 14 02    D              LD      (RANGE),HL           ;
131 0044 21 16 02    D              LD      HL,MISTUNE           ;Set MISTUNE to enable SWEEPER
132 0047 CB C6                      SET     0,(HL)               ;
133                                                                         ;
134 0049 21 1B 02    D              LD      HL,FAULT_CNTR        ;Set an allowed number of TRIES
135 004C 36 0A                      LD      (HL),TRIES           ;
136                                                                         ;
137 004E CD 95 00    C              CALL    ANALYSIS             ;Call ANALYSIS "direct" (SEE NOTE)
138                                                                         ;
139 0051 21 31 02    D              LD      HL,FAILURE           ;
140 0054 CB 46                      BIT     0,(HL)               ;
141 0056 CA 63 00    C              JP      Z,COLD1              ;
142                                                                         ;
143 0059 21 00 00    E              LD      HL,CONN_LED          ;Signal acceptance
144 005C CB 86                      RES     0,(HL)               ;Disable led...
145 005E CB 8E                      RES     1,(HL)               ; ...if not already enabled
146                                                                         ;
```

```
147 00ED C3 8D 00    C           JP     COLD2          ;
148                       COLD1                        ;
149 00ED CD A1 02    C           CALL   POSTCHARGE     ;
150                                                    ;
151 00EE 21 00 00    E           LD     HL,CONN_LED    ;Signal acceptance
152 00EF CB C6                   SET    0,(HL)         ;Enable led...
153 00EE CB CE                   SET    1,(HL)         ; ...if not already enabled
154                       COLD2                        ;
155 00ED 21 00 00    E           LD     HL,RELAPSE     ;Null the timer contents
156 0070 CB C6                   SET    0,(HL)         ;
157                                                    ;
158 0072 21 00 00    E           LD     HL,MID_C       ;Point to the SONG
159 0075 22 00 00    E           LD     (MELODY),HL    ;
160 0078 21 00 00    E           LD     HL,RYTHM       ;Set the RYTHM for audio feedback
161 007B 36 08                   LD     (HL),8         ;
162 007D 21 00 00    E           LD     HL,CONDUCTOR   ;Set the CONDUCTOR's queue
163 0080 CB C6                   SET    0,(HL)         ;
164 0082 21 00 00    E           LD     HL,NOTE        ;
165 0085 36 00                   LD     (HL),0         ;
166                                                    ;
167                       EX_COLD                      ;
168 0087 21 12 02    D           LD     HL,BLINK       ;Deactivate the CONN_LED BLINK
169 008A 36 00                   LD     (HL),0         ;
170                                                    ;
171 008C 21 16 02    D           LD     HL,MISTUNE     ;Ignore, conditions not right
172 008F CB 8E                   RES    1,(HL)         ;
173                                                    ;

174 0091 CD 8A 03    C           CALL   VCO_OFF        ;
175                                                    ;
176 0094 C9                      RET                   ;
177                                                    ;
178                       ANALYSIS                     ;
179                                                    ;
180 0095 CD B3 03    C           CALL   VCO_ON         ;
181                                                    ;
182 0098 A7                      AND    A              ;
183 0099 2A 14 02    D           LD     HL,(RANGE)     ;RANGE = MINIMUM ?
184 009C 01 00 00                LD     BC,MINIMUM     ;Do 16 bit subtraction
185 009F ED 42                   SBC    HL,BC          ;If false, continue with SWEEPER
186 00A1 CA 15 01    C           JP     Z,LEAVE        ; otherwise, LEAVE
187                                                    ;
188 00A4 21 00 00    E           LD     HL,LOOP        ;Disable MINIMIZER
189 00A7 CB 86                   RES    0,(HL)         ; Reset it's enable flag
190                                                    ;
191 00A9 CD 40 02    C           CALL   WINDOW         ;
192                                                    ;
193 00AC CD 97 02    C           CALL   PRECHARGE      ;
194                                                    ;
```

```
195 00AF 21 00 00    E            LD    HL,BOUNDRY        ;Get power BOUNDRY value
196 00B2 7E                       LD    A,(HL)            ; (minimum power is req'd)
197 00B3 F5                       PUSH  AF                ;Save old BOUNDRY on the STACK
198 00B4 36 3C                    LD    (HL),NOMINAL      ;Set NOMINAL BOUNDRY value
199                  SWPR2                                ;
200 00B6 21 0A 02    D            LD    HL,P_SLOPE        ;Clear the slope detection flags
201 00B9 CB 86                    RES   0,(HL)            ;
202 00BB 21 0B 02    D            LD    HL,N_SLOPE        ;
203 00BE CB 86                    RES   0,(HL)            ;
204                                                       ;Establish the defaults
205 00C0 21 00 00                 LD    HL,MINIMUM        ;
206 00C3 22 05 02    D            LD    (SWEEP_FREQ),HL   ;
207 00C6 22 00 00    E            LD    (HERTZ),HL        ;
208 00C9 22 FF 01    D            LD    (I_PEAK),HL       ;
209 00CC 22 17 02    D            LD    (RESONANCE),HL    ;
210 00CF 22 08 02    D            LD    (SLOPE),HL        ;
211                  SWPR3                                ;
212 00D2 CD 16 01    C            CALL  PEAK              ;Peak current resonance finder
213                                                       ;
214                  VALIDATE                             ;
215 00D5 21 1B 02    D            LD    HL,FAULT_CNTR     ;Check the number of unsuccessful
216 00D8 35                       DEC   (HL)              ; attempts
217 00D9 3E 00                    LD    A,0               ;
218 00DB BE                       CP    (HL)              ;
219 00DC C2 EA 00    C            JP    NZ,SWPR4A         ;If TRIES not exhausted, continue
220                                                       ; otherwise, flag an error
221 00DF CD 00 00    E            CALL  ERROR4            ;Notify user
222 00E2 21 31 02    D            LD    HL,FAILURE        ;Indicate FAILURE
223 00E5 CB C6                    SET   0,(HL)            ;
224 00E7 C3 F8 00    C            JP    SWPR4             ;
225                  SWPR4A                               ;
226 00EA CD 67 02    C            CALL  CHK_LIMIT         ;Make sure it's within limits
227 00ED 21 1C 02    D            LD    HL,RAILED         ;Check RAILED flag
228 00F0 CB 46                    BIT   0,(HL)            ;If false, limits not exceeded
229 00F2 C2 B6 00    C            JP    NZ,SWPR2          ; otherwise, deal with extreme case
230                                                       ;Do it again until it's right
231 00F5 CD 9E 03    C            CALL  SET_VCO           ;Adjust the VCO setting 232                                                       ;
233                  SWPR4                                ;
234 00F8 21 1B 02    D            LD    HL,FAULT_CNTR     ;Restart the FAULT_CNTR
235 00FB 36 00                    LD    (HL),0            ;
236                                                       ;
237 00FD 21 16 02    D   SWPR4B   LD    HL,MISTUNE        ;Reset MISTUNE
238 0100 36 00                    LD    (HL),0            ;
239                                                       ;
240                  SWPR5                                ;
241 0102 F1                       POP   AF                ;Restore previous BOUNDRY
242 0103 21 00 00    E            LD    HL,BOUNDRY        ;Point to BOUNDRY
```

```
243 0105 77                       LD     (HL),A              ;Put previous value there
244                                                          ;
245 0107 21 00 00    E            LD     HL,LOOP             ;Enable MINIMIZER
246 010A CB C6                    SET    0,(HL)              ; Set it's enable flag
247 010C 21 00 00                 LD     HL,MINIMUM          ;Null RANGE before leaving
248 010F 22 14 02    D            LD     (RANGE),HL          ;
249 0112 22 FF 01    D            LD     (I_PEAK),HL         ;NULL IT JUST IN CASE !!!!!!!!!!!!
250                                                          ;
251                        LEAVE                             ;
252 0115 C9                       RET                        ;Frequency sweep completed
253                                                          ;
254                        ;
255                        ;------ Search for the PEAK current, that will be the mechanical resonance
256                        ;
257 0116                   PEAK
258 0116 CD E0 02    C            CALL   DELAY               ;
259 0119 CD E0 02    C            CALL   DELAY               ;
260 011C CD E0 02    C            CALL   DELAY               ;
261                                                          ;
262 011F 2A 00 00    E            LD     HL,(HERTZ)          ;HERTZ < MAX_FREQ ?
263 0122 ED 4B 03 02 D            LD     BC,(MAX_FREQ)       ;Do 16 bit comparison
264 0126 ED 42                    SBC    HL,BC               ;Subtract and watch flags
265 0128 D2 7B 01    C            JP     NC,EX_PEAK          ;If false, leave
266                                                          ; otherwise, increment frequency
267 012B ED 4B 05 02 D            LD     BC,(SWEEP_FREQ)     ;SWEEP_FREQ = SWEEP_FREQ + 1
268 012F 03                       INC    BC                  ;
269 0130 ED 43 05 02 D            LD     (SWEEP_FREQ),BC     ;Write new frequency to VCO
270                                                          ;
271 0134 ED 4B 05 02 D            LD     BC,(SWEEP_FREQ)     ;HERTZ = SWEEP_FREQ
272 0138 ED 43 00 00 E            LD     (HERTZ),BC          ;
273                                                          ;
274 013C 2A FF 01    D            LD     HL,(I_PEAK)         ;CURRENT > I_PEAK ?
275 013F ED 4B 00 00 E            LD     BC,(CURRENT)        ;Do 16 bit comparison
276 0143 A7                       AND    A                   ;Clear the carry flag
277 0144 ED 42                    SBC    HL,BC               ;Subtract and watch the flags
278 0146 D2 6F 01    C            JP     NC,AGAIN            ;Ignore < or = values of current
279                                                          ;
280 0149 A7                       AND    A                   ;Clear the carry flag
281 014A 2A 05 02    D            LD     HL,(SWEEP_FREQ)     ;SWEEP_FREQ < TRANSIENT ?
282 014D 01 F4 01                 LD     BC,BUFF_SIZE        ;Disregard transient zone
283 0150 ED 42                    SBC    HL,BC               ;Subtract and watch flags
284 0152 EA 6F 01    C            JP     PE,AGAIN            ;Ignore overflow results
285 0155 DA 6F 01    C            JP     C,AGAIN             ;If true, reject as TRANSIENT
286                                                          ; otherwise, keep it
287 0158 A7                       AND    A                   ;Clear the carry flag
288 0159 2A 05 02    D            LD     HL,(SWEEP_FREQ)     ;SWEEP_FREQ > F9Ch ? (REJECT HI 100)
289 015C 01 9C 0F                 LD     BC,0F9CH            ;Disregard transient zone 290 015F ED 42                    SBC    HL,BC               ;Subtract and watch flags
```

```
291 0161 D2 6F 01      C              JP     NC,AGAIN         ;If true, reject as TRANSIENT
292                                                            ; otherwise, keep it
293 0164 ED 4B 00 00   E              LD     BC,(CURRENT)     ;Do 16 bit comparison
294 0168 ED 43 FF 01   D              LD     (I_PEAK),BC      ;Record magnitude...
295                                                            ;
296 016C CD 17 02      C              CALL   DETECTOR         ; ...and point of occurence
297                                                            ;
298 016F                       AGAIN
299 016F CD 7C 01      C              CALL   RECORDER         ;Record current
300                                                            ;
301 0172 2A 00 00      E              LD     HL,(CURRENT)     ;Get the value from the A/D
302 0175 22 00 00      E              LD     (SDAC01),HL      ; ...before shipping it out
303                                                            ;
304 0178 C3 16 01      C              JP     PEAK             ;Continue across entire range
305                            EX_PEAK
306 017B C9                           RET                     ;
307                                                            ;
308                            ;
309                            ;------ Store CURRENT data in circular buffer
310                            ;
311                            ;
312 017C                       RECORDER
313 017C ED 4B 25 02   D              LD     BC,(COUNTR)      ;Decrement the counter
314 0180 0B                           DEC    BC               ;
315 0181 0B                           DEC    BC               ;
316 0182 ED 43 25 02   D              LD     (COUNTR),BC      ;
317                                                            ;
318 0186 78                           LD     A,B              ;COUNTR = 0 ?
319 0187 B1                           OR     C                ;
320 0188 C2 92 01      C              JP     NZ,OFFSET        ;If COUNTR <> 0, then continue
321                            RELOAD                          ; otherwise, restart COUNTR
322 018B 01 F4 01                     LD     BC,BUFF_SIZE     ;Reload count
323 018E ED 43 25 02   D              LD     (COUNTR),BC      ;
324                            OFFSET                          ;
325 0192 21 02 00      D              LD     HL,BUFFER        ;POINTR = BUFFER + COUNTR
326 0195 ED 5B 25 02   D              LD     DE,(COUNTR)      ;
327 0199 19                           ADD    HL,DE            ;
328 019A 22 27 02      D              LD     (POINTR),HL      ;
329                                                            ;
330 019D 21 02 00      D              LD     HL,BUFFER        ;POINTR < BUFFER ?
331 01A0 ED 5B 27 02   D              LD     DE,(POINTR)      ;
332 01A4 CD 00 00      E              CALL   CMP16            ;
333 01A7 D2 C2 01      C              JP     NC,LOGGER        ;
334                                                            ;
335 01AA 2A 27 02      D              LD     HL,(POINTR)      ;POINTR > DATA_BASE ?
336 01AD 11 00 00      E              LD     DE,A_TO_D        ;
337 01B0 CD 00 00      E              CALL   CMP16            ;
338 01B3 D2 C2 01      C              JP     NC,LOGGER        ;
339                                                            ;
340 01B6 01 02 00                     LD     BC,2             ;BUFFER[POINTR] = CURRENT
341 01B9 21 00 00      E              LD     HL,CURRENT       ;
342 01BC ED 5B 27 02   D              LD     DE,(POINTR)      ;
343 01C0 ED B0                        LDIR                    ;
344                            LOGGER                          ;
345 01C2 2A 00 00      E              LD     HL,(CURRENT)     ;TOP = CURRENT
346 01C5 22 21 02      D              LD     (TOP),HL         ;
```

```
348 01C8 2A 27 02      D        LD      HL,(POINTR)        ;Check POINTER
349 01CB ED 5B 02 00   D        LD      DE,(BUFFER)        ;
350 01CF CD 00 00      E        CALL    CMP16              ;
351 01D2 D2 E0 01      C        JP      NC,CONTINUE        ;If < 0, continue
352                             LOOPBACK                   ; otherwise LOOPBACK to top
353 01D5 21 02 00      D        LD      HL,BUFFER          ;Get base address of BUFFER...
354 01D8 11 F4 01               LD      DE,BUFF_SIZE       ; ...as well as last address
355 01DB ED 5A                  ADC     HL,DE              ;
356 01DD C3 E5 01      C        JP      UPDATE             ;Jump with pointer in HL
357                             CONTINUE                   ;
358 01E0 2A 27 02      D        LD      HL,(POINTR)        ;Normally, old pointer is OK
359 01E3 2B                     DEC     HL                 ;
360 01E4 2B                     DEC     HL                 ;
361                             UPDATE                     ;
362 01E5 01 02 00               LD      BC,2               ;Fetch BOTTOM
363 01E8 11 23 02      D        LD      DE,BOTTOM          ;
364 01EB ED B0                  LDIR                       ;
365                                                        ;
366 01ED 21 21 02      D        LD      HL,TOP             ;SLOPE = TOP - BOTTOM
367 01F0 11 23 02      D        LD      DE,BOTTOM          ;
368 01F3 06 02                  LD      B,2                ;Prep for 2 byte SUBTRACTION
369 01F5 CD 00 00      E        CALL    SUBTRACTION        ;
370                                                        ;
371 01F8 2A 21 02      D        LD      HL,(TOP)           ;Pass result to SLOPE
372 01FB 22 08 02      D        LD      (SLOPE),HL         ;
373
374 01FE 11 90 01               LD      DE,400             ;
375 0201 CD 00 00      E        CALL    CMP16              ;
376 0204 EA 16 02      C        JP      PE,EX_RECORD       ;
377 0207 D2 16 02      C        JP      NC,EX_RECORD       ;
378                                                        ;
379 020A 22 08 02      D        LD      (SLOPE),HL         ;Pass result to SLOPE
380 020D 29                     ADD     HL,HL              ;
381 020E 29                     ADD     HL,HL              ;
382 020F 11 FF 07               LD      DE,2047            ;Offset result, (negate sign)
383 0212 19                     ADD     HL,DE              ;
384 0213 22 00 00      E        LD      (SDAC03),HL        ; on an oscilloscope
385                             EX_RECORD                  ;
386 0216 C9                     RET                        ;
387                                                        ;
388                             TAG                        ;
389                             ;       LD      HL,(TOP)   ;
390                             ;       LD      (SDAC03),HL ;
391                             ;       LD      HL,(BOTTOM) ;
392                             ;       LD      (SDAC01),HL ; ...before shipping it out
393                                                        ;
394                             ;
```

```
395                    ;------ Check slope before resonance to qualify the result
396                    ;
397                    DETECTOR                          ;
398                                                     ;RESONANCE criteria: 1 < SLOPE < 10
399 0217 2A 08 02   D          LD    HL,(SLOPE)        ;SLOPE < MIN_SLOPE ?
400 021A 11 1E 00              LD    DE,MIN_RISE       ;
401 021D CD 00 00   E          CALL  CMP16             ;
402 0220 DA 31 02   C          JP    C,DISCARD         ;If so, RESONANCE invalid
403                    KEEP                             ;
404 0223 2A 05 02   D          LD    HL,(SWEEP_FREQ)   ;RESONANCE = SWEEP_FREQ
405 0226 22 17 02   D          LD    (RESONANCE),HL    ;

406
407 0229 21 31 02   D          LD    HL,FAILURE        ;
408 022C CB 86                 RES   0,(HL)            ;
409                                                    ;
410 022E C3 3F 02   C          JP    LEV_DETECTOR      ;
411                                                    ;
412                    DISCARD                         ;
413 0231 21 00 00              LD    HL,0              ;Null I_PEAK to allow
414 0234 22 FF 01   D          LD    (I_PEAK),HL       ; continued search
415 0237 22 17 02   D          LD    (RESONANCE),HL    ;
416                                                    ;
417 023A 21 1C 02   D          LD    HL,RAILED         ;
418 023D CB C6                 SET   0,(HL)            ;
419                                                    ;
420                    LEV_DETECTOR                    ;
421 023F C9                    RET                     ;Detection completed
422                                                    ;
423                    ;
424                    ;------ Establish acquisition window (upper and lower sweep limits)
425                    ;
426                    WINDOW                          ;
427 0240 A7                    AND   A                 ;Clear carry flag
428 0241 2A 17 02   D          LD    HL,(RESONANCE)    ;MIN_FREQ = RESONANCE - RANGE
429 0244 ED 4B 14 02 D         LD    BC,(RANGE)        ;
430 0248 ED 42                 SBC   HL,BC             ;
431 024A D2 50 02   C          JP    NC,W1             ;If no carry,equation is valid
432 024D 21 00 00              LD    HL,MINIMUM        ; otherwise, MIN_FREQ = MINIMUM
433 0250 22 01 02   D  W1      LD    (MIN_FREQ),HL     ;
434                                                    ;
435 0253 A7                    AND   A                 ;Clear carry flag
436 0254 2A 17 02   D          LD    HL,(RESONANCE)    ;MIN_FREQ = RESONANCE + RANGE
437 0257 ED 4B 14 02 D         LD    BC,(RANGE)        ;
438 025B ED 4A                 ADC   HL,BC             ;
439 025D D2 63 02   C          JP    NC,W2             ;If no carry, equation is valid
440 0260 21 FF 0F              LD    HL,MAXIMUM        ; otherwise, MAX_FREQ = MAXIMUM
441 0263 22 03 02   D  W2      LD    (MAX_FREQ),HL     ;
442                    EX_WINDOW                       ;
```

```
443 026: C9                          RET                      ;With WINDOW set, leave
444                                                           ;
445                     ;
446                     ;------ See if sweep is at the extreme range
447                     ;
448                     CHK_LIMIT                              ;
449 0267 21 1C 02    D          LD    HL,RAILED              ;Reset the RAILED flag
450 026A CB 86                  RES   0,(HL)                 ;
451                                                           ;
452 026C 2A 17 02    D          LD    HL,(RESONANCE)         ;RESONANCE > HI_RAIL ?
453 026F 11 00 0C               LD    DE,3072                ;
454 0272 CD 00 00    E          CALL  CMP16                  ;
455 0275 D2 86 02    C          JP    NC,BACKWARD            ;
456                                                           ;
457                     ;       LD    HL,(RESONANCE)         ;RESONANCE < LO_RAIL ?
458                     ;       LD    DE,1024                ;
459                     ;       CALL  CMP16                  ;
460                     ;       JP    C,FORWARD              ;
461 0278 C3 96 02    C          JP    EX_LIMIT               ;
462                     FORWARD                                ;
463 027B 2A 00 00    E          LD    HL,(COURSE)            ;COURSE = COURSE - STEP 464 027E 11 48 00               LD    DE,STEP                ;
465 0281 ED 52                  SBC   HL,DE                  ;
466 0283 C3 8E 02    C          JP    PROBLEM                ;
467                     BACKWARD                               ;
468 0286 2A 00 00    E          LD    HL,(COURSE)            ;COURSE = COURSE + STEP
469 0289 11 48 00               LD    DE,STEP                ;
470 028C ED 5A                  ADC   HL,DE                  ;
471                     PROBLEM                                ;
472 028E 22 00 00    E          LD    (COURSE),HL            ;
473 0291 21 1C 02    D          LD    HL,RAILED              ;Assume that result is RAILED
474 0294 CB C6                  SET   0,(HL)                 ;
475                                                           ;
476                     EX_LIMIT                               ;
477 0296 C9                     RET                          ;Limits checked, leave
478                                                           ;
479                     ;
480                     ;------ Boost charge the inductor before doing PEAK analysis
481                     ;
482                     PRECHARGE                              ;Inductor has nasty .4 sec
483                                                           ; transfer characteristic
484 0297 21 00 00               LD    HL,MINIMUM             ;Establish the defaults
485 029A 22 00 00    E          LD    (HENRY),HL             ;
486 029D CD EC 02    C          CALL  STALL                  ;Wait A second, then procede
487                                                           ;
488 02A0 C9                     RET                          ;
489                                                           ;
490                     ;
```

```
491                     ;------ Elevate power to permit inductor servo to stabilize
492                     ;
493                     POSTCHARGE                          ;
494                                                         ;
495 02A1 21 32 02   D       LD    HL,TUNED                 ;Enable POWER once TUNED
496 02A4 CB C6              SET   0,(HL)                   ; Set it's enable flag
497                                                         ;
498 02A6 21 00 00   E       LD    HL,LOOP                  ;Enable MINIMIZER
499 02A9 CB C6              SET   0,(HL)                   ; Set it's enable flag
500                                                         ;
501 02AB 21 00 00   E       LD    HL,FS_DOWN               ;Simulate a depressed footpedal
502 02AE CB C6              SET   0,(HL)                   ;
503                                                         ;
504 02B0 21 C8 0C           LD    HL,PREDICTED             ;Set HENRY to PREDICTED
505 02B3 22 00 00   E       LD    (HENRY),HL               ; near the typical op. point
506                                                         ;
507 02B6 21 00 00   E       LD    HL,BOUNDRY               ;Raise BOUNDRY (power level)
508 02B9 7E                 LD    A,(HL)                   ;
509 02BA F5                 PUSH  AF                       ;
510 02BB 36 78              LD    (HL),120                 ;
511                                                         ;
512 02BD CD EC 02   C       CALL  STALL                    ;Stall for a second
513 02C0 CD EC 02   C       CALL  STALL                    ;   ..   ..   ..   ..
514 02C3 CD EC 02   C       CALL  STALL                    ;   ..   ..   ..   ..
515 02C6 CD EC 02   C       CALL  STALL                    ;   ..   ..   ..   ..
516 02C9 CD EC 02   C       CALL  STALL                    ;   ..   ..   ..   ..
517 02CC CD EC 02   C       CALL  STALL                    ;   ..   ..   ..   ..
518 02CF CD EC 02   C       CALL  STALL                    ;   ..   ..   ..   ..
519 02D2 CD EC 02   C       CALL  STALL                    ;   ..   ..   ..   ..
520                                                         ;
521 02D5 F1                 POP   AF                       ;Restore BOUNDRY 522 02D6 21 00 00   E       LD    HL,BOUNDRY               ;
523 02D9 77                 LD    (HL),A                   ;
524                                                         ;
525 02DA 21 00 00   E       LD    HL,FS_DOWN               ;Simulate a released foootpedal
526 02DD CB 86              RES   0,(HL)                   ;
527                                                         ;
528 02DF C9                 RET                            ;Wait is over, go back
529                                                         ;
530                     ;
531                     ;------ Loop delay
532                     ;
533                     DELAY                               ;
534 02E0 C5                 PUSH  BC                       ;
535 02E1 01 08 00           LD    BC,8    ;=2 SECONDS      ;Load delay counter (28cnts/SEC)
536 02E4                DLY1
537 02E4 0B                 DEC   BC                       ;Subtract 1
538 02E5 79                 LD    A,C                      ;Sum upper with lower
```

```
539 02E6 B0                          OR    B               ;
540 02E7 C2 E4 02    C               JP    NZ,DLY1         ;Continue until it is zero
541 02EA C1                          POP   BC              ;
542 02EB C9                          RET                   ;
543                                                        ;
544                  ;
545                  ;------ Loop delay
546                  ;
547                  STALL                                 ;
548 02EC 01 FF FF           LD    BC,0FFFFH   ;2 SECS ;Load delay counter (28cnts/SEC)
549                  STLL1                                 ;
550 02EF 0B                  DEC   BC              ;Subtract 1
551 02F0 79                  LD    A,C             ;Sum upper with lower
552 02F1 B0                  OR    B               ;
553 02F2 C2 EF 02    C       JP    NZ,STLL1        ;Continue until it is zero
554 02F5 C9                  RET                   ;
555                                                ;
556                  ;
557                  ;------ Call user attention to the handpiece connector
558                  ;
559 02F6            WINK
560 02F6 3A 12 02    D       LD    A,(BLINK)       ;BLINK > 0 ?
561 02F9 FE 00               CP    0               ;
562 02FB CA 1F 03    C       JP    Z,CLR_BLINKR    ;
563                                                ;
564 02FE 21 13 02    D       LD    HL,BLINKR       ;Increment the rate counter
565 0301 34                  INC   (HL)            ;
566                                                ;
567 0302 BE                  CP    (HL)            ;BLINKR >= BLINK ?
568 0303 D2 24 03    C       JP    NC,STANDBY      ;
569                                                ;
570 0306 3A 00 00    E       LD    A,(CONN_LED)    ;CONNLED = NOT(CONN_LED)
571 0309 2F                  CPL                   ;
572 030A E6 03               AND   00000011B       ;
573 030C 32 00 00    E       LD    (CONN_LED),A    ;
574                                                ;
575 030F 21 2C 00    E       LD    HL,SCALE+44     ;Short bleep with each state change
576 0312 22 00 00    E       LD    (MELODY),HL     ;
577 0315 21 00 00    E       LD    HL,RYTHM        ;Set the RYTHM for audio feedback
578 0318 36 01               LD    (HL),1          ;
579 031A 21 00 00    E       LD    HL,CONDUCTOR    ;Set the CONDUCTOR's queue 580 031D CB C6               SET   0,(HL)          ;
581                  CLR_BLINKR                    ;
582 031F 21 13 02    D       LD    HL,BLINKR       ;BLINKR = 0
583 0322 36 00               LD    (HL),0          ;
584                  STANDBY                       ;
585 0324 C9                  RET                   ;
586                                                ;
```

```
587                     ;
588                     ;------
589                     ;
590                     TWEEKR
591 033E 2A 00 00   E           LD    HL,(HENRY)        ;Keep HENRY
592 0339 E5                      PUSH  HL                ;
593                                                      ;
594 033A 21 00 00   E           LD    HL,LOOP           ;Deactivate the MINIMIZER
595 033D CB 86                  RES   0,(HL)            ;
596                                                      ;
597 033F 21 00 00               LD    HL,MINIMUM        ;Set HENRY to MINIMUM
598 0332 22 00 00   E           LD    (HENRY),HL        ;
599                                                      ;
600 0334 3A 00 00   E           LD    A,(BOUNDRY)       ;
601 0337 F5                     PUSH  AF                ;
602 0338 3E 3C                  LD    A,NOMINAL         ;Set BOUNDRY
603 033A 32 00 00   E           LD    (BOUNDRY),A       ;
604                                                      ;
605 033D CD 53 03   C           CALL  TOTH              ;Find the Top-Of-The-Hill
606                                                      ;
607 0340 F1                     POP   AF                ;Restore BOUNDRY
608 0341 32 00 00   E           LD    (BOUNDRY),A       ;
609                                                      ;
610 0344 E1                     POP   HL                ;Restore HENRY
611 0345 22 00 00   E           LD    (HENRY),HL        ;
612                                                      ;
613 0348 21 00 00   E           LD    HL,LOOP           ;Reactivate the MINIMIZER
614 034B CB C6                  SET   0,(HL)            ;
615                                                      ;
616                     TWEEKD
617 034D 21 00 00   E           LD    HL,HSERVICE       ;Reset the flag to acknowledge
618 0350 CB 86                  RES   0,(HL)            ; the completion of the task
619                                                      ;
620 0352 C9                     RET                     ;
621                                                      ;
622                     ;
623                     ;------ Locate the Top-Of-The-Hill
624                     ;
625                     TOTH
626 0353 01 00 F0               LD    BC,0F000H         ;Start timer
627 0356 ED 43 29 02 D           LD    (TIMR),BC         ;
628                     TOTH0
629 035A CD 7C 01   C           CALL  RECORDER          ;Determine the SLOPE
630                                                      ;
631 035D 21 00 00               LD    HL,0              ;SLOPE > OR < 0 ?
632 0360 ED 5B 08 02 D           LD    DE,(SLOPE)        ;
633 0364 CD 00 00   E           CALL  CMP16             ;
634 0367 FA 70 03   C           JP    M,TOTH1           ;If negative, use minus correction
635                                                      ; otherwise, positive correct
636 036A CD 9E 03   C           CALL  POS               ;Positive correction called for
637 036D C3 73 03   C           JP    TOTH2             ;Continue
```

```
638                         TOTH1                                ;
639 0370 CD 96 03    C      CALL    NEG                          ;Negative correction called for
640                         TOTH2                                ;
641 0373 ED 4B 29 02 D      LD      BC,(TIMR)                    ;Tick the TIMR
642 0377 0B                 DEC     BC                           ;
643 0378 ED 43 29 02 D      LD      (TIMR),BC                    ;
644                                                              ;
645 037C CD E0 02    C      CALL    DELAY                        ;Wait, this will help reject
646 037F CD E0 02    C      CALL    DELAY                        ;transient corrections due to
647                                                              ; noisy acquisition
648 0382 78                 LD      A,B                          ;Have we timed out yet ?
649 0383 B1                 OR      C                            ;
650 0384 C2 5A 03    C      JP      NZ,TOTH0                     ;
651                                                              ;
652 0387 2A 00 00    E      LD      HL,(HERTZ)                   ;RESONANCE = HERTZ
653 038A 22 17 02    D      LD      (RESONANCE),HL               ;Note that HERTZ has been TWEEK'D
654                                                              ;
655 038D C9                 RET                                  ;
656                                                              ;
657                                                              ;
658                         ;------ Increment the VCO setting
659                         ;
660                         POS                                  ;
661 038E 2A 00 00    E      LD      HL,(HERTZ)                   ;HERTZ = HERTZ + 1
662 0391 23                 INC     HL                           ;
663 0392 22 00 00    E      LD      (HERTZ),HL                   ;
664                    ;    LD      (SDAC03),HL                  ;Also set the service dac
665                         POS60                                ;
666 0395 C9                 RET                                  ;
667                                                              ;
668                         ;
669                         ;------ Decrement the VCO setting
670                         ;
671                         NEG                                  ;
672 0396 2A 00 00    E      LD      HL,(HERTZ)                   ;HERTZ = HERTZ - 1
673 0399 2B                 DEC     HL                           ;
674 039A 22 00 00    E      LD      (HERTZ),HL                   ;
675                    ;    LD      (SDAC03),HL                  ;Also set the service dac
676                         NEG60                                ;
677 039D C9                 RET                                  ;
678                                                              ;
679                         ;
680                         ;------ Set the VCO to the resultant point of RESONANCE
681                         ;
682                         SET_VCO                              ;
683 039E 2A 17 02    D      LD      HL,(RESONANCE)               ;Fetch acquired point of resonance
684                                                              ;
685 03A1 11 C8 00           LD      DE,DELTAF                    ;Subtract static offset
686 03A4 ED 52               SBC     HL,DE                        ;
687 03A6 EA B2 03    C      JP      PE,VAL1                      ;If overflow, don't change VCO
688 03A9 DA B2 03    C      JP      C,VAL1                       ;If carry, don't change VCO
689                                                              ;
690 03AC 22 00 00    E      LD      (HERTZ),HL                   ;Set VCO to acquired peak point
```

```
691 03AF 22 19 02      D            LD      (LAST_RES),HL        ;keep for later reference
692                         VAL1                                  ;
693 03B2 C9                          RET                          ;
694                                                               ;
695                         ;
```

```
696                         ;------ Restore the OLD_COURSE setting to reactivate the VCO
697                         ;
698                         VCO_ON                                 ;
699                                                               ;
700 03B3 2A 00 00      D             LD     HL,(OLD_COURSE)       ;
701 03B6 22 00 00      E             LD     (COURSE),HL           ;
702                                                               ;
703 03B9 C9                          RET                          ;
704                                                               ;
705                         ;
706                         ;------ Completely deactivate the VCO
707                         ;
708                         VCO_OFF                                ;
709                                                               ;
710 03BA 2A 00 00      E             LD     HL,(COURSE)           ;
711 03BD 11 FF 0F                    LD     DE,0FFFH              ;
712 03C0 CD 00 00      E             CALL   CMP16                 ;
713 03C3 CA D2 03      C             JP     Z,VCO_EXIT            ;
714                                                               ;
715 03C6 2A 00 00      E             LD     HL,(COURSE)           ;
716 03C9 22 00 00      D             LD     (OLD_COURSE),HL       ;
717                                                               ;
718 03CC 21 FF 0F                    LD     HL,0FFFH              ;
719 03CF 22 00 00      E             LD     (COURSE),HL           ;
720                         VCO_EXIT                               ;
721 03D2 C9                          RET                          ;
722                                                               ;
723                                                                                                              ;
724                         ;===================================================================;
725                         ;         DATA SEGMENT                                              ;
726                         ;===================================================================;
727                         ;
= 728 03D3                           INCLUD EQU.INC        ;INCLUDE CONSTANTS IN ASSEMBLY
= 729                       ;===================================================================;
= 730                       ;                                                                   ;
= 731                       ;         EQU.INC           PHACO SYSTEM GLOBAL EQUATES             ;
= 732                       ;                                                                   ;
= 733                       ;===================================================================;
= 734                       ;                                                                   ;
= 735                       ;              !!!!!!!!! CHANGE HISTORY !!!!!!!!!                   ;
= 736                       ;                                                                   ;
= 737                       ;         AUTHOR         DATE          CHANGE PURPOSE               ;
= 738                       ;         ----------------------------------------------------      ;
```

```
= 739                ;        T. Lo         3 FEB 86      CREATION                       ;
= 740                ;        F. Lian       10 Feb. 86    Update                         ;
= 741                ;        F. Lian       10 April 86   Update                         ;
= 742                ;        T. Escorcio   24 June 86    Update                         ;
= 743                ;        T. Escorcio   7 July 86     Update                         ;
= 744                ;        T. Escorcio   4/1/87        add adaptive tuning constants  ;
= 745                ;                                                                   ;
= 746                ;-------------------------------------------------------------------;
= 747                ;
= 748                ;------ TOP OF RAM MARKER
= 749                ;
= 750 8000           RAM_END       EQU      8000H         ;32K CONFIGURATION
= 751                ;
= 752                ;------ INTERRUPT LOOP TIMING CONSTANTS
= 753                ;

= 754 01E3           SAMPFRQ       EQU      489+2         ;INTERRUPT SAMPLING FREQUENCY
= 755 0002           DIV480HZ      EQU      2             ;480 HZ DIVIDER
= 756 0004           DIV240HZ      EQU      4             ;240 HZ DIVIDER
= 757 0008           DIV120HZ      EQU      8             ;120 HZ DIVIDER
= 758 0010           DIV60HZ       EQU      16            ; 60 HZ DIVIDER
= 759 0020           DIV30HZ       EQU      32            ; 30 HZ DIVIDER
= 760 0060           DIV10HZ       EQU      96            ; 10 HZ DIVIDER
= 761                                                     ;
= 762                ;
= 763                ;------ System counter parameters
= 764                ;
= 765 0168           ELAPS1        EQU      168H          ;3 SECOND TIMER VALUE (HUNTER)
= 766 05A0           ELAPS2        EQU      5A0H          ;3 SECOND TIMER VALUE (COM. REPLY)
= 767 0020           ELAPS3        EQU      020H          ;BEEPER DURATION
= 768 0300           ELAPS4        EQU      0300H         ;BEEPER COUNTER SAMPLING RATE
= 769 0078           ELAPS5        EQU      120           ;SCANNER INTERVAL
= 770                                                     ;
= 771                ;
= 772                ;------ PROGRAM THRESHOLD LEVELS
= 773                ;
= 774 0000           MIN           EQU      00H           ;
= 775 00FF           MAX           EQU      0FFH          ;
= 776 0001           TRUE          EQU      00000001B     ;
= 777 0000           FALSE         EQU      00000000B     ;
= 778 01F4           BUFF_SIZE     EQU      500           ;
= 779 000A           KEY_RYTHM     EQU      10            ;Key music duration time
= 780 0004           KEY_TIME      EQU      4             ;
= 781 000F           BEEP_TIME     EQU      15            ;
= 782 0640           BEGINNING     EQU      1600          ;
= 783 0800           FULL          EQU      2048          ;
= 784                                                                                   ;
= 785                ;==================================================================;
= 786 0300
```

```
= 787 03::
  788 000A         TRIES      EQU    10           ;
  789                         ;
  790                         ;------ SWEEPER parameters
  791                         ;
  792                         ;STEP      EQU    36           ;400 Hz ;VCO COURSE ADJUST step 11Hz/CNT
  793 0048         STEP       EQU    72           ;800 Hz ;VCO COURSE ADJUST step 11Hz/CNT
  794 001E         MIN_RISE   EQU    30           ;
  795                         ;
  796                         ;------ ADAPTIVE TUNING CONSTANTS
  797                         ;
  798 00C8         DELTAF     EQU    200          ;300Hz ;ERROR CORRECTION FACTOR
  799 000A         MAX_RATE   EQU    10           ;Max slope countr threshold
  800 000A         MIN_RATE   EQU    10           ;Min slope countr threshold
  801 0001         MIN_SLOPE  EQU    1            ;Minimum permitted absolute slope
  802 0001         ALLOWED    EQU    1  ;q1 DEGREE  ;ALLOWED MARGIN BEFORE CORRECTION
  803 0878         THETA      EQU    2168         ;REFERENCE PHASE ANGLE (7FFH = 0)
  804 0000         MINIMUM    EQU    0000H        ;REFERENCE CONSTANT
  805 0FFF         MAXIMUM    EQU    0FFFH        ;REFERENCE CONSTANT
  806 003C         NOMINAL    EQU    60           ;ALTERNATE POWER LEVEL OFFSET
  807 0000         NORMAL     EQU    MINIMUM      ;RESTORED POWER LEVEL VALUE
  808 0000         ZERO       EQU    MINIMUM      ;REFERENCE CONSTANT
  809 0FFF         MAX_HENRY  EQU    MAXIMUM      ;EXTREME INDUCTOR ADJUSTMENT
  810 0CC8         PREDICTED  EQU    3272         ;EXPECTED OPERATING POINT OF HENRY
  811 0EE8         RETREAT    EQU    3800         ;POINT TO FALLBACK TO WHEN UNSTABLE 812 0F5C         HI_LIMIT   EQU    3932         ;4.8V ;SET BOUNDS ON HENRY
  813 0948         LO_LIMIT   EQU    2376         ;2.9V ; WHERE COUNT = (V. / 5) * 4096
  814                         ;
  815                         ;
  816                         ;------ HANDPIECE STATUS INFORMATION
  817                         ;
  818 0040         PHACOPC    EQU    01000000B    ;TEST FOR PHACO HANDPIECE
  819 0080         FRAGPC     EQU    10000000B    ; "  "  FRAG       "
  820 00C0         AUXPC      EQU    11000000B    ; "  "  AUXILARY  "+
  821 0000         NO_PC      EQU    00000000B    ; "  "  NO HANDPIECE CONNECTED
  822                         ;
  823 03C0
  824                         ;
  825                                  DSEG       ;
  826                         ;
  827 0000 00 00   OLD_COURSE DEFW   0            ;
  828 00C2         BUFFER     DS     BUFF_SIZE    ;Revolving buffer space
  829 01F6         BUFF_END   DS     1            ;
  830 01F7 00 00   MARGIN     DEFW   0            ;DIFFERENCE BETWEEN TARGET PHASE AND ACTUAL
  831 01F9 00 00   MIN_MARGIN DEFW   0            ;CURRENT MIN MARGIN
  832 01FB 00 00   MAX_MARGIN DEFW   0            ;ABSOLUTE MAX ACCEPTABLE
  833 01FD 00 00   LAST_MARGIN DEFW  0            ;REFERENCE PREVIOUS VALUE
  834 01FF 00 00   I_PEAK     DEFW   0            ;PEAK MAGNITUDE OF CURRENT DURING SWEEP
```

```
835 02:: 00 00         MIN_FREQ      DEFW   0    ;ESTABLISHED LOWER SWEEP RANGE
836 02:: 00 00         MAX_FREQ      DEFW   0    ;ESTABLISHED UPPER SWEEP RANGE
837 02:: 00 00         SWEEP_FREQ    DEFW   0    ;LATEST SWEEP VALUE
838 02:: 00            FIRST_TIME    DB     0    ;FLAG TUNER AT FIRST OCCURENCE OF LOCKOUT
839 02:: 00 00         SLOPE         DEFW   0    ;Current rate of rise or decline
840 02:: 00            P_SLOPE       DB     0    ;Indicate pass/fail
841 02:: 00            N_SLOPE       DB     0    ;Indicate pass/fail
842 02:: 00 00         P_RATE        DEFW   0    ;Rising slope interval counter
843 02:: 00 00         N_RATE        DEFW   0    ;Falling slope interval counter
844 02:: 00 00         OLD_CURRENT   DEFW   0    ;
845 02:: 00            BLINK         DB     0    ;Store duration of BLINK
846 02:: 00            BLINKR        DB     0    ;Store working value of BLINK
847 02:: 00 00         RANGE         DEFW   0    ;PLACE TO HOLD CURRENT SWEEP RANGE
848 02:: 00            MISTUNE       DB     0    ;FLAG NEEDED TO INVOKE SWEEPER
849 02:: 00 00         RESONANCE     DEFW   0    ;HOLD CURRENT RESULT OF SWEEPER
850 02:: 00 00         LAST_RES      DEFW   0    ;HOLD LAST RESULT OF SWEEPER
851 02:: 00            FAULT_CNTR    DB     0    ;COUNT ATTEMPTS TO OBTAIN RESONANCE
852 02:: 00            RAILED        DB     0    ;INDICATE MAX SWEEP LIMITS IN EFFECT
853 02:: 00 00         LATENCY       DEFW   0    ;MONITOR THE INTERVAL BETWEEN SWEEPS
854 02:: 00 00         NEW_CURRENT   DEFW   0    ;
855 02:: 00 00         TOP           DEFW   0    ;
856 02:: 00 00         BOTTOM        DEFW   0    ;
857 02:: 00 00         COUNTR        DEFW   0    ;
858 02:: 00 00         POINTR        DEFW   0    ;
859 02:: 00 00         TIMR          DEFW   0    ;
860 02:: 00 00         TLIM          DEFW   0    ;
861 02:: 00 00         BLIM          DEFW   0    ;
862 02:: 00 00         PAST          DEFW   0    ;
863 02:: 00            FAILURE       DB     0    ;
864 02:: 00            TUNED         DB     0    ;
865                                              ;
866
867                    ;-----------------------------------------------------------------;
868                    ;                                                                 ;
869                    ;        EXTERNAL VARIABLE DECLARATION                            ;

870                    ;                                                                 ;
871                    ;-----------------------------------------------------------------;
872                    ;
873                            EXTRN    NOTE, SCALE, HERTZ, CURRENT, BOUNDRY, LOOP, HENRY, ERROR1
874                            EXTRN    CMP16, SUBTRACTION, A_TO_D, PEDAL, HANDPC, CONN_LED
875                            EXTRN    CONDUCTOR, MID_C, RYTHM, MELODY
876                            EXTRN    SDAC01, SDAC02, SDAC03, ERROR4
877                            EXTRN    FS_DOWN, COURSE, HSERVICE, RELAPSE
878                                                                                      ;
879                    ;-----------------------------------------------------------------;
880                    ;                                                                 ;
881                    ;        PUBLIC VARIABLE DECLARATION                              ;
882                    ;                                                                 ;
```

```
983
984          ;
985                  PUBLIC  NEW_CURRENT, TOP, BOTTOM, COUNTR, POINTR, SWEEPER, WINK
986                  PUBLIC  OLD_CURRENT, BLINK, RANGE, MISTUNE, RESONANCE, LAST_RES
987                  PUBLIC  FAULT_CNTR, RAILED, LATENCY, TAG, VCO_ON, VCO_OFF
988                  PUBLIC  OLD_COURSE, TUNED
989
990          ;===============================================================
991          ;
992          ;:::::::::::::::::::::::::::::::::::::::::::::::::::::::::::::::
993          ;
994 02::           END

ERRORS = 0000
```

PHACO ADAPTIVE INDUCTOR CONTROLLER            1

```
1                   TITLE   'PHACO ADAPTIVE INDUCTOR CONTROLLER'
2                   NAME    PHENRY_MODULE
3                   PAGES   66
4                   CSEG
5
6           ;:::::::::::::::::::::::::::::::::::::::::::::::::::::::::::::::
7           ;
8           ;           PHACO ADAPTIVE INDUCTOR CONTROLLER
9           ;
10          ;===============================================================
11          ;         :::::::: CHANGE HISTORY ::::::::
12          ;
13          ;    Author        Date        Change Purpose
14          ;    ---------------------------------------------------------
15          ;    Tony Escorcio  3/31/87    Creation
16          ;    Tony Escorcio  7/31/87    Add test for conditional
17          ;                              execution; LOCKOUT and LOOP
18          ;    Tony Escorcio  8/21/87    Replace LOCKOUT with FS_DOWN
19          ;
20          ;===============================================================
21          ;
22          ;---------------------------------------------------------------
23          ;
24          ;    Function: Maintain minimal phase margin by tweaking the
25          ;                   tuning inductor
26          ;
27          ;    Registers: AF, BC, HL
28          ;      Accepts: LOOP, MIN_MARGIN
29          ;      Returns: MARGIN, HENRY
30          ;        Flags: C, P, LOOP, FS_DOWN
31          ;    Variables: MARGIN, TWEAK, HENRY, DELTA
32          ;    Constants: THETA, ALLOWED
33          ;
```

```
34                  ;       Pseudo Code:
35                  ;       MINIMIZER
36                  ;               if (LOOP) AND (FS_DOWN)) then
37                  ;                       if (MARGIN > ALLOWED) then
38                  ;                               TWEAK = DELTA / 2
39                  ;                               HENRY = HENRY + TWEAK
40                  ;                       endif
41                  ;                       DELTA = PHASE - THETA
42                  ;                       if (not(DELTA)) then
43                  ;                               MARGIN = 0 - DELTA
44                  ;                       else
45                  ;                               MARGIN = DELTA
46                  ;                       endif
47                  ;               endif
48                  ;       return
49                  ;
50                  ;----------------------------------------------------------
51                  ;------    ------------------------------------------------
52                  ;
53                  ;       Notes:
54                  ;       - The algorythm uses successive approximation.
55                  ;       - This routine is intended to be utilized as an interrupt
56                  ;               process.
57                  ;       - THETA = reference phase angle in counts (0 degrees)

58                  ;       - ALLOWED = range of permissible minor deviations
59                  ;       - MARGIN = current deviation from THETA
60                  ;       - DELTA = signed correction to be subsequently added to HENRY
61                  ;       - LOLIMIT = lower extreme of servo capture range.
62                  ;       - UPLIMIT = upper     "       "       "       "       "
63                  ;
64                  ;----------------------------------------------------------
65                  ;
66                          MINIMIZER                               ;Execute if both flags true
67 0000 3A 00 00  E         LD      A,(FS_DOWN)                     ;Check if footpedal depressed
68 0003 21 05 00  D         LD      HL,LOOP                         ;Check process enable flag
69 0006 A6                  AND     (HL)                            ;Do Boolean addition
70 0007 CB 47               BIT     0,A                             ;If false, continue
71 0009 C2 14 00  C         JP      NZ,MN0                          ; otherwise, null timer
72 000C 21 00 00  D         LD      HL,SUPPRESS                     ;
73 000F 36 00               LD      (HL),0                          ;
74 0011 C3 20 00  C         JP      DEFAULT                         ;Leave
75                          MN0                                     ;
76 0014 3A 00 00  D         LD      A,(SUPPRESS)                    ;SUPPRESS > value ?
77 0017 FE 1E               CP      30                              ;
78 0019 D2 29 00  C         JP      NC,MN1                          ;If true, continue
79 001C 3C                  INC     A                               ; otherwise, keep waiting
80 001D 32 00 00  D         LD      (SUPPRESS),A                    ;
```

```
81                      DEFAULT
82 0020 21 FF 07                LD      HL,DFAULT       ;DEFAULT THE PHASE
83 0023 22 00 00    E           LD      (PHASE),HL      ;
84                                                      ;
85 0026 C3 A6 00    C           JP      EXIT            ;
86                      MN1                             ;
87 0029 2A 00 00    E           LD      HL,(PHASE)      ;
88 002C 11 6C 07                LD      DE,LOLIMIT      ;
89 002F CD 00 00    E           CALL    CMP16           ;
90 0032 D2 3E 00    C           JP      NC,MN1B         ;
91                                                      ;
92 0035 21 00 0C                LD      HL,UPLIMIT      ;DEFAULT THE PHASE
93 0038 22 00 00    E           LD      (PHASE),HL      ;
94 003B 22 00 00    E           LD      (HENRY),HL      ;
95                      ;       CALL    WHINER          ;
96                      MN1B                            ;
97 003E 2A 06 00    D           LD      HL,(MARGIN)     ;MARGIN > ALLOWED ?
98 0041 01 01 00                LD      BC,ALLOWED      ;Do 16 bit comparison
99 0044 ED 42                   SBC     HL,BC           ;Subtract and watch flags
100 0046 DA 7E 00   C           JP      C,READING       ;If true, merely take reading
101                                                     ;
102 0049 ED 4B 01 00 D          LD      BC,(DELTA)      ;TWEAK = DELTA / 2
103 004D CB 28                  SRA     B               ;Shift upper byte
104 004F CB 19                  RR      C               ;Shift lower byte
105 0051 ED 43 03 00 D          LD      (TWEAK),BC      ;Record new TWEAK
106 0055 2A 00 00   E           LD      HL,(HENRY)      ;HENRY = HENRY + TWEAK
107 0058 ED 4A                  ADC     HL,BC           ;Adjust HENRY
108                                                     ;
109 005A 22 00 00   E           LD      (HENRY),HL      ;Write to buffer
110                                                     ;
111                     VERIFY                          ;
112                     LO_RAIL                         ;
113 005D 11 48 09               LD      DE,LO_LIMIT     ;VALUE > LO_LIMIT ?
114 0060 CD 00 00   E           CALL    CMP16           ;
115 0063 D2 6F 00   C           JP      NC,HI_RAIL      ;If true, check next limit
                                                        ; otherwise, override it
117 0066 21 D8 0E               LD      HL,RETREAT      ;Set HENRY to LO_LIMIT
118 0069 22 00 00   E           LD      (HENRY),HL      ;Write to buffer
119 006C C3 7E 00   C           JP      READING         ;
120                     HI_RAIL                         ;
121 006F 11 5C 0F               LD      DE,HI_LIMIT     ;VALUE < HI_LIMIT ?
122 0072 CD 00 00   E           CALL    CMP16           ;
123 0075 DA 7E 00   C           JP      C,READING       ;If true, keep this as a good value
124                                                     ; otherwise, override it
125 0078 21 5C 0F               LD      HL,HI_LIMIT     ;Set HENRY to HI_LIMIT
126 007B 22 00 00   E           LD      (HENRY),HL      ;Write to buffer
127                                                     ;
128                     READING                         ;
```

```
129 007E 2A 00 00      E          LD      HL,(PHASE)         ;DELTA = PHASE - THETA
130 0081 01 78 08                 LD      BC,THETA           ;Do 16 bit comparison
131 0084 ED 42                    SBC     HL,BC              ;Subtract and watch flags
132                                                          ;
133                                                          ;*** ADJUST THE CORRECTION ***
134 0086 CB 2C                    SRA     H                  ;Divide DELTA correction by 8
135 0088 CB 1D                    RR      L                  ; for dampened loop response
136 008A CB 2C                    SRA     H                  ;
137 008C CB 1D                    RR      L                  ;
138 008E CB 2C                    SRA     H                  ;
139 0090 CB 1D                    RR      L                  ;
140 0092 3E 01                    LD      A,1                ;Unconditionally OR an increment
141 0094 B5                       OR      L                  ; to the correction as a minimum
142 0095 6F                       LD      L,A                ;
143                                                          ;
144 0096 22 01 00      D          LD      (DELTA),HL         ;Record new DELTA
145 0099 F2 A3 00      C          JP      P,READ_MARGIN      ; otherwise, negate
146 009C 44                       LD      B,H                ;Prep for negation
147 009D 4D                       LD      C,L                ; by passing it to subtrahend
148 009E 21 00 00                 LD      HL,0000H           ;Subtract DELTA from zero and
149 00A1 ED 42                    SBC     HL,BC              ; record positive result
150                    READ_MARGIN                           ;
151 00A3 22 06 00      D          LD      (MARGIN),HL        ;Log current phase MARGIN
152                    EXIT                                   ;
153 00A6 C9                       RET                        ;Continue seeking min. phase
154                                                          ;
155                                                                                          ;
156                    ;============================================================;
157                    ;       DATA SEGMENT                                          ;
158                    ;============================================================;
159                    ;
= 160 00A7              INCLUD  EQU.INC        ;Include constants in assembly
= 161                  ;============================================================;
= 162                  ;
= 163                  ;       EQU.INC         PHACO SYSTEM GLOBAL EQUATES           ;
= 164                  ;
= 165                  ;============================================================;
= 166                  ;                                                             ;
= 167                  ;            ********* CHANGE HISTORY *********                ;
= 168                  ;                                                             ;
= 169                  ;       AUTHOR          DATE            CHANGE PURPOSE        ;
= 170                  ;       ------------------------------------------------------;
= 171                  ;       T. Lo           3 FEB 86        CREATION
= 172                  ;       F. Lian         10 Feb. 86      Update
= 173                  ;       F. Lian         10 April 86     Update = 174                  ;       T. Escorcio     24 June 86      Update
= 175                  ;       T. Escorcio     7 July 86       Update
= 176                  ;       T. Escorcio     4/1/87          add adaptive tuning constants
```

```
= 177                    ;                                                                  ;
= 178                    ;------------------------------------------------------------------;
= 179                    ;
= 180                    ;------ TOP OF RAM MARKER
= 181                    ;
= 182 8000               RAM_END       EQU    8000H              ;32K CONFIGURATION
= 183                    ;
= 184                    ;------ INTERRUPT LOOP TIMING CONSTANTS
= 185                    ;
= 186 01E3               SAMPFRQ       EQU    489+2              ;INTERRUPT SAMPLING FREQUENCY
= 187 0002               DIV480HZ      EQU    2                  ;480 HZ DIVIDER
= 188 0004               DIV240HZ      EQU    4                  ;240 HZ DIVIDER
= 189 0008               DIV120HZ      EQU    8                  ;120 HZ DIVIDER
= 190 0010               DIV60HZ       EQU    16                 ; 60 HZ DIVIDER
= 191 0020               DIV30HZ       EQU    32                 ; 30 HZ DIVIDER
= 192 0060               DIV10HZ       EQU    96                 ; 10 HZ DIVIDER
= 193                                                            ;
= 194                    ;
= 195                    ;------ System counter parameters
= 196                    ;
= 197 0168               ELAPS1        EQU    168H               ;3 SECOND TIMER VALUE (HUNTER)
= 198 05A0               ELAPS2        EQU    5A0H               ;3 SECOND TIMER VALUE (COM. REPLY)
= 199 0020               ELAPS3        EQU    020H               ;BEEPER DURATION
= 200 0300               ELAPS4        EQU    0300H              ;BEEPER COUNTER SAMPLING RATE
= 201 0078               ELAPS5        EQU    120                ;SCANNER INTERVAL
= 202                                                            ;
= 203                    ;
= 204                    ;------ PROGRAM THRESHOLD LEVELS
= 205                    ;
= 206 0000               MIN           EQU    00H                ;
= 207 00FF               MAX           EQU    0FFH               ;
= 208 0001               TRUE          EQU    00000001B          ;
= 209 0000               FALSE         EQU    00000000B          ;
= 210 01F4               BUFF_SIZE     EQU    500                ;
= 211 000A               KEY_RYTHM     EQU    10                 ;Key music duration time
= 212 0004               KEY_TIME      EQU    4                  ;.
= 213 000F               BEEP_TIME     EQU    15                 ;
= 214 0640               BEGINNING     EQU    1600               ;
= 215 0800               FULL          EQU    2048               ;
= 216                                                            ;
= 217                    ;==================================================================;
= 218 00A7
= 219 00A7
  220                                                     ;
  221                    ;
  222                    ;------ ADAPTIVE TUNING CONSTANTS
  223                    ;
  224 00C8               DELTAF        EQU    200    ;300Hz  ;ERROR CORRECTION FACTOR
  225 000A               MAX_RATE      EQU    10            ;Max slope countr threshold
  226 000A               MIN_RATE      EQU    10            ;Min slope countr threshold
  227 0001               MIN_SLOPE     EQU    1             ;Minimum permitted absolute slope
  228 0001               ALLOWED       EQU    1  ;q1 DEGREE ;ALLOWED MARGIN BEFORE CORRECTION
  229 0878               THETA         EQU    2168          ;REFERENCE PHASE ANGLE (7FFH = 0)
  230                    ;THETA        EQU    2336          ;HiPOT TESTER VERSION
  231 0000               MINIMUM       EQU    0000H         ;REFERENCE CONSTANT
```

```
232 0FFF              MAXIMUM    EQU    0FFFH            ;REFERENCE CONSTANT
233 003C              NOMINAL    EQU    60               ;ALTERNATE POWER LEVEL OFFSET
234 0000              NORMAL     EQU    MINIMUM          ;RESTORED POWER LEVEL VALUE
235 0000              ZERO       EQU    MINIMUM          ;REFERENCE CONSTANT
236 0FFF              MAX_HENRY  EQU    MAXIMUM          ;EXTREME INDUCTOR ADJUSTMENT
237 0CC8              PREDICTED  EQU    3272             ;EXPECTED OPERATING POINT OF HENRY
238 0ED8              RETREAT    EQU    3800             ;POINT TO FALLBACK TO WHEN UNSTABLE
239 0F5C              HI_LIMIT   EQU    3932    ;4.8V    ;SET BOUNDS ON HENRY
240 0948              LO_LIMIT   EQU    2376    ;2.9V    ; WHERE COUNT = (V / 5) * 4096
241                                                      ;
242 07FF              DFAULT     EQU    2047             ;
243 076C              LOLIMIT    EQU    1900             ;
244 0C00              UPLIMIT    EQU    3072             ;
245                                                      ;
246                          DSEG                        ;
247 0000 00           SUPPRESS   DB     0                ;
248 0001 00 00        DELTA      DEFW   0                ;MONITOR ABSOLUTE DIFFERENCE BETWEEN
249                                                      ; TARGET MARGIN AND MEASURED
250 0003 00 00        TWEAK      DEFW   0                ;ADJUSTMENT TO CURRENT HENRY
251 0005 00           LOOP       DB     0                ;MINIMIZER ENABLE/DISABLE FLAG
252 0006 00 00        MARGIN     DEFW   0                ;
253                                                      ;
254                                                      ;
255                                                                                              ;
256                   ;----------------------------------------------------------------;
257                   ;                                                                ;
258                   ;     EXTERNAL VARIABLE DECLARATION                              ;
259                   ;                                                                ;
260                   ;----------------------------------------------------------------;
261                   ;
262                          EXTRN   HENRY, PHASE, FS_DOWN, CMP16, WHINER
263                                                                                       ;
264                   ;----------------------------------------------------------------;
265                   ;                                                                ;
266                   ;     PUBLIC VARIABLE DECLARATION                                ;
267                   ;                                                                ;
268                   ;----------------------------------------------------------------;
269                   ;
270                          PUBLIC  MINIMIZER, LOOP
271                                                                                    ;
272                   ;================================================================;
273                   ;
274                   ;IIIIIIIIIIIIIIIIIIIIIIIIIIIIIIIIIIIIIIIIIIIIIIIIIIIIIIIIIIIIIIII;
275                   ;
276 0008                     END

ERRORS = 0000
```

What is claimed is:

1. A phacoemulsification apparatus for driving an ultrasonic handpiece, comprising:
   driver means for supplying a variable electrical driving signal to said handpiece;
   an electrically tunable inductor in said driver means for coupling said driver means to said handpiece and for altering the source impedance of said driver means; and
   frequency tuning means coupled to said driver means and to said electrically tunable inductor means, for electrically tuning said tunable inductor to have a minimum inductance during a resonance tuning phase and for altering the frequency of said driving signal and measuring load current flowing through said ultrasonic handpiece at each frequency of said driver means to define a function of load current versus drive frequency and continuing to measure load current at various frequencies until a peak in the load current is found where the slope of said function of load current versus frequency at the frequency where said peak in said load current function occurs satisfies a predetermined criteria, and for causing said driver means to alter the driving frequency so as to drive said handpiece at the frequency of said peak load current; and
   phase adjusting means coupled to said frequency tuning means and to said electrically tunable inductor for controlling the inductance of said electrically tunable inductor so as to minimize the phase angle between the voltage waveform and the load current waveform of said variable frequency electrical driving signal after the frequency of said driving signal has been adjusted by said frequency tuning means to said mechanical resonance frequency.

2. The apparatus of claim 1 wherein said frequency tuning means includes slope checking means to reject spurious peaks in said load current versus frequency function by comparing the slope of said load current versus frequency function of every peak in load current to a predetermined minimum positive slope.

3. The apparatus of claim 1 wherein said driver means includes a voltage controlled oscillator for creating said driving signal, said voltage controlled oscillator having a coarse tuning input for receiving a coarse tuning signal that alters the frequency of said driving signal by a first factor per unit change in said coarse tuning signal and has a fine tuning input for receiving a fine tuning signal that alters the frequency of said driving signal by a second factor per unit change in said fine tuning signal.

4. The apparatus of claim 3 wherein said frequency tuning means includes a computer means for generating said coarse and fine tuning signals in such a manner that said load current peak having a slope satisfying said predetermined criteria is located by setting said coarse tuning signal at a predetermined value and then sweeping said fine tuning signal through a predetermined range, and, if said peak is not found, for setting said coarse signal at a new value and then sweeping said fine tuning signal through a predetermined range and for repeating the above steps until said peak is located.

5. The apparatus of claim 4 wherein said slope checking means rejects said peak if said peak is found at a frequency lying within the upper or lower 25% of the range of frequencies which said driving signal can assume for any fixed level of said coarse signal and full excursion of said fine tuning signal.

6. An apparatus for driving an ultrasonic probe comprising:
   first means for generating an alternating current driving signal for said probe thereby causing load current to flow in said probe and having an input for receiving a first control signal to determine the frequency of said driving signal;
   second means coupled to said first means to determine the mechanical resonant frequency of said probe under then existing conditions at predetermined times by causing said first means to generate said driving signal at a first frequency and for recording the load current flowing through said probe which results, and for causing said first means to increment the frequency of said driving signal to a second frequency and for recording the resulting load current through said probe at said second frequency, and, if the load current at said second frequency is less than the load current at said first frequency, for calculating the slope of said load current versus frequency function for the load current samples adjacent said load current peak, and for comparing the calculated slope to a constant which is positive and greater than the slope at any false peak in the load current versus frequency function, and, if the slope is greater than said constant, for generating said first control signal to control said first means so as to generate said driving signal at said mechanical resonant frequency of said probe which caused said peak load current to flow;
   a tuning inductor means for coupling said driving signal to said probe and having an input for receiving a second control signal which controls the amount of inductance of said tuning inductor and for changing inductance in accordance with said second control signal;
   means coupled to said tuning inductor and to said first means and to said second means for determining the actual phase angle between the driving signal for said probe and the resulting load current and for determining the difference between said actual phase angle and a desired range of phase angles and for generating said second control signal to tune said tuning inductor to bring said phase angle within said desired range of phase angles after said second means has tuned said first means to generate said driving signal at said mechanical resonance frequency of said probe.

7. The apparatus of claim 6 wherein said second means includes means for determining said mechanical resonant frequency by sweeping the frequency of said driving signal through a predetermined range of frequencies and measuring the load current drawn by said probe and for selecting as said mechanical resonant frequency, that frequency where said load current is at a peak and the slope of a function relating load current versus frequency is greater than a predetermined value if and only if the frequency at said peak load current is within a predetermined band of frequencies.

8. An apparatus as defined in claim 7 wherein said first means includes a voltage controlled oscillator for generating said driving signal and having an input for receiving a power control signal which controls the amplitude of said driving signal generated by said voltage controlled oscillator and wherein said apparatus further comprises means coupled to said first means and including a foot operated control, for determining the desired amount of power to be dissipated in said probe from the position of said foot operated control and for generating said power control signal controlling said voltage controlled oscillator such that the amplitude of said driving signal is altered in accordance with the desired power to be dissipated in said probe.

9. An apparatus for driving an ultrasonic probe comprising:

first means for generating a driving signal for said probe thereby causing load current to flow in said probe and having an input for receiving a first control signal to determine the frequency of said driving signal;

second means coupled to said first means to occasionally determine the mechanical resonant frequency of said probe under then existing conditions and to generate said first control signal to tune said first means for generating a driving signal at said mechanical resonant frequency of said probe;

a tuning reactance means for coupling said drive signal to said probe and having an input for receiving a second control signal which controls the amount of reactance coupled to said load and for changing the amount of said reactance in accordance with the value of said second control signal;

third means coupled to said tuning reactance means for determining the actual phase angle between the driving signal voltage for said probe and the resulting load current and for determining the difference between said actual phase angle and a predetermined minimum phase angle and for generating said second control signal to tune said tuning reactance means to change its reactance so as to minimize said phase angel;

and wherein said first means also has an input for receiving a third control signal which controls the amplitude of the driving signal generated by said first means and wherein said apparatus further comprises means coupled to said first means and including a foot operated control with a range of deflection, for determining the desired amount of power to be dissipated in said probe by determining the percentage of full deflection of said foot operated control and for generating said third control signal so as to control the amplitude of said driving signal such that the power dissipated in said probe is a linear function of the deflection of said foot operated control;

and wherein said second means includes means for generating said second control signal so as to cause said tuning reactance means to assume a minimum inductance and then for sweeping the frequency of said drive signal through a band of frequencies and for recording the resulting drive current drawn by said probe for each frequency and for comparing said drive signal current at each said frequency to the highest drive current previously recorded and for calculating the slope of a function relating each said load current value to the corresponding frequency of said drive signal at least at said peak load current and for comparing the value of said slope to a minimum slope value, and for generating said first control signal to set the drive frequency to the frequency which results in a peak load current having a slope greater than said minimum slope; and wherein said third means includes means to calculate one-half the difference between said actual phase angle and said predetermined minimum phase angle and for generating said second control signal so as to adjust the inductance of said tuning inductor means to alter the actual phase angle by one-half said phase angle difference and to continue this process of altering said inductance of said tuning inductor means until the difference between said actual phase angle and said predetermined minimum phase angle is within a specified tolerance.

10. An apparatus for driving an ultrasonic probe having a piezoelectric crystal excitation device for exciting a metal rod comprising:

first means for finding and tracking the mechanical resonance frequency of said probe by monitoring the load current and the slope of the load current versus driving frequency functions and for generating a driving signal and applying it to said crystal, said driving signal having a frequency substantially equal to the mechanical resonance frequency of said probe;

tunable reactance means coupled to said piezoelectric crystal for cancelling the reactive component of the load impedance represented by said piezoelectric crystal excitation device such that the output impedance of said first means is substantially the complex conjugate of the load impedance; and further comprising resonance tuning means in said first means for tuning said tunable reactance means so as to have minimum reactance during a resonance tuning phase and for sweeping the frequency of said driving signal during said resonance tuning phase until a peak load current occurs which has a slope of change of load current per unit change in frequency greater than a predetermined minimum value, and for fixing the frequency of said drive signal at the frequency which caused said peak load current to occur which satisfies said minimum slope value criteria, and then for allowing said tunable reactance means to tune out said reactive component at said resonant frequency of said driving signal.

11. An apparatus for driving an ultrasonic probe having a piezoelectric crystal excitation transducer mechanically coupled to a metal rod comprising:

means for generating a periodic driving signal having a frequency which can be tuned; and means, coupled to said means for generating, for automatically tuning the frequency of said means for generating so that the frequency of the periodic driving signal matches the mechanical resonant frequency of said probe by incrementally changing said driving signal frequency and monitoring the value of load current drawn by said probe at each frequency and calculating the slope of a load current versus driving signal frequency function at least at each frequency where successive measurements of load current indicates a peak load current has been found, and for controlling said means for generating so as to set the frequency of said driving signal at the frequency where said slope of load current versus frequency is greater than a predetermined minimum.

12. The apparatus of claim 11 further comprising an electronically tunable tuning reactance coupled to said probe and means coupled to said electronically tunable reactance and to said means for automatically tuning for tuning said electronically tunable reactance so as to have minimum reactance during the time when said frequency of said driving signal is being incrementally altered, and, after said mechanical resonant frequency has been found, for sensing the phase angle difference between the voltage of said driving signal and said load current and tuning said reactance so as to cause the overall load impedance represented by said probe and said electrically tunable reactance to be substantially resistive with little or no reactance component.

13. A method of driving an ultrasonically driven probe comprising the steps of:
 (1) generating a driving signal to said probe having a frequency within a band of frequencies which encompasses the mechanical resonance frequency of said probe and applying said driving signal to said probe;
 (2) sampling and storing the amount of drive current drawn by said probe at said frequency;
 (3) comparing said drive current sample to the highest drive current sample previously recorded for other drive signal frequencies in said band of frequencies;
 (4) calculating the slope of a function relating each said drive current sample to the corresponding drive signal frequency which caused that drive current to flow for substantially all said drive current samples;
 (5) incrementing the frequency of said driving signal;
 (6) repeating steps 1 through 5 until a mechanical resonant frequency is found where the corresponding drive current sample is larger than all other drive current samples and where the slope of said function at said mechanical resonant frequency which caused said highest load current to flow is greater than a predetermined constant selected to eliminate spurious current peaks caused by phenomena other than mechanical resonance from being mistaken as the load current peak associated with the actual mechanical resonance.

14. The method of claim 13 wherein said step of incrementing said frequency of said driving signal includes the steps of setting a coarse tuning signal at a predetermined value and incrementing a fine tuning signal to sweep through a range of frequencies defining a window, and if said resonance frequency is not found, for changing said coarse tuning signal to a new value and incrementing said fine tuning signal to sweep through a range of frequencies defining a new window, and repeating the above described steps until said resonance frequency is found, or a determination is made that said resonance frequency cannot be found.

15. The method of claim 14 wherein steps 5 and 6 include the steps of continuing to alter said coarse tuning and fine tuning signals until said resonance frequency is located within the center 50% of frequencies of any one of said windows or frequencies swept by the incrementation of said fine tuning signal.

16. The method of claim 15 wherein said step of altering said coarse tuning signal is carried out such that each said window of frequencies somewhat overlaps each other said window of frequencies.

17. The method of claim 13 further comprising the step of tuning the reactance of an electronically controlled reactance coupled to said probe such that during the process of incrementing the frequency of the driving signal and taking load current samples, the reactance is controlled so as to not affect this process of locating the mechanical resonant frequency, and such that, after the mechanical resonant frequency is found, the reactance is tuned so as to substantially cancel the reactance of said load so as to increase the efficiency of power transfer to said load.

* * * * *